United States Patent [19]
Chong et al.

[11] Patent Number: 6,083,743
[45] Date of Patent: *Jul. 4, 2000

[54] HAEMOPHILUS OUTER MEMBRANE PROTEIN

[75] Inventors: Pele Chong, Richmond Hill, Canada; Wayne Thomas, Nedlands, Australia; Yan Ping Yang, Willowdale, Canada; Sheena Loosmore, Aurora, Canada; Dwe Yuan Charles Sia, Thornhill, Canada; Michel Klein, Willowdale, Canada

[73] Assignee: Connaught Laboratories Limited, North York, Canada

[*] Notice: This patent is subject to a terminal disclaimer.

[21] Appl. No.: 09/135,166

[22] Filed: Aug. 18, 1998

Related U.S. Application Data

[63] Continuation of application No. 08/433,522, filed as application No. PCT/CA93/00501, Nov. 23, 1993.

[30] Foreign Application Priority Data

Nov. 23, 1992 [GB] United Kingdom ............... 9224584

[51] Int. Cl.$^7$ ............... A61K 39/102; C07K 14/285; C12N 15/31
[52] U.S. Cl. ............... 435/320.1; 424/185.1; 424/192.1; 424/193.1; 424/197.11; 424/203.1; 424/234.1; 424/256.1; 435/69.1; 435/69.3; 435/69.7; 530/300; 530/350; 536/23.7
[58] Field of Search ............... 424/190.1, 185.1, 424/192.1, 193.1, 197.11, 203.1, 234.1, 256.1; 435/69.1, 69.3, 71.1, 71.2, 91.4, 252.1, 320.1, 69.7; 514/44; 530/350, 300; 536/23.1, 23.7

[56] References Cited

U.S. PATENT DOCUMENTS

| | | |
|---|---|---|
| 4,888,170 | 12/1989 | Curtis, III . |
| 5,013,664 | 5/1991 | Brodeur et al. . |
| 5,194,254 | 3/1993 | Barber et al. . |
| 5,580,859 | 12/1996 | Felgner et al. . |
| 5,589,466 | 12/1996 | Felgner et al. . |
| 5,593,972 | 1/1997 | Weiner et al. . |
| 5,620,896 | 4/1997 | Hermann et al. . |

FOREIGN PATENT DOCUMENTS

| | | |
|---|---|---|
| 0281673 | 9/1988 | European Pat. Off. . |
| 0378929 | 7/1990 | European Pat. Off. . |
| WO 91/06652 | 5/1991 | WIPO . |
| WO 92/17167 | 10/1992 | WIPO . |

OTHER PUBLICATIONS

Thomas, W. et al—Molecular Cloning of DNA Coding for Outer Membrane Proteins of Haemophilus Type b—Inf. and Imm. Jun. 1986, pp. 812–817.

Whalen, Robert G.—Emerging Infectious Diseases—vol. 2, No. 3—Jul.–Sep. 1996, pp. 168–175.
Roth, Jack A. et al—Journal of National Cancer Institute—vol. 89, No. 1, Jan. 1, 1997—pp. 21–40.
Report and Recommendations of the Panel to Assess the NIH Investment in Research on Gene Therapy, Dec. 7, 1995. Orkin et al.
Thomas, W.R.—Infection and Immunity—vol. 58, No. 4, Apr. 1990, pp. 1909–1913.
O'Hagan, Clin. Pharmacokinet. vol. 22, No. 1, pp. 1–10 (1992).
Ulmer et al. Curr. Opin. Invest. Drugs. vol. 2, No. 9, pp. 983–989 (1993).
Berns, C.A. et al,—J. Mol. Biol. 11:476–490—(1965).
Carlone, G.M. et al—J. Clin. Microbiol. 24:330–331—(1986).
Smith, D.B. et al—Gene 67:31–40—(1988).
Harkness, R. et al,—J. Bacteriol. 174:2425–2430—(1992).
Hamel et al,—J. Med. Microbiol.—23:163–170 (1987).
Mills et al, Infect. Immun. 61:399–410 (1993).
Trinchieri, Immunology Today 14:335–338 (1993).
Hopp, T.P.—J. Immunol. Methods—88:1–18 (1986).
Zangwill et al, MMWR 42:1–15, (1993).
Loeb et al—Infect. Immun. 55:2612–2618—(1987).
Panezutti, Infect. Immun. 61:1867–1872—(1993).
Loeb, M.R. et al—Outer Membrane Protein Composition in Disease Isolates of Haemophilus Influenzae: Pathogenic and Epidemiological Implications—Inf. And Imm. Dec. 1980, pp. 709–717.
Barenkamp, S.J. et al—Subtyping Isolates of Haemophilus Influenzae Type b by Outer–Membrane Protein Profiles—J. of Inf Diseases, vol. 143, No. 5, May 1981.
Gulig, P.A. et al.—Antibody Response of Infants to Cell Surface–Exposed Outer Membrane Proteins of Haemophilus Infleunzae type b After Systemic Haemophilus Disease—Inf. And Imm, Jul. 1982, pp. 82–88.
Vachon V.—Transmembrane Permeability Channels across the Outer Membrane of Haemophilus Influenzae Type b—J. of Bacteriology, Jun. 1985, pp. 918–924.
Coglan, New Scientist, 25 No. 1995, pp. 14–15.

*Primary Examiner*—Phuong T. Bui
*Attorney, Agent, or Firm*—Sim & McBurney

[57] ABSTRACT

Purified and isolated nucleic acid from specific strains of *Haemophilus influenzae* is provided which encodes at least a portion of the D15 outer membrane protein of Haemophilus. The nucleic acid is used to produce peptides, polypeptides and proteins free of contaminant associated with Haemophilus for purposes of diagnosis and medical treatment. Furthermore, the nucleic acid may be used in the diagnosis of Haemophilus infection. Antisera obtained following immunization with the nucleic acid D15 outer membrane protein or peptides also may be used for the purpose of diagnosis and medical treatment.

10 Claims, 82 Drawing Sheets

FIG.1A-1

H. influenzae b Ca strain D15 sequence

```
                    Hind III                          -35
GATTACGCCAAGCTTAACGGTGTGTTTGCATTATTTAAATGATTTTTACGTCTATAATTTAT
         10           20            30           40           50           60
                                                                         -10

RBS        MET LYS LYS LEU LEU ILE ALA SER LEU LEU PHE GLY THR THR THR T
ATAGGATACAATCGATGAAAAAACTTCTAATCGCAAGTTTATTATTCGGTACGACAACGA
         70           80           90          100          110          120 start truncated GST/D15
HR VAL PHE ALA ALA PRO PHE VAL ALA LYS ASP ILE ARG VAL ASP GLY VAL GLN GLY ASP L
CTGTGTTTGCCGCACCTTTTGTGGCAAAAGATATTCGTGTGGATGGTGTTCAAGGTGACT
        130          140          150          160          170          180

EU GLN GLN ILE ARG ALA SER LEU PRO VAL THR CYS VAL PRO GLY GLN ARG VAL THR ASP ASN A
TAGAACAACAAATCCGAGCAAGTTTACCCTGTTACCTGCGTTCCGGGTCAGCGTGTGACAATG
        190          200          210          220          230          240
                     spurious thrombin site
SP VAL ALA ASN ILE VAL ARG SER LEU PHE VAL SER GLY ARG PHE ASP ASP VAL LYS ALA H
ATGTGGCTAATATTGTCCGCTCTCTTTATTCGTAAGTGGTCGATTCGATGATGTGAAAGCGC
        250          260          270          280          290          300

IS GLN GLU GLY ASP VAL LEU VAL VAL SER VAL VAL ALA LYS SER ILE ILE SER ASP VAL L
ATCAAGAAGGCGATGTGCTTGTTGTTAGCGTTGTGGCTAAATCGATCATTTCAGATGTTA
        310          320          330          340          350          360
```

FIG.1A-2

```
YS  ILE LYS GLY ASN SER VAL ILE PRO THR GLU ALA LEU LYS GLN ASN LEU ASP ALA ASN G
A A ATCAAAGGTAACTCTGTTATTCCCACTGAAGCACTTAAACAAAACTTAGATGCTAACG
        370             380             390             400             410         420

LY  PHE LYS VAL GLY ASP VAL LEU ILE ARG GLU LYS ASN GLU PHE ALA LYS SER VAL L
G G TTTAAAGTTGGCGATGTTTTAATTCGAGAAAAATTAAATGAATTTGCCAAAAGTGTAA
        430             440             450             460             470         480

YS  GLU HIS TYR ALA SER VAL GLY ARG TYR ASN ALA THR VAL GLU PRO ILE VAL ASN THR L
A A GAGCACTATGCAAGTGTAGGTCGCTATAACGCAACAGTTGAACCTATTGTCAATACGC
        490             500             510             520             530         540

EU  PRO ASN ASN ARG ALA GLU ILE LEU ILE ASN GLN ILE ASN SER THR GLU ASP LYS ALA LYS LEU A
T A CCAAATAATCGCGCTGAAATTTTAATTCAAATCAATTCAACAGAAGATAAAGCAAAATTGG
        550             560             570             580             590         600

LA  SER LEU THR PHE LYS GLN GLY ASN GLU SER VAL SER SER THR LEU GLN GLU GLN MET G
C A TCATTAACTTTCAAGGGGAACGAATCTGTTAGCAGTACATTACAAGAACAAATGG
        610             620             630             640             650         660

LU  LEU GLN PRO ASP SER TRP TRP LYS LEU TRP GLY ASN LYS PHE GLU GLY ALA GLN PHE G
A A TTACAACCCTGATTCTTGGTGGAAATTATGGGGAAATAAATTTGAAGGTGCGCAATTCG
        670             680             690             700             710         720
   end truncated GST/D15
LU  LYS ASP LEU GLN SER ILE ARG ASP TYR TYR LEU ASN GLY TYR ALA LYS ALA GLN I
A G AAAGATTTGCAGTCAATTCGTGATTATTATTTAAATAATGGCTATGCCAAAGCACAAA
        730             740             750             760             770         780
```

FIG.1A-3

```
LE  THR LYS THR ASP VAL GLN LEU ASN ASP GLU LYS THR LYS VAL ASN VAL THR ILE ASP V
TTACTAAAACGGATGTTCAGCTAAATGATGAAAAAACAAAAGTTAATGTAACCATTGATG
          790                 800                 810                 820                 830                 840

AL  ASN GLU GLY LEU GLN TYR ASP LEU ARG SER ALA ARG ILE ILE GLY ASN LEU GLY GLY M
TAAATGAAGGTTTACAGTATGACCTTCGTAGTGCACGCATTATAGGTAATCTGGGAGGTA
          850                 860                 870                 880                 890                 900

ET  SER ALA GLU LEU GLU PRO LEU LEU GLU ASN ALA LEU HIS LEU SER ALA PHE ARG ARG S
TGTCTGCCGAGCTTGAACCTTTACTTGAAAATGCATTACATTTAAATGATACTTTCCGCCGTA
          910                 920                 930                 940                 950                 960

ER  ASP ILE ALA ASP VAL GLU ASN SER VAL GLU ASN LYS ALA ILE LYS ALA ILE LYS LEU GLY GLU ARG GLY TYR GLY S
GTGATATTGCAGATGTAGAGAATTCAGTAGAAAATAAAGCAATTAAAGCAAAACTTGGAGAACGCGGTTACGGTA
          970                 980                 990                1000                1010                1020

ER  ALA THR VAL ASN SER VAL PRO ASP PHE ASP ALA ASN LYS THR LEU ALA ILE THR L
GCGCAACGGTAAATTCAGTACCTGATTTTGATGCAAATAAAACATTAGCGATAACCC
         1030                1040                1050                1060                1070                1080

EU  VAL VAL ASP ALA GLY ARG ARG ARG ASP GLY LEU THR VAL ARG GLN LEU ARG PHE GLU GLY ASN THR V
TTGTTGTTGATGCTGGACGACGTTCGCCAACTGTTCGCCAAACTTCGCCTTTGAAGGAAATACCG
         1090                1100                1110                1120                1130                1140
```

FIG.1A-4

```
AL  SER ALA ASP SER THR LEU ARG GLN GLU MET ARG GLN GLU GLY THR TRP TYR ASN S
    TTTCTGCTGATAGCACTTTACGTCAGGAAATGCGCCAACAAGAAGGAACTTGGTATAATT
         1150          1160          1170          1180          1190          1200

ER  GLN LEU VAL GLU LEU GLY LYS ILE ARG LEU ASP ARG THR GLY PHE PHE GLU THR VAL G
    CACAATTAGTTGAGTTAGGAAAAATTCGCTTAGATCGTACAGGTTTCTTCGAAACAGTCG
         1210          1220          1230          1240          1250          1260

LU  ASN ARG ILE ASP PRO ILE ASN GLY SER ASN ASP GLU VAL ASP VAL TYR LYS VAL L
    AAAACCGAATTGATCCTATCAATGGTAGTAATGATGAAGTGGATGTCGTATATAAAGTCA
         1270          1280          1290          1300          1310          1320

YS  GLU ARG ASN THR GLY SER ILE ASN PHE GLY TYR ILE GLY THR GLU SER GLY ILE S
    AAGAACGTAACACGGGTAGTATCAACTTTGGTTATTGGTTACGGTACAGAGAGTGGTATTA
         1330          1340          1350          1360          1370          1380

ER  TYR GLN ALA SER VAL LYS GLN ASP ASN PHE LEU GLY THR GLY ALA ALA VAL SER ILE A
    GTTATCAAGCAAGTGTTAAACAAGATAATTTCTTGGGAACAGGCGGCCAGTAAGTATAG
         1390          1400          1410          1420          1430          1440

LA  GLY THR LYS ASN ASP TYR GLY THR SER VAL ASN LEU GLY TYR THR GLU PRO TYR PHE T
    CTGGTACGAAAAATGATTATGGTACGAGTGTCAATTTGGGTTATACCGAGCCCTATTTTA
         1450          1460          1470          1480          1490          1500

HR  LYS ASP GLY VAL SER LEU GLY GLY ASN VAL PHE PHE GLU ASN TYR ASP ASN SER LYS S
    CTAAAGATGGTGTAAGTCTTGGTGGAAATGTTTTCTTTGAAAACTACGATAACTCTAAAA
         1510          1520          1530          1540          1550          1560
```

FIG.1A-5

```
ER  ASP THR SER SER ASN TYR LYS ARG THR THR TYR GLY SER ASN VAL THR LEU GLY PHE P
    GTG ATA CAT CCT CTA AAC TAT AAG CGT ACG ACT TAC GGA AGT AAT GTT ACT TTA GGT TTC C
       1570            1580            1590            1600            1610            1620

RO  VAL ASN GLU ASN ASN SER TYR TYR VAL GLY LEU GLY HIS THR TYR ASN LYS ILE SER A
    CTG TAA ATG AAA AAT AAC TCC TAT TAT GTA GGA TTA GGT CAT ACC TAT AAA ATT AGT A
       1630            1640            1650            1660            1670            1680

SN  PHE ALA LEU GLU TYR ILE ASN ARG ASN LEU TYR ILE GLN SER MET LYS PHE LYS GLY ASN G
    ACT TTG CTC TAG AAT ATA TCA ATA ACC GTA ATT TTA TAT ATT CAA TCA ATG AAA TTT AAA GGT AAT G
       1690            1700            1710            1720            1730            1740

LY  ILE LYS THR ASN ASP PHE ASP PHE PHE GLY TRP ASN TYR ASN SER LEU ASN ARG G
    GCA TTA AAA CAA ATG ACT TTT TTC TTT TGG TTG GAA ACT ATA ACA GCC TTA ATA GAG
       1750            1760            1770            1780            1790            1800

LY  TYR PHE PRO THR LYS GLY VAL LYS ALA SER LEU GLY ARG VAL THR ILE PRO GLY S
    GCT ATT TCC CAA CTA AAA GGG GTT AAA GCA AGT CTT GGA CGA GTT ACT ATT CCA GGT T
       1810            1820            1830            1840            1850            1860

ER  ASP ASN LYS TYR TYR LYS LEU SER ALA ASP VAL GLN GLY PHE TYR PRO LEU ASP ARG A
    CT GAT AAC AAA TAC TAC AAA CTA AGT GCA GAT GTA CAG GGT TTC TAC CCA TTA GAC AGA G
       1870            1880            1890            1900            1910            1920

SP  HIS LEU TRP VAL VAL SER ALA LYS ALA LYS ALA SER ALA GLY TYR ALA ASN GLY PHE GLY ASN L
    AT CAC CTC TGG GTT GTA TCT GCA AAA GCA TCT GCA GGA TAT GCA AAT GGT TTT GGA AAA CA
       1930            1940            1950            1960            1970            1980
```

FIG.1A-6

```
YS  ARG LEU PRO PHE TYR GLN THR TYR THR ALA GLY GLY ILE GLY SER LEU ARG GLY PHE A
A G C G T T T A C C G T T C T A T C A A A C T T A T A C A G C G G G T G G C A T C G G T T C A T T A C G T G G T T T T G
              1990                2000                2010                2020                2030            2040

LA  TYR GLY SER ILE GLY PRO ASN ALA ILE TYR ALA GLU TYR GLY ASN GLY SER GLY THR G
C T T A T G G T A G T A T T G G A C C T A A C G C A A T T T A T G C C G A A T A T G G T A A T G G T A G T G G T A C T G
              2050                2060                2070                2080                2090            2100

LY  THR PHE LYS LYS ILE SER SER ASP VAL ILE GLY GLY VAL ASN ALA ILE ALA THR ALA SER A
G T A C T T T T A A A G A A G A T A A G T T C T G A T G T G A T T G G T G G T A A T G C A A T C G C T A C A G C T A G C G
              2110                2120                2130                2140                2150            2160

LA  GLU LEU ILE VAL PRO THR PRO PHE VAL SER ASP LYS SER GLN ASN THR VAL ARG THR S
C A G A G T T A A T T G T G C C A A C T C C A T T T G T G A G C G A T A A G A G C C A A A A T A C G G T C C G A A C C T
              2170                2180                2190                2200                2210            2220

ER  LEU PHE VAL ASP ALA ALA SER VAL TRP ASN THR LYS TRP LYS SER ASP LYS ASN GLY L
C C T T T A T T T G T T G A T G C G G C A A G T G T T T G G A A T A C T A A A T G G A A A T C A G A T A A A A A T G G A T
              2230                2240                2250                2260                2270            2280

EU  PHE VAL ASP VAL LEU LYS ARG LEU LYS LYS ARG LEU PRO ASP TYR GLY LYS SER SER ARG ILE ARG ALA S
C T T T T T G T T G A T G T A T T A A A A A G A T T G C C T G A T T A T G G C A A A T C A A G C C G T A T T C G C G C C T
              2290                2300                2310                2320                2330            2340

EU  SER ASP VAL LEU LYS ARG LEU LYS LYS ARG LEU PRO ASP TYR GLY LYS SER SER ARG ALA S
T A G A G A G C G A T G T A T T A A A A A G A T T G C C T G A T T A T G G C A A A T C A A G C C G T A T T C G C G C C T
              2290                2300                2310                2320                2330            2340
```

FIG.1A-7

```
ER  THR GLY VAL GLY PHE GLN TRP GLN SER PRO ILE GLY PRO LEU VAL PHE SER TYR ALA L
C T A C A G G T G T C G G A T T C C A A T G G C A A T C T C C T A T T G G G C C A T T G G T A T T C T T A T G C C A
              2350                    2360                    2370                    2380                    2390                    2400

YS  PRO ILE LYS LYS TYR GLU ASN ASP VAL GLU GLN PHE GLN PHE SER ILE GLY GLY S
A A C C A A T T A A A A A A A T A T G A A A A T G A T G T C G A A C A G T T C C A A T T T A G T A T T G G A G G T T
              2410                    2420                    2430                    2440                    2450                    2460

ER  PHE *** ***
C T T T C T A A T A A A T T G A A C T T T T T T T C T T C A T C A G A A C T C A A A A A C A A C G T T C T C T G C C T A A
              2470                    2480                    2490                    2500                    2510                    2520

```
AGCAAAAAAGAAGTTGATGATAAAAATTGCTGCTCGTAAAAAGTAGAAGCAAAAGTT
        2770            2780            2790            2800            2810            2820
GCGGCTTTAGAAAAAGATGCACCCTCGCTTACGTCAAGCTGATATTCAAAAACGCCAACAG
        2830            2840            2850            2860            2870            2880
GAGATTAATAAATTAGGTGCGGCTGAAGATGCTGAATTACAAAAATTAATGCAAGAACAA
        2890            2900            2910            2920            2930            2940
GATAAAAAAA
```

FIG.1B-1

DS-712-2-1 DNA, Eagan D15 sequence
IS THE SEQUENCE BEING TRANSLATED

```
                    MET LYS LYS LEU LEU ILE ALA SER LEU LEU PHE GLY THR THR THR
T A G G A T A C A A T C G A T G A A A A A A C T T C T A A T C G C A A G T T T A T T C G T A C G A C A A C G A C
                                    380               390               400               410               420

VAL PHE ALA ALA PRO PHE VAL ALA LYS ASP ILE ARG VAL ASP GLY VAL GLN GLY ASP LEU
T G T G T T T G C C G C A C C T T T T G T G G C A A A A G A T A T T C G T G T G G A T G G T G T T C A A G G T G A C T T
            430               440               450               460               470               480

GLU GLN ILE ARG ALA SER LEU PRO VAL ARG ALA GLY GLN ARG VAL THR ASP ASN ASP
A G A A C A A A T C C G A G C A A G T T T A C C T G T T C G T G C C G G T C A G C G T G T G A C T G A C A A T G A
            490               500               510               520               530               540

VAL ALA ASN ILE VAL ARG SER LEU PHE VAL SER GLY ARG PHE ASP ASP VAL LYS ALA HIS
T G T G G C T A A T A T T G T C C G C T C T T T A T T C G T A A G T G G T C G A T T C G A T G A T G T G A A A G C G C A
            550               560               570               580               590               600

GLN GLU GLY ASP VAL VAL LEU VAL VAL SER VAL ALA LYS SER ILE ILE SER ASP VAL LYS
T C A A G A A G G C G A T G T G T G C T T G T T G T T A G C G T T G T G G C T A A A T C G A T C A T T T C A G A T G T T A A A
            610               620               630               640               650               660

ILE LYS GLY ASN SER VAL ILE PRO THR GLU ALA LEU LYS GLN ASN LEU ASP ALA ASN GLY
A A T C A A A G G T A A C T C T G T T A T T C C C A C T G A A G C A C T T A A A C A A A A C T T A G A T G C T A A C G G
            670               680               690               700               710               720
```

FIG.1B-3

```
PHE LYS VAL GLY ASP VAL LEU ILE ARG GLU LYS LEU ASN GLU PHE ALA LYS SER VAL LYS
GTTTAAAGTTGGCGATGTGTTTAATTCGAGAAAAATTAAATGAATTTGCCAAAAGTGTAAA
        730                 740                 750                 760                 770                 780

GLU HIS TYR ALA SER VAL GLY ARG TYR ARG ALA THR ASN ALA THR VAL GLU PRO ILE VAL ASN THR LEU
AGAGCACTATGCAAGTGTAGGTCGCTATAACGCAACAGTTGAACCTATTGTCAATACGCT
        790                 800                 810                 820                 830                 840

PRO ASN ARG ALA GLU ILE LEU PHE LYS ILE GLN ILE LEU ASN ASP LYS ASP LYS ALA LYS LEU ALA
ACCAAATCGCGCTGAAATTTTAATTCAAATCAATGAAGATGATAAAGCAAAATTGGGC
        850                 860                 870                 880                 890                 900

SER LEU THR PHE LYS GLY ASN GLU SER VAL SER SER THR LEU GLN MET GLU
ATCATTAACTTTCAAGGGAACGAATCTGTTAGTAGCAGTACATTACAAGAACAAATGGA
        910                 920                 930                 940                 950                 960

LEU GLN PRO ASP SER TRP TRP LYS LEU TRP GLY ASN LYS PHE GLU GLY ALA GLN PHE GLU
ATTACAACCTGATTCTTGGTGGAAATTATGGGGAAATAAATTTGAAGGTGCGCAATTCGA
        970                 980                 990                 1000                1010                1020

LYS ASP LEU GLN SER ILE ARG ASP TYR TYR LEU ASN ASN GLY TYR ALA LYS ALA GLN ILE
GAAAGATTTGCAGTCAATTCGTGATTATTATTTAAATAATGGCTATGCCAAAGCACAAAT
        1030                1040                1050                1060                1070                1080

THR LYS THR ASP VAL GLN LEU ASN ASP VAL SER GLU LYS VAL ASN THR ILE ASP VAL
TACTAAAACGGATGTTCAGCTAAATGATGTAAGCTAAAAAAGTTAATGTAACCATTGATGT
        1090                1100                1110                1120                1130                1140
```

FIG.1B-4

```
ASN GLU GLY LEU GLN TYR ASP LEU ARG SER ALA ARG ILE ILE GLY ASN LEU GLY GLY MET
AAATGAAGGTTTACAGTATGACCTTCGTAGTGCACGCATTATAGGTAATCTGGGAGGTAT
     1150              1160              1170              1180              1190              1200

SER ALA GLU LEU GLU PRO LEU LEU SER ALA LEU HIS LEU ASN ASP THR PHE ARG ARG SER
GTCTGCCGAGCTTGAACCCTTTACTTTCAGCATTACATTTAAATGATACTTTCCGCCGTAG
     1210              1220              1230              1240              1250              1260

ASP ILE ALA ASP VAL GLU ASN ALA ILE LYS ALA LYS ASN LEU GLY GLU ARG GLY TYR GLY SER
TGATATTGCAGATGTAGAAAATGCAATTAAAGCAAAAACTTGGAGAACGCGGTTACGGGTAG
     1270              1280              1290              1300              1310              1320

ALA THR VAL ASN SER VAL PRO ASP PHE ASP ASP ALA ASN LYS THR LEU ALA ILE THR LEU
CGCAACGGTAAATTCAGTACCTGATTTTGATGATGCAAATAAAACATTAGCGATAACCCT
     1330              1340              1350              1360              1370              1380

VAL VAL ASP ALA GLY ARG ARG LEU THR VAL ARG GLN LEU ARG PHE GLU GLY ASN THR VAL
TGTTGTTGATGCTGGACGACGTTAACTGTTCGCCAACTTTCGCTTTGAAGGAAATACCGT
     1390              1400              1410              1420              1430              1440

SER ALA ASP SER THR LEU ARG GLN GLN MET ARG GLN GLU GLY GLY THR TRP TYR ASN SER
TTCTGCTGATAGCACTTTACGTCAGCAGATGCGCCAACAAGAAGGAACTTGGTATAATTC
     1450              1460              1470              1480              1490              1500
```

FIG.1B-5

```
GLN LEU VAL GLU LEU GLY LYS ILE ARG LEU ASP ARG THR GLY PHE PHE GLU THR VAL GLU
ACAATTAGTTGAGTTAGGAAAAATTCGCTTAGATCGTACAGGTTTCTTCGAAACAGTCGA
         1510                1520               1530              1540              1550              1560

ASN ARG ILE ASP PRO ILE ASN GLY SER ASN ASP GLU VAL ASP VAL VAL TYR LYS VAL LYS
AAACCGAATTGATCCTATCAATGGTAGTAATGATGAAGTGGATGTCGTATATAAAGTCAA
         1570              1580              1590              1600              1610              1620

GLU ARG ASN THR GLY SER ILE ASN PHE GLY ILE GLY TYR GLY THR GLU SER GLY ILE SER
AGAACGTAACACGGGTAGTATCAACTTTGGTATTGGTTACGGTACAGAGAGTGGTATTAG
         1630              1640              1650              1660              1670              1680

TYR GLN ALA SER VAL LYS GLN ASP ASN PHE LEU GLY THR GLY ALA ALA VAL SER ILE ALA
TTATCAAGCAAGTGTTAAACAAGATAATTTCTTGGGAACAGGCGGCCAGTAAGTATAGC
         1690              1700              1710              1720              1730              1740

GLY THR LYS ASN ASP TYR GLY TYR ASN LEU VAL ASN LEU GLY TYR GLU PRO TYR PHE THR
TGGTACGAAAAATGATTATGGTACGAGTGTCAATTTGGGTTATACCGAGCCCTATTTTAC
         1750              1760              1770              1780              1790              1800

LYS ASP GLY VAL SER LEU GLY GLY ASN VAL PHE PHE GLU ASN TYR ASP ASN SER LYS SER
TAAAGATGGTGTAAGTCTTGGTGGAAATGTTTTCTTTGAAAACTACGATAACTCTAAAAG
         1810              1820              1830              1840              1850              1860
```

FIG.1B-6

```
ASP THR SER SER ASN TYR LYS ARG THR THR TYR GLY SER ASN VAL THR LEU GLY PHE PRO
TGATACATCCCTCTAACTATAAGCCGTACGACTTACGGAAGTAATGTTACTTTAGGTTTCCC
       1870          1880          1890          1900          1910          1920

VAL ASN GLU ASN ASN ASN SER TYR TYR VAL GLY LEU GLY LEU GLY HIS THR TYR ASN LYS ILE SER ASN
TGTAAATGAAAATAACTCCTATTATGTAGGATTAGGTCATACCTATAATAAAATTAGTAA
       1930          1940          1950          1960          1970          1980

PHE ALA LEU GLU TYR ASN ARG ASN LEU TYR ILE GLN SER MET LYS PHE LYS GLY ASN GLY
CTTTGCTCTAGAATATAACCGTAATTTATATATTCAATCAATGAAATTTAAAGGTAATGG
       1990          2000          2010          2020          2030          2040

ILE LYS THR ASN ASP PHE ASP PHE SER PHE GLY TRP ASN TYR ASN SER LEU ASN ARG GLY
CATTAAAACAAATGACTTTGATTTTTCTTTTGGTTGGAACTATAACAGCCTTAATAGAGG
       2050          2060          2070          2080          2090          2100

TYR PHE PRO THR LYS GLY VAL LYS ALA SER LEU GLY ARG VAL THR ILE PRO GLY SER
CTATTTCCCAACTAAAGGGGTTAAAGCAAGTCTTGGTGGACGAGTTACTATTCCAGGTTC
       2110          2120          2130          2140          2150          2160

ASP ASN LYS TYR TYR LYS LEU SER ALA ASP VAL GLN GLY PHE TYR PRO LEU ASP ARG ASP
TGATAACAAATACTACAAACTAAGTGCAGATGTACAGGGTTTCTACCCATTAGACAGAGA
       2170          2180          2190          2200          2210          2220

HIS LEU TRP VAL VAL SER ALA LYS ALA LYS SER ALA TYR ALA ASN GLY PHE GLY ASN LYS
TCACCTCTGGGTTGTATCTGCAAAAAGCATCTGCAGGATATGCAAATGGTTTTGGAAACAA
       2230          2240          2250          2260          2270          2280
```

FIG.1B-7

```
ARG LEU PRO PHE TYR GLN THR TYR THR ALA GLY GLY ILE GLY SER LEU ARG GLY PHE ALA
GCGTTTACCGTTCTATCAAACTTATACAGCGGTGGCATCGGTTCATTACGTGGTTTTGC
     2290              2300              2310              2320              2330              2340

TYR GLY SER ILE GLY PRO ASN ALA ILE TYR ALA GLU TYR GLY ASN GLY SER GLY THR GLY
TTATGGTAGTATTGGACCTAACGCAATTTATGCCGAATATGGTAATGGTAGTGGTACTGG
     2350              2360              2370              2380              2390              2400

THR PHE LYS LYS ILE SER SER ASP VAL ILE GLY GLY ASN ALA ALA ILE ALA THR ALA SER ALA
TACTTTTAAAGAAGATAAGTTCTGATGTGATTGGTGGTAATGCAATCGCTACAGCTAGCGC
     2410              2420              2430              2440              2450              2460

GLU LEU ILE VAL PRO THR PRO PHE VAL SER GLN ASN THR LYS SER VAL ARG THR SER
AGAGTTAATTGTGCCAACTCCATTTGTGAGCCAAAATACGGTCCGAACCTC
     2470              2480              2490              2500              2510              2520

LEU PHE VAL ASP ALA ALA SER VAL TRP ASN THR LYS TRP LYS SER ASP LYS ASN GLY LEU
CTTATTTGTTGATGCGGCAAGTGTTTGGAATACTAAATGGAAATCAGATAAAAATGGATT
     2530              2540              2550              2560              2570              2580

GLU SER ASP VAL LEU LYS ARG LEU LYS ARG GLY LYS LEU SER SER ARG ILE ARG ALA SER
AGAGAGCGATGTATTAAAAAGATTGCCCTGATTATGGCAAATCAAGCCGTATTCGCGCCTC
     2590              2600              2610              2620              2630              2640
```

FIG.1B-8

```
THR GLY VAL GLY PHE GLN TRP GLN SER PRO ILE GLY PRO LEU VAL PHE SER TYR ALA LYS
TACAGGTGTCGGATTCCAATGGCAATCTCCTATTGGGCCATTGGTATTCTCTTATGCCAA
    2650                2660                2670                2680                2690                2700

PRO ILE LYS LYS TYR GLU ASN ASP ASP VAL GLU GLN PHE GLN PHE SER ILE GLY GLY SER
ACCAATTAAAAAATATGAAAATGATGATGTCGAACAGTTCCAATTTAGTATTGGAGGTTC
    2710                2720                2730                2740                2750                2760

PHE *** ***
TTTCTAATAAATTGAACTTTTTTCTTCATCAGAACTCAAAAACAACGTTCTCTGCCTAAT
    2770                2780                2790                2800                2810                2820

TTAATTGGGCAGAGAAAATATTAAACCCATCATTTAATTAAGGATATTTATCAAATGAAA
    2830                2840                2850                2860                2870                2880

AACATCGCAAAAGTAACCGCACTTGCTTTAGGTATTGCACTTGCTTTCAGGCTATGCTTCC
    2890                2900                2910                2920                2930                2940

GCTGAAGAAAAAATTGCTTTCATTAATGCACTTATATTTTCAA
    2950                2960                2970                2980
```

FIG.1C-1

DS-691-1-5 DNA, Minn A D15 sequence
IS THE SEQUENCE BEING TRANSLATED

```
                                                        MET LYS LEU LEU ILE ALA SER LEU
TTTTACGTCTATAATTTATATAGGATACAATCGATGAAAAACTTCTAATCGCAAGTTTA
         310               320               330               340               350               360

LEU PHE GLY THR THR THR VAL PHE ALA ALA PRO PHE VAL ALA LYS ASP ILE ARG VAL
TTATTCGGTACGACAACGACTGTGTTTGCCGCCACCCTTTTGTGGCAAAAGATATTCGTGTG
         370               380               390               400               410               420

ASP GLY VAL GLN GLY ASP LEU GLU GLN ILE ARG ALA SER LEU PRO VAL ARG ALA GLY
GATGGTGTTCAAGGTGACTTAGAACAAATCCGAGCAAGTTTACCTGTTCGTGCCGGT
         430               440               450               460               470               480

GLN ARG VAL THR ASP ASN ILE VAL ALA ASN ILE VAL ARG SER LEU PHE VAL SER GLY ARG
CAGCGTGTGACTGACAATATTGTCGCTAATATTGTCCGCTCTCTTTATTCGTAAGTGGTCGA
         490               500               510               520               530               540

PHE ASP ASP VAL LYS ALA HIS GLN GLU GLY ASP VAL LEU VAL VAL SER VAL VAL ALA LYS
TTCGATGATGTGAAAGCGCATCAAGAAGGCGATGTGCTTGTTGTTAGCGTTGTGGCTAAA
         550               560               570               580               590               600

SER ILE ILE SER ASP VAL LYS ILE LYS GLY ASN SER VAL ILE PRO THR GLU ALA LEU LYS
TCGATCATTTCAGATGTTAAAATCAAAGGTAACTCTGTTATTCCCACTGAAGCACTTAAA
         610               620               630               640               650               660
```

FIG.1C-3

```
GLN ASN LEU ASP ALA ASN GLY PHE LYS VAL GLY ASP VAL LEU ILE ARG GLU LYS LEU ASN
CAAAACTTAGATGCTAACGGGTTTAAAGTTGGCGATGTTTTAATTCGAGAAAATTAAAT
       670              680              690              700              710              720

GLU PHE ALA LYS SER VAL LYS GLU LYS SER VAL LYS TYR ALA SER VAL GLY ARG TYR ASN ALA THR VAL
GAATTTGCCAAAAGTGTAAAAGAGAGCACTATGCAAGTGTAGGTCGCTATAACGCAACAGTT
       730              740              750              760              770              780

GLU PRO ILE VAL ASN THR LEU PRO ASN ARG ALA GLU ILE LEU ILE GLN ILE ASN GLU
GAACCTATTGTCAATACGCTACCAAATAATCGCGCTGAAATTTTAATTCAAATCAATGAA
       790              800              810              820              830              840

ASP ASP LYS ALA LYS LEU ALA SER LEU THR PHE LYS GLY ASN GLU THR PHE LYS ASN GLU SER VAL SER SER
GATGATAAAGCAAAATTGGCATCATTAACTTTCAAGGGAACGAATCTGTTAGTAGCAGT
       850              860              870              880              890              900

THR LEU GLN GLU GLN MET GLU LEU GLN PRO ASP SER TRP TRP LYS LEU TRP GLY ASN LYS
ACATTACAAGAACAAATGGAATTACAACCTGATTCTTGGTGGAAATTATGGGAAATAAA
       910              920              930              940              950              960

PHE GLU GLY ALA GLN PHE GLU LYS ASP LEU GLN SER ILE ARG ASP TYR TYR LEU ASN ASN
TTTGAAGGTGCGCAATTCGAGAAAGATTTGCAGTCAATTCGTGATTATTATTTAAATAAT
       970              980              990              1000             1010             1020
```

FIG.1C-4

```
GLY TYR ALA LYS ALA GLN ILE THR LYS THR ASP VAL GLN LEU ASN ASP GLU LYS THR LYS
GGCTATGCCAAAGCACAAATTACTAAAACGGATGTTCAGCTAAAATGATGAAAAACAAAA
         1030              1040              1050              1060              1070              1080

VAL ASN VAL THR ILE ASP VAL ASN GLU GLY LEU GLN TYR ASP LEU ARG SER ALA ARG ILE
GTTAATGTAACCATTGATGTAAATGAAGGTTTACAGTATGACCTTCGTAGTGCACGCATT
         1090              1100              1110              1120              1130              1140

ILE GLY ASN LEU GLY GLY MET SER ALA GLU LEU GLU PRO LEU LEU SER ALA LEU HIS LEU
ATAGGTAATCTGGGAGGTATGTCTGCCGAGCTTGAACCCTTTACTTTCAGCATTACATTTA
         1150              1160              1170              1180              1190              1200

ASN ASP THR PHE ARG ARG SER ASP ILE ALA ASP VAL GLU ASN ALA ILE LYS ALA LYS LEU
AATGATACTTTCCGCCGTAGTGATATTGCAGATGTAGAAAATGCAATTAAAGCAAAACTT
         1210              1220              1230              1240              1250              1260

GLY GLU ARG GLY TYR GLY SER ALA THR VAL ASN SER VAL PRO ASP PHE ASP ASP ALA ASN
GGAGAACGCGGTTACGGGTAGCGCAACGGTAAATTCAGTACCTGATTTTGATGATGCAAAT
         1270              1280              1290              1300              1310              1320

LYS THR LEU ALA ILE THR LEU VAL VAL ASP ALA GLY ARG ARG LEU THR VAL ARG GLN LEU
AAAACATTAGCGATAACCCTGTTGTTGATGCTGGACGACGTTTAACTGTTCGCCAACTT
         1330              1340              1350              1360              1370              1380
```

FIG.1C-5

```
ARG PHE GLU GLY ASN THR VAL SER ALA ASP SER THR LEU ARG GLN GLU MET ARG GLN GLN
CGC TTT GAA GGA AAT ACC GTT TCT GCT GAT AGC ACT TTA CGT CAG GAA ATG CGC CAA CAA
        1390            1400            1410            1420            1430            1440

GLU GLY THR TRP TYR ASN SER GLN LEU VAL GLU LEU GLY LYS ILE ARG LEU ASP ARG THR
GAA GGA ACT TGG TAT AAT TCA CAA TTA GTT GAG TTA GGA AAA ATT CGC TTA GAT CGT ACA
        1450            1460            1470            1480            1490            1500

GLY PHE PHE GLU THR VAL GLU ASN ARG ILE ASP PRO ILE ASN GLY SER ASN ASP GLU VAL
GGT TTC TTC GAA ACA GTC GAA AAC CGA ATT GAT CCT ATC AAT GGT AGT AAT GAT GAA GTG
        1510            1520            1530            1540            1550            1560

ASP VAL VAL TYR LYS VAL LYS GLU ARG ASN THR GLY SER ILE ASN PHE GLY ILE GLY TYR
GAT GTC GTA TAT AAA GTC AAA GAA CGT AAC ACG GGT AGT ATC AAC TTT GGT ATT GGT TAC
        1570            1580            1590            1600            1610            1620

GLY THR GLU SER GLY ILE VAL LEU SER TYR GLN ALA SER VAL LYS GLN ASP ASN PHE LEU GLY THR
GGT ACA GAG AGT GGT ATT AGT TAT CAA GCA AGT GTT AAA CAA GAT AAT TTC TTT GGG AAC A
        1630            1640            1650            1660            1670            1680

GLY ALA ALA VAL SER ILE ALA GLY THR LYS ASN ASP TYR GLY THR SER VAL ASN LEU GLY
GGG GCG CAG TAA GTA GCT GGT ACG AAA AAT GAT TAT GGT ACG AGT GTC AAT TTG GGT
        1690            1700            1710            1720            1730            1740
```

FIG.1C-6

| TYR | THR | GLU | PRO | TYR | PHE | THR | LYS | ASP | GLY | VAL | SER | LEU | GLY | GLY | ASN | VAL | PHE | PHE | GLU |
TAT ACC GAG CCC TAT TTT ACT AAA GAT GGT GTA AGT CTT GGT GGA AAT GTT TTC TTT GAA
             1750              1760              1770              1780              1790              1800

| ASN | TYR | ASP | ASN | SER | LYS | SER | ASP | THR | SER | SER | ASN | TYR | LYS | ARG | THR | THR | TYR | GLY | SER |
AAC TAC GAT AAC TCT AAA AGT GAT ACA TCC TCT AAC TAT AAG CGT ACG ACT TAC GGA AGT
             1810              1820              1830              1840              1850              1860

| ASN | VAL | THR | LEU | GLY | PHE | PRO | VAL | ASN | GLU | ASN | ASN | SER | TYR | VAL | GLY | LEU | GLY | HIS |
AAT GTT ACT TTA GGT TTT CCC CTG TAA ATG AAA ATA ACT CCT ATT GTA GGA TTA GGT CAT
             1870              1880              1890              1900              1910              1920

| THR | TYR | ASN | LYS | ILE | SER | ASN | PHE | ALA | LEU | GLU | TYR | ASN | ARG | ASN | LEU | TYR | ILE | SER |
ACC TAT AAT AAA ATT AGT AAC TTT GCT CTA GAA TAT AAC CGT AAT TTA TAT TCA ATC A
             1930              1940              1950              1960              1970              1980

| MET | LYS | PHE | LYS | GLY | ASN | GLY | ILE | LYS | THR | ASN | ASP | PHE | SER | PHE | GLY | TRP | ASN |
ATG AAA TTT AAA GGT AAT GGC ATT AAA ACA AAA TGA CTT TGA TTT TCT TTG GTT GGA AAC
             1990              2000              2010              2020              2030              2040

| TYR | ASN | SER | LEU | ASN | ARG | GLY | TYR | PHE | PRO | THR | LYS | GLY | VAL | LYS | ALA | SER | LEU | GLY | GLY |
TAT AAC AGC CCT TAA TAG AGG CTA TTT CCC AAC TAA AGG GTT AAA AGC AAG TCT TGG TGG A
             2050              2060              2070              2080              2090              2100

FIG.1C-7

```
ARG VAL THR ILE PRO GLY SER ASP ASN LYS TYR TYR LYS LEU SER ALA ASP VAL GLN GLY
CGAGTTACTATTCCAGGTTCTGATAACAAATACTACAAACTAAGTGCAGATGTACAGGGT
      2110                2120                2130                2140                2150              2160

PHE TYR PRO LEU ASP ARG ASP HIS LEU ASP ARG LEU ASP TRP VAL VAL SER ALA LYS ALA LYS SER ALA GLY TYR
TTCTACCCATTAGACAGAGATCACCTCTCTGGGTTGTATCTGCAAAAGCATCTGCAGGATAT
      2170                2180                2190                2200                2210              2220

ALA ASN GLY PHE GLY ASN LYS ARG LEU PRO PHE TYR GLN THR LYS ARG LEU PRO ASN ALA GLY ILE
GCAAATGGTTTTGGAAACAAGCGTTTACCGTTTCTATCAAACTTACAGCGGGTGGCATC
      2230                2240                2250                2260                2270              2280

GLY SER LEU ARG GLY PHE ALA TYR GLY SER ILE GLY PRO ASN ALA ILE TYR ALA GLU TYR
GGTTCATTACGTGGTTTTGCTTATGGTAGTATTGGACCTAACGCAATTTATGCCGAATAT
      2290                2300                2310                2320                2330              2340

GLY ASN GLY SER GLY THR GLY THR PHE LYS LYS ILE LYS LYS ILE LEU SER SER ASP VAL
GGTAATGGTAGTGGTACTGGTACTTTTAAGAAGATAAGTTCTGATGTGATTGGTGGTAAT
      2350                2360                2370                2380                2390              2400

ALA ILE ALA THR ALA SER ALA GLU LEU ILE VAL PRO THR PRO PHE VAL SER ASP LYS SER
GCAATCGCTACAGCGCTAGCGGAGTTAATTGTGCCAACTCCATTTGTGAGCGATAAGAGC
      2410                2420                2430                2440                2450              2460
```

FIG. 1C-8

```
GLN ASN THR VAL ARG THR SER LEU PHE VAL ASP ALA ALA SER VAL TRP ASN THR LYS TRP
CAAAATACGGTCCGAACCCTTCCTTATTTGTTGATGCCGGCAAGTGTTTGGAATACTAAATGG
         2470              2480              2490              2500              2510              2520

LYS SER ASP LYS ASN GLY LEU GLU SER ASP VAL LEU LYS ARG LEU PRO ASP TYR GLY LYS
AAATCAGATAAAAATGGATTAGAGAGCGATGTATTAAAAAGATTGCCTGATTATGGCAAA
         2530              2540              2550              2560              2570              2580

SER SER ARG ILE ARG ALA SER THR GLY VAL GLY PHE GLN TRP GLN SER PRO ILE GLY PRO
TCAAGCCCGTATTCGCGCCCTCTACAGGTGTCGGATTCCAATGGCAATCTCCTATTGGGCCA
         2590              2600              2610              2620              2630              2640

LEU VAL PHE SER TYR ALA LYS PRO ILE LYS LYS TYR GLU ASN ASP ASP VAL GLU GLN PHE
TTGGTATTCTCTTATGCCAAACCAATTAAAAAATATGAAAATGATGTCGAACAGTTC
         2650              2660              2670              2680              2690              2700

GLN PHE SER ILE GLY GLY SER PHE *** *** ***
CAATTTAGTATTGGAGGTTCTTTCTAATAAATTGAACTTTTTCTTCATCAGAACTCAAA
         2710              2720              2730              2740              2750              2760
```

FIG.1C-9

```
AACAACGTTCTCTGCCTAATTTAATTGGGCAGAGAAAATATTAAACCCATCATTTAATTA
     2770          2780          2790          2800          2810          2820

AGGATATTTATCAAATGAAAAACATCGCAAAAGTAACCGCACTTGCTTTAGGTATTGCAC
     2830          2840          2850          2860          2870          2880

TTGCTTCAGGCTATGCTTCCGCTGAAGAAAAAAATTGCTTTCATTAATGCGGGTTATANTT
     2890          2900          2910          2920          2930          2940

TNCAAGGCNAAGG
     2950
```

FIG.1D-1

SB33 D15
IS THE SEQUENCE BEING TRANSLATED

```
GGCATTGAAAAACAGGACAGCTTTCCCTTTTAACCCTTGAAAATATTAGGGAAATTACTT
         10         20         30         40         50         60

ACTGGCGATTTGTCATTAAATAATTTAAGTGGGCCAATTTCTATTGCAAAAGGTGCTGGC
         70         80         90        100        110        120

GCATCAGCAAATATTGGATTGGTGTATTTTTAAGTTTTATGGCATTGATTAGTGTAAAT
        130        140        150        160        170        180

TTAGGGATTATGAATTTTATTTCCATTACCAGTATTAGATGGCGGTCATTTAGTTTTTTA
        190        200        210        220        230        240

ACAAATGGAAAGCTGTTAAAGGAAAACCTGTTTCTGAGCGGGTGCAAAGCATCTGTTATCGA
        250        260        270        280        290        300
```

FIG.1D-2

```
ATTGGCGCAGCACTGTTATTAAGCTTAACGGGTGTTTGCATTATTTAATGATTTTTACGT
           310          320          330          340          350          360

MET LYS LYS LEU LEU ILE ALA SER LEU LEU PHE GLY
CTATAATTTATATAGGATACAATCGATGAAAAAACTTCTAATCGCAAGTTTATTATTCGG
           370          380          390          400          410          420

THR THR THR VAL PHE ALA ALA PRO PHE VAL ALA LYS ASP ILE ARG VAL ASP GLY VAL
TACGACAACGACTGTGTTTGCCCGCACCTTTGTGGCAAAAGATATTCGTGTGGATGGTGT
           430          440          450          460          470          480

GLN GLY ASP LEU GLU GLN GLN ILE ARG ALA SER LEU PRO VAL ARG ALA GLY GLN ARG VAL
TCAAGGTGACTTAGAACAACAAATCCGAGCAAGTTTACCTGTTCGTGCCGGGTCAGCGTGT
           490          500          510          520          530          540

THR ASP ASN ASP VAL ALA ASN ILE VAL ARG SER LEU PHE VAL SER GLY ARG PHE ASP ASP
GACTGACAATGATGTGGCTAATATTGTCCGCTCTCTTTATTCGTAAGTGGTTCGATTGATGA
           550          560          570          580          590          600

VAL LYS ALA HIS GLN GLU GLY ASP VAL LEU VAL VAL SER VAL VAL ALA LYS SER ILE ILE
TGTGAAAGCGCATCAAGAAGGCGATGTGCTTGTTGTTAGCGTTGTGGCTAAATCGATCAT
           610          620          630          640          650          660
```

FIG.1D-3

```
SER ASP VAL LYS ILE LYS GLY ASN SER ILE ILE PRO PRO GLU ALA LEU LYS GLN ASN LEU
TTCAGATGTTAAAATCAAAGGTAACTCTATTATTCCACCTGAAGCACTAAAACAAACTT
        670             680             690             700             710             720

ASP ALA ASN GLY PHE LYS VAL GLY ASP ILE LEU ARG GLU LYS LEU ASN GLU PHE ALA
AGATGCTAACGGGTTTAAAGTTGGCGATATTTTAATTCGAGAAAAATTAAATGAATTTGC
        730             740             750             760             770             780

GLN SER VAL LYS GLU HIS TYR ALA SER VAL ARG TYR ASN ALA THR VAL GLU PRO ILE
CCAAAGTGTAAAAGAGCACTATGCAAGTGTAGGTCGCTATAACGCAACCGTTGAACCTAT
        790             800             810             820             830             840

VAL ASN THR LEU PRO ASN ASN ARG ALA GLU ILE LEU ILE ASN GLN ILE ASN GLU ASP ASP LYS
TGTCAATACGCTACCAAATAATCGCGCTGAAATTTTAATTCAAATCAATGAAGATGATAA
        850             860             870             880             890             900

ALA LYS LEU ALA SER LEU THR PHE LYS GLY ASN GLU THR VAL SER SER SER THR LEU GLN
AGCCAAATTGGCATCATTAACTTTCAAGGGGAACGAATCTGTTAGTAGCAGTACATTACA
        910             920             930             940             950             960

GLU GLN MET GLU LEU GLN PRO ASP SER TRP TRP LYS LEU TRP GLY ASN LYS PHE GLU GLY
AGAACAAATGGAATTACAACCTGATTCTTGGTGGAAATTATGGGGAAATAAATTTGAAGG
        970             980             990             1000            1010            1020
```

FIG.1D-4

```
ALA GLN PHE GLU LYS ASP LEU GLN ALA ILE ARG ASP TYR TYR LEU ASN ASN GLY TYR ALA
TGCGCAATTCGAGAAAGATTTGCAGGCAATTCGTGATTATTTAAAATGGCTATGC
     1030           1040           1050           1060           1070           1080

LYS ALA GLN ILE THR LYS ALA ASP VAL GLN LEU ASN ASP GLU LYS THR LYS VAL ASN VAL
CAAAGCACAAATCACTAAAGCGGATGTTCAGCTAAATGATGAAAAAACAAAAGTTAATGT
     1090           1100           1110           1120           1130           1140

THR ILE ASP VAL ASN GLU VAL ASN GLU GLY LEU GLN TYR ASP LEU ARG SER ALA ARG ILE ILE GLY ASN
AACCATTGATGTAAATGAAGGTTTACAGTATGACCTTCGTAGTGCACGCATTATAGGTAA
     1150           1160           1170           1180           1190           1200

LEU GLY GLY MET SER ALA GLU LEU LEU GLU PRO LEU LEU SER ALA LEU HIS LEU ASN ASP THR
TCTGGGAGGTATGTCTGCCGAGCTTGAACCCTTTACTTTCAGCATTACATTAAATGATAC
     1210           1220           1230           1240           1250           1260

PHE ARG ARG SER ASP ILE ALA ASP VAL GLU ASN ALA ILE LYS ALA LYS LEU GLY GLU ARG
TTTCCGCCGTAGTGATATTGCAGATGTAGAAAATGCAATTAAAGCAAAACTTGGGGAACG
     1270           1280           1290           1300           1310           1320

GLY TYR GLY ASN THR THR VAL ASN SER VAL PRO ASP PHE ASP ASP ALA ASN LYS THR LEU
AGGTTACGGTAACACAACAGTAAATTCTGTACCTGATTTTGACGATGCAAATAAAACATT
     1330           1340           1350           1360           1370           1380
```

FIG.1D-5

```
ALA ILE THR PHE VAL VAL ASP ALA GLY ARG ARG LEU THR VAL HIS GLN LEU ARG PHE GLU
AGCGATAACCTTTGTTGTTGATGCTGGACGACGTTTAACTGTTCACCAACTTCGCTTTGA
         1390              1400              1410              1420              1430              1440

GLY ASN THR VAL SER ALA ASP SER THR LEU ARG GLN GLN MET ARG GLN GLN GLU GLY THR
AGGAAATACCGTTTCTGCTGATAGTACTTTACGTCAGGAAATGCGCCAACAAGAAGGAAC
         1450              1460              1470              1480              1490              1500

TRP TYR ASN SER GLN LEU VAL GLU LEU GLY LYS LYS ILE ARG LEU ASP ARG THR GLY PHE PHE
TTGGTATAATTCACAATTAGTTGAGTTAGGAAAAATTCGCTTAGATCGTACAGGTTTCTT
         1510              1520              1530              1540              1550              1560

GLU THR VAL GLU ASN ARG ILE ASP PRO ILE ASN GLY SER ASN ASP GLU VAL ASP VAL VAL
CGAAACAGTTGAAAACCGAATTGATCCTATCAATGGTAGCAATGATGAAGTGGATGTCGT
         1570              1580              1590              1600              1610              1620

TYR LYS VAL LYS GLU ARG ASN THR GLY SER ILE ASN PHE GLY ILE GLY TYR GLY THR GLU
ATATAAAGTCAAAGAACGTAACACGGGTAGTATCAACTTTGGTATTGGTTACGGTACAGA
         1630              1640              1650              1660              1670              1680

SER GLY ILE SER TYR GLN ALA SER VAL LYS GLN ASP ASN PHE LEU GLY THR GLY ALA ALA
GAGTGGTATTAGTTATCAAGCAAGTGTCAAACAAGATAATTTCTTGGGAACAGGGGCGGC
         1690              1700              1710              1720              1730              1740
```

FIG.1D-6

```
VAL SER ILE ALA GLY THR LYS ASN ASP TYR GLY THR SER VAL ASN LEU GLY TYR THR GLU
AGTAAGTATAGCTGGTACGGAAAAATGATTATGGTACGAGTGTCAATTTGGGTTATACCGA
        1750            1760            1770            1780            1790            1800

PRO TYR PHE THR LYS ASP GLY VAL SER LEU GLY GLY ASN VAL PHE PHE GLU ASN TYR ASP
GCCCTATTTTACTAAAGATGGTGTAAGTCTTGGTGGAAATGTTTTCTTTGAAAACTACGA
        1810            1820            1830            1840            1850            1860

ASN SER LYS SER ASP THR SER SER ASN TYR LYS ARG THR THR TYR GLY SER ASN VAL THR
TAACTCTAAAAGTGATACATCCTCTAACTATAAGCGTACGACTTATGGAAGTAATGTTAC
        1870            1880            1890            1900            1910            1920

LEU GLY PHE PRO VAL ASN SER TYR TYR VAL GLY LEU GLY HIS THR TYR ASN
TTTAGGTTTCCCTGTAAATAACTCCTATTATGTAGGATTAGGCCATACCTATAA
        1930            1940            1950            1960            1970            1980

LYS ILE SER ASN PHE ALA LEU GLU TYR ASN ARG ASN LEU TYR ILE GLN SER MET LYS PHE
TAAAATTAGTAACTTTGCTCTAGAATATAACCGTAATTTATATATTCAATCAATGAAATT
        1990            2000            2010            2020            2030            2040

LYS GLY ASN GLY ILE LYS THR ASN ASP PHE ASP PHE SER PHE GLY TRP ASN TYR ASN SER
TAAAGGTAATGGCATTAAAACAAATGACTTTGATTTTTCTTTTGGTTGGAACTATAACAG
        2050            2060            2070            2080            2090            2100
```

FIG.1D-7

| LEU | ASN | ARG | GLY | TYR | PHE | PRO | THR | LYS | GLY | VAL | LYS | ALA | SER | LEU | GLY | GLY | ARG | VAL | THR |
|---|---|---|---|---|---|---|---|---|---|---|---|---|---|---|---|---|---|---|---|
CCTTAATAGAGGCTATTTCCCAACTAAAGGGGTTAAAGCAAGTCTTGGTGGACGAGTTAC
      2110              2120              2130              2140              2150              2160

| ILE | PRO | GLY | SER | ASP | ASN | LYS | TYR | TYR | LYS | LEU | SER | ALA | ASP | VAL | GLN | GLY | PHE | TYR | PRO |
|---|---|---|---|---|---|---|---|---|---|---|---|---|---|---|---|---|---|---|---|
AATTCCAGGTTCTGATAACAAATACTACAAACTAAGTGCAGATGTACAGGGTTTCTACCC
      2170              2180              2190              2200              2210              2220

| LEU | ASP | ARG | ASP | HIS | LEU | TRP | VAL | VAL | SER | ALA | LYS | ALA | GLY | TYR | ALA | ASN | GLY |
|---|---|---|---|---|---|---|---|---|---|---|---|---|---|---|---|---|---|
ATTAGACAGAGATCACCTCTCTGGGTTTGTATCTGCAAAAGCATCTGCAGGATATGCAAATGG
      2230              2240              2250              2260              2270              2280

| PHE | GLY | ASN | LYS | ARG | LEU | PRO | PHE | TYR | GLN | THR | THR | ALA | GLY | GLY | ILE | GLY | SER | LEU |
|---|---|---|---|---|---|---|---|---|---|---|---|---|---|---|---|---|---|---|
TTTTGGAAACAAGCGTTTACCGTTTCTATCAAACTTATACAGCGGGTGGCATTGGTTCATT
      2290              2300              2310              2320              2330              2340

| ARG | GLY | PHE | ALA | TYR | GLY | SER | ILE | GLY | PRO | ASN | ALA | ILE | TYR | GLN | GLY | ASN | ASN | LYS |
|---|---|---|---|---|---|---|---|---|---|---|---|---|---|---|---|---|---|---|
ACGCGGTTTGCTTATGGTAGCATTGGGCCTAACGCAATTTATCAAGGTCAAAATAATAA
      2350              2360              2370              2380              2390              2400

| PHE | ASN | LYS | ILE | SER | SER | ASP | VAL | ILE | GLY | GLY | ASN | ALA | ILE | ALA | THR | ALA | SER | ALA | GLU |
|---|---|---|---|---|---|---|---|---|---|---|---|---|---|---|---|---|---|---|---|
ATTTAAATAAGATAAGTTCTGATGTGATTGGTGGTAATGCAATCGCTACAGCTAGCGCAGA
      2410              2420              2430              2440              2450              2460

FIG.1D-8

```
LEU  ILE  VAL  PRO  THR  PRO  PHE  VAL  SER  ASP  LYS  SER  GLN  ASN  THR  VAL  ARG  THR  SER  LEU
G T T A A T T G T G C C A A C T C C A T T T G T G A G T G A T A A G A G T C A A A T A C A G T C C G A A C C T C C C T
              2470                    2480                    2490                    2500                    2510                    2520

PHE  VAL  ASP  ALA  ALA  SER  VAL  TRP  ASN  THR  LYS  TRP  LYS  SER  ASP  LYS  ASN  GLY  LEU  GLU
A T T T G T T G A T G C G G G C A A G T G T T T G G A A T A C T A A A T G G A A A T C A G A T A A A A A T G G A T T A G A
              2530                    2540                    2550                    2560                    2570                    2580

SER  ASN  VAL  LEU  LYS  ASP  LEU  PRO  ASP  TYR  GLY  LYS  SER  SER  ARG  THR  ARG  ALA  SER  THR
G A G C A A T G T C T T G A A A G A C T T A C C C G A T T A T G G C A A A T C A A G C C G T A C T C G C C T C T A C
              2590                    2600                    2610                    2620                    2630                    2640

GLY  VAL  GLY  PHE  GLN  TRP  GLN  SER  PRO  GLY  PRO  VAL  VAL  PHE  SER  TYR  ALA  LYS  PRO
A G G T G T C G G A T T C C A A T G G C A A T C T C C T A G T G G A C C A G T G G T A T T T T C T T A T G C T A A A C C
              2650                    2660                    2670                    2680                    2690                    2700

ILE  LYS  LYS  TYR  GLU  ASN  ASP  ASP  VAL  GLU  GLN  PHE  GLN  PHE  SER  ILE  GLY  GLY  SER  PHE
A G G T C G G A T T C C A A T G G C A A T C T C C T A G T G G A C C A G T G G T A T T T T C T T A T G C T A A A C C
              2710                    2720                    2730                    2740                    2750                    2760

```
ATTGGGCAGAGAAATATTAAAACCATCATTTAATTAAGGATATATTTATCAAATGAAAAAC
         2830          2840          2850          2860          2870          2880

ATCGCCAAAGTAACCGCACTTGCTTTAGGTATTGCACTTGCTTCAGGCTATGCTGCAGCT
         2890          2900          2910          2920          2930          2940

GAAGAAAAAATTGCTTTTATTAATGCAGGTTATA
         2950          2960          2970
```

FIG.1E-1

JB-1042-9-4 DNA, PAK D15
IS THE SEQUENCE BEING TRANSLATED

```
AAAAGGCATTGAAAAAACAGGACAACTTTCCCTTTTAACCCTTGAAAATATTAGGGAAATT
         10        20        30        40        50        60

ACTTACTGGCGATTTGTCATTAAATAATTTAAGTGGGCCAATTTCTATTGCAAAAGGTGC
         70        80        90       100       110       120

TGGTGCATCAGCAAAATATTGGATTGGTGTATTTTTTAAGTTTTATGGCATTGATTAGTGT
        130       140       150       160       170       180

AAATTTAGGGATTATGAATTTATTTCCATTACCAGTATTAGATGGCCGGTCATTTAGTTTT
        190       200       210       220       230       240

TTTAACAATGGAAGCTGTTAAAGGAAAAACCTGTTTCTGAGCGGGTGCAAAGCATCTGTTA
        250       260       270       280       290       300

TCGAATTGGCGCAGCACTGTTATTAAGCTTAACGGTGTTTGCATTATTAATGATTTTT
        310       320       330       340       350       360
```

FIG.1E-2

```
                                            MET LYS LYS LEU LEU ILE ALA SER LEU LEU P
ACGTCTATAATTTATATAGGATACAATCGATGAAAAAACTTCTAATCGCAAGTTTATTAT
        370               380               390               400               410               420

HE  GLY THR THR THR VAL PHE ALA ALA PRO PHE VAL ALA LYS ASP ILE ARG VAL ASP G
TCGGTACGACAACGACTGTGTTTGCCCGCACCTTTTGTGGCAAAAGATATTCGTGTGGATG
        430               440               450               460               470               480

LY  VAL GLN GLY ASP LEU GLU ASN ASP ILE ARG ALA SER LEU PRO VAL ARG ALA GLY GLN A
GTGTTCAAGGTGACTTAGAAAATGATATCCGAGCAAGTTTACCTGTTCGTGCTGGTCAGC
        490               500               510               520               530               540

RG  VAL THR ASP ASN ASP VAL ALA ASN ILE VAL ARG SER LEU PHE VAL SER GLY ARG PHE A
GTGTGACTGACAATGATGTGGCTAATATTGTCCGCTCTTTATTCGTAAGTGGTCGATTCG
        550               560               570               580               590               600

SP  ASP VAL LYS ALA HIS GLN GLU GLY ASP VAL VAL LEU VAL SER VAL ALA LYS SER I
ATGATGTGAAAGCGCATCAAGAAGGCGATGTGTTGTTGTTAGCGTTGTGGCTAAATCGA
        610               620               630               640               650               660

LE  ILE SER ASP VAL LYS ILE LYS GLY ASN SER VAL ILE PRO THR GLU ALA LEU LYS GLN A
TCATTTCAGATGTTAAAATCAAAGGTAACTCTGTTATTCCCACTGAAGCACTTAAACAAA
        670               680               690               700               710               720
```

FIG.1E-3

```
SN  LEU ASP ALA ASN GLY PHE LYS VAL GLY ASP VAL LEU ILE ARG GLU LYS LEU ASN GLU P
    ACT TAG ATG CTA ACG GGG TTT AAA GTT GGC GAT GTT TTA ATT CGA GAA AAA TTA AAT GAA T
            730             740             750             760             770             780

HE  ALA LYS SER VAL LYS GLU HIS TYR ALA SER VAL GLY ARG TYR ASN ALA THR VAL GLU P
    TTG CCA AAA GTG TAA AAG AGC ACT ATG CAA GTG TAG GTC GCA AGT GCA ACC GTT GAA C
            790             800             810             820             830             840

RO  ILE VAL ASN THR LEU PRO ASN ASN ARG ALA GLU ILE LEU ILE GLN ILE ASN GLU ASP A
    CTA TTG TCA ATA CGC TGC CAA ATA ATC GTG CTG AAA TTT AAT TCA AAT CAA TGA AGA TG
            850             860             870             880             890             900

SP  LYS ALA LYS LEU ALA SER LEU ILE THR PHE LYS GLY ASN GLU SER VAL SER SER THR L
    ATA AAG CAA AAT TGG CAT CAT TAA CTT TCA AGG GAA CGA ATC TGT TAG TAG CAG TAC AT
            910             920             930             940             950             960

EU  GLN GLU GLN MET GLU LEU GLN PRO ASP SER TRP TRP LYS LEU TRP GLY ASN LYS PHE G
    TAC AAG AAC AAA TGG AAT TAC AAC CTG ATT CTT GGT GGA AAT TAT GGG AAA TAA ATT TG
            970             980             990             1000            1010            1020

LU  GLY ALA GLN PHE GLU LYS ASP LYS GLN ALA ILE ARG ASP TYR TYR LEU ASN ASN GLY T
    AAG GTG CGC AAT TCG AGA AAG ATA AGC AAG CTG CAG GCA ATT CGT GAT TAT TTA AAT AAT GGC T
            1030            1040            1050            1060            1070            1080

YR  ALA LYS ALA GLN ILE THR LYS THR ASP VAL GLN LEU ASN ASP GLU LYS THR LYS VAL A
    ATG CCA AAG CAC AAA TCA CTA AAA ACG GAT GTT CAG CTA AAT GAT GAA AAA CAA AGT TA
            1090            1100            1110            1120            1130            1140
```

FIG.1E-4

```
SN  VAL THR ILE ASP VAL ASN GLU GLY LEU GLN TYR ASP LEU ARG SER ALA ARG ILE ILE G
    ATGTAACCATTGATGTAAATGAAGGTTTACAGTATGACCTTCGTAGTGCACGCATTATAG
         1150          1160          1170          1180          1190          1200

LY  ASN LEU GLY MET GLY SER ALA GLU LEU GLU PRO LEU LEU SER ALA LEU HIS LEU ASN A
    GTAATCTGGGAGGTATGTCTGCCGAGCTTGAACCCTTACTTTCAGCATTACATTTAAATG
         1210          1220          1230          1240          1250          1260

SP  THR PHE ARG ARG SER ASP ILE ALA ASP VAL GLU ASN ALA ILE LYS ALA LYS LEU GLY G
    ATACTTTCCGCCGTAGTGATATTGCAGATGTAGAAAATGCAATTAAAGCAAAACTTGGGG
         1270          1280          1290          1300          1310          1320

LU  ARG GLY TYR GLY ASN THR THR VAL ASN SER VAL PRO ASP PHE ASP ALA ASN LYS T
    AACGAGGGTTACGGTAACACAACAGTAAATTCTGTACCTGATTTTGACGATGCAAATAAAA
         1330          1340          1350          1360          1370          1380

HR  LEU ALA ILE THR PHE VAL VAL ASP ALA GLY ARG ARG LEU THR VAL ARG GLN LEU ARG P
    CATTAGCGATAACCTTTGTTGTTGATGCTGGACGACGTTAACTGTTCGCCAACTTCGCT
         1390          1400          1410          1420          1430          1440

HE  GLU GLY ASN THR VAL SER ALA ASP SER THR LEU ARG GLN MET ARG GLN GLN GLU G
    TTGAAGGAAATACCGTTTCTGCTGATAGTACTTTACGTCAGGAAATGCGACAACAAGAAG
         1450          1460          1470          1480          1490          1500
```

FIG.1E-5

```
LY  THR  TRP  TYR  ASN  SER  GLN  LEU  VAL  GLU  LEU  GLY  LYS  ILE  ARG  LEU  ASP  ARG  THR  GLY  P
GAACTTGGTATAATTCACAATTAGTTGAGTTAGGAAAAATTCGCTTAGATCGTACAGGTT
         1510           1520           1530           1540           1550           1560

HE  PHE  GLU  THR  VAL  GLU  ASN  ARG  ILE  ASP  PRO  ILE  ASN  GLY  SER  ASN  ASP  GLU  VAL  ASP  V
TCTTCGAAACAGTTGAAAACCGAATTGATCCTATCAATGGTAGCAATGATGAAGTGGATG
         1570           1580           1590           1600           1610           1620

AL  VAL  TYR  LYS  VAL  LYS  GLU  ARG  ASN  THR  GLY  SER  ILE  ASN  PHE  GLY  ILE  GLY  TYR  GLY  T
TCGTATATAAAGTCAAAGAACGTAACACGGGTAGTATCAACTTTGGTATTGGTTACGGTA
         1630           1640           1650           1660           1670           1680

HR  GLU  SER  GLY  ILE  SER  TYR  GLN  THR  SER  ILE  LYS  GLN  ASP  ASN  PHE  LEU  GLY  THR  GLY  A
CAGAGAGTGGTATCAGTTATCAAACAAGATATTAAACAAGATAATTTCTTGGGAACAGGGG
         1690           1700           1710           1720           1730           1740

LA  ALA  VAL  SER  ILE  ALA  GLY  THR  LYS  ASN  ASP  TYR  GLY  THR  SER  VAL  ASN  LEU  GLY  TYR  T
CGGCAGTAAGTATAGCTGGTACGAAAAATGATTATGGTACGAGTGTCAATTTGGGTTATA
         1750           1760           1770           1780           1790           1800

HR  GLU  PRO  TYR  PHE  THR  LYS  ASP  GLY  VAL  SER  LEU  GLY  GLY  ASN  ILE  PHE  PHE  GLU  ASN  T
CCGAAACCCTATTTTACTAAAGATGGTGTAAGTCTTGGTGGAAATATTTTCTTTGAAAACT
         1810           1820           1830           1840           1850           1860
```

FIG.1E-6

```
YR  ASP ASN SER LYS SER ASP THR SER SER ASN TYR LYS ARG THR THR TYR GLY SER ASN V
A C G A T A A C T C T A A A A G T G A T A C A T C C C T A A C T A T A A G C G T A C G A C T T A T G G A A G T A A T G
                  1870                1880                1890                1900                1910                1920

AL  THR LEU GLY PHE PRO VAL ASN GLU ASN ASN SER TYR TYR VAL GLY LEU GLY HIS THR T
T T A C T T T A G G T T T C C C T G T A A A T G A A A A T A A C T C C T A T T A T G T A G G A T T A G G C C A T A C C T
                  1930                1940                1950                1960                1970                1980

YR  ASN LYS ILE SER ASN PHE ALA LEU GLU TYR ASN ARG ASN LEU TYR ILE GLN SER MET L
A T A A A T A A A A T T A G T A A C T T T G C T C T A G A A T A T A A C C G T A A T T T A T A T A T T C A A T C A A T G A
                  1990                2000                2010                2020                2030                2040

YS  PHE LYS GLY ASN GLY ILE LYS THR ASN ASP PHE ASP PHE SER PHE TRP GLY TYR ASN TYR A
A A T T T A A A G G T A A T G G C A T T A A A A C A A A T G A C T T T G A T T T T T C T T T T T G G T T G G A A C T A T A
                  2050                2060                2070                2080                2090                2100

SN  SER LEU ASN ARG GLY TYR PHE PRO THR LYS GLY VAL LYS LEU ALA SER LEU GLY GLY ARG V
A C A G C C T T A A A T A G A G G C T A T T T C C C A A C T A A A G G G G T T A A A G C A A G T C T T G G T G G A C G A G
                  2110                2120                2130                2140                2150                2160

AL  THR ILE PRO GLY SER PHE LEU ASP ASN LYS TYR TYR LYS LEU SER ALA ASP VAL GLN GLY PHE T
T T A C T A T T C C A G G T T C T T T C T T G A T A A C A A A T A C T A C A A A C T A A G T G C A G A T G T A C A G G G T T T C T
                  2170                2180                2190                2200                2210                2220

YR  PRO LEU ASP ARG ASP HIS ARG TRP VAL VAL SER ALA LYS ALA SER ALA GLY TYR ALA A
A C C C A T T A G A C A G A G A T C A C C G C T G G G T T G T A T C T G C A A A A G C A T C T G C A G G A T A T G C A A
                  2230                2240                2250                2260                2270                2280
```

FIG.1E-7

```
SN  GLY PHE GLY ASN LYS ARG LEU PRO PHE TYR GLN THR TYR THR ALA GLY GLY ILE GLY S
    ATGGTTTTGGAAACAAGCGTTTACCGTTCTATCAAACTTATACAGCGGGTGGCATTGGTT
                 2290           2300          2310          2320          2330          2340

ER  LEU ARG GLY PHE ALA TYR GLY SER ILE GLY PRO ASN ALA ILE TYR ALA GLU HIS GLY A
    CATTACGCGGTTTTGCTTATGGTAGTATTGGGCCTAATGCAATTTATGCCGAACATGGTA
                 2350          2360          2370          2380          2390          2400

SN  GLY THR PHE ASN LYS ILE SER SER ASP VAL ILE GLY GLY ASN ALA ILE THR THR ALA S
    ATGGTACTTTTAATAAGATAAGTTCTGATGTGATTGGTGGTAATGCAATCACAACTGCGA
                 2410          2420          2430          2440          2450          2460

ER  ALA GLU LEU ILE VAL PRO THR PRO PHE VAL SER ASP LYS SER GLN ASN THR VAL ARG T
    GTGCAGAACTTATTGTACCAACTCCATTTGTGAGTGATAAAGCCAAAATACAGTCCGAA
                 2470          2480          2490          2500          2510          2520

HR  SER LEU PHE VAL ASP ALA ALA SER VAL TRP ASN THR LYS TRP LYS SER ASP LYS ASN G
    CCTCCCTATTTGTTGATGCGGCAAGTGTTTGGAATACTAAATGGAAATCAGATAAAATG
                 2530          2540          2550          2560          2570          2580

LY  LEU GLU SER LYS VAL LEU LEU LYS ASP TYR GLY LYS SER SER ARG ILE ARG A
    GATTAGAGAGCAAGGTCTTGAAAAGACTTACCTGATTATGGCAAATCAAGCCGTATTCGCG
                 2590          2600          2610          2620          2630          2640
```

FIG.1E-8

```
LA  SER  THR  GLY  VAL  GLY  PHE  GLN  TRP  GLN  SER  PRO  ILE  GLY  PRO  LEU  VAL  PHE  SER  TYR  A
CCTCTACAGGTGTCGGATTCCAATGGCAATCTCCTATTGGACCATTGGTATTTCTTATG
         2650                2660                2670                2680                2690                2700

LA  LYS  PRO  ILE  LYS  LYS  TYR  GLU  ASN  ASP  VAL  GLU  GLN  PHE  GLN  PHE  SER  ILE  GLY  G
CTAAACCAATTAAAAAATATGAAAAATGATGATGTCGAACAGTTCCAATTTAGTATTGGGG
         2710                2720                2730                2740                2750                2760

LY  SER  PHE  ***  ***
GCTCTTTCTAATAAATTGAACTTTTTTTCGTCATCAGAACTCAAAAACGACGTTCTCTGCC
         2770                2780                2790                2800                2810                2820

TAATTGAATTGGGCAGAGAAAATATTAAACCCATCATTTAATTAAGGATATTTATCAAAT
         2830                2840                2850                2860                2870                2880

GAAAAACATCGCAAAAGTAACCGCACTTGCTTTAGGTTTTGCACTTGCTTTCAGGCTATGC
         2890                2900                2910                2920                2930                2940

TTCCGCTGAAGAAAAAAATTGCTTTCATTAATGCAGGTTATATTTTTCAA
         2950                2960                2970                2980
```

FIG.1F-1

```
1. cad15      (1-2949)
3. minnad15   (1-2953)
2. eagand15   (1-2984)
4. pakd15     (1-2989)
5. sb33d15    (1-2974)

cad15      1
minnad15   1
eagand15   1                                    ACAGGACAgCTTTCCCTTTTAACCTTGAAAATATATTAGGGAAATTA
                                                |||||||||||||||||||||||||||||||||||||||||||||||
pakd15     1       aaaaGGCATTGAAAAAACAGGACAaCTTTCCCTTTTAACCTTGAAAATATATTAGGGAAATTA
                   ||||||||||||||||||||||||||||||||||||||||||||||||||||||||||||||
sb33d15    1       GGCATTGAAAAAACAGGACAgCTTTCCCTTTTAACCTTGAAAATATATTAGGGAAATTA
consensus      aaaaggcattgaaaaaacaggacagctttccctttttaaccttgaaaatattagggaaatta cad15      1
```

FIG.1F-2

```
minnad15    6   CTTaCTGGCGATTTGTCATTAAATAATTTAAGTGGGCCAATTTCTATTGCAAAAGGTGCTG
                |||  |||||||||||||||||||||||||||||||||||||||||||||||||||||||
eagand15   46   CTTcCTGGCGATTTGTCATTAAATAATTTAAGTGGGCCAATTTCTATTGCAAAAGGTGCTG
                ||| |||||||||||||||||||||||||||||||||||||||||||||||||||||||||
pakd15     62   CTTACTGGCGATTTGTCATTAAATAATTTAAGTGGGCCAATTTCTATTGCAAAAGGTGCTG
                ||||||||||||||||||||||||||||||||||||||||||||||||||||||||||||
sb33d15    58   CTTACTGGCGATTTGTCATTAAATAATTTAAGTGGGCCAATTTCTATTGCAAAAGGTGCTG consensus       cttactggcgatttgtcattaaataatttaagtgggccaatttctattgcaaaggtgctg cad15       1 minnad15   67   GCaCATCAGCAAATATTGGATTGGTGTATTTTTAAGTTTTATGGCACTGATTAGTGTAAA
                || ||||||||||||||||||||||||||||| ||||||||||||||||||||||||||||
eagand15  107   GCcCATCAGCAAATATTGGATTGGTGTATTTTTTAAGTTTTATGGCACTGATTAGTGTAAA
                || |||||||||||||||||||||||||||||  |||||||||||||| |||||||||||
pakd15    123   GtGCATCAGCAAATATTGGATTGGTGTATTTTTTAAGTTTTTATGGCATTGATTAGTGTAAA
                |  |||||||||||||||||||||||||||||  ||||||| |||||| ||||||||||||
sb33d15   119   GcGCATCAGCAAATATTGGATTGGTGTATTTTTTAAGTTTTTATGGCATTGATTAGTGTAAA consensus       gcgcatcagcaaatattggattggtgtattttttaagttttatggca-tgattagtgtaaa
```

FIG.1F-3

```
cad15      1   gATTAC
                   ||||||
minnad15  128  TTTAGGGATTATGAATTTATTTCCATTACCAGTATTAGATGGCGGTCATTTAGTTTTTTTA
               ||||||||||||||||||||||||||||||||||||||||||||||||||||||||||||
eagand15  168  TTTAGGGATTATGAATTTATTTCCATTACCAGTATTAGATGGCGGTCATTTAGTTTTTTTA
               ||||||||||||||||||||||||||||||||||||||||||||||||||||||||||||
pakd15    184  TTTAGGGATTATGAATTTATTTCCATTACCAGTATTAGATGGCGGTCATTTAGTTTTTTTA
               ||||||||||||||||||||||||||||||||||||||||||||||||||||||||||||
sb33d15   180  TTTAGGGATTATGAATTTATTTCCATTACCAGTATTAGATGGCGGTCATTTAGTTTTTTTA consensus      tttagggattatgaatttatttccATTACcagtattagatggcggtcatttagttttttta cad15      7   ACAATGGAAGCTGTTAAAGGAAAACCTGTTTCTGAGCGGGTGCAAAGCATCTGTTATCGAA
               ||||||||||||||||||||||||||||||||||||||||||||||||||||||||||||
minnad15  189  ACAATGGAAGCTGTTAAAGGAAAACCTGTTTCTGAGCGGGTGCAAAGCATCTGTTATCGAA
               ||||||||||||||||||||||||||||||||||||||||||||||||||||||||||||
eagand15  229  ACAATGGAAGCTGTTAAAGGAAAACCTGTTTCTGAGCGGGTGCAAAGCATCTGTTATCGAA
               ||||||||||||||||||||||||||||||||||||||||||||||||||||||||||||
pakd15    245  ACAATGGAAGCTGTTAAAGGAAAACCTGTTTCTGAGCGGGTGCAAAGCATCTGTTATCGAA
               ||||||||||||||||||||||||||||||||||||||||||||||||||||||||||||
sb33d15   241  ACAATGGAAGCTGTTAAAGGAAAACCTGTTTCTGAGCGGGTGCAAAGCATCTGTTATCGAA
```

FIG.1F-4

```
consensus      acaatggaagctgttaaaggaaaacctgtttctgagcgggtgcaaagcatctgttatcgaa cad15        7                           gccAAGCTTAACGGTGTTTGCATTATTTAATGATTTTTACGTCT
                                          ||||||||||||||||||||||||||||||||||||||||||||
minnad15   250 TTGGCGCAGCACTGTTATTAAGCTTAACGGTGTTTGCATTATTTAATGATTTTTACGTCT
               ||||||||||||||||||||||||||||||||||||||||||||||||||||||||||||
eagand15   290 TTGGCGCAGCACTGTTATTAAGCTTAACGGTGTTTGCATTATTTAATGATTTTTACGTCT
               ||||||||||||||||||||||||||||||||||||||||||||||||||||||||||||
pakd15     306 TTGGCGCAGCACTGTTATTAAGCTTAACGGTGTTTGCATTATTTAATGATTTTTACGTCT
               ||||||||||||||||||||||||||||||||||||||||||||||||||||||||||||
sb33d15    302 TTGGCGCAGCACTGTTATTAAGCTTAACGGTGTTTGCATTATTTAATGATTTTTACGTCT consensus      ttggcgcagcactgttattaAGCTTAACGGTGTTTGCATTATTTAATGATTTTTACGTCT cad15       52 ATAATTTATATAGGATACAATCGATGAAAAAACTTCTAATCGCAAGTTTATTATTCGGTAC
               ||||||||||||||||||||||||||||||||||||||||||||||||||||||||||||
minnad15   311 ATAATTTATATAGGATACAATCGATGAAAAAACTTCTAATCGCAAGTTTATTATTCGGTAC
               ||||||||||||||||||||||||||||||||||||||||||||||||||||||||||||
eagand15   351 ATAATTTATATAGGATACAATCGATGAAAAAACTTCTAATCGCAAGTTTATTATTCGGTAC
               ||||||||||||||||||||||||||||||||||||||||||||||||||||||||||||
pakd15     367 ATAATTTATATAGGATACAATCGATGAAAAAACTTCTAATCGCAAGTTTATTATTCGGTgC
```

FIG.1F -5

```
sb33d15      363  ATAATTTATATAGGATACAATCGATGAAAAAACTTCTAATCGCAAGTTTATTATTCGGTaC consensus         ATAATTTATATAGGATACAATCGATGAAAAAACTTCTAATCGCAAGTTTATTATTCGGTaC cad15        113  GACAACGACTGTGTTTGCCCGCACCTTTTGTGGCAAAAGATATTCGTGTGGATGGTGTTCAA
                  ||||||||||||||||||||||||||||||||||||||||||||||||||||||||||||
minnad15     372  GACAACGACTGTGTTTGCCCGCACCTTTTGTGGCAAAAGATATTCGTGTGGATGGTGTTCAA
                  ||||||||||||||||||||||||||||||||||||||||||||||||||||||||||||
eagand15     412  GACAACGACTGTGTTTGCCCGCACCTTTTGTGGCAAAAGATATTCGTGTGGATGGTGTTCAA
                  ||||||||||||||||||||| ||||||||||||||||||||||||||||||||||||||
pakd15       428  GACAACGACTGTGTTTGCCCGCACCTTTTGTGCCAAAAGATATTCGTGTGGATGGTGTTCAA
                  ||||||||||||||||||||||||||||||||||||||||||||||||||||||||||||
sb33d15      424  GACAACGACTGTGTTTGCCCGCACCTTTTGTGgCAAAAGATATTCGTGTGGATGGTGTTCAA consensus         GACAACGACTGTGTTTGCCCGCACCTTTTGTGCCAAAAGATATTCGTGTGGATGGTGTTCAA cad15        174  GGTGACTTAGAACAACAAATCCGAGCAAGTTTACCTGTTCGTGCCGGTCAGCCGTGTGACTG
                  ||||||||||||||||||||||||||||||||||||||||||||||||||||||||||||
minnad15     433  GGTGACTTAGAACAACAAATCCGAGCAAGTTTACCTGTTCGTGCCGGTCAGCCGTGTGACTG
                  ||||||||||||||||||||||||||||||||||||||||||||||||||||||||||||
eagand15     473  GGTGACTTAGAACAACAAATCCGAGCAAGTTTACCTGTTCGTGCCGGTCAGCCGTGTGACTG
```

FIG.1F-6

```
pakd15    489  GGTGACTTAGAACAACAAATCCGAGCAAGTTTACCTGTCTTCGTCGTCTGGTCAGCGTGTGACTG
               ||||||||||||||||||||||||||||||||||||||||||  |||||| ||||||||||||||
sb33d15   485  GGTGACTTAGAACAACAAATCCGAGCAAGTTTACCTGTTCGTGCCGGTCAGCGTGTGACTG consensus      GGTGACTTAGAACAACAAATCCGAGCAAGTTTACCTGTTCGTGCCGGTCAGCGTGTGACTG cad15     235  ACAATGATGTGGCTAATATTGTCCGCTCTTTATTCGTAAGTGGTCGATTCGATGATGTGAA
               ||||||||||||||||||||||||||||||||||||||||||||||||||||||||||||
minnad15  494  ACAATGATGTGGCTAATATTGTCCGCTCTTTATTCGTAAGTGGTCGATTCGATGATGTGAA
               ||||||||||||||||||||||||||||||||||||||||||||||||||||||||||||
eagand15  534  ACAATGATGTGGCTAATATTGTCCGCTCTTTATTCGTAAGTGGTCGATTCGATGATGTGAA
               ||||||||||||||||||||||||||||||||||||||||||||||||||||||||||||
pakd15    550  ACAATGATGTGGCTAATATTGTCCGCTCTTTATTCGTAAGTGGTCGATTCGATGATGTGAA
               ||||||||||||||||||||||||||||||||||||||||||||||||||||||||||||
sb33d15   546  ACAATGATGTGGCTAATATTGTCCGCTCTTTATTCGTAAGTGGTCGATTCGATGATGTGAA consensus      ACAATGATGTGGCTAATATTGTCCGCTCTTTATTCGTAAGTGGTCGATTCGATGATGTGAA cad15     296  AGCCGCATCAAGAAGGCGATGTGCTTGTGTTGTTAGCGTTGTGGCTAAATCGATCATTTCAGAT
               |||||||||||||||||||||||||||||||||||||||||||||||||||||||||||||||
minnad15  555  AGCCGCATCAAGAAGGCGATGTGCTTGTGTTGTTAGCGTTGTGGCTAAATCGATCATTTCAGAT
```

FIG.1F-7

```
eagand15   595  AGCGCATCAAGAAGGCGATGTGCTTGTTGTTAGCGTTGTGGCTAAATCGATCATTCAGAT
                ||||||||||||||||||||||||||||||||||||||||||||||||||||||||||||
pakd15     611  AGCGCATCAAGAAGGCGATGTGCTTGTTGTTAGCGTTGTGGCTAAATCGATCATTCAGAT
                ||||||||||||||||||||||||||||||||||||||||||||||||||||||||||||
sb33d15    607  AGCGCATCAAGAAGGCGATGTGCTTGTTGTTAGCGTTGTGGCTAAATCGATCATTCAGAT
                ||||||||||||||||||||||||||||||||||||||||||||||||||||||||||||
consensus       AGCGCATCAAGAAGGCGATGTGCTTGTTGTTAGCGTTGTGGCTAAATCGATCATTCAGAT cad15      357  GTTAAAATCAAAGGTAACTCTGTTATTCCCACTGAAGCACTTAAACAAAACTTAGATGCTA
                ||||||||||||||||||||||||||||||||||||||||||||||||||||||||||||
minnad15   616  GTTAAAATCAAAGGTAACTCTGTTATTCCCACTGAAGCACTTAAACAAAACTTAGATGCTA
                ||||||||||||||||||||||||||||||||||||||||||||||||||||||||||||
eagand15   656  GTTAAAATCAAAGGTAACTCTGTTATTCCCACTGAAGCACTTAAACAAAACTTAGATGCTA
                |||||||||||||||||||||||||||||||||||||||||
pakd15     672  GTTAAAATCAAAGGTAACTCTGTTATTCCCACTGAAGCACTTAAACAAAACTTAGATGCTA
                |||||||||||||||||||||||||||||| |||||||||||||||||||||||||||||
sb33d15    668  GTTAAAATCAAAGGTAACTCTaTTATTCCacCTGAAGCACTaAAACAAAACTTAGATGCTA
                ||||||||||||||||||||||||||||||||||||||||||||||||||||||||||||
consensus       GTTAAAATCAAAGGTAACTCTgTTATTCCcaCTGAAGCACTtAAACAAAACTTAGATGCTA cad15      418  ACGGGTTTAAAGTTGGCGATGTTTTAATTCGAGAAAAATTAAATGAATTGCCAAAAGTGT
                ||||||||||||||||||||||||||||||||||||||||||||||||||||||||||||
```

FIG.1F-8

```
minnad15   677  ACGGGTTTAAAGTTGGCCGATGTTTTAATTCGAGAAAATTAAATGAATTTGCCAAAGTGT
                     ||||||||||||||||||||||||||||||||||||||||||||||||||||||||
eagand15   717  ACGGGTTTAAAGTTGGCCGATGTTTTAATTCGAGAAAATTAAATGAATTTGCCAAAGTGT
                     ||||||||||||||||||||||||||||||||||||||||||||||||||||||||
pakd15     733  ACGGGTTTAAAGTTGGCCGATGTTTTAATTCGAGAAAATTAAATGAATTTGCCAAAGTGT
                     |||||||||||||||||||||||||   |||||||||||||||||||||   ||||||||
sb33d15    729  ACGGGTTTAAAGTTGGCCGATaTTTTAATTCGAGAAAATTAAATGAATTTGCCcAAAGTGT
                     ||||||||||||||||||| |||||||||||||||||||||||||||||| ||||||||
consensus       ACGGGTTTAAAGTTGGCCGATgTTTTAATTCGAGAAAATTAAATGAATTTGCcAAAGTGT cad15      479  AAAAGAGCACTATGCAAGTGTAGGTCGCTATAACGCAACAGTTGAACCTATTGTCAATACG
                     ||||||||||||||||||||||||||||||||||||||||||||||||||||||||
minnad15   738  AAAAGAGCACTATGCAAGTGTAGGTCGCTATAACGCAACAGTTGAACCTATTGTCAATACG
                     ||||||||||||||||||||||||||||||||||||||||||||||||||||||||
eagand15   778  AAAAGAGCACTATGCAAGTGTAGGTCGCTATAACGCAACAGTTGAACCTATTGTCAATACG
                     ||||||||||||||||||||||||||||||||||||||||||||||||||||||||
pakd15     794  AAAAGAGCACTATGCAAGTGTAGGTCGCTATAACCGTTGAACCGTTGAACCTATTGTCAATACG
                     ||||||||||||||||||||||||||||||||||||||||||||||||||||||||
sb33d15    790  AAAAGAGCACTATGCAAGTGTAGGTCGCTATAACGCAACCGTTGAACCTATTGTCAATACG
                     |||||||||||||||||||||||||||||||||||| |||||||||||||||||||||
consensus       AAAAGAGCACTATGCAAGTGTAGGTCGCTATAACGCAACaGTTGAACCTATTGTCAATACG
```

FIG. 1F-9

| | | |
|---|---|---|
| cad15 | 540 | CTACCAAATAATCGCGCTGAAATTTTAATTCAAATCAATGAAGATGATAAAGCAAAATTGG |
| minnad15 | 799 | CTACCAAATAATCGCGCTGAAATTTTAATTCAAATCAATGAAGATGATAAAGCAAAATTGG |
| eagand15 | 839 | CTACCAAATAATCGCGCTGAAATTTTAATTCAAATCAATGAAGATGATAAAGCAAAATTGG |
| pakd15 | 855 | CTgCCAAATAATCGtGCTGAAATTTTAATTCAAATCAATGAAGATGATAAAGCAAAATTGG |
| sb33d15 | 851 | CTaCCAAATAATCGCGCTGAAATTTTAATTCAAATCAATGAAGATGATAAAGCcAAATTGG |
| consensus | | CTaCCAAATAATCGcGCTGAAATTTTAATTCAAATCAATGAAGATGATAAAGCaAAATTGG |

| | | |
|---|---|---|
| cad15 | 601 | CATCATTAACTTTCAAGGGGAACGAATCTGTTAGTAGCAGTACATTACAAGAACAAATGGA |
| minnad15 | 860 | CATCATTAACTTTCAAGGGGAACGAATCTGTTAGTAGCAGTACATTACAAGAACAAATGGA |
| eagand15 | 900 | CATCATTAACTTTCAAGGGGAACGAATCTGTTAGTAGCAGTACATTACAAGAACAAATGGA |
| pakd15 | 916 | CATCATTAACTTTCAAGGGGAACGAATCTGTTAGTAGCAGTACATTACAAGAACAAATGGA |
| sb33d15 | 912 | CATCATTAACTTTCAAGGGGAACGAATCTGTTAGTAGCAGTACATTACAAGAACAAATGGA |
| consensus | | CATCATTAACTTTCAAGGGGAACGAATCTGTTAGTAGCAGTACATTACAAGAACAAATGGA |

FIG.1F-10

```
cad15      662  ATTACAACCTGATTCTTGGTGTGGAAATTATGGGGAAATAAATTTGAAGGTGCGCAATTCGAG
                |||||||||||||||||||||||||||||||||||||||||||||||||||||||||||||||
minnad15   921  ATTACAACCTGATTCTTGGTGTGGAAATTATGGGGAAATAAATTTGAAGGTGCGCAATTCGAG
                |||||||||||||||||||||||||||||||||||||||||||||||||||||||||||||||
eagand15   961  ATTACAACCTGATTCTTGGTGTGGAAATTATGGGGAAATAAATTTGAAGGTGCGCAATTCGAG
                |||||||||||||||||||||||||||||||||||||||||||||||||||||||||||||||
pakd15     977  ATTACAACCTGATTCTTGGTGTGGAAATTATGGGGAAATAAATTTGAAGGTGCGCAATTCGAG
                |||||||||||||||||||||||||||||||||||||||||||||||||||||||||||||||
sb33d15    973  ATTACAACCTGATTCTTGGTGTGGAAATTATGGGGAAATAAATTTGAAGGTGCGCAATTCGAG consensus       ATTACAACCTGATTCTTGGTGTGGAAATTATGGGGAAATAAATTTGAAGGTGCGCAATTCGAG cad15      723  AAAGATTTGCAGTCAATTCGTGATTATTATTTAAATAATGGCTATGCCAAAGCACAAATTA
                |||||||||||||||||||||||||||||||||||||||||||||||||||||||||||||
minnad15   982  AAAGATTTGCAGTCAATTCGTGATTATTATTTAAATAATGGCTATGCCAAAGCACAAATTA
                |||||||||||||||||||||||||||||||||||||||||||||||||||||||||||||
eagand15   1022 AAAGATTTGCAGTCAATTCGTGATTATTATTTAAATAATGGCTATGCCAAAGCACAAATTA
                |||||||||||||||||||||||||||||||||||||||||||||||||||||||||||||
pakd15     1038 AAAGATCTGCAGGCAATTCGTGATTATTATTTAAATAATGGCTATGCCAAAGCACAAATCA
                |||||| |||||  |||||||||||||||||||||||||||||||||||||||||||||||
sb33d15    1034 AAAGATtTGCAGtCAATTCGTGATTATTATTTAAATAATGGCTATGCCAAAGCACAAATCA consensus       AAAGATtGCAGtCAATTCGTGATTATTATTTAAATAATGGCTATGCCAAAGCACAAATtA
```

FIG.1F-11

```
cad15      784 CTAAAACGGATGTGTTCAGCTAAATGATGAAAAAACAAAAGTTAATGTAACCATTGATGTAAA
minnad15  1043 CTAAAACGGATGTGTTCAGCTAAATGATGAAAAAACAAAAGTTAATGTAACCATTGATGTAAA
eagand15  1083 CTAAAACGGATGTGTTCAGCTAAATGATGAAAAAACAAAAGTTAATGTAACCATTGATGTAAA
pakd15    1099 CTAAAACGGATGTGTTCAGCTAAATGATGAAAAAACAAAAGTTAATGTAACCATTGATGTAAA
sb33d15   1095 CTAAAgCGGATGTGTTCAGCTAAATGATGAAAAAACAAAAGTTAATGTAACCATTGATGTAAA consensus      CTAAAaCGGATGTGTTCAGCTAAATGATGAAAAAACAAAAGTTAATGTAACCATTGATGTAAA cad15      845 TGAAGGTTTACAGTATGACCTTCGTAGTGCACGCATTATAGGTAATCTGGGAGGTATGTCT
minnad15  1104 TGAAGGTTTACAGTATGACCTTCGTAGTGCACGCATTATAGGTAATCTGGGAGGTATGTCT
eagand15  1144 TGAAGGTTTACAGTATGACCTTCGTAGTGCACGCATTATAGGTAATCTGGGAGGTATGTCT
pakd15    1160 TGAAGGTTTACAGTATGACCTTCGTAGTGCACGCATTATAGGTAATCTGGGAGGTATGTCT
sb33d15   1156 TGAAGGTTTACAGTATGACCTTCGTAGTGCACGCATTATAGGTAATCTGGGAGGTATGTCT consensus      TGAAGGTTTACAGTATGACCTTCGTAGTGCACGCATTATAGGTAATCTGGGAGGTATGTCT
```

FIG.1F-12

```
cad15       906  GCCGAGCTTGAACCTTTACTTTCAGCATTACATTTAAATGATACTTTCCGCCGTAGTGATA
                 ||||||||||||||||||||||||||||||||||||||||||||||||||||||||||||
minnad15   1165  GCCGAGCTTGAACCTTTACTTTCAGCATTACATTTAAATGATACTTTCCGCCGTAGTGATA
                 ||||||||||||||||||||||||||||||||||||||||||||||||||||||||||||
eagand15   1205  GCCGAGCTTGAACCTTTACTTTCAGCATTACATTTAAATGATACTTTCCGCCGTAGTGATA
                 ||||||||||||||||||||||||||||||||||||||||||||||||||||||||||||
pakd15     1221  GCCGAGCTTGAACCTTTACTTTCAGCATTACATTTAAATGATACTTTCCGCCGTAGTGATA
                 ||||||||||||||||||||||||||||||||||||||||||||||||||||||||||||
sb33d15    1217  GCCGAGCTTGAACCTTTACTTTCAGCATTACATTTAAATGATACTTTCCGCCGTAGTGATA consensus        GCCGAGCTTGAACCTTTACTTTCAGCATTACATTTAAATGATACTTTCCGCCGTAGTGATA cad15       967  TTGCAGATGTAGAAAATGCAATTAAAGCAAAACTTGGAGAACGCGGTTACGGTAGCGCAAC
                 ||||||||||||||||||||||||||||||||||||||||||||||||||||||||||||
minnad15   1226  TTGCAGATGTAGAAAATGCAATTAAAGCAAAACTTGGAGAACGCGGTTACGGTAGCGCAAC
                 ||||||||||||||||||||||||||||||||||||||||||||||||||||||||||||
eagand15   1266  TTGCAGATGTAGAAAATGCAATTAAAGCAAAACTTGGAGAACGCGGTTACGGTAGCGCAAC
                 ||||||||||||||||||||||||||||||||||||||||||||||||||||||||||||
pakd15     1282  TTGCAGATGTAGAAAATGCAATTAAAGCAAAACTTGGGAACGAGGTTACGGTAACACAAC
                 ||||||||||||||||||||||||||||||||||||||||||||||||||||||||||||
sb33d15    1278  TTGCAGATGTAGAAAATGCAATTAAAGCAAAACTTGGGGAACGAGGTTACGGTAACACAAC consensus        TTGCAGATGTAGAAAATGCAATTAAAGCAAAACTTGGaGAACGcGGTTACGGTAgCgCAAC
```

```
cad15     1150  ATAGCACTTTACGTCAGGAAATGCGCCAACAAGAAGGAACTTGGTATAATTCACAATTAGT
                ||||||||||||||||||||||||||||||||||||||||||||||||||||||||||||
minnad15  1409  ATAGCACTTTACGTCAGGAAATGCGCCAACAAGAAGGAACTTGGTATAATTCACAATTAGT
                ||||||||||||||||||||||||||||||||||||||||||||||||||||||||||||
eagand15  1449  ATAGCACTTTACGTCAGGAAATGCGCCAACAAGAAGGAACTTGGTATAATTCACAATTAGT
                ||||         |||||||||||||||||||||||||||||||||||||||||||||||
pakd15    1465  ATAGTACTTTACGTCAGGAAATGCGaCAACAAGAAGGAACTTGGTATAATTCACAATTAGT
                ||||  ||||||||||||||||||| ||||||||||||||||||||||||||||||||||
sb33d15   1461  ATAGTACTTTACGTCAGGAAATGCGCCAACAAGAAGGAACTTGGTATAATTCACAATTAGT consensus       ATAGCACTTTACGTCAGGAAATGCGCCAACAAGAAGGAACTTGGTATAATTCACAATTAGT cad15     1211  TGAGTTAGGAAAAATTCGCTTAGATCGTACAGGTTTCTTCGAAACAGTCGAAAACCGAATT
                ||||||||||||||||||||||||||||||||||||||||||||||||||||||||||||
minnad15  1470  TGAGTTAGGAAAAATTCGCTTAGATCGTACAGGTTTCTTCGAAACAGTCGAAAACCGAATT
                ||||||||||||||||||||||||||||||||||||||||||||||||||||||||||||
eagand15  1510  TGAGTTAGGAAAAATTCGCTTAGATCGTACAGGTTTCTTCGAAACAGTCGAAAACCGAATT
                ||||||||||||||||||||||||||||||||||||||||||||||| ||||||||||||
pakd15    1526  TGAGTTAGGAAAAATTCGCTTAGATCGTACAGGTTTCTTCGAAACAGTTGAAAACCGAATT
                |||||||||||||||||||||||||||||||||||||||||||||||| |||||||||||
sb33d15   1522  TGAGTTAGGAAAAATTCGCTTAGATCGTACAGGTTTCTTCGAAACAGTcGAAAACCGAATT consensus       TGAGTTAGGAAAAATTCGCTTAGATCGTACAGGTTTCTTCGAAACAGTcGAAAACCGAATT
```

FIG.1F-15

```
cad15      1272  GATCCTATCAATGGTAGTAATGATGAAGTGGATGTCGTATATAAAGTCAAAGAACGTAACA
                 ||||||||||||||||||||||||||||||||||||||||||||||||||||||||||||
minnad15   1531  GATCCTATCAATGGTAGTAATGATGAAGTGGATGTCGTATATAAAGTCAAAGAACGTAACA
                 ||||||||||||||||||||||||||||||||||||||||||||||||||||||||||||
eagand15   1571  GATCCTATCAATGGTAGTAATGATGAAGTGGATGTCGTATATAAAGTCAAAGAACGTAACA
                 ||||||||||||||||||||||||||||||||||||||||||||||||||||||||||||
pakd15     1587  GATCCTATCAATGGTAGCAATGATGAAGTGGATGTCGTATATAAAGTCAAAGAACGTAACA
                 ||||||||||||||||| ||||||||||||||||||||||||||||||||||||||||||
sb33d15    1583  GATCCTATCAATGGTAGCAATGATGAAGTGGATGTCGTATATAAAGTCAAAGAACGTAACA consensus        GATCCTATCAATGGTAGtAATGATGAAGTGGATGTCGTATATAAAGTCAAAGAACGTAACA cad15      1333  CGGGTAGTATCAACTTTGGTATTGGTTACGGTACAGAGAGTGGTATTAGTTATCAAGCAAG
                 ||||||||||||||||||||||||||||||||||||||||||||||||||||||||||||
minnad15   1592  CGGGTAGTATCAACTTTGGTATTGGTTACGGTACAGAGAGTGGTATTAGTTATCAAGCAAG
                 ||||||||||||||||||||||||||||||||||||||||||||||||||||||||||||
eagand15   1632  CGGGTAGTATCAACTTTGGTATTGGTTACGGTACAGAGAGTGGTATTAGTTATCAAGCAAG
                 ||||||||||||||||||||||||||||||||||||||||||||||||||||||||||||
pakd15     1648  CGGGTAGTATCAACTTTGGTATTGGTTACGGTACAGAGAGTGGTATcAGTTATCAAaCAAG
                 ||||||||||||||||||||||||||||||||||||||||||||||| |||||||| |||
sb33d15    1644  CGGGTAGTATCAACTTTGGTATTGGTTACGGTACAGAGAGTGGTATtAGTTATtAAgCAAG consensus        CGGGTAGTATCAACTTTGGTATTGGTTACGGTACAGAGAGTGGTATtAGTTATCAAgCAAG
```

FIG.1F-16

```
cad15     1394  TGTTAAACAAGATAATTTCTTGGGAACAGGGCGGCAGTAAGTATAGCTGGTACGAAAAAT
                ||||||||||||||||||||||||||||||||||||||||||||||||||||||||||||
minnad15  1653  TGTTAAACAAGATAATTTCTTGGGAACAGGGCGGCAGTAAGTATAGCTGGTACGAAAAAT
                ||||||||||||||||||||||||||||||||||||||||||||||||||||||||||||
eagand15  1693  TGTTAAACAAGATAATTTCTTGGGAACAGGGCGGCAGTAAGTATAGCTGGTACGAAAAAT
                |||||||||||||||||| |||||||||||||||||||||||||||||||||||||||||
pakd15    1709  TaTTAAACAAGATAATTCTTGGGAACAGGGCGGCAGTAAGTATAGCTGGTACGAAAAAT
                ||  ||||||||||||||||||||||||||||||||||||||||||||||||||||||||
sb33d15   1705  TgTcAAACAAGATAATTTCTTGGGAACAGGGCGGCAGTAAGTATAGCTGGTACGAAAAAT consensus       TgTtAAACAAGATAATTTCTTGGGAACAGGGCGGCAGTAAGTATAGCTGGTACGAAAAT cad15     1455  GATTATGGTACGAGTGTCAATTTGGGTTATACCGAGCCCTATTTTACTAAAGATGGTGTAA
                ||||||||||||||||||||||||||||||||||||||||||||||||||||||||||||
minnad15  1714  GATTATGGTACGAGTGTCAATTTGGGTTATACCGAGCCCTATTTTACTAAAGATGGTGTAA
                ||||||||||||||||||||||||||||||||||||||||||||||||||||||||||||
eagand15  1754  GATTATGGTACGAGTGTCAATTTGGGTTATACCGAGCCCTATTTTACTAAAGATGGTGTAA
                ||||||||||||||||||||||||||||||||||||||||||||||||||||||||||||
pakd15    1770  GATTATGGTACGAGTGTCAATTTGGGTTATACCGAaCCCTATTTTACTAAAGATGGTGTAA
                |||||||||||||||||||||||||||||||||||| |||||||||||||||||||||||
sb33d15   1766  GATTATGGTACGAGTGTCAATTTGGGTTATACCGAgCCCTATTTTACTAAAGATGGTGTAA consensus       GATTATGGTACGAGTGTCAATTTGGGTTATACCGAgCCCTATTTTACTAAAGATGGTGTAA
```

FIG.1F-17

```
cad15     1516  GTCTTGGTGGAAATGTTTTCTTTGAAAACTACGATAACTCTAAAAGTGATACATCCTCTAA
                |||||||||||||||||||||||||||||||||||||||||||||||||||||||||||| 
minnad15  1775  GTCTTGGTGGAAATGTTTTCTTTGAAAACTACGATAACTCTAAAAGTGATACATCCTCTAA
                |||||||||||||||||||||||||||||||||||||||||||||||||||||||||||| 
eagand15  1815  GTCTTGGTGGAAATGTTTTCTTTGAAAACTACGATAACTCTAAAAGTGATACATCCTCTAA
                |||||||||||||||||||||||||||||||||||||||||||||||||||||||||||| 
pakd15    1831  GTCTTGGTGGAAATaTTTTCTTTGAAAACTACGATAACTCTAAAAGTGATACATCCTCTAA
                |||||||||||||||  ||||||||||||||||||||||||||||||||||||||||||| 
sb33d15   1827  GTCTTGGTGGAAATgTTTTCTTTGAAAACTACGATAACTCTAAAAGTGATACATCCTCTAA
                ||||||||||||||| |||||||||||||||||||||||||||||||||||||||||||| 
consensus       GTCTTGGTGGAAATgTTTTCTTTGAAAACTACGATAACTCTAAAAGTGATACATCCTCTAA cad15     1577  CTATAAGCGTACGACTTACGGAAGTAATGTTACTTTAGGTTTCCCTGTAAATGAAAATAAC
                ||||||||||||||||||||||||||||||||||||||||||||||||||||||||||||
minnad15  1836  CTATAAGCGTACGACTTACGGAAGTAATGTTACTTTAGGTTTCCCTGTAAATGAAAATAAC
                ||||||||||||||||||||||||||||||||||||||||||||||||||||||||||||
eagand15  1876  CTATAAGCGTACGACTTACGGAAGTAATGTTACTTTAGGTTTCCCTGTAAATGAAAATAAC
                ||||||||||||||||||||||||||||||||||||||||||||||||||||||||||||
pakd15    1892  CTATAAGCGTACGACTTATGGAAGTAATGTTACTTTAGGTTTCCCTGTAAATGAAAATAAC
                ||||||||||||||||||  ||||||||||||||||||||||||||||||||||||||||
sb33d15   1888  CTATAAGCGTACGACTTATGGAAGTAATGTTACTTTAGGTTTCCCTGTAAATGAAAATAAC
                ||||||||||||||||||  ||||||||||||||||||||||||||||||||||||||||
consensus       CTATAAGCGTACgACTTAcGGAAGTAATGTTACTTTAGGTTTCCCTGTAAATGAAAATAAC
```

FIG.1F-18

```
cad15     1638  TCCTATTATGTAGGATTAGGTCATACCTATAATAAAATTAGTAACTTTGCTCTAGAATATA
                ||||||||||||||||||||||||||||||||||||||||||||||||||||||||||||
minnad15  1897  TCCTATTATGTAGGATTAGGTCATACCTATAATAAAATTAGTAACTTTGCTCTAGAATATA
                ||||||||||||||||||||||||||||||||||||||||||||||||||||||||||||
eagand15  1937  TCCTATTATGTAGGATTAGGTCATACCTATAATAAAATTAGTAACTTTGCTCTAGAATATA
                ||||||||||||||||||||||||||||||||| ||||||||||||||||||||||||||
pakd15    1953  TCCTATTATGTAGGATTAGGCCATACCTATAATAAAATTAGTAACTTTGCTCTAGAATATA
                ||||||||||||||||||||||||||||||||||||||||||||||||||||||||||||
sb33d15   1949  TCCTATTATGTAGGATTAGGCCATACCTATAATAAAATTAGTAACTTTGCTCTAGAATATA consensus       TCCTATTATGTAGGATTAGGtCATACCTATAATAAAATTAGTAACTTTGCTCTAGAATATA cad15     1699  ACCGTAATTTATATATTCAATCAATGAAATTTAAAGGTAATGGCATTAAAACAAATGACTT
                ||||||||||||||||||||||||||||||||||||||||||||||||||||||||||||
minnad15  1958  ACCGTAATTTATATATTCAATCAATGAAATTTAAAGGTAATGGCATTAAAACAAATGACTT
                ||||||||||||||||||||||||||||||||||||||||||||||||||||||||||||
eagand15  1998  ACCGTAATTTATATATTCAATCAATGAAATTTAAAGGTAATGGCATTAAAACAAATGACTT
                ||||||||||||||||||||||||||||||||||||||||||||||||||||||||||||
pakd15    2014  ACCGTAATTTATATATTCAATCAATGAAATTTAAAGGTAATGGCATTAAAACAAATGACTT
                ||||||||||||||||||||||||||||||||||||||||||||||||||||||||||||
sb33d15   2010  ACCGTAATTTATATATTCAATCAATGAAATTTAAAGGTAATGGCATTAAAACAAATGACTT consensus       ACCGTAATTTATATATTCAATCAATGAAATTTAAAGGTAATGGCATTAAAACAAATGACTT
```

FIG.1F -19

```
cad15    1760  TGATTTTTCTTTTGGTTGGAACTATAACAGCCTTAATAGAGGCTATTCCCAACTAAAGGG
               ||||||||||||||||||||||||||||||||||||||||||||||||||||||||||||
minnad15 2019  TGATTTTTCTTTTGGTTGGAACTATAACAGCCTTAATAGAGGCTATTCCCAACTAAAGGG
               ||||||||||||||||||||||||||||||||||||||||||||||||||||||||||||
eagand15 2059  TGATTTTTCTTTTGGTTGGAACTATAACAGCCTTAATAGAGGCTATTCCCAACTAAAGGG
               ||||||||||||||||||||||||||||||||||||||||||||||||||||||||||||
pakd15   2075  TGATTTTTCTTTTGGTTGGAACTATAACAGCCTTAATAGAGGCTATTCCCAACTAAAGGG
               ||||||||||||||||||||||||||||||||||||||||||||||||||||||||||||
sb33d15  2071  TGATTTTTCTTTTGGTTGGAACTATAACAGCCTTAATAGAGGCTATTCCCAACTAAAGGG consensus      TGATTTTTCTTTTGGTTGGAACTATAACAGCCTTAATAGAGGCTATTCCCAACTAAAGGG cad15    1821  GTTAAAGCAAGTCTTGGTGGACGAGTTACTATTCCAGTTCTGATAACAAATACTACAAAC
               ||||||||||||||||||||||||||||||||||||||||||||||||||||||||||||
minnad15 2080  GTTAAAGCAAGTCTTGGTGGACGAGTTACTATTCCAGTTCTGATAACAAATACTACAAAC
               ||||||||||||||||||||||||||||||||||||||||||||||||||||||||||||
eagand15 2120  GTTAAAGCAAGTCTTGGTGGACGAGTTACTATTCCAGTTCTGATAACAAATACTACAAAC
               ||||||||||||||||||||||||||||||||||||||||||||||||||||||||||||
pakd15   2136  GTTAAAGCAAGTCTTGGTGGACGAGTTACTATTCCAGTTCTGATAACAAATACTACAAAC
               ||||||||||||||||||||||||||||||||||||||||||||||||||||||||||||
sb33d15  2132  GTTAAAGCAAGTCTTGGTGGACGAGTTACaATTCCAGTTCTGATAACAAATACTACAAAC consensus      GTTAAAGCAAGTCTTGGTGGACGAGTTACTATTCCAGTTCTGATAACAAATACTACAAAC
```

FIG. 1F-20

```
cad15     1882  TAAGTGCAGATGTACAGGGTTTCTACCCATTAGACAGAGATCACCTCTGGGTTGTATCTGC
                ||||||||||||||||||||||||||||||||||||||||||||||||||||||||||||
minnad15  2141  TAAGTGCAGATGTACAGGGTTTCTACCCATTAGACAGAGATCACCTCTGGGTTGTATCTGC
                ||||||||||||||||||||||||||||||||||||||||||||||||||||||||||||
eagand15  2181  TAAGTGCAGATGTACAGGGTTTCTACCCATTAGACAGAGATCACCTCTGGGTTGTATCTGC
                ||||||||||||||||||||||||||||||||||||||||||||||||||||||||||||
pakd15    2197  TAAGTGCAGATGTACAGGGTTTCTACCCATTAGACAGAGATCACCgCTGGGTTGTATCTGC
                ||||||||||||||||||||||||||||||||||||||||||||| ||||||||||||||
sb33d15   2193  TAAGTGCAGATGTACAGGGTTTCTACCCATTAGACAGAGATCACCtCTGGGTTGTATCTGC consensus       TAAGTGCAGATGTACAGGGTTTCTACCCATTAGACAGAGATCACCtCTGGGTTGTATCTGC cad15     1943  AAAAGCATCTGCAGGATATGCAAATGGTTTTGGAAACAAGCGTTTACCGTTCTATCAAACT
                ||||||||||||||||||||||||||||||||||||||||||||||||||||||||||||
minnad15  2202  AAAAGCATCTGCAGGATATGCAAATGGTTTTGGAAACAAGCGTTTACCGTTCTATCAAACT
                ||||||||||||||||||||||||||||||||||||||||||||||||||||||||||||
eagand15  2242  AAAAGCATCTGCAGGATATGCAAATGGTTTTGGAAACAAGCGTTTACCGTTCTATCAAACT
                ||||||||||||||||||||||||||||||||||||||||||||||||||||||||||||
pakd15    2258  AAAAGCATCTGCAGGATATGCAAATGGTTTTGGAAACAAGCGTTTACCGTTCTATCAAACT
                ||||||||||||||||||||||||||||||||||||||||||||||||||||||||||||
sb33d15   2254  AAAAGCATCTGCAGGATATGCAAATGGTTTTGGAAACAAGCGTTTACCGTTCTATCAAACT
```

```
sb33d15  2376  CAATTTATcaaGgtCAaaaTAAT                              aaaTTTAATAAGATAAGTTCTGA consensus       CAATTTATgccGaatAtggTAATggtagtggtactggtactTTTAAgAAGATAAGTTCTGA cad15    2126  TGTGATTGGTGGTAATGCAATCGCTACAGCTAGCGGCAGAGTTAATTGTGCCAACTCCATTT
                ||||||||||||||||||||||||||||||||||||||||||||||||||||||||||||
minnad15 2385  TGTGATTGGTGGTAATGCAATCGCTACAGCTAGCGGCAGAGTTAATTGTGCCAACTCCATTT
                ||||||||||||||||||||||||||||||||||||||||||||||||||||||||||||
eagand15 2425  TGTGATTGGTGGTAATGCAATCGCTACAGCTAGCGGCAGAGTTAATTGTGCCAACTCCATTT
                ||||||||||||||||||||||||||||||||||||||||||||||||||||||||||||
pakd15   2429  TGTGATTGGTGGTAATGCAATCaCaACtGCgAGtGCAGAAcTtATTGTaCCAACTCCATTT
                ||||||||||||||||||||||| ||  ||  ||  ||||||| |||||| |||||||||
sb33d15  2422  TGTGATTGGTGGTAATGCAATCgCtACaGCtAGcGGCAGAGtTaATTGTgCCAACTCCATTT
                ||||||||||||||||||||| || || | ||||||||| | ||||| |||||||||||| consensus       TGTGATTGGTGGTAATGCAATCGCTACAGCTAGCGGCAGAGTTAATTGTGCCAACTCCATTT cad15    2187  GTGAGCGATAAGAGCCAAAATACGGTCCGAACCTCCTTATTTGTTGATGCGGCAAGTGTTT
                ||||||||||||||||||||||||||||||||||||||||||||||||||||||||||||
minnad15 2446  GTGAGCGATAAGAGCCAAAATACGGTCCGAACCTCCTTATTTGTTGATGCGGCAAGTGTTT
                ||||||||||||||||||||||||||||||||||||||||||||||||||||||||||||
eagand15 2486  GTGAGCGATAAGAGCCAAAATACGGTCCGAACCTCCTTATTTGTTGATGCGGCAAGTGTTT
                ||||||||||||||||||||||||||||||||||||||||||||||||||||||||||||
```

FIG.1F-23

```
pakd15    2490  GTGAGTGATAAaAGCCAAAATACAGTCCGAACCTCCCTATTTGTTGATGCGGCAAGTGTTT
                |||||||||||| ||||| ||||||||||||||||||||||||||||||||||||||||
sb33d15   2483  GTGAGTGATAAgAGtCAAAATACAGTCCGAACCTCCCTATTTGTTGATGCGGCAAGTGTTT consensus       GTGAGcGATAAgAGCCAAAATACgGTCCGAACCTCCtTATTTGTTGATGCGGCAAGTGTTT cad15     2248  GGAATACTAAATGGAAATCAGATAAAAATGGATTAGAGAGCCGATGTATTAAAAGATTGCC
                ||||||||||||||||||||||||||||||||||||||||||||||||||||||||||||
minnad15  2507  GGAATACTAAATGGAAATCAGATAAAAATGGATTAGAGAGCCGATGTATTAAAAGATTGCC
                ||||||||||||||||||||||||||||||||||||||||||||||||||||||||||||
eagand15  2547  GGAATACTAAATGGAAATCAGATAAAAATGGATTAGAGAGCCGATGTATTAAAAGATTGCC
                ||||||||||||||||||||||||||||||||||| || ||||||||||| |||||||||
pakd15    2551  GGAATACTAAATGGAAATCAGATAAAAATGGATTAGAGAGCCAAgGTCTTGAAAGACTTACC
                ||||||||||||||||||||||||||||||||||| ||||||||| |||||||||||||
sb33d15   2544  GGAATACTAAATGGAAATCAGATAAAAATGGATTAGAGAGCCAAtGTCTTGAAAGACTTACC consensus       GGAATACTAAATGGAAATCAGATAAAAATGGATTAGAGAGCgatGTaTTaAAAagaTTgcc cad15     2309  TGATTATGGCAAATCAAGCCGTATTCGCGCCCTCTACAGGTGTCGGATTCCAATGGCAATCT
                |||||||||||||||||||||||||||||||||||||||||||||||||||||||||||||
minnad15  2568  TGATTATGGCAAATCAAGCCGTATTCGCGCCCTCTACAGGTGTCGGATTCCAATGGCAATCT
```

FIG.1F-24

```
eagand15   2608  TGATTATGGCAAAATCAAGCCCGTATTCGCGCCTCTACAGGTGTGTCGGATTCCAATGGCAATCT
                 ||||||||||||||||||||||||||||||||||||||||||||||||||||||||||||||||
pakd15     2612  TGATTATGGCAAAATCAAGCCCGTATTCGCGCCTCTACAGGTGTGTCGGATTCCAATGGCAATCT
                 ||||||||||||||||||||||||||||||| ||||||||||||||||||||||||||||||||
sb33d15    2605  cGATTATGGCAAAATCAAGCCCGTACTCGCGCCTCTACAGGTGTGTCGGATTCCAATGGCAATCT
                 ||||||||||||||||||||||| ||||||||||||||||||||||||||||||||||||||||
consensus        tGATTATGGCAAAATCAAGCCCGTAtCGCGCCTCTACAGGTGTGTCGGATTCCAATGGCAATCT cad15      2370  CCTATTGGGCCATTGGTATTCTCTTATGCCAAACCAATTAAAAAATATGAAAATGATGATG
                 ||||||||||||||||||||||||||||||||||||||||||||||||||||||||||||
minnad15   2629  CCTATTGGGCCATTGGTATTCTCTTATGCCAAACCAATTAAAAAATATGAAAATGATGATG
                 ||||||||||||||||||||||||||||||||||||||||||||||||||||||||||||
eagand15   2669  CCTATTGGGCCATTGGTATTTCTCTTATGCCAAACCAATTAAAAAATATGAAAATGATGATG
                 ||||||||||||||||||||| ||||||||||||||||||||||||||||||||||||||
pakd15     2673  CCTATTGGACCATTGGTATTTTCTTATGCTAAACCAATTAAAAAATATGAAAATGATGATG
                 |||| ||| ||||||||||| |||||||| ||||||||||||||||||||||||||||||
sb33d15    2666  CCTAgTGGACCATTGGTATTCTCTTATGCCAAACCAATTAAAAAATATGAAAATGATGATG
                 |||| ||| |||||||||||||||||||||||||||||||||||||||||||||||||||
consensus        CCTAtTGGgCCATTGGTATTCTCTTATGCCAAACCAATTAAAAAATATGAAAATGATGATG cad15      2431  TCGAACAGTTCCAATTTAGTATTGGAGGTTCTTTTCTAATAAATTGAACTTTTTTCTTCATC
                 ||||||||||||||||||||||||||||||||||||||||||||||||||||||||||||||
```

FIG.1F -25

```
minnad15  2690  TCGAACAGTTCCAATTTAGTATTGGAGGTTCTTTCTAATAAATTGAACTTTTTCTTCATC
                |||||||||||||||||||||||||||||||||||||||||||||||||||| |||||||
eagand15  2730  TCGAACAGTTCCAATTTAGTATTGGAGGTTCTTTCTAATAAATTGAACTTTTTCTTCATC
                |||||||||||||||||||||||||| ||||  |||||||||||||||||||| ||||||
pakd15    2734  TCGAACAGTTCCAATTTAGTATTGGGGGCTCTTTCTAATAAATTGAACTTTTTCGTCATC
                ||||||||||||||||||||||||| ||| |||||||||||||||||||||||||||||
sb33d15   2727  TCGAACAGTTCCAATTTAGTATTGGGGGtTCTTTCTAATAAATTGAACTTTTTCGTCATC consensus       TCGAACAGTTCCAATTTAGTATTGGaGGtTCTTTCTAATAAATTGAACTTTTTCtTCATC cad15     2492  AGAACTCAAAAACAACGTTCTCTGCCTAATTTAATTGGGCAGAGAAAATATTAAACCCATC
                ||||||||||||||||||||||||||||||||||||||||||||||||||||||||||||
minnad15  2751  AGAACTCAAAAACAACGTTCTCTGCCTAATTTAATTGGGCAGAGAAAATATTAAACCCATC
                ||||||||||||||||||||||||||||||||||||||||||||||||||||||||||||
eagand15  2791  AGAACTCAAAAACAACGTTCTCTGCCTAATTTAATTGGGCAGAGAAAATATTAAACCCATC
                |||||||||||| ||||||||||||||||||| ||| ||||||||||||||||||||||
pakd15    2795  AGAACTCAAAAACgACGTTCTCTGCCTAATTgAATTGGGCAGAGAAAATATTAAACCCATC
                |||||||||||| |||||||||||||||||| |||||||||||||||||||||| |||||
sb33d15   2788  AGAACTCAAAAACaACGTTCTCTGCCTAATTtAATTGGGCAGAGAAAATATTAAaCCCATC consensus       AGAACTCAAAAACaACGTTCTCTGCCTAATTtAATTGGGCAGAGAAAATATTAAACCCATC
```

FIG.1F-26

```
cad15     2553  ATTTAATTAAGGATATATTTATCAAATGAAAAAACATCGCAAAGTAACCGCACTTGCTTTAGG
                |||||||||||||||||||||||||||||||||||||||||||||||||||||||||||||||
minnad15  2812  ATTTAATTAAGGATATATTTATCAAATGAAAAAACATCGCAAAGTAACCGCACTTGCTTTAGG
                |||||||||||||||||||||||||||||||||||||||||||||||||||||||||||||||
eagand15  2852  ATTTAATTAAGGATATATTTATCAAATGAAAAAACATCGCAAAGTAACCGCACTTGCTTTAGG
                |||||||||||||||||||||||||||||||||||||||||||||||||||||||||||||||
pakd15    2856  ATTTAATTAAGGATATATTTATCAAATGAAAAAACATCGCAAAGTAACCGCACTTGCTTTAGG
                |||||||||||||||||||||||||||||||||||||||||||||||||||||||||||||||
sb33d15   2849  ATTTAATTAAGGATATATTTATCAAATGAAAAAACATCGCCAAAGTAACCGCACTTGCTTTAGG consensus       ATTTAATTAAGGATATTTATCAAATGAAAAAACATCGCaAAGTAACCGCACTTGCTTTAGG cad15     2614  TATTGCACTTGCTTCAGGCTATGCTTCCGCTGAAGAAAAAATTGCTTTCATTAATGCaGGT
                |||||||||||||||||||||||||||||||||||||||||||||||||||||||||||||
minnad15  2873  TATTGCACTTGCTTCAGGCTATGCTTCCGCTGAAGAAAAAATTGCTTTCATTAATGCgGGT
                |||||||||||||||||||||||||||||||||||||||||||||||||||||||||||||
eagand15  2913  TATTGCACTTGCTTCAGGCTATGCTTCCGCTGAAGAAAAAATTGCTTTCATTAATGC AcT
                |||||||||||||||||||||||||||||||||||||||| |||||||||||||||||
pakd15    2917  TtTTGCACTTGCTTCAGGCTATGCTTCCGCTGAAGAAAAAATTGCTTTCATTAATGC AGG
                |||||||||||||||||||||||||||||||||||||||||||||||||||||||||||
sb33d15   2910  TaTTGCACTTGCTTCAGGCTATGCTgCaGCTGAAGCTGAAGAAAAAATTGCTTTtATTAATGC AGG consensus       TaTTGCACTTGCTTcCGCTGAAGAAAAAATTGCTTTcATTAATGC-agt
```

FIG.1F-27

```
cad15    2675  atattTTTcaAcatCacccagatcgcccaagcggtagcagataaacttgatgctgaatttaa
                    ||||||  || ||    |||||  |||||||||||||||||||||||||
minnad15 2934                    TATAnTTTnCAAggCnaagg
                                 |||| ||| ||||
eagand15 2973                    TATAtTTTTCAA
                                 |||| |||||
pakd15   2977                    TTTATATTTTtcAa
                                 ||||| ||
sb33d15  2970                    TTTATA consensus       ttat-ttttcaaa-c-----gatcgccaagcggtagcagataaacttgatgctgaatttaa cad15    2736  acctgtagctgagaaattagcagcaagcaaaaagaagttgatgataaaattgctgctgct
minnad15 2954
eagand15 2985
pakd15   2990
sb33d15  2975 consensus       acctgtagctgagaaattagcagcaagcaaaaagaagttgatgataaaattgctgctgct
```

FIG.1F-28

```
cad15    2797   cgtaaaaagtagaagcaaaagttgcgggctttagaaaaagatgcacctcgcttacgtcaag
minnad15 2954
eagand15 2985
pakd15   2990
sb33d15  2975
consensus       cgtaaaaagtagaagcaaaagttgcgggctttagaaaaagatgcacctcgcttacgtcaag cad15    2858   ctgatattcaaaacgccaacaggagattaataaattaggtgcggctgaagatgctgaatt
minnad15 2954
eagand15 2985
pakd15   2990
sb33d15  2975
consensus       ctgatattcaaaacgccaacaggagattaataaattaggtgcggctgaagatgctgaatt
```

FIG.1F-29

| | | |
|---|---|---|
| cad15 | 2919 | acaaaaattaatgcaagaacaagataaaaa |
| minnad15 | 2954 | |
| eagand15 | 2985 | |
| pakd15 | 2990 | |
| sb33d15 | 2975 | |
| consensus | | acaaaaattaatgcaagaacaagataaaaa |

D15 CLONES pUC19/D15

DS-712-2-1

DS-691-1-5

JB-1042-5-1

JB-1042-9-4

D15 SEQUENCE COMPARISON

```
MKKLLIASLLFGITTVFAAPFVAKDIRVDGVQGDLEQQIRASLPVRAGQRVTINDVANIVRSLFVSGRFDDVKAHQEGIVLVVSVVAKSIISDVKIKGN    Ca
.................................................................................................    Eagan
.................................................................................................    MinnA
.................................................................................................    SB33
.................................................................................................    PAK SVIPTEALKQNLDANGFKVGDVLIREKLNEFAKSVKEHYASVGRYNAIVEPIVNILPNNRAEILIQINEDIKAKLASLIFKGNESVSSSTLQEQMELQPD    Ca
.................................................................................................    Eagan
........I........................................................................................    MinnA
.................................................................................................    SB33
.................................................................................................    PAK SMWKLMGNKFEGAQFEKDLQSIRDYLNNGYAKAQITKIDVQLNDEKTKVNVTIDMNEGLQYDLRSARIIGNLQGMSAELEPLLSALHINDITFRRSDIAD    Ca
.................................................................................................    Eagan
.......................A.........................................................................    MinnA
.......................A.........................................................................    SB33
.................................................................................................    PAK VENAIKAKLGERGYCSAIVNSVPFDDANKTLATTLVVDAGRRLTVRQLRFEGNIVSADSTLRQEMRQQEGTWNSQLVELGKIRLDRIGFFEIVENRID    Ca
.................................................................................................    Eagan
.................................................................................................    MinnA
....NT......................................F.........H..........................................    SB33
....NT......................................F....................................................    PAK
```

FIG.3A.

| | | |
|---|---|---|
| PINGSNDEVDVVYKERNIGSINFGIGYGTESGISYQASVKQDNFLGIGAAVSLAGTKNDYGTSVNLGYTEPYFTKDGVSLGGNVFFENYINSKSDISS | Ca | |
| . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . | Eagan | |
| . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . | MinnA | |
| . . . . . . . . . . . . . . . . . . . . . . . . . . . . . . . . . . . . . . . . . . . . . . . . . . . . . . . . . . . . . . . . . T . I . . . . . . . . . . . . . . . . . . . . . . . | SB33 | |
| . . . . . . . . . . . . . . . . . . . . . . . . . . . . . . . . . . . . . . . . . . . . . . . . . . . . . . . . . . . . . . . . . . . . . . . . . . . . . . . . . . . I . . . . . . . . | PAK | |
| | | |
| NYKRITYGSNVTLGFPVNENNSYYVGLGHTYNKISNFALEYNFRNLYIQSMKFFKGNGIKINDFDFSFGMNVNSLNRGYFPTKGVKASLGGRVTIPGSDNKY | Ca | |
| . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . | Eagan | |
| . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . | MinnA | |
| . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . | SB33 | |
| . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . | PAK | |
| | | |
| YKLSADMQGFYPLDRDHLMVVSAKASAGYANGFGNKRLPFYQITYTAGGIGSLRGFAYGSIGPNAIYAEYGNSSGTIGFKKLSSDVIGGNAIATASAELIV | Ca | |
| . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . | Eagan | |
| . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . | MinnA | |
| . . . . . . . . . . . . . . . . . . . . . . . . . . . . . . . - - Q . QNNK - - - . N . . . . . . . . . . . . . . . . . . . . . . . . . . . . . . . . . . . . . . . . | SB33 | |
| . . . R . . . . . . . . . . . . . . . . . . . . . . . . . . . . . . . . . . . . . . . . . . . . . . . . . . . . . H . - - - - . . N . . . . . . . . . . . . . . . . . . . . . . . T . . . . | PAK | |
| | | |
| PTPFVSDKSQNIVRISLFVDAASWVNITKWKSDKNGLESDMLKRLPDYGKSSRIRASTGMGFQMQSPIGPLVFSYAKPIKKYENDMBQFQFSIGGSF** | Ca | |
| . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . ** | Eagan | |
| . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . . ** | MinnA | |
| . . . . . . . . . . . . . . . . . . . . . . . . . . . N . . D . . . . . . . . . . . . . . . . . . . . . . . . . . . . . . . . . . . . . . . . . . . . . . . . . . . . . . . . . . . . . ** | SB33 | |
| . . . . . . . . . . . . . . . . . . . . . . . . . . . K . . D . . . . . . . . . . . . . . . . . . . . . . . . . . . . . . . . . . . . . . . . . . . . . . . . . . . . . . . . . . . . . ** | PAK | |

FIG.3B.

PURIFICATION OF D15 FROM A NON-TYPEABLE
HAEMOPHILUS INFLUENZAE STRAIN 30

A 1  2  3  4

PROTEIN STAIN

B 1  2  3  4

WESTERN BLOT

1. Low MW markers

2. Strain 30

3. Native D15 crude extract

4. D15 after anti-D15 affinity chromatography

PURIFICATION OF FULL LENGTH RECOMBINANT D15

1. Protein M.W. Markers

2. Lysate of E. coli expressed rD15

3. Soluble protein in Tris-HC1 buffer extract

4. Soluble proteins in Tris/Triton X-100/ EDTA extraction buffer 5. rD15 inclusion bodies

PURIFICATION OF TRUNCATED D15 FROM D15-GST FUSION PROTEIN

1. Prestain low MW markers

2. GST standard

3. GST-(D15 fragment) fusion protein

4. Fusion protein cleaved by thrombin 5. rD15 fragment

6. GST

7. Low MW markers

HAEMOPHILUS OUTER MEMBRANE PROTEIN

REFERENCE TO RELATED APPLICATIONS

This application is a continuation of co-pending U.S. patent application Ser. No. 08/433,522 filed Sep. 12, 1995, which itself is a U.S. national phase filing under 35 USC 371 of PCT/CA93/00501 filed Nov. 23, 1993.

FIELD OF INVENTION

The present invention is related to the field of molecular genetics and is particularly concerned with the cloning of an outer membrane protein D15 of Haemophilus.

BACKGROUND OF THE INVENTION

*Haemophilus influenzae* type b (Hib) is a major cause of bacterial meningitis in children under the age of five years. Protective antibodies to the disease are induced by the capsular polysaccharide of the organism and a vaccine was developed that utilises the purified polyribosyl ribitol phosphate (PRP) as the antigen. This vaccine provides 90% protection in adults and in children over 24 months of age, but was ineffective in children under 24 months Zangwill et al 1993 (The references are identified in a list of reference at the end of this disclosure). Like other polysaccharide antigens, PRP does not induce the proliferation of T-helper cells, and re-immunisation fails to elicit either a booster response or an increase in memory cells. Conjugation of the PRP polysaccharide with protein carriers confers T-cell dependent characteristics to the vaccine and substantially enhances the immunologic response to the PRP antigen. Currently, there are four PRP-carrier conjugate vaccines available. These are vaccines based upon *H. influenzae* type b capsular polysaccharide conjugated to diphtheria toxoid, tetanus toxoid, or *Neisseria meningitidis* outer membrane protein (reviewed in Zangwill et al 1993).

However, the current Haemophilus conjugate vaccines only protect against meningitis caused by *Haemophilus influenzae* type b. They do not protect against other invasive typeable strains (types a and c) and, more importantly, against non-typeable (NTHi) strains which are a common cause of postpartum and neonatal sepsis, pneumonia and otitis media. In the United States alone, treatment of otitis media costs between 1 and 2 billion dollars per year for antibiotics and surgical procedures, such as tonsillectomies, adenoidectomies and insertion of tympanostomy tubes. To achieve universal protection against *H. influenzae* related diseases in the 2 to 6 month age group and certain high risk groups, the provision of conserved, cross-reactive non-capsular *H. influenzae* immunogens is desirable. Methods for inducing immunity against disease are constantly improving and there is presently a move to use subunits and better defined materials as antigens. This is being undertaken to minimise or eliminate potential side-effects caused by certain native immunogens, while preserving their immunogenicity to confer protection against the disease. Therefore, it would be very attractive to develop a universal vaccine against Haemophilus using cross-reactive outer membrane proteins, fragment, analogs, and/or peptides corresponding thereto as protective antigens. Such antigens may be incorporated into the conventional *H. influenzae* type b conjugate vaccines as additional immunogens or used as autologous carriers for *H. influenzae* capsular polysaccharides. A high molecular weight outer membrane protein D15 found in non-typeable and type b stains of *H. influenzae* has been identified as a cross-reactive antigen (Thomas et al., 1990). D15 appears to be cell surface-exposed in its natural state and exhibits a molecular mass of about 80 kDa as judged by SDS-PAGE analysis. It would be desirable to provide the sequence of the DNA molecule that encodes this D15 outer membrane protein and peptides corresponding to portions thereof for diagnosis, immunization and the generation of diagnostic and immunological reagents. The diseases caused by Haemophilus are serious and improved methods for preventing, detecting and treating diseases such as otitis media, epiglottitis, pneumonia, and tracheobronchitis, are required.

The present invention is directed towards the provision of purified and isolated nucleic acid molecules comprising at least a portion coding for a D15 outer membrane protein of a species of Haemophilus. The nucleic acid molecules comprising at least a portion coding for D15 outer membrane protein are useful for the specific detection of strains of Haemophilus, and for diagnosis of infection by Haemophilus. The purified and isolated nucleic acid molecules, such as DNA comprising at least a portion coding for D15 outer membrane protein, are also useful for expression of the D15 gene by recombinant DNA means for providing, in an economical manner, purified and isolated D15 outer membrane protein.

The D15 outer membrane protein or fragments thereof or analogs thereof are useful immunogenic compositions for the preparation of vaccines against diseases caused by Haemophilus, the diagnosis of infection by Haemophilus and as tools for the generation of immunological reagents. mono- or polyclonal antisera (antibodies) raised against the D15 outer membrane protein produced in accordance with aspects of the present invention are useful for the diagnosis of infection by Haemophilus, specific detection of Haemophilus (in, for example, an vitro and in vivo assays) and for the treatment of diseases caused by infection by Haemophilus.

Peptides corresponding to portions of the D15 outer membrane protein or analogs thereof are useful immunogenic compositions for the preparation of vaccines against disease caused by Haemonhilus, the diagnosis of infection by Haemophilus and as tools for the generation of immunological reagents. Mono- or polyclonal antisera raised against these peptides, produced in accordance with aspects of the present invention, are useful for the diagnosis of infection by Haemophilus, specific detection of Haemophilus (in, for example, in vitro and in vivo assays) and for use in passive immunization as a treatment of disease caused by infection by Haemophilus. In accordance with one aspect of the present invention, therefore, there is provided a purified and isolated nucleic acid molecule, the molecule comprising at least a portion coding for a D15 outer membrane protein. The nucleic acid molecule has a DNA sequence selected from:

(a) the DNA sequence set out in any one of FIGS. 1A to 1E (as described below) or its complementary strand; and (b) DNA sequences which hybridize under stringent conditions to the DNA sequences defined in (a). The DNA sequences defined in (b) preferably has at least 90% sequence identity with the sequences defined in (a). The DNA sequence defined in (b) particularly may comprise the consensus sequence set forth in FIG. 1F (as described below).

In another aspect of the present invention, there is provided a purified and isolated D15 outer membrane protein or a portion thereof. The D15 outer membrane protein may be a Haemophilus D15 outer membrane protein and more particularly an *H. influenzae* D15 outer membrane protein and the *H. influenza* strain may be an *H. influenzae* type b strain, such as *H. influenzae* type b strains Ca or Eagan or MinnA or a non-typeable *H. influenzae* strain, such as PAK 12085 or SB33.

In an additional embodiment, the present invention also includes a recombinant plasmid adapted for transformation of a host, the recombinant plasmid comprising a plasmid vector into which has been inserted a DNA segment comprising the purified and isolated DNA molecule provided herein. Such recombinant plasmid comprises a plasmid vector into which a DNA segment which comprises at least an 18 bp fragment selected from the DNA molecules as recited above is inserted. The recombinant plasmid may be plasmid DS-712-2-1 having ATCC accession number 75604, deposited Nov. 4, 1993 and plasmid JB-1042-5-1 having ATCC accession number 75006, deposited Nov. 4, 1993.

The plasmids may be adapted for expression of the encoded D15 outer membrane protein in a host cell, which may be a heterologous or homologous host, by incorporation into a recombinant vector, provided in accordance with a further aspect of the invention. The recombinant vector may comprise at least a DNA segment comprising at least an 18 bp fragment selected from the DNA molecules as recited above and expression means operatively coupled to the DNA segment for expression of the gene product encoded thereby in the host cell. The plasmid for expression of the encoded D15 outer membrane protein may be plasmid DS-880-1-2 having ATCC accession number 75605, deposited Nov. 4, 1993 being adapted for expression at the D15 outer membrane protein in *E. coli*. The selected DNA segment may encode a polypeptide of at least 6 residues and, in particular, may be selected from those segments encoding a polypeptide of Table 2 (below). The DNA segment may further comprise a nucleic acid sequence encoding a leader sequence for export of the gene product from the host. The host for expression may be selected from, for example, *Escherichia coli,* Bacillus, Haemophilus, fungi, yeast or the baculovirus expression system may be used.

Additional aspects of the invention include the protein encoded by the DNA molecule comprising at least a portion coding for the D15 outer membrane protein, fragment or a functional analog of such protein, the use of the protein or analog in vaccination and diagnosis, and the generation of immunological reagents. The invention also includes antisera (antibodies) raised against the D15 outer membrane protein encoded by the DNA molecule comprising at least a portion coding for a D15 outer membrane protein and purified peptides corresponding to portions of the D15 outer membrane protein and there are in passive immunization and treatment of diseases caused by Haemophilus.

According to another aspect of the invention, a purified and isolated peptide containing an amino acid sequence corresponding to the amino acid sequence of at least a portion of the D15 outer membrane protein or variant or mutant which retains immunogenicity. The peptide may be produced by recombinant methods or peptide synthesis whereby the purified peptide is free from contaminants associated with bacteria normally containing the D15 outer membrane protein. Such synthetic peptides preferably have an amino acid sequence selected from those presented in Table 2.

In accordance with an additional aspect of the invention, an immunogenic composition is provided which comprises the D15 outer membrane protein, fragments thereof, functional analogs thereof, or peptides as recited above and a physiologically-acceptable carrier therefor. Such immunogenic composition is particularly formulated as a vaccine for in vivo administration to protect against diseases caused by Haemophilus. For such purpose, the immunogenic composition may be formulated as a microparticle preparation, capsule preparation or liposome preparation. In addition, such immunogenic composition may be provided in combination with a targeting molecule for delivery to specific cells of the immune system or to mucosal surfaces.

In accordance with a further aspect of the invention, there is provided a method for inducing protection against disease caused by Haemophilus, comprising the step of administering to a subject, including a mammal, such as a human, an effective amount of the immunogenic composition or the nucleic acid molecule as recited above to provide protective immunity against Haemophilus infection.

The present invention further includes a chimeric molecule comprising a D15 protein or peptide corresponding thereto as provided herein linked to another polypeptide or protein or a polysaccharide. The linked polypeptide or protein may comprise a surface protein or peptide corresponding thereto from a pathogenic bacteria, which may be the P1, P2 or P6 outer membrane protein of *H. influenzae*. The linked polysaccharide preferably comprise a PRP molecule from *H. influenzae*.

BRIEF DESCRIPTION OF THE FIGURES

The present invention will be further understood from the following description with reference to the drawings, in which:

FIGS. 1A1–1A8 show the nucleotide sequence of the D15 gene from *H. influenzae* type b Ca strain (SEQ ID NO: 1) and its deduced amino acid sequence (SEQ ID NO: 2);

FIGS. 1B1–1B8 show the nucleotide sequence of the D15 gene from *H. influenzae* type b Eagan strain (SEQ ID NO. 3) and its deduced amino acid sequence (SEQ ID NO: 4);

FIGS. 1C1–1C9 show the nucleotide sequence of the D15 gene from *H. influenzae* type b MinnA strain (SEQ ID NO. 5) and its deduced amino acid sequence (SEQ ID NO: 6);

FIGS. 1D1–1D9 show the nucleotide sequence of the D15 gene from *H. influenzae* non-typeable SB33 (SEQ ID NO. 7) and its deduced amino acid sequence (SEQ ID NO: 8);

FIGS. 1E1–1E8 show the nucleotide sequence of the D15 gene from *H. influenzae* non-typeable PAK 12085 (SEQ ID NO. 9) and its deduced amino acid sequence (SEQ ID NO: 10);

FIGS. 1F1–1F29 show an alignment of the nucleotide sequences of the D15 genes (SEQ ID NOS: 1, 3, 5, 7 and 9) obtained from different *H. influenzae* isolates (typeable, Ca, Eagan and MinnA; nontypeable SB33 and PAK 12085) and the consensus sequence (SEQ ID NO: 55)for the D15 gene;

FIGS. 3A and 3B show an alignment of the amino acid sequences of D15 outer membrane proteins (SEQ ID NOS: 2, 4, 6, 8 and 10) obtained from different *H. influenzae* isolates (typeable, Ca, Eagan and MinnA; nontypeable, SB33 and PAK 12085). Amino acids are represented by the conventional one-letter code. The Ca D15 sequence is used as reference and the dots indicate amino acid residues which are identical to those of the Ca D15 outer membrane protein;

FIGS. 8A–8B show mouse IgG antibody responses to full length rD15. The arrows indicate the immunization schedule. Bleeds were taken at 0, 1, 4, 5 and 7 weeks. The bars represent the standard deviation;

FIG. 9 shows an SDS-PAGE analysis of the N-terminal rD15 fragment purified from GST-(D15 fragment) fusion protein. Lanes: 1, prestained low molecular weight markers (14 kDa, 21 kDa, 31 kDa, 45 kDa, 68 kDa, 97 kDa); 2, GST standard; 3, GST-(D15 fragment) fusion protein; 4, fusion protein cleaved by thrombin; 5, N-terminal rD15 fragment; 6, GST; 7, low molecular weight markers;

GENERAL DESCRIPTION OF THE INVENTION

Figure 2:
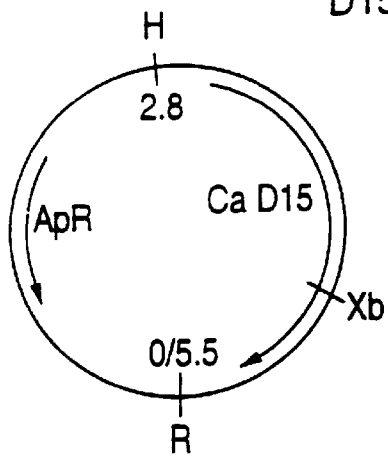
FIG. 2 shows restriction maps of clones pUC19/D15 (Ca), DS-712-2-1 (Eagan), DS-691-1-5 (MinnA), JB-1042-5-1 (SB33), and JB-1042-9-4 (PAK 12085). H=HIII; R=EcoRI; S=Sau3A I; and Xb=XbaI.
Figure 2:
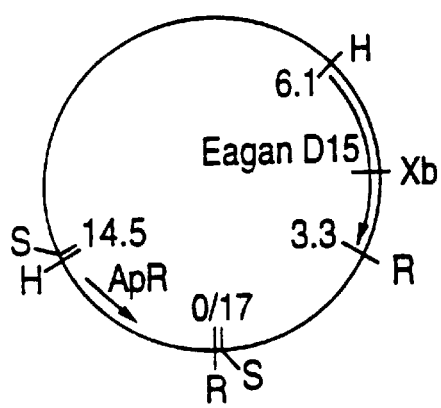
Figure 2:
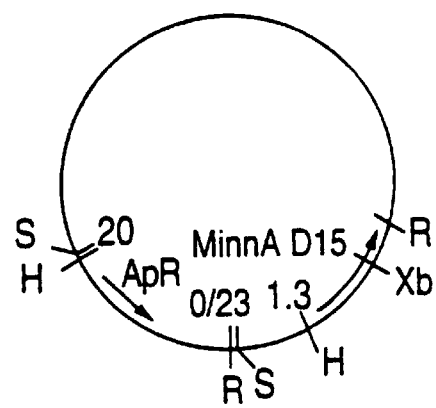
Figure 2:
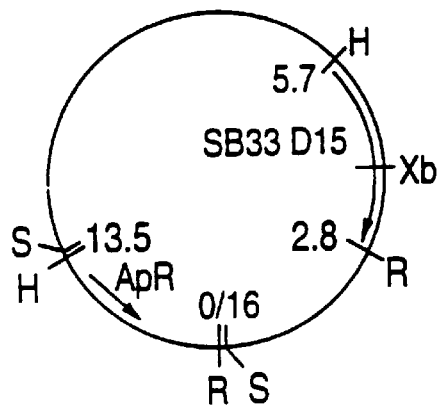
Figure 2:
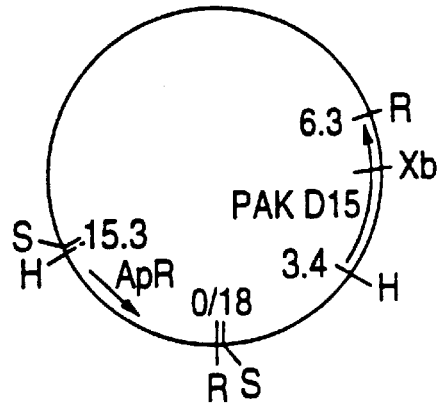

Any Haemophilus strains that have D15 genes may be conveniently used to provide the purified and isolated nucleic acid molecules (which may be in the form of DNA molecules), comprising at least a portion coding for a D15 outer membrane protein as typified by embodiments of the present invention. Such strains are generally available from clinical sources and from bacterial culture collections, such as the American Type Culture Collection. *H. influenzae* strains may include types a, b and c strains, non-typeable strains and other bacteria that produce a D15 protein, fragment or analog thereof. Appropriate strains of Haemophilus include:

*H. influenzae* type b strain Ca;

*H. influenzae* type b strain MinnA;

*H. influenzae* type b strain Egan;

*H. influenzae* non-typeable b strain SB33; or

*H. influenzae* non-typeable b strain PAK 12085.

In this application, the term D15 outer membrane protein is used to define a family of D15 proteins which includes those having naturally occurring variations in their amino acid sequences as found in various strains of, for example, Haemophilus. The purified and isolated DNA molecules comprising at least a portion coding for D15 outer membrane protein of the present invention also include those having naturally occuring variations in their nucleic acid sequences as found in various strains of, for example Haemophilus and those DNA molecules encoding functional analogs of D15 outer membrane protein. In this application, a first protein is a functional analog of a second protein if the first protein is immunologically related with and/or has the same function as the second protein. The functional analog may be, for example, a fragment of the protein or a substitution, addition or deletion mutant thereof.

Figure 1A-7:
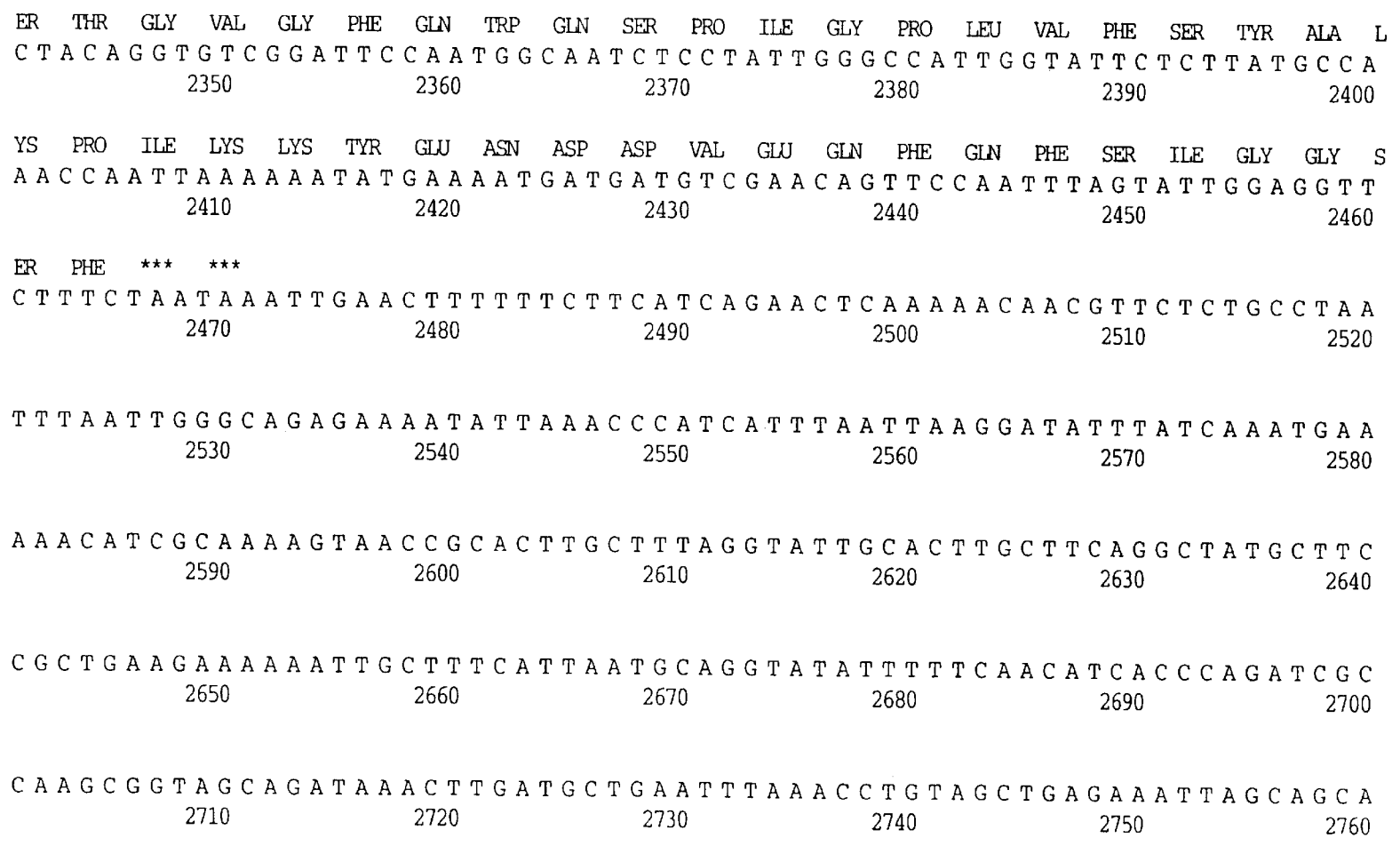
Figure 1B-1:
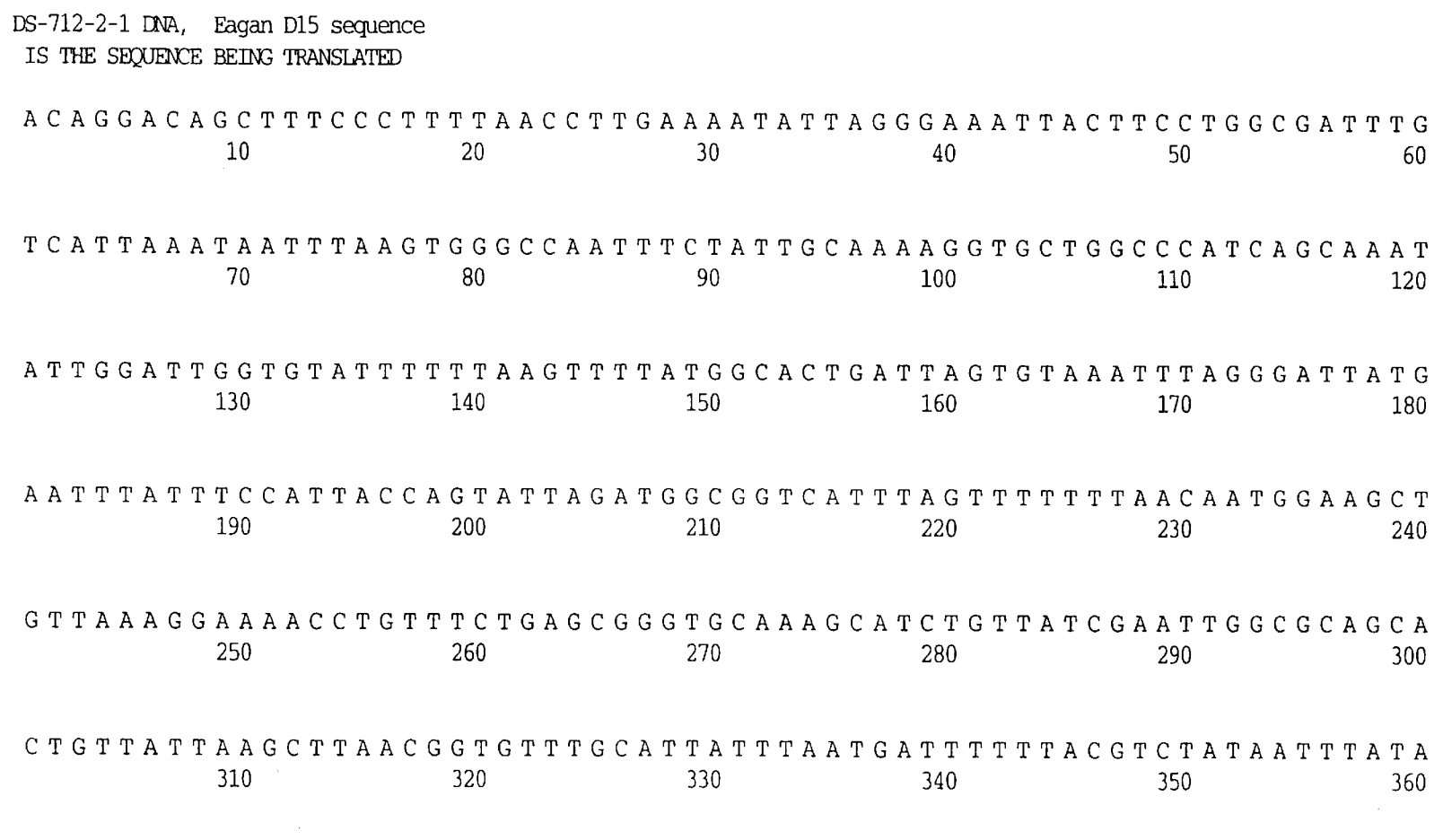

In aspects of the present invention, the D15 gene was isolated from *H. influenzae* type b strain Ca as shown in FIG. 1A; *H. influenzae* type B Egan, FIG 1B; *H. influenzae* type b MinnA, FIG. 1C; non-typeable *H. influenzae* SB33, FIG. 1D; non-typeable *H. influenzae* PAK 12085, FIG. 1E. A comparison of the nucleic acid sequences of the D15 genes and of the deduced amino acid sequences of the D15 outer membrane proteins from these strains of *H. influenzae* showed the genes and proteins to be highly conserved (FIGS. 1F and 3). The consensus sequence (SEQ ID NO: 55) for the D15 gene is shown in FIG. 1F.

The purified and isolated DNA molecules comprising at least a portion coding for a D15 outer membrane protein of a species of Haemophiius, typified by the embodiments described herein, are advantageous as:

nucleic acid probes for the specific identification of Haemophilus strains in vitro or in vivo;

the products encoded by the DNA molecules are useful as diagnostic reagents, antigens for the production of Haemophilus-specific antisera, for vaccination against the diseases caused by species of Haemophilus and detecting infection by Haemophilus; and peptides corresponding to portions of the D15 outer membrane protein as typified by the embodiments described herein are advantageous as diagnostic reagents, antigens for the production of Haemophilus-specific antisera, for vaccination against the diseases caused by species of Haemophilus and for detecting infection by Haemophilus.

Reference will now be made in detail to the presently preferred embodiments of the invention, which together with the following Examples, serve to explain the principle of the invention. For clarity of disclosure, and not by way of limitation, the detailed description of the invention is divided into the following sections:

(i) The DNA Sequences Coding for the Outer Membrane Protein D15 from *H. influenza* Type b Ca Strain A clone producing the outer membrane protein designated D15 of *H. influenzae* type b (Hib) was isolated by screening a genomic library with *H. influenzae* type b OMP-specific polyclonal antibodies as previously described by Berns and Thomas 1965; Thomas and Rossi 1986. The DNA fragment encoding the D15 protein was isolated, subcloned into pUC19 to produce pUC19/D15 (FIG. 2) and used to transform *E. coli* HB101 as described in Example 1. Plasmid DNA was prepared from two individual colonies of *E. coli* HB101 containing the pUC19/D15 plasmid. Sequencing was performed on an ABI DNA sequencer model 370A using dye-terminator chemistry and oligonucleotide primers which had been synthesized on an ABI DNA synthesizer model 380B, and purified by chromatography. Nucleotide sequence analysis of the D15 gene revealed that it contains a putative promoter and an open reading frame encoding 789 amino acids (FIG. 1A).

The first 19 amino acid residues of the translated open reading frame form a typical leader sequence as found in other *H. influenzae* type b outer membrane proteins, such as P1 and P2. The N-terminal sequence of immuno-affinity purified native D15 antigen was determined by automated Edman degradation using the ABI 477A protein sequencer and was found to be Ala-Pro-Phe, which is identical to the N-terminal amino acid sequence Ala-Pro-Phe-Val-Ala-Lys- (SEQ ID NO: 11) predicted from an analysis of the sequence of the D15 gene presented in FIG. 1A.

(ii) The Sequence of D15 Genes from Other *H. influenzae* Strains

D15 genes were isolated from other *H. influenzae* strains by screening the chromosomal libraries of *H. influenzae* type b strains Eagan, Minn A and the non-typeable *H. influenzae* (NTHi) strains SB33 and PAK 12085, as described in Examples 2, 3 and 4. Hybridization-positive clones were plated and submitted to a second round of screening. The restriction maps of the clones obtained are shown in FIG. 2. The nucleotide sequences of the D15 genes were determined for all these clones (FIGS. 1B to 1E) and their derived amino acid sequences compared (FIG. 3). The D15 amino acid sequences of the three *H. influenzae* type b strains were identical and only a few amino acid differences were observed in the amino acid sequence of the D15 protein from the non-typeable strains (FIG. 3).

(iii) Expression of D15 and its Fragments in *E. coli*

Since D15 is expressed in small quantities by strains of *H. influenzae*, it is advantageous to either express this antigen as a recombinant protein in a heterologous system, such as *E. coli*, or to modify the *H. influenzae* organism to enhance native D15 expression. The Hind III/Eco RI fragment of *H. influenzae* type b Ca strain DNA encoding the full length D15 protein was expressed in pUCl9 but not pUC18, suggesting that the lac promoter is helping to express the D15 gene in *E. coli*, even though the native D15 gene promoter is present. The T7 expression system is a tightly controlled, inducible system which has great utility in expression of heterologous proteins in *E. coli*. The T7 expression system is described in U.S. Pat. No. 4,952,496. Clones were, therefore, constructed which utilize the T7 system to express a mature D15 protein that contains an additional methionine residue at the amino terminus. The D15 signal sequence was removed during this construction process. A full length recombinant D15 (termed rD15) was expressed in inclusion bodies which allow the D15 protein to be readily purified. The D15 genes from *H. influenzae* type b strain Ca and *H. influenzae* non-typeable SB33 strain have been expressed at high levels in *E. coli* using the T7 system to permit production of large quantities of rD15 protein. The construction of clone DS-880-1-2 which expresses the SB33 D15 gene is described herein (see FIG. 4 and Example 5). The rD15 protein was immunologically similar to its native counterpart isolated from *H. influenzae* typeable and non-typeable strains (see below). Thus, rD15 may be used as a cross-reactive antigen in a diagnostic kit to detect many, if not all, strains of *H. influenzae* and other bacteria that produce a D15 outer membrane protein or analog thereof. Alternatively, rD15 can be used as an antigen to specifically detect the presence of *H. influenza* in a sample.

A truncated D15 fragment was expressed in *E. coli* as a fusion protein with glutathione S-transferase (GST), as described in Example 6. The construction was designed to express the N-terminal fragment of the D15 protein. The fusion protein was expressed at high levels from a pGEX-2T construction and the N-terminal fragment was cleaved from the GST carrier protein by treatment with thrombin. This procedure generated a molecule termed the N-terminal rDi5 fragment which encompasses amino acids 63–223 of the D15 protein. This N-terminal rD15 fragment was highly immunogenic and elicited protective antibodies against challenge with live *H. influenzae*.

(iv) Purification of Native D15 from *H. influenzae* Cell Paste

Figure 5:
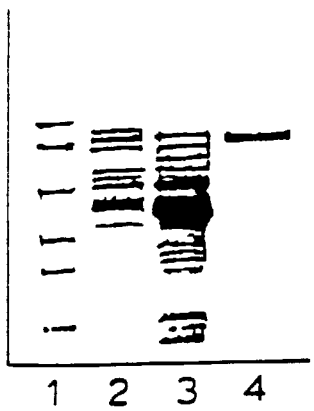
FIGS. 5A and 5B show an SDS-PAGE analysis of native D15 affinity-purified from *H. influenzae* strain 30.
Figure 5:
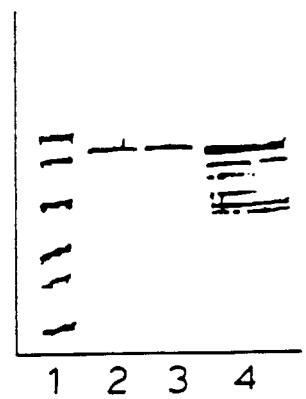

The present invention also provides a method to prepare purified native D15 protein from *H. influenzae*. The protein is extracted and affinity-purified from the cell pastes of either *H. influenzae* typeable or non-typeable isolates by a procedure involving the dissolution of the protein in an aqueous detergent solution (see Example 13). The native D15 protein from a non-typeable *H. influenzae* strain 30 was solubilized with a 50 mM Tris-HCl/0.5% Triton X-100/10 mM EDTA buffer, pH 8.0 and further purified on a D15-specific monoclonal antibody affinity column (FIG. 5A). An 80 kDa protein was eluted from the column with 50 mM diethylamine, pH 12.0 and shown to react with a D15-specific monoclonal antibody on immunoblot analysis (FIG. 5B). The native D15 is also highly immunogenic in experimental animals. Rabbit anti-D15 antisera reacted with all *H. influenzae* isolates as determined by immunoblot analyses.

(v) Purification of a Full-length Recombinant D15 Protein Expressed in *E. coli*.

Figure 6:
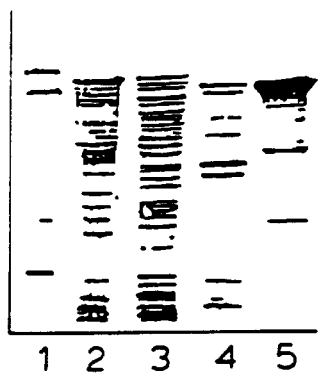
FIG. 6 shows an SDS-PAGE analysis of sequential fractions obtained during the purification of the full-length rD15 expressed in *E. coli* containing plasmid DS-880-1-2.

A full-length recombinant D15 (rD15) protein was expressed in inclusion bodies in *E. coli*. As shown in FIG. 6, purification of rD15 inclusion bodies was achieved by a sequential extraction of the *E. coli* cell lysate with 50 mM Tris-HCl, pH 8.0, then 50 mM Tris containing 0.5% Triton X-100 and 10 mM EDTA, pH 8.0. After centrifugation, more than 95% of the proteins in the resulting pellet was an 80 kDa protein by SDS-PAGE analysis, that reacted with a D15-specific monoclonal antibody on an immunoblot. The N-terminal sequence of the rD15 was found to be Met-Ala-Pro-Phe-Val-Lys-Asp- (SEQ ID NO: 54) which is identical to the predicted amino acid sequence.

The rD15 inclusion bodies were solubilized with a mixture of PBS, 0.5% Triton X-100, 10 mM EDTA and 8 M urea (see Example 8). After dialysis against PBS to remove urea, more than 80% of the D15 protein remained soluble. This soluble rD15 antigen was used for the immunogenicity studies described below. From shake-flask experiments, it was estimated that about 10 mg of soluble rD15 protein was obtained from 1 L of *E. coli* bacterial culture. It is clear that growing the recombinant *E. coli* strains under optimised fermentation conditions significantly increase the level of rD15 production.

(vi) Immunogenicity of the Full-length Recombinant D15 Protean (rD15)

Figure 7:
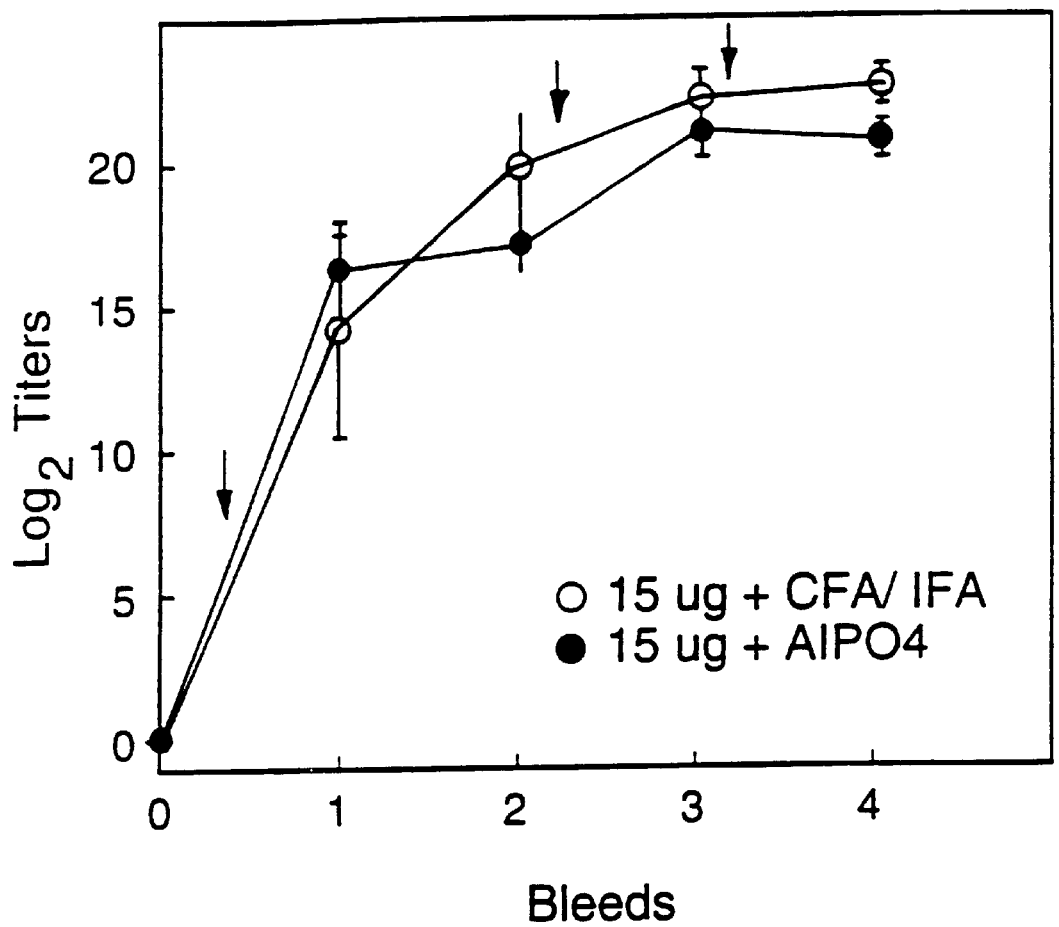
FIG. 7 shows guinea pig IgG antibody responses to full length rD15. The arrows indicate the immunization schedule. Bleeds were taken at 0, 2, 4, 6 and 8 weeks. The bars represent the standard deviation.
Figure 8:
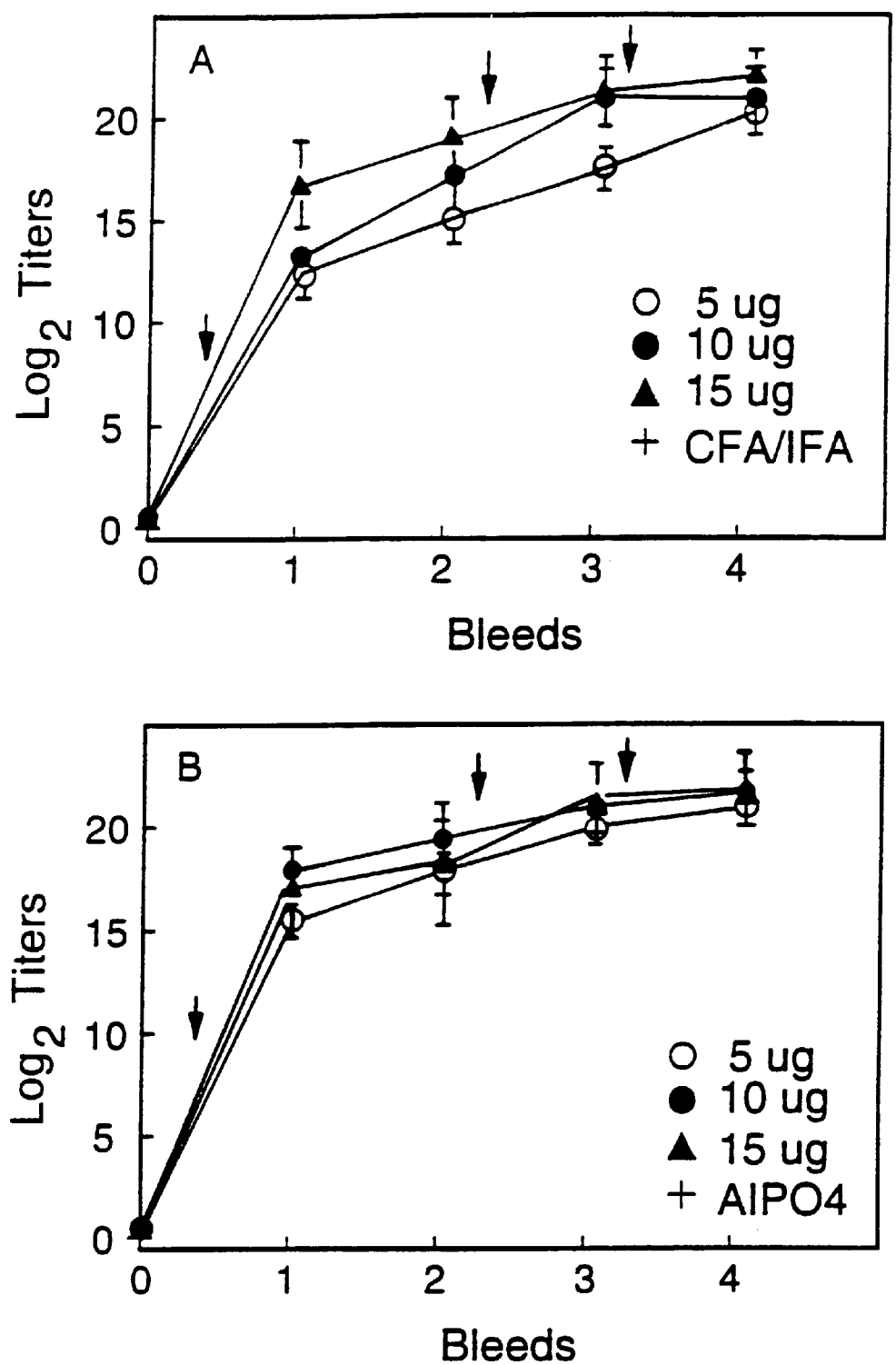

The immunogenicity of the full-length rD15 protein was studied in guinea pigs and mice. Using the immunization protocols described in FIG. 7, a 15 μg dose of rD15 induced high IgG titers in guinea pigs when administered in the presence of either Freund's adjuvant or AlPO$_4$. In the mouse dose-response study, the protein appeared to be immunogenic at a dose as low as 5 μg in either Freund's adjuvant (FIG. 8A) or AlPO$_4$ (FIG. 8B).

The protective ability of rD15 against *H. influenzae* type b infection was examined in the infant rat model of bacteremia essentially as described by Loeb (1987). Thus, infant rats passively immunized with guinea pig anti-rD15 antisera were significantly less bacteremic than controls injected with pre-bleed sera, which is consistent with the previous report by Thomas et al. (1990).

(vii) Purification and Characterization of the N-terminal rD15 Fragment

Figure 9:
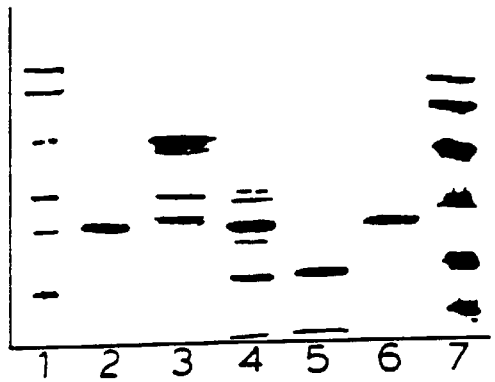

The truncated rD15 fragment corresponding to the N-terminus of the D15 protein (residues 22 to 223) as described in Example 6, was expressed in *E. coli* as a soluble protein fused to GST. The fusion protein (46 kDa) was readily extracted using phosphate buffered saline (PBS). Purification of the GST-D15 fragment fusion protein was achieved by a single-step affinity purification process on a glutathione-Sepharose 4B column (FIG. 9, Lane 3). Cleavage of the 46 kDa fusion protein with thrombin yielded two fragments (FIG. 9, Lane 4), a 26 kDa protein which corresponded to a purified GST standard (FIG. 9, Lane 2), and a 20 kDa polypeptide which had the size expected for the N-terminal rD15 fragment (amino acid residues 63 to 223), respectively. Separation of these two proteins was achieved by a second round of glutathione-Sepharose 4B affinity chromatography. From shake-flask experiments, it was estimated that about 1 mg of purified N-terminal rD15 fragment was recovered from 1 L of E. coli bacterial culture. It is clear that growing the recombinant E. coli strains under optimised fermentation conditions will significantly increase the level of N-terminal rD15 fragment production.

The identity of the 20 kDa polypeptide and the 26 kDa protein was confirmed by both immunoblotting and protein sequencing. The N-terminal sequence of the 20 kDa polypeptide was found to be $NH_2$-Ser-Leu-Phe-Val-Ser-Gly-Arg-Phe-Asp-Asp-Val-Lys-Ala-His-Gln-Glu-Gly-Asp-Val-Leu-Val-Val-Ser- (SEQ ID NO: 12), which corresponds to residues 63 to e5 of the primary sequence of D15. This result indicates that there is a spurious thrombin cleavage site within the D15 sequence and that the first 42 amino acids of the rD15 fragment are cleaved off during thrombin digestion. Thus, the final N-terminal rD15 fragment was 161 amino acids in length corresponding to residues 63 to 223 of the primary sequence of D15. The N-terminal sequence obtained for the 26 kDa protein ($NH_2$-Met-Ser-Pro-Ile-Leu-Gly-Tyr-Trp-Lys-—SEQ ID NO: 13) confirmed that it was GST.

(viii) *Immogenicity of the N-terminal rD15 fragment*

Figure 10:
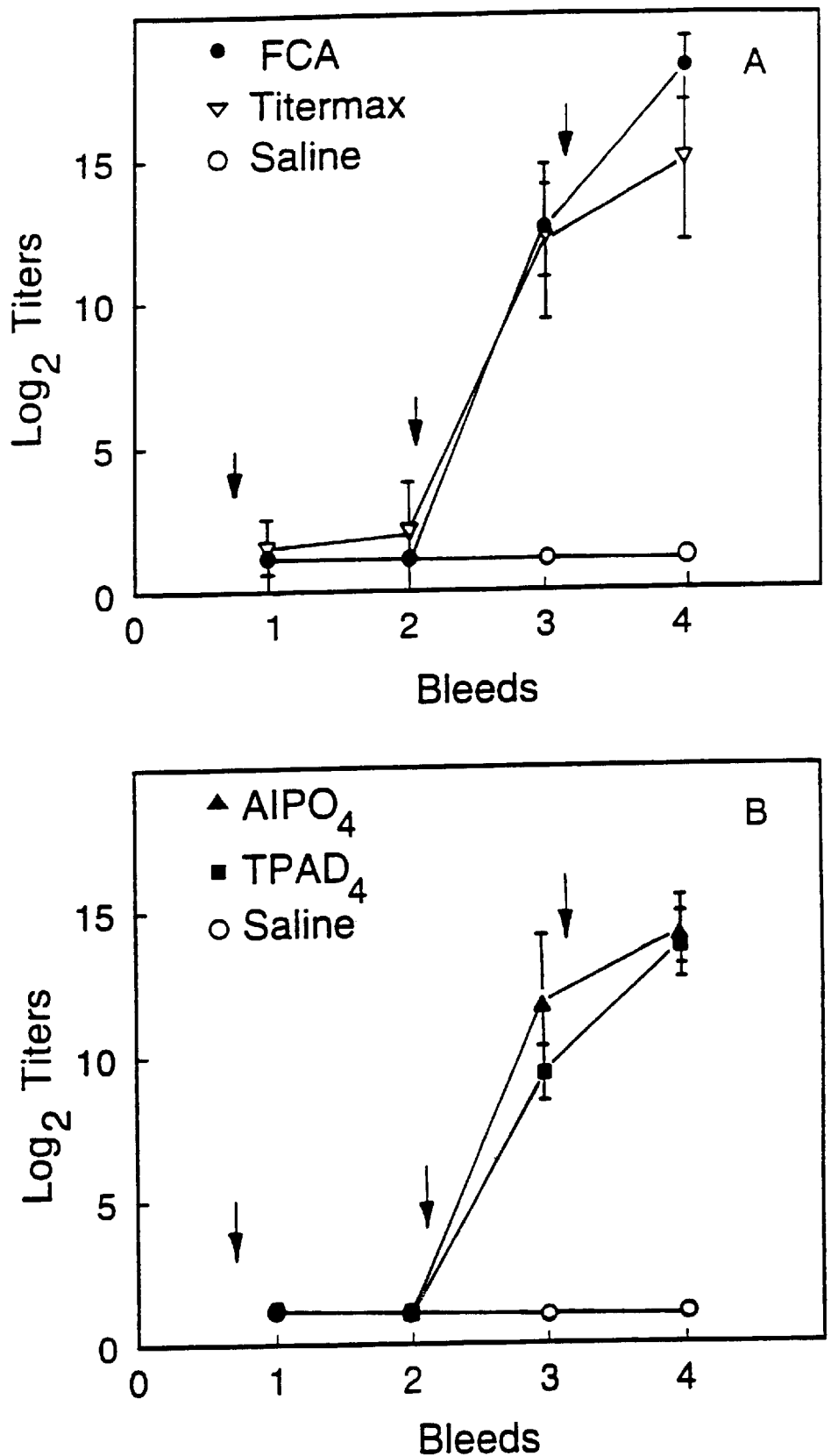
FIGS. 10A and 10B show guinea pig IgG antibody response to N-terminal rD15 fragment. The arrows indicate the immunization schedule. Bleeds were taken at 2, 4, 6 and 8 weeks. The bars represent the standard deviation.

The immunogenicity of the N-terminal rD15 fragment was tested in guinea pigs using various adjuvants. Using the immunization protocols described in FIG. 10, a 10 $\mu$g dose of N-terminal rD15 fragment induced a good booster response in guinea pigs with almost all the adjuvants tested. The highest anti-D15 IgG titer was observed in the group of guinea pigs immunized with N-terminal rD15 fragment in Freund's adjuvant. The second best adjuvant was Titermax (CytRx Inc.). The other two adjuvants, TPAD4 (tripalmityl-Cys-Ser-$Glu_4$) and $AlPO_4$ were equally potent.

(ix) *Protective Ability of the N-terminal rD15 Fragment Against H. influenzae Type b Challange*

An in vivo challenge model for a assessing the protective abilities of antigen against diseases caused by Haemophilus is the infant rat model of bacteremia as described by Loeb 1987. The protective ability of the N-terminal rD15 fragment against *H. influenzae* type b challenge was examined in this rat model. As illustrated in Table 1, infant rats passively immunized with rabbit anti-N-terminal rD15 fragment antisera showed significantly lower bacteremia compared to those injected with pre-bleed sera.

Since passively transferred antisera against the N-terminal rD15 fragment were found to be protective in the infant rat model of bacteremia, it was of interest to identify the protective epitope(s) of this N-terminal rD15 fragment. The first nine overlapping peptides of the D15 protein as listed in Table 2 were chemically synthesized based upon the amino acid sequence derived from the sequence of the D15 gene from *H. influenzae* type b Ca (FIG. 1). These synthetic peptides were assessed for their reactivities with either rabbit or guinea pig antisera raised against purified N-terminal rD15 fragment by ELISAs. As shown in Table 3, both guinea pig and rabbit antisera reacted with a cluster of D15 peptides, including peptides D15-P4 to D15-P8 encompassing residues 93 to 209 of the D15 primary sequence.

Further studies were performed to determine whether the protection against H. influenzae type b observed using rabbit anti-D15 antisera in infant rats could be neutralized by D15 peptides. In the first experiment, a rabbit anti-N-terminal rD15 fragment antiserum was injected into a group of seven infant rats in the presence or absence of a mixture of the nine D15 peptides (D15-P2 to D15-P10). Animals in the positive control group were injected with the rabbit anti-N-terminal rD15 fragment antiserum mixed with purified D15 fragment and the negative control group was injected with a mixture of the nine peptides only. As illustrated in Table 4, infant rats passively immunized with a rabbit anti-N-terminal rD15 fragment antiserum (group #1) showed a significantly lower bacteremia level (3%, p=$1.2 \times 10^{-7}$) compared to those in the negative control group (group #4, 100%), which was consistent with the previously obtained results. The protection mediated by the rabbit anti-N-terminal rD15 fragment antiserum was largely neutralized by the addition of purified N-terminal rD15 fragment (group #3, 64%), as indicated by the lack of significant difference in the bacteremia level between group #3 and group #4 (p=0.09). Although the addition of the mixture of nine D15 peptides only slightly neutralized the protection conferred by the antiserum (group #2, 13%) as compared to group #1 (3%), the difference in bacteria counts between these two groups was statistically significant (p=0.0037).

To more clearly define the protective epitope(s) of the N-terminal rD15 fragment, the above experiment was repeated with a mixture of five peptides (peptides D15-P4 to D15-P8) which were chosen for their strong reactivities with the rabbit anti-N-terminal rD15 fragment antiserum. The results obtained from this second experiment showed that the protection observed using rabbit anti-N-terminal rD15 fragment (Table 5, group #1) was completely blocked by the addition of this mixture of five peptides (Table 5, group #2, 106%, p=$0.53 \times 10^{-8}$). These results strongly indicate that a cocktail of D15 synthetic peptides may be used as immunogens to induce protective antibodies against *H. influenzae*.

(x) *Epitope Prediction and Peptide Synthesis*

Figure 11:
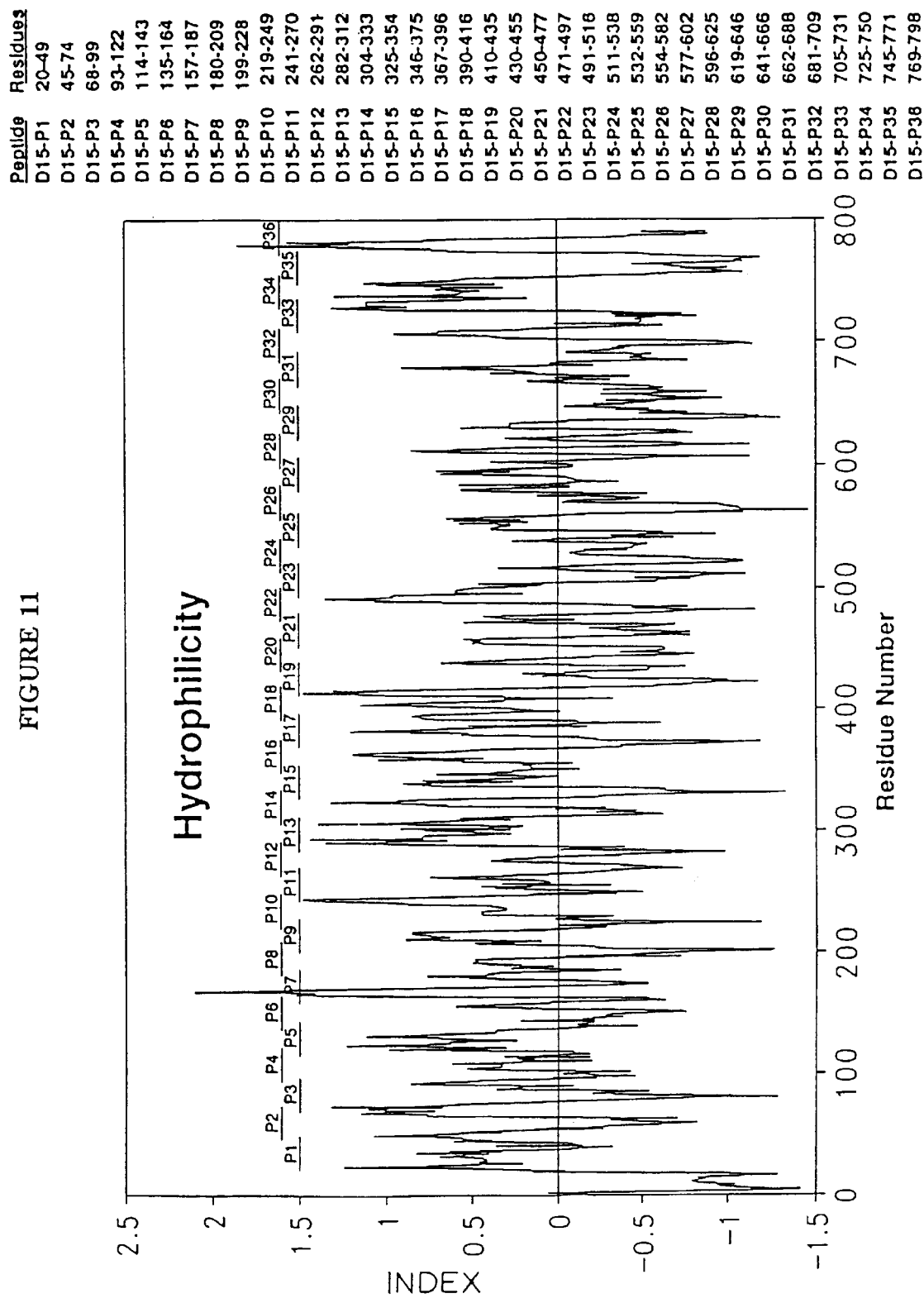
FIG. 11 shows the hydrophilicity plot of D15 established by using a window average across 7 residues according to Hope, 1986.

To map the immunodominant T-cell or B-cell epitopes of D15, overlapping synthetic peptides covering the entire D15 protein sequence (Table 2—SEQ ID NO: 14 to 49) were synthesized using the t-Boc solid-phase peptide synthesis as described in Example 15. The peptides were chosen based on their high index of hydrophillic $\beta$-turns estimated by secondary structure prediction analysis (FIG. 11). Such peptides are likely to be surface-exposed and antigenic. Peptides more than 25 residues in length were selected to better mimic native epitopes.

(xi) *Identification and charaterization of Immunodominant Epitopes of D15 Using Synthetic Peptides*

To map the linear B-cell epitopes of D15, overlapping synthetic peptides representing the entire sequence of D15 were individually coated onto ELISA plates and probed with several anti-rD15 antisera as described in Example 19. The results are summarized in Table 6. Mouse antisera raised against rD15 reacted with all D15 peptides, but the major epitopes were located within peptides D15-P8 (residues 180–209—SEQ ID NO: 21), D15-P10 (residues 219–249—SEQ ID NO: 23), D15-P11 (residues 241–270—SEQ ID NO: 24), and D15-P26 (residues 554–582—SEQ ID NO: 39), respectively. Rabbit anti-D15 antisera recognized only peptides D15-P4 (residues 93–122—SEQ ID NO: 17), D15-P14 (residues 304–333—SEQ ID NO: 27) and D15-P36 (residues 769–798—SEQ ID NO: 49). Guinea pig antisera raised against rD15 reacted with peptides D15-P2 (residues 45–72—SEQ ID NO: 15), D15-P4 (residues 93–122—SEQ ID NO: 17), D15-P6 (residues 135–164—SEQ ID NO: 19), D15-P8 (residues 180–209—SEQ ID NO: 21), DS-P14 (residues 304–333—SEQ ID NO: 27), D15-P27 (residues 577–602—SEQ ID NO: 40). The immunodominant linear B-cell epitopes of D15 were thus found to be located within peptides D15-P4 (residues 93–122—SEQ ID NO: 17) and D15-P14 (residues 304–333—SEQ ID NO: 27), since these are the only two peptides recognized by rD15-specific antisera from all three animal species. These results indicate that the peptides containing the linear B-cell epitope sequences described above can be used as target antigens in, for example, diagnostic kits to detect the presence of anti-D15 and anti-*H. influenzae* antibodies in samples.

(xii) Identification and Characterization of Immunodominant T-cell Epitopes of D15 Using Synthetic Peptides The importance of cytokine networks in the immune and inflammatory responses in immunity and inflammation and their alteration in pathology is becoming more evident as new members of the cytokine family are identified and characterized. Mills et al. (1993) have recently reported that there is a rapid clearance of *B. pertussis* from the lungs of mice on challenge six weeks after respiratory infection or following two immunizations with the whole-cell pertussis vaccine. Spleen cells from these immunized mice were found to secrete high levels of IL-2 and IFN-γ and low levels of IL-5 in the presence of pertussis antigen (pertussis toxoid, filamentous haemagglutinin (FHA) and pertactin). This result suggests that Th1 cell (T-cells producing high levels of IL-2 and IFN-γ) proliferation is very important for recovering from respiratory infection. The generation of Th1 and Th2 cell subsets is regulated by the balance between different groups of cytokines, predominantly IL-12 and IL-4 (Trinchieri, 1993). IL-12 and IL-4 are responsible for Th1 and Th2 cells differentiation, respectively. One of the roles of Th2 cells in the immune system is to provide helper activity for eliciting high levels of antigen-specific antibodies following immunization. Antigens containing Th1 epitope(s) stimulate antigen-specific T-cells to produce high levels of IL-2 and IFN-γ, whereas Th2 epitope(s) induce high levels of IL-4 expression. Th0 epitope(s) stimulate the synthesis of IFN-γ and IL-4.

Little is known about the cellular immune response to outer membrane proteins of *H. influenzae* and its role in the protection against *H. influenzae* infection and diseases. To this end, the inventors performed studies of the cellular response elicited in mice following rD15 immunization. D15-specific T-cell epitopes were determined using D15 peptides and T-cell lines obtained from five BALB/c mice immunized with rD15 (see Example 23). The lymphocyte proliferative responses of the D15-specific T-cell lines to overlapping D15 peptides were determined in conventional cytokine assays as described in Example 24. The results summarized in Table 7, revealed that stimulation only with certain synthetic peptides elicited proliferative responses and the release of specific cytokines. Synthetic peptides corresponding to residues 114–143 (D15-P5—SEQ ID NO: 18), 282–312 (D15-P13—SEQ ID NO: 26) and 577–602 (D15-P27—SEQ ID NO: 40), and 219–249 (D15-P10—SEQ ID NO: 23), 262–291 (D15-P12—SEQ ID NO: 25), 390–416 (D15-P18—SEQ ID NO: 31), 410–435 (D15-P19—SEQ ID NO: 32) 554–582 (D15-P26—SEQ ID NO: 39), 596–625 (D15-P28—SEQ ID NO: 41), 725–750 (D15-P34—SEQ ID NO: 47) and 745–771 (D1S-P35—SEQ ID NO: 48) were shown to be highly stipulatory for rD15-specific BALB/c Th0 cells and Th1 cells, respectively. Therefore, these immunodominant T-cell epitopes can be used as autologous carriers for PRP, and/or OMP B-cell epitopes to enhance their immunogenicity. The Th1 cell epitopes identified above may be useful in the *H. influenzae* vaccine formulations to induce *H. influenzae*-specific cellular immune responses.

(xiii) Immuogenicity of D15 Peptides

To determine whether synthetic D15 peptides were immunogenic free peptides were assessed individually for their immunogenicity. Rabbit and guinea pig anti-peptide antisera were tested for their reactivities with the immunizing peptides as well as with native D15 and rD15 by ELISA and immunoblotting. As shown in Table 8, all guinea pig anti-D15 peptide antisera except those raised against D15-P26 (SEQ ID NO: 39), D15-P29 (SEQ ID NO: 42), D15-P30 (SEQ ID NO: 43) and D15-P31 (SEQ ID NO: 44) were shown to be immunogenic by ELISAS. The induction of high titers of peptide-specific IgG antibodies by free peptides clearly indicates that most peptides contain both a functional T-helper determinant and a B-cell epitope(s). In addition, these anti-peptide antisera recognised D15 in the immunoblot assay. Since most peptides contain potent functional T-helper determinant(s) and induce strong IgG antibody responses in mammals, they are candidate immunogens for inclusion in an *H. influenzae* vaccine preparation. D15 peptide-specific antisera cross-reacted with D15 from non-typeable strains of *H. influenzae* as judged by immunoblotting. This finding indicates that immunogenic D15 peptides contain epitopes which are highly conserved among typeable and non-typeable strains of H. influenzae. In addition, polyclonal antibodies against these epitopes are useful to detect *H. influenzae* in biological samples.

Therefore, these conserved epitopes of D15 can be used either individually or in combination to prepare cross-reactive synthetic immunogens against typeable and non-typeable strains of *H. influenzae* and other bacteria that produce D15 protein, a fragment or an analog thereof. Peptides described above can be further polymerized, or modified with lipids as lipopeptides, or linked to polysaccharides including PRP as synthetic glycopeptide or lipoglycopeptide conjugates to produce alternate vaccines. These vaccines can be used to immunize against diseases caused by *H. influenzae* when administered to mammals, for example, by the intramuscular or parenteral route, or when delivered using microparticles, capsules, liposomes and targeting molecules, such as toxins or fragments thereof, and antibodies, to cells of the immune system or mucosal surfaces.

(xiv) Utility of D15 as Carrier Protein for the Production of Glycoconjugates

To determine whether D15 may serve both as a protective antigen and a carrier, D15-PRP conjugation experiments were performed as described in Example 14. The D15-PRP conjugates were found to be highly immunogenic in rabbits and able to elicit both anti-D15 and anti-PRP IgG antibody responses as judged by D15-specific ELISA and PRP-BSA immunoassay (Table 9). These results clearly demonstrate the practical utility of D15 as a carrier protein for glycoconjugation technology.

In preferred embodiments of the present invention, the carrier function of D15 can be generally utilized to prepare chimeric molecules and conjugate vaccines against pathogenic bacteria, including encapsulated bacteria. Thus, the glycoconjugates of the present inventions may be applied to vaccinations to confer protection against infection with any bacteria having polysaccharide antigens, including, for example, *Haemophilus influenzae, Streptococcus pneumoniae, Escherichia coli, Neisseria meningitidis, Salmonella typhi, Streptococcus mutans, Cryptococcus neoformans,* Klebsiella, *Staphylococcus aureus* and *Pseudomonas aeruginosa.*

In another embodiment, the carrier function of D15 may be used, for example, to induce immunity toward abnormal polysaccharides of tumor cells, or to produce anti-tumor antibodies that can be conjugated to chemotherapeutic or bioactive agents.

Accordingly, the present invention provides the primary sequence and the preparation of an antigen (D15) of *H. influenzae* that can be used in the prevention and diagnosis of diseases caused by Haemophilus. In particular, the inventors discovered that recombinant D15 or its fragments, can elicit protective antibody responses against live *H. influenzae* type b bacteria challenge. Thus, the present inventions have utility in vaccines. The invention also discloses the nucleotide sequences of the D15 genes isolated from both *H. influenzae* type b strains and non-typeable isolates. The DNA segments encoding D15 are disclosed and show minor polymorphism in both their nucleotide and derived amino acid sequences (FIGS. 1F and 3). These DNA segments may be used to provide an immunogen essentially free from other *H. influenzae* antigens (such as PRP and lipooligosaccharides (LOS)) through the application of recombinant DNA technology. The present disclosure further provides novel techniques which can be employed for preparing essentially pure D15 or fragments thereof, as well as functional analogs. The recombinant D15 protein, fragment or analog thereof, may be produced in a suitable expression system, such as *E. coli*, Haemophilus Bordetella, Bacillus, Fungi, Yeast, Baculovirus, Poxvirus, vaccinia or mammalian expression systems.

In one embodiment, the present invention concerns the process of preparing vaccine compositions which include purified recombinant D15 protein (rD15) or rD15 fragments that are immunologically cross-reactive with native D15. In particular, the gene coding the entire D15 protein and a DNA segment encoding an N-terminal rD15 fragment fused to the glutathione-S-transferase gene have been constructed and expressed in *E. coli*. The expressed rD15 protein and its fragments were found to cross-react immunologically with the native DS antigen isolated from both typeable and non-typeable *H. influenzae* isolates and thus represent cross-reactive immunogens for inclusion in a vaccine against diseases caused by *H. influenzae*. Furthermore, Haemophilus convalescent serum recognized D15 purified from *H. influenzae* as described herein, rD15 and N-terminal rD15 fragment.

In another embodiment, the present invention provides a gene coding for the outer membrane protein D15 from *H. influenzae* having the specific nucleotide sequences described herein or ones substantially homologous thereto (i.e. those which hybridize under stringent conditions to such sequences), for genetically engineering hybrids or chimeric proteins containing a D15 fragment fused to another polypeptide or protein or a polysaccharide, such as *H. influenza* outer membrane proteins, for example, P1, P2, or P6 or PRP. As a result, the hybrids, chimeric proteins or glycoconjugates may have higher protectivity against *H. influenzae* than D15, or P1, or P2, or P6, or PRP alone.

Thus, D15 outer membrane protein can function both as a protective antigen and as a carrier in a conjugate vaccine to provide autologous T-cell priming, wherein the hapten part of the conjugate is the capsular polysaccharide moiety (PRP) of *H. influenzae*. This D15-carbohydrate conjugate can elicit antibodies against both PRP and D15, and thus should enhance the level of protection against *H. influenzae*-related diseases, especially in infants.

In another embodiment, the present invention comprises an essentially pure form of at least one protein or peptide containing an amino acid sequence corresponding to at least one antigenic determinant of DIS, which peptide is capable of eliciting polyclonal antibodies against *H. influenzae* in mammals. These D15 -specific antibodies are useful in test kits for detecting the presence of *H. influenzae* in biological samples. The peptides can have, for example, the amino acid sequences corresponding to residues 20–49, 45–74, 68–99, 93–122, 114–143, 135–164, 157–187, 180–209, 199–228, 219–249, 241–270, 262–291, 282–312, 304–333, 325–354, 346–375, 367–396, 390–416, 410–435, 430–455, 450–477, 471–497, 491–516, 511–538, 532–559, 554–582, 577–602, 596–625, 619–646, 641–666, 662–688, 681–709, 705–731, 725–750, 745–771, 769–798 (SEQ ID NOS: 14 to 49) of the D15 protein of the *H. influenzae* type b Ca strain, respectively, as set forth in Table 2 below, or any portion, variant or mutant thereof which retains immunogenicity.

In yet another embodiment, the present invention provides pure native D15 protein, extracted and chromatographically purified from cultures of *H. influenzae* typeable or non-typeable isolates. The novel procedures involves extraction of the D15 protein from cell paste by techniques known for other outer membrane proteins, with an aqueous detergent solution, followed by purification by centrifugation and chromatography. The purified native D15 antigen can be used to immunize mammals against diseases caused by *H. influenzae*, for example, by the intramuscular or the parenteral routes, or by delivering it using microparticles, capsules, liposomes and targeting molecules, such as toxins or fragments thereof, and antibodies.

Another aspect of the present invention is that the D15 outer membrane protein, fragments or analogs thereof or peptides corresponding to portions of D15 may be components of a multivalent vaccine against otitis media. This multivalent vaccine comprises at least one immunogenic determinant of D15 as described herein, along with at least one protective antigen isolated from *Strentococcus pneumoniae, Branhamella* (Moroxella) *gatarhalis, Staphylococcus aureus,* or respiratory syncytial virus, in the presence or absence of adjuvant.

The D15 peptides (Table 2) or any portion, variant or mutant thereof, can easily be synthesized either manually or with a commercially available peptide synthesizer, such as the Applied Biosystems Model 430A synthesizer.

It is clearly apparent to one skilled in the art, that the various embodiments of the present invention have many applications in the fields of vaccination, diagnosis, and treatment of diseases caused by Haemophilus infections, and the generation of immunological reagents. A further non-limiting discussion of such uses is further presented below.
1. Vaccine Preparation and Use Immunogenic compositions, suitable for use as vaccines, may be prepared from immunogenic D15 outer membrane protein, fragments or analogs thereof and/or peptides corresponding to portions of D15 as disclosed herein. The vaccine elicits an immune response which produces antibodies, including anti-D15 outer membrane protein antibodies and antibodies against D15 that are opsonizing or bactericidal. Should the vaccinated subject be challenged by Haemophilus, the antibodies bind to the D15 outer membrane protein and thereby inactivate the bacterium. Opsonizing and bactericidal antibodies represent examples of antibodies useful in protection against disease.

Vaccines containing peptides are generally well known in the art, as exemplified by U.S. Pat. Nos. 4,601,903; 4,599,231; 4,599,230; and 4,596,792; all of which references are incorporated herein by reference. As to any further reference to patents and references in this description, they are as well hereby incorporated by reference without any further notice to that effect. Vaccines may be prepared as injectables, as liquid solutions or emulsions. The D15 outer membrane protein, fragments or analogs thereof or peptides corresponding to portions of D15 may be mixed with physiologically-acceptable excipients which are compatible with the D15 outer membrane protein, fragments, analogs or peptides. Excipients may include, water, saline, dextrose, glycerol, ethanol, and combinations thereof. The vaccine may further contain minor amounts of auxiliary substances such as wetting or emulsifying agents, pH buffering agents, or adjuvants to enhance the effectiveness of the vaccines. Methods of achieving adjuvant effect for the vaccine includes use of agents, such as aluminum hydroxide or phosphate (alum), commonly used as 0.05 to 0.1 percent solution in phosphate buffered saline. Vaccines may be administered parenterally, by injection subcutaneously or intramuscularly. Alternatively, other modes of administration including suppositories and oral formulations may be desirable. For suppositories, binders and carriers may include, for example, polyalkalene glycols or triglycerides. Oral formulations may include normally employed incipients such as, for example, pharmaceutical grades of saccharine, cellulose, magnesium carbonate and the like. These compositions take the form of solutions, suspensions, tablets, pills, capsules, sustained release formulations or powders and contain 10–95% of the D15 outer membrane protein, fragment analogs and/or peptides.

The vaccines are administered in a manner compatible with the dosage formulation, and in an amount which is therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the D15 outer membrane protein, analog, fragment and/or peptides. Suitable regimes for initial administration and booster doses are also variable, but may include an initial administration followed by subsequent administrations. The dosage of the vaccine may also depend on the route of administration and varies according to the size of the host.

The nucleic acid molecules encoding the D15 outer membrane protein of the present invention may also be used directly for immunization by administration of the DNA directly, for example, by injection for genetic immunization or by constructing a live vector, such as Salmonella, BCG, adenovirus, poxvirus or vaccinia. A discussion of some live vectors that have been used to carry heterologous antigens to the immune system are discussed in, for example, O'Hagan (1992). Processes for the direct injection of DNA into test subjects for genetic immunization are described in, for example, Ulman et al. (1993).

The use of peptides in vivo may first require their chemical modification since the peptides themselves may not have a sufficiently long serum and/or tissue half-life. Such chemically modified peptides are referred to herein as peptide analogs. The term peptide analog extends to any functional chemical equivalent of a peptide characterized by its increased stability and/or efficacy in vivo or in vitro in respect of the practice of the invention. The term peptide analog is also used herein to extend to any amino acid derivative of the peptides as described herein. Peptide analogs contemplated herein are produced by procedures that include, but are not limited to, modifications to side chains, incorporation of unnatural amino acids and/or their derivatives during peptide synthesis and the use of cross-linkers and other methods which impose conformational constraint on the peptides or their analogs.

Examples of side chain modifications contemplated by the present invention include modification of amino groups, such as by reductive alkylation by reaction with an aldehyde followed by reduction with $NaBH_4$; amidation with methylacetimidate; acetylation with acetic anhydride; carbamylation of amino groups with cyanate; trinitrobenzylation of amino groups with 2, 4, 6, trinitrobenzene sulfonic acid (TNBS); alkylation of amino groups with succinic anhydride and tetrahydrophthalic anhydride; and pyridoxylation of lysine with pyridoxa-5'-phosphate followed by reduction with $NABH_4$. The guanidino group of arginine residues may be modified by the formation of heterocyclic condensation products with reagents such as 2,3-butanedione, phenylglyoxal and glyoxal.

The carboxyl group may be modified by carbodiimide activation via o-acylisourea formation followed by subsequent derivatisation, for example, to a corresponding amide.

Sulfhydryl groups may be modified by methods, such as carboxymethylation with iodoacetic acid or iodoacetamide; performic acid oxidation to cysteic acid; formation of mixed disulphides with other thiol compounds; reaction with maleimide; maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamylation with cyanate at alkaline pH.

Tryptophan residues may be modified by, for example, oxidation with N-bromosuccinimide or alkylation of the indole ring with 2-hydroxy-5-nitrobenzyl bromide or sulphonyl halides. Tryosine residues may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

2. Immunoassays

The D15 outer membrane protein, analog, fragment and/or peptides of the present invention are useful as antigens in immunoassays, including enzyme-linked immunosorbent assays (ELISA), RIAs and other non-enzyme linked antibody binding assays or procedures known to the art for the detection of anti-bacterial, Haemophilus, D15 and/or peptide antibodies. In ELISA assays, the D15 outer membrane protein, fragment or analogs thereof and/or peptides corresponding to portions of D15 outer membrane protein are immobilized onto a selected surface, for example, a surface exhibiting a protein affinity, such as the wells of a polystyrene microtiter plate. After washing to remove incompletely adsorbed D15 outer membrane protein, analog, fragment and/or peptides, a nonspecific protein, such as bovine serum albumin (BSA) or casein, that is known to be antigenically neutral with regard to the test sample may be bound to the selected surface. This allows for blocking of nonspecific adsorption sites on the immobilizing surface and thus decreases the background caused by nonspecific bindings of antisera onto the surface. Normally, the peptides employed herein are in the range of 12 residues and up and preferably 14 to 30 residues.

The immobilizing surface is then contacted with a sample such as clinical or biological materials to be tested in a manner conducive to immune complex (antigen/antibody)

formation. This may include diluting the sample with diluents, such as BSA, bovine gamma globulin (BGG) and/or phosphate buffered saline (PBS)/Tween. The sample is then allowed to incubate for from 2 to 4 hours, at temperatures, such as of the order of 25° to 37° C. Following incubation, the sample-contacted surface is washed to remove non-immunocomplexed material. The washing procedure may include washing with a solution such as PBS/Tween, or a borate buffer.

Following formation of specific immunocomplexes between the test sample and the bound D15 outer membrane protein, analog, fragment and/or peptides, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and, in general, IgG. To provide detecting means, the second antibody may have an associated activity, such as an enzymatic activity that will generate, for example, a color development upon incubating with an appropriate chromogenic substrate. Quantification may then achieved by measuring the degree of color generation using, for example, a visible spectra spectrophotometer.

3. Use of Sequences an Hybridization Probes

The nucleotide sequences of the present invention comprising the sequence of the D15 outer membrane protein, now allow for the identification and cloning of the D15 outer membrane protein genes from any species of Haemophilus and other bacteria that have genes encoding D15 outer membrane proteins.

The nucleotide sequences comprising the sequence encoding the D15 outer membrane protein of the present invention are useful for their ability to selectively form duplex molecules with complementary stretches of other D15 genes. Depending on the application, a variety of hybridization conditions may be employed to achieve varying degrees of selectivity of the probe toward the other D15 genes. For a high degree of selectivity, stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 20° C. to 55° C. Hybridization conditions can also be rendered more stringent by the addition of increasing amounts of formamide, to destabilize the hybrid duplex. Thus, particular hybridization conditions can be readily manipulated, and will generally be a method of choice depending on the desired results.

In a clinical diagnostic embodiment, the nucleic acid sequences of the D15 outer membrane protein genes of the present invention may be used in combination with an appropriate means, such as a label, for determining hybridization. A wide variety of appropriate indicator means are known in the art, including radioactive, enzymatic or other ligands, such as avidin/biotin, which are capable of providing a detectable signal. In some diagnostic embodiments, an enzyme tag, such as urease, alkaline phosphatase or peroxidase, instead of a radioactive tag may be used. In the case of enzyme tags, calorimetric indicator substrates are known which can be employed to provide means visible to the human eye or spectrophotometrically, to identify specific hybridization with samples containing D15 gene sequences.

The nucleic acid sequences of D15 genes of the present invention are useful as hybridization probes in solution hybridizations and in embodiments employing solid-phase procedures. In embodiments involving solid phase procedures, the test DNA (or RNA) from samples, such as clinical samples, including exudates, body fluids (e.g., serum, amniotic fluid, middle ear effusion, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the D15 genes or fragments thereof of the present invention under desired conditions. The selected conditions will depend on the particular circumstances based on the particular criteria required depending on, for example, on the G+C contents, type of target nucleic acid, source of nucleic acid, size of hybridization probe etc. Following washing of the hybridization surface so as to remove non-specifically bound probe molecules, specific hybridization is detected, or even quantified, by means of the label. The selected probe should be at least 18 bp and may be in the range of 30 bp to 90 bp long.

4. Expression of the D15 Outer Membrane Protein Genes

Plasmid vectors containing replicon and control sequences which are derived from species compatible with the host cell may be used for the expression of the D15 outer membrane protein genes in expression systems. The vector ordinarily carries a replication site, as well as marking sequences which are capable of providing phenotypic selection in transformed cells. For example, *E. coli* may be transformed using pBR322 which contains genes for ampicillin and tetracycline resistance and thus provides easy means for identifying transformed cells. The pBR322 plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as a transforming vector in connection with these hosts. For example, the phage in lambda GEM™-11 may be utilized in making recombinant phage vectors which can be used to transform host cells, such as *E. coli* LE392.

Promoters commonly used in recombinant DNA construction include the β-lactamase (penicillinase) and lactose promoter systems and other microbial promoters, such as the T7 promoter system. Details concerning the nucleotide sequences of promoters are known, enabling a skilled worker to ligate them functionally with plasmid vectors. The particular promoter used generally is a matter of choice depending upon the desired results. Hosts that are appropriate for expression of the transferrin receptor genes, fragment analogs or variants thereof include *E. coli,* Bacillus, Haemophilus, Bordetella, fungi, yeast, or the baculovirus and poxvirus expression systems may be used.

In accordance with an aspect of this invention, it is preferred to make the D15 outer membrane protein, fragment or analog thereof by recombinant methods, particularly since the naturally occurring D15 protein as purified from culture of a species of Haemophilus may include undesired contaminants, including trace amounts of toxic materials. This problem can be avoided by using recombinantly produced D15 outer membrane protein in heterologous systems which can be isolated from the host in a manner to minimize toxins in the purified material. Particularly desirable hosts for expression in this regard include Gram positive bacteria which do not have lipopolysaccharide (LPS) and are, therefore, endotoxin free. Such hosts include species of Bacillus and may be particularly useful for the production of non-pyrogenic D15 outer membrane protein, fragments or analogs thereof.

Biological Deposits

Certain plasmids that contain at least a portion coding for a D15 outer membrane protein from strains of *Haemophilus influenzae* that are described and referred to herein have been deposited with the American Type Culture Collection (ATCC) located at 10801 University Boulevard, Manassas, Va. 20110-2209 U.S.A. pursuant to the Budapest Treaty and prior to the filing of this application. Samples of the deposited plasmids will become available to the public upon grant of a patent based upon this United States patent application. The invention described and claimed herein is not to be limited in scope by plasmids deposited, since the deposited embodiment is intended only as an illustration of the invention. Any equivalent or similar plasmids that encode similar or equivalent antigens as described in this application are within the scope of the invention.

DEPOSITE SUMMARY

| Clone | *H. influenzae* | ATCC Designation | Date Deposited |
|---|---|---|---|
| DS-712-2-1 | Eagan | 75604 | November 4, 1993 |
| JB-1042-5-1 | SB33 | 75606 | November 4, 1993 |
| DS-880-1-2 | Eagan | 75605 | November 4, 1993 |

The above disclosure generally describes the present inversion. A more complete understanding can be obtained by reference to the following specific Examples. These Examples are described solely for purposes of illustration and are not intended to limit the scope of the invention. Although specific terms have been employed herein, such terms are intended in a descriptive sense and not for purposes of limitations. Immunological and recombinant DNA methods may not be explicitly described in this disclosure but are well within the scope of those skilled in the art.

EXAMPLES

Methods of molecular genetics, protein biochemistry, and immunology used but not explicitly described in this disclosure and these EXAMPLES are amply reported in the scientific literature and are well within the ability of those skilled in the art.

Example 1

This Example illustrates the cloning and sequencing of the D15 genes.

Genomic DNA was purified from the *Haemophilus influenzae* type b strain Ca by lysis of the bacteria with pronase and sodium dodecylsulphate followed by phenol extraction and isopropanol precipitation, according to Berns and Thomas, 1965. The DNA was then partially digested with EcoRI and the DNA fraction containing 6–10 kb fragments was isolated following electrophoresis in low-melting point agarose. These fragments were ligated into a lambda gt11 Amp1 vector (Thomas and Rossi, 1986) and cloned as a lysogen into *E. coli* strain BTA282. Recombinant clones were selected for their ampicillin resistance conferred by the vector. To identify clones producing *H. influenzae* type b antigen, the clones were replica-plated on nitrocellulose filters and duplicate colonies induced for expression by temperature switch to 42° C. for 2 hours. Colonies were lysed by wetting the filters with 1% sodium dodecylsulphate (SDS). The filters were then placed into a chloroform-saturated atmosphere for 15 min. The filters were then assayed by colony radioimmuno-assay using a hyperimmune rabbit anti-*H. influenzae* type b antiserum absorbed with *E. coli* lysate for antigen expression. Clones shown by autoradiography to be producing *H. influenzae* type b antigens were further purified and their replicates retested for reactivity with the hyperimmune anti-*H. influenzae* type antiserum. The antiserum absorbed with $10^{10}$ intact *H. influenzae* type b bacteria (strain Ca) was used as negative control.

A number of clones were identified which reacted with the unabsorbed, but not with the absorbed antiserum and were further analysed. One of the clones, D15, was purified, grown and found to produce a *H. influenzae* type b antigen which migrated in sodium dodecyl sulphate polyacrylamide gels with a $M_r$ of about 80 kDa. Lysates from the D15 clone were coupled to Sepharose™ 4B gel and used to affinity-purify anti-D15 antibodies. This procedure is described by Thomas et al, 1990, except that the apparent $M_r$ was initially reported to be about 103 kDa. The affinity-purified antibodies to D15 were then shown to react with an $M_r$ 80 kDa protein in an outer membrane protein preparation of *H. influenzae* type b (sarcosyl insoluble fraction—Carlone et al, 1986). Radioimmuno dot blots and Western blots analyses of membrane preparations from both type b and nontypeable *Haemophilus influenzae* strains showed that affinity-purified anti-D15 antibodies reacted with all isolates. These antibodies were found to be capable of passively protecting infant rats from bacteraemia following intraperitoneal injection of live *H. influenzae* type b bacteria. The specificity of the protection was confirmed by absorbing out the protective activity of anti-D15 antibodies with a lysate of *E. coli* expressing D15 coupled to Sepharose. The protection studies have been described in detail by Thomas et al, 1990.

DNA from the lambda gt11 Amp1 D15 phage was isolated 35 and a 5.7 kb fragment was released by EcoRI digestion. This fragment was subcloned into pUC19 and the resulting plasmid transformed into *E. coli* HB101. Recombinant bacteria were found to produce the expected $M_r$ 80 kDa *H. influenzae* type b antigen when examined by Western blotting. The insert DNA was then characterised by restriction endonuclease mapping. A 2.8 kb HindIII-EcoRI fragment was subcloned into pUC19 to generate plasmid PCT/CA93100, pUC19/D15, which was transformed into *E. coli* HB101. The recombinant bacteria expressed a $M_r$ 80 kD protein recognized by D15-specific antibodies on Western blot analysis of *E. coli* lysates.

Plasmid DNA was prepared from two individual colonies of recombinant *E. coli* HB101 containing the pUC19/D15 plasmid using standard techniques. Oligonucleotide sequencing primers of 17–25 bases in length were synthesized on the ABI model 380B DNA Synthesizer and purified by chromatography using OPC cartridges obtained from Applied Biosystems Inc., and used in accordance with the manufactures recommendations. Samples were sequenced using the ABI model 370A DNA Sequencer and dye terminator chemistry according to manufacturers' protocols. This sequence analysis indicated that the D15 gene contains an open reading frame encoding for 789 amino acids, including a putative signal sequence (FIG. 1). The derived amino acid sequence was found to contain the sequence of an internal peptide obtained by thrombin digestion of native D15 that had been chemically determined. The amino acid composition of D15 derived from the D15 gene sequence was comparable (within experimental error) to that of the native protein as determined by amino acid analysis.

Example 2

This Example illustrates the preparation of hromosomal DNA from *Haemophilus influenzae* strains Eagan, Minna, SB33, and PAK 12085.

*H. influenzae* strains were grown on Mueller-Hinton agar or in brain heart infusion broth as described by Harkness et al., 1992.

Eagan Chromosomal DNA

Bacteria from 50 mL of culture were pelleted by centrifugation at 5,000 rpm, 20 minutes, 4° C. The pellet was resuspended in 25 mL TE (10 mM Tris, 1 mM EDTA, pH 8.0) and 2×5 mL aliquots used for chromosomal DNA preparation. To each aliquot were added 0.6 mL of 10% 10 sarkosyl and 0.15 mL of 20 mg/mL proteinase K and the samples incubated at 37° C. for 1 hour. The lysate was extracted once with Tris-saturated phenol (pH 8.0) and three times with chloroform:isoamyl alcohol (24:1). The aqueous phase was pooled for a final volume of 7 mL. Then, 0.7 mL of 3M sodium acetate (pH 5.2) and 4.3 mL of isopropanol were added to precipitate the DNA which was spooled, rinsed with 70% ethanol, dried, and resuspended in 1 mL of water.

MinnA. SB33. and PAK 12085 Chromosomal DNA

Bacteria from 50 mL of culture were pelleted by centrifugation at 5,000 rpm for 15–20 minutes, at 4° C, in a Sorvall RC-3B centrifuge. The cell pellet was resuspended in 10 mL of TE (10 mM Tris-HCl, 1 mM EDTA, pH 7.5), pronase was added to 500 μg/mL, and SDS to 1%. The sample was incubated at 37° C. for about 4 hours until a clear lysate was obtained. The lysate was extracted once with Tris-saturated phenol, once with Tris-saturated phenol/chloroform (1:1), and once with chloroform. The final aqueous phase was dialysed for 24 hours against 2×500 mL of 1M NaCl at 4° C., changing the buffer once, and for 24 hours against 2×500 mL of TE at 4° C., changing the buffer once. The final dialysate was aliquotted for subsequent use.

Example 3

This Example illustrates the preparation of *Haemophilus influenzae* chromosomal libraries.

*H. influenzae* Eagan and PAK 12085 chromosomal DNAs were digested with Sau3A I (0.5 unit/10 μg DNA) at 37° C. for 15 minutes and size-fractionated by agarose gel electrophoresis. Gel slices corresponding to DNA fragments of 15–23 kb were excised and DNA was electroeluted overnight in dialysis tubing containing 3 mL of TAE (40 mM Tris-acetate, 1 mM EDTA, pH 8.0) at 14V. The DNA was precipitated twice and resuspended in water before overnight ligation with EMBL3 BamH I arms (Promega). The ligation mixture was packaged using the Lambda in vitro packaging kit (Amersham) according to the manufacturer's instructions and plated onto *E. coli* NM539 cells. The library was titrated, then amplified and stored at 4° C. under 0.3% chloroform.

MinnA chromosomal DNA (10 μg) was digested with Sau3A I (40 units) for 2, 4, and 6 minutes then size-fractionated on a 10–30% sucrose gradient in TNE (20 mM Tris-HCl, SmM NaCl, 1 mM EDTA, pH 8.0). Fractions containing DNA fragments>5 kb were pooled and precipitated. in a second experiment, chromosomal DNA (2.6 μg) was digested with Sau3A I (4 units) for 1, 2, and 3 minutes and size-fractionated by preparative agarose gel electrophoresis. Gel slices containing DNA fragments of 10–20 kb were excised and DNA extracted by a standard freeze/thaw technique. The size-fractionated DNA from the two experiments was pooled for ligation with BamH I arms of EMBL3 (Promega). The ligation mix was packaged using the Gigapack II packaging kit (Amersham) and plated on *E. coli* LE392 cells. The library was titrated, then amplified and stored at 4° C. under 0.3% chloroform.

SB33 chromosomal DNA (20 μg) was digested with Sau3A I (40 units) for 2, 4, or 6 minutes and size-fractionated on a 10–30% sucrose gradient in TNE (20 mM Tris-HCl, 5 mM NaCl, 1 mM EDTA, pH 8.0). Fractions containing fragments>5 kb were pooled. In a second experiment, SB33 chromosomal DNA (2 μg) was digested with Sau3A I (4 units) for 2, 4, or 6 minutes and size-fractionated on a preparative agarose gel. Gel slices containing DNA fragments of 10–20 kb were excised and DNA extracted by a standard freeze/thaw technique. The size-fractionated DNA from both experiments was pooled for ligation with BamH I arms of EMBL3 (Promega). The ligation mix was packaged using the Gigapack II packaging kit and plated on LE392 cells. The library was titrated, then amplified and stored at 4° C. under 0.3% chloroform.

Example 4

This Example illustrates the screening of the DNA libraries.

The Eagan, MinnA, SB33, and PAK 12085 DNA libraries were plated onto LE392 cells on NZCYM plates using 0.7% top agarose in NZCYM as overlay. Plaque lifts onto nitrocellulose filters were performed following standard procedures, and filters were processed and hybridized with a digoxigenin-labelled D15 probe prepared according to the manufacturer's specifications (Boehringer Mannheim). The probe was the ECoR I/Hind III fragment from pUC19/D15 containing the entire Ca D15 gene (FIG. 2). Putative plaques were plated and submitted to a second round of screening using the same procedures. Phage DNA was prepared from 500 mL of culture using standard techniques, the insert DNA was excised by Sal I digestion, and cloned into pUC to generate clones DS-712-2-1 (Eagan), DS-691-1-5 (MinnA), JB-1042-5-1 (SB33), and JB-1042-9-4 (PAK 12085), which are shown in FIG. 2.

The nucleotide sequences of the D15 genes from *H. influenzae* type b strains Eagan and MinnA the non-typeable *H. influenzae* strains SB33 and PAK 12085 were determined and compared with that for strain Ca, as seen in FIGS. 1*b*, 1C, 1D, 1E and 1F. The desired amino acid sequence are shown in FIGS. 1B, 1C, 1D and 1E and are compared with the amino acid sequence of the D15 protein of *H. influenzae* type b Ca (FIG. 3).

Example 5

This Example illustrates the expression of rD15 protein in *E. coli*.

A 2.8 kb fragment HindIII-EcoRI was subcloned into pUC19 and this pUC19/D15 plasmid was transformed into *E. coli* HB101. Upon induction, the positive clones expressed an 80 kDa protein which was recognized by D15-specific antisera on Western blot analysis. A HindIII-Pst I fragment was also subcloned into pUC19 and shown to express a 67 kDa protein. According to the restriction map, this 67 kDa protein corresponded to a C-terminal truncated D15 protein. On Western blot analysis, this truncated D15 was still recognized by the D15-specific antisera.

Figure 4:
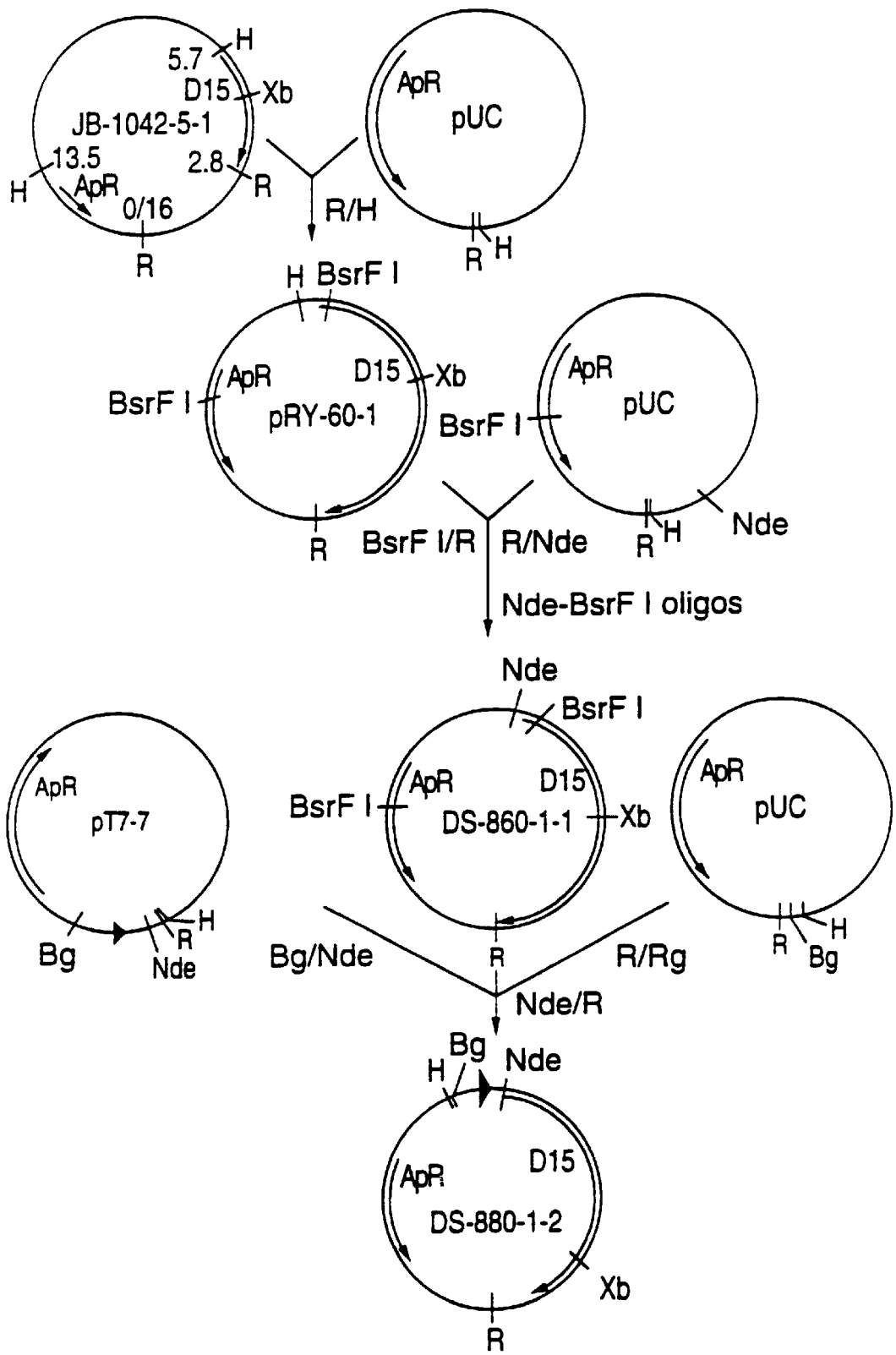
FIG. 4 shows the construction of a plasmid (DS-880-1-2) expressing full-length SB33 D15 (rD15) from the strong inducible T7 promoter.

Plasmids to express the D15 gene of the non-typeable strain SB33 in *E. coli* were constructed. Plasmid JB-1042-5-1 containing the SB33 D15 gene and its flanking regions, was digested with EcoR I and Hind III and the 3 kb D15 insert subcloned into pUC to give plasmid pRY-60-1 (FIG. 4). Appropriate oligonucleotides were synthesized to restore the native D15 sequence between the ATG codon of the expression plasmid pT7-7 and the BsrF I site within the D15 gene. These oligonucleotides had the following sequence:

```
       Nde
5'-   TATGGCACCTTTTGTGGCAAAAGATATTCGTGTGGATGGTGTTC

ACCGTGGAAAACACCGTTTTCTATAAGCACACCTACCACAAGTTCCACT

AGGTGACTTAGAATCAACAAACCGAGCAAGTTTACC

GAATCTTGGTTGTTTAGGCTCGTTCAAATGGACAAGC

TGTTCGTG - SEQ ID NO: 50

ACGGCC-5' - SEQ ID NO: 51
BsrF I
```

Plasmid pRY-60-1 was digested with EcoR I and Bsr I and the DNA fragment containing most of the D15 gene was purified. pUC was digested with EcoR I and Nde I and the vector fragment purified. A multi-component ligation between the pUC and D15 fragments and the oligonucleotides generated plasmid DS-860-1-1 which contains a D15 sequence without a promoter. pT7-7 was digested with Nde I and EcoR I and the vector fragment purified. DS-860-1-1 was digested with Nde I and EcoR I and the D15 insert was purified and ligated with the T7-7 vector generating plasmid DS-880-1-2 (FIG. 4).

The plasmid constructions were performed using *E. coli* JM109 as host. For expression, plasmid DS-880-1-2 was transformed into *E. coli* BL21/DE3, BL21/DE3/pLysS, or JM109/DE3 cells. Transformation of the cells was performed using either calcium chloride-treated competent cells or by electroporation using a BioRad 15 electroporator. Transformed cells were grown in YT, M9, or NZCYM media and induced with IPTG or other inducing agents.

Example 6

This Example illustrates the construction and expression of the GST-D15 fragment hybrid gene in *E. coli*.

A forward sense primer (primer 1) 5'-GGGGAATTCCAAAAGATGTTCGT (SEQ ID NO: 52) and a reverse antisense primer CACGAATTCCCTGCAAATC-5' (primer 7—SEQ ID NO: 53) were used to amplify a 2.8 Kb fragment HindIII-EcoRI of the D15 gene by the polymerase chain reaction that encodes the N-terminal amino acid residues 22 to 223 of the primary sequence of D15 protein (FIG. 1A). The nucleotide sequence of the 609 bp amplified fragment was confirmed by DNA sequencing. The amplified gene segment was ligated into the pGEX-2T vector downstream from the GST gene and transformed into *E. coli* TG-1. Colonies expressing the *H. influenzae* type b antigen were screened with a rabbit anti-*H. influenzae* type b antiserum by colony radioimmunoassay and isolated. The glutathione-S-transferase-D15 fragment fusion protein produced by transformed *E. coli* was isolated by affinity purification on glutathione agarose.

Example 7

This Example describes alternative expression systems for rD15.

The D15 gene or fragments thereof are also expressed in *E. coli* under the control of other regulated promoters. The D15 gene or fragments thereof are expressed in the absence of the leader peptide, or in other cloning systems where toxicity of D15 expression to the host is not problematic. The gene or fragments thereof are synthesized de novo or by employing the polymerase chain reaction using suitable primers. These genes are cloned into suitable cloning vectors or bacteriophage vectors in *E. coli* or other suitable hosts directly when toxicity can be avoided. Expression systems are Gram-positive bacteria (such as Bacillus species), pox virus, adenovirus, baculovirus, yeast, fungi, BCG or mammalian expression systems.

Example 8

This Example illustrates the protocol for extraction and purification of rD15 from *E. coli* expression system.

The cell pellet from a 250 mL culture, prepared as described in Example 5, was resuspended in 40 mL of 50 mM Tris, pH 8.0, and disrupted by sonication (3×10 min, 70% duty circle). The extract was centrifuged at 20,000×g and the resulting pellet saved. The initial pellet was re-extracted with 40 mL of 50 mM Tris, 0.5% Triton X-100, 10 mM EDTA, pH 8.0. The suspension was then sonicated for 10 minutes at 70% duty circle. The extract was centrifuged at 300×g for 5 minutes. The resulting supernatant was centrifuged again at 20,000×g for 30 min and the resulting pellet was saved. The pellet was resuspended in 50 mM Tris, 0.5% Triton X-100, 10 mM EDTA, pH 8.0. The suspension was then mixed with PBS/8 M urea to a final urea concentration of 6 M. The solution was then dialyzed against PBS to remove urea. After dialysis, the solution was centrifuged at 300×g for 10 min., the supernatant was saved and stored at 4° C.

Example 9

This Example demonstrates the purification of GST-(D15 fragment) fusion protein using glutathione-Sepharose 4B affinity chromatography.

Five mg of GST-(D15 fragment) fusion protein crude extract, prepared as described in Example 6, were dissolved in 5 mL of phosphate buffer saline (PBS) containing 1i Triton X-100. The solution was then loaded onto a Glutathione-Sepharose 4B column (2 mL) equilibrated with PBS containing 1% Triton X-100. The run-through of the column was discarded. The column was washed with 20 mL of PBS and the GST-(D15 fragment) fusion protein was eluted with 50 mM Tris-HCl buffer, pH 8.0, containing 5 mM glutathione. Elution was monitored by absorbance at 280 nm. Protein-containing fractions (2 mL/fraction) were collected and pooled. The purity of the protein was assessed by SDS-PAGE (FIG. 9, lane 3). The final volume of the purified fusion protein was 6 mL.

Example 10

This Example illustrates the protocol used for thrombin digestion of proteins to release the truncated D15 molecule.

The GST-(D15 fragment) fusion protein sample from Example 9 (0.1 to 0.5 mg protein/mL) was dialyzed against 1 L of 50 mM Tris-HCl buffer (pH 8.5) 3 times with at least 2 hour intervals at 4° C. to remove protease inhibitors. After dialysis, the solution was treated with human thrombin (Sigma) at a ratio of 1 mL of solution to 25 units of thrombin. The cleavage reaction was carried out at 37° C. for 2 hr and analysed by SDS-PAGE (FIG. 9, lane 4). The reaction was stopped by placing the solution in ice.

Example 11

This Example illustrates the procedure used for N-terminal rD15 fragment purification from GST using Glutathione-sepharose 4B affinity chromatography.

A thrombin-digested GST-(D15 fragment) sample, prepared as described in Example 10, was loaded onto a Glutathione-Sepharose 4B column (2 mL) equilibrated with PBS containing 1% Triton X-100. The run-through of the column containing the N-terminal rD15 fragment was saved. After washing the column with 20 mL of PBS, the affinity column was regenerated by removing GST using 50 mM Tris-HCl buffer, pH 8.0, containing 5 mM glutathione. The purity of rD15 fragment was analysed by SDS-PAGE (FIG. 9, lane 5). This N-terminal RD15 fragment contains amino acids 63–223 of the D15 protein as a result of cleavage at the spacious thrombin site shown in FIG. 1A.

Example 12

This Example illustrates the protocol used for the purification of D15 -specific polyclonal antibodies by affinity chromatography using GST-(D15 fragment) fusion protein.

The recombinant GST-(D15 fragment) fusion protein, prepared as described in Example 9, was conjugated to cyanogen bromide-activated Sepharose. The affinity column was then used to purify antibodies from a rabbit hyperimmune anti-*H. influenzae* type b antiserum. The affinity purified-antibodies were shown by immunoblotting to react with a 80 kDa component present in the lysates of *E. coli* transformed with pUC9/D15 and in the lysates of several typeable and nontypeable *H. influenzae* isolates. These results confirmed that the DNA segment encoding the D15 fragment of the fusion protein was part of the open reading frame of the D15 gene.

Similarly, antisera raised against the recombinant fusion protein (Example 9) or the purified N-terminal rD15 fragment (Example 11) reacted with the D15 protein produced by *H. influenzae* strains (Example 13).

Example 13

This Example describes the protocol used for the purification of native D15 from *H. influenzae*.

Cell paste of the non-typeable *H. influenzae* SE33 strain, prepared from a culture grown in brain heart infusion medium supplemented with NAD (2 $\mu$g/mL) and HEMIN (2 $\mu$g/mL) at 37° C., as described in Panezutti, et al, 1993, was resuspended in 50 mM Tris-HCl, pH 8.0, containing 0.5% Triton X-100 and 10 mM EDTA (20 mL per 1 g of cell paste). The mixture was stirred at room temperature for 2 hr, then centrifuged at 20,000×g for 30 minutes. The D15 was located in the supernatant and further purified.

Purification of native D15 was achieved by affinity chromatography using a D15-specific monoclonal antibody (see Example 24). The D15 extract (25 mL) was mixed with the affinity matrix (1 mL) at room temperature for 2 hr. The mixture was packed into a column and the run-through fraction was discarded. The column was washed sequentially with the following buffers: 50 mM Tris-HCl, pH 8.0, containing 0.5% Triton X-100 and 10 mM EDTA; 1 M HEPES buffer, pH 6.8; 50 mM Tris-HCl, pH 8.0, containing 0.5% Triton X-100 and 10 mM EDTA; and 10 mM phosphate buffer, pH 8.0. D15 was then eluted from the column with 3 mL of 50 mM diethylamine, pH 12.0 and the protein solution was neutralized by 1 M HEPES, pH 6.8 (1/10 volume). The affinity-purified native D15 was analysed by SDS-PAGE and stored at −20° C.

Example 14

This Example describes the procedure used for the preparation of D15-PRP conjugates.

*Haemophilus influenzae* type b oligosaccharides (PRP) prepared by controlled acid hydrolysis were conjugated either with the purified native (Example 13) or recombinant D15 (Example 8) as well as with its fragments (Example 11) using periodate oxidation as described in U.S. Pat. No. 4,356,170 and further details of which are presented in Example 17. The mean molecular size of the PRP molecules used for conjugation was determined as being approximately 20,000 Daltons. The conjugation was carried out without a linker molecule but may also be carried out with a linker molecule. A PRP/D15 molar ratio of approximately 7 was used to provide an excess of PRP hapten.

The PRP/rD15 conjugate was tested according to the protocol of Example 18 for immunogenicity in rabbits and elicited both primary and secondary anti-PRP IgG and anti-D15 antibody responses (Table 9). Rabbit anti-rD15-PRP antisera also strongly reacted with both native D15 and rD15 as judged by immunoblot analysis. These data indicate that rD15 can be used as a carrier protein in a conjugate vaccine. In addition, a rD15-PRP conjugate vaccine should ensure a more consistent protection against *H. influenzae* type b disease, particularly in infants, as a result of the additional homotypic protection provided by antibodies directed against the D15 protein.

Example 15

This Example describes the preparation of D15 peptides.

D15 peptides (Table 2) were synthesized using an ABI 430A peptide synthesizer and optimized t-Boc chemistry as described by the manufacturer, then cleaved from the resin by hydrofluoric acid (HF). The peptides were purified by reversed-phase high performance liquid chromatography (RP-HPLC) on a Vydac C4 semi-preparative column (1×30 cm) using a 15 to 55% acetonitrile gradient in 0.1% trifluoryl acetic acid (TFA) developed over 40 minutes at a flow rate of 2 mL/min. All synthetic peptides (Table 2) used in biochemical and immunological studies were>95% pure as judged by analytical HPLC. Amino acid composition analyses of these peptides performed on a Waters Pico-Tag system were in good agreement with their theoretical compositions.

Example 16

This Example describes the protocol used for D15 peptide-specific antisera production.

Guinea pigs and rabbits were immunized with individual peptides (50 to 200 $\mu$g) emulsified with Freund's complete adjuvant and injected intramuscularly. After two booster doses with the same amount of peptide 10 in incomplete Freund's adjuvant at +14 and +28 days, the anti-peptide antisera were collected on day +42 and tested by ELISAs and immunoblotting. Both rabbit and guinea pig antisera were shown to be monospecific for their respective immunizing peptides by the peptide-specific ELISAs (Table 6). In addition, both guinea pig and rabbit antisera raised against D15 peptides reacted with both *H. influenzae* type b and non-typeable D15 on immunoblot analyses. Since most D15 peptides induced strong anti-peptide antibody responses in at least one animal species, they are appropriate immunogens to be included in immunogenic compositions including vaccine preparations.

Example 17

This Example describes the procedure used for the preparation of PRP-BSA conjugates.

0.5 mL of periodate-oxidized PRP (25mg in 1 mL of 0.1 M sodium phosphate buffer, pH 6.0), prepared from native PRP treated with aqueous periodic acid (Carlone et al, 1986), was added to bovine serum albumin (BSA) (1.32 mg ; 0.02 μmol) in 0.5 mL of 0.2 M sodium phosphate buffer, pH 8.0, followed by the addition of sodium cyanoborohydride (14 μg ; 0.22 μmol ; 10 eqv. to BSA). After incubation at 37° C. for 5 days, the reaction mixture was dialysed against 4 L of 0.1 M phosphate buffer, pH 7.5. The resulting solution was applied onto an analytical Superose 12 column (15×300 mm, Pharmacia) equilibrated with 0.2 M sodium phosphate buffer, pH 7.2, and eluted with the same buffer. Fractions were monitored for absorbance at 230 nm. The first major protein peak was pooled and concentrated in a Centriprep 30 to 2.2 mL. The amount of protein was determined using the Bio Rad protein assay, and was found to be 300 μg/mL. The presence of PRP in the protein conjugate fraction was confirmed by the Orcinol test.

Example 18

This Example describes the protocol used for the production of anti-PRP antisera in animals using rD15-PRP conjugates.

Rabbits were immunized intramuscularly with rD15-PRP conjugates (Example 14) (5 to 50 μg PRP equivalent) mixed with 3 mg $AlPO_4$ per mL, followed by two booster doses (half amount of the same immunogen) at 2 week intervals. Antisera were collected every 2 weeks after the first injection, heat-inactivated at 56° C. for 30 minutes and stored at −20° C.

Example 19

This Example illustrates the reactivity between D15 peptides and anti-peptide and D15-specific antisera using D15-specific and peptide-specific ELISAs.

Microtiter wells (Nunc-Immunoplate, Nunc, Denmark) 25 were coated with 200 ng of purified rD15 or 500 ng of individual peptides in 50 μL of coating buffer (15 mM $Na_2CO_3$, 35 mM $NaHCO_3$, pH 9.6) for 16 hours at room temperature. The plates were then blocked with 0.1% (w/v) BSA in phosphate buffer saline (PBS) for 30 minutes at room temperature. Serially diluted antisera were added to the wells and incubated for 1 hour at room temperature. After removal of the antisera, the plates were washed five times with PBS containing 0.1% (w/v) Tween-20 and 0.1% (w/v) BSA. F(ab')$_2$ fragments from goat anti-rabbit, guinea pig, mouse, or human IgG antibodies conjugated to horseradish peroxidase (Jackson ImmunoResearch Labs Inc., PA) were diluted (1/8,000) with washing buffer, and added onto the microtiter plates. After 1 hr incubation at room temperature, the plates were washed five times with the washing buffer. The plates were then developed using the substrate tetramethylbenzidine (TMB) in $H_2O_2$ (ADI, Toronto). The reaction was stopped with 1N $H_2SO_4$ and the optical density was measured at 450 nm using a Titretek Multiskan II (Flow Labs., Virginia). Two irrelevant peptides as negative controls in the peptide-specific ELISAs. Assays were performed in triplicate, and the reactive titer of each antiserum was defined as the dilution consistently showing 2-fold increase absorbance value over those obtained from the negative controls. The results obtained are summarized in Tables 3, 6 and 8 and in the DETAILED DESCRIPTION OF THE INVENTION above.

Example 20

This Example illustrates the measurement of the anti-PRP IgG titers in rabbit anti-PRP-D15 conjugate antisera using a PRP-specific ELISA.

Microtiter wells (Nunc-Immunoplate, Nunc, Denmark) were coated with 200 ng of purified PRP-BSA (see Example 17) in 200 μL of coating buffer (15 mM $Na_2CO_3$, 35 mM $NaHCO_3$, pH 9.6) for 16 hours at room temperature. The plates were then blocked with 0.1% (w/v) BSA in phosphate buffer saline (PBS) for 30 minutes at room temperature. Serially diluted rabbit antisera raised against PRP-D15 conjugates were added to the wells and incubated for 1 hour at room temperature. After removal of the antisera, the plates were washed five times with PBS containing 0.1% (w/v) Tween-20 and 0.1% (w/v) BSA. F(ab')$_2$ fragment from goat anti-rabbit IgG antibodies conjugated to horseradish peroxidase (Jackson ImmunoResearch Labs Inc., PA) were diluted (1/8,000) with washing buffer, and added onto the microtiter plates. After 1 hour incubation at room temperature, the plates were washed five times with the washing buffer. The plates were then developed using the substrate tetramethylbenzidine (TMB) in $H_2O_2$ (AD:, Toronto). The reaction was stopped with 1N $H_2SO_4$ and the optical density measured at 450 nm using a Titretek Multiskan II (Flow Labs., Virginia). A standard anti-PRP antiserum of known titer was included as positive control. Assays were performed in triplicate, and the reactive titer of each antiserum was defined as the reciprocal of the dilution consistently showing a 2-fold increase in O.D. value over that obtained with the pre-immune serum (Table 9).

Example 21

This Example describes the protocol used for the production of D15-specific antisera using purified D15, rD15 or N-terminal rD15 fragment.

New Zealand White rabbits (Maple Lane) and guinea pigs (Charles River) were immunized intramuscularly (IM) with a 10 μg dose of either affinity-purified native D15 (Example 13), recombinant D15 (Example 8) or N-terminal rD15 fragment (Example 11) emulsified in Freund's complete adjuvant (Difco). Animals were boosted on day 28 with another 10 μg dose of affinity-purified D15 or rD15 or rD15 fragment emulsified in Freund's incomplete adjuvant and bled on day 42 via the marginal ear vein.

D15-specific polyclonal antibodies were purified from this material as described in Example 12.

Example 22

This Example illustrates the protective activity of D15-specific antisera against *H. influenzae* type b challenge using the infant rat model of bacteremia.

Five-day old infant rats were inoculated subcutaneously (SC) on the dorsum with 0.15 mL of two different rabbit anti-N-terminal rD15 fragments. Pre-immune sera were used as negative controls. One day after immunization, the infant rats were injected intraperitoneally (IP) with 200 colony-forming units (cfu) of *Haemophilus influenzae* type b Minn A strain (0.1 ml) freshly grown in brain heart infusion (BHI) medium supplemented with cofactors and diluted in PBS containing 0.5 mM $MgCl_2$ and 0.15 mM $CaCl_2$. One day later, blood samples were collected via cardiac puncture under methoxyflurane anaesthesia and plated on chocolate agar plates. The number of bacteria per mL, of blood was quantified after 24 hr. The statistical significance of differences observed in the levels of bacteremia relative to controls was analyzed by the Student's t-test. The results are summarized in Table 1.

Example 23

This Example describes the protocol used for the generation of D15-specific T-cell lines.

BALB/c (H-2$^d$) mice purchased from Charles River Animal Farm (Montreal, Canada) were individually primed subcutaneously with 20 μg of rD15 adsorbed to 1.5 mg of aluminium phosphate (alum). The animals were boosted twice with the same dose of immunogen at 3 week intervals. Ten days after the final boost, spleens of immunized mice were removed. Splenocytes were cultured at 5.75×10$^5$ cells per well in a final volume of 200 μL of RPMI 1640 medium (Flow Lab.) supplemented with 10% heat-inactivated fetal calf serum (Gibco), 2 mM L-glutamine (Flow Lab.), 100 U/mL) penicillin (Flow Lab.) and 5×10$^{-5}$ M 2-mercaptoethanol (Sigma) in the presence of varying concentrations (1, 10 and 100 μg per mL) of individual D15 peptides (Table 2) in 96-well plates (Nunc, Denmark). Cultures were kept in a humidified incubator in the presence of 5% $CO_2$/air. Triplicate cultures were performed for each concentration of each peptide. Five days later, 150 μL of 10% rat concanavalin A culture supernatant diluted in culture medium was added to the microtiter plate wells as a source of Interleukin-2 (IL-2) to expand peptide-specific T-cells. Six days later, 150 μL of supernatant were removed from each microculture, and 150 μL of fresh IL-2 containing culture supernatant added to further expand and maintain the viability of the peptide-specific T-cells. After a further 6 day-incubation, the cells were washed three times, each time with 200 μL of culture medium.

Each set of cultures was then stimulated with the corresponding concentrations (1, 10 and 100 μg per mL) of the peptide in the presence of 2×10$^5$ irradiated (1,500 rad) BALB/c spleen cells in a final volume of 200 μL of culture medium. Sixty μL of supernatant were then removed from each microculture. The supernatants from each triplicate cultures set were pooled. All supernatants were assayed for IL-2, Interleukin-4 and Interferon-gamma (IFN-γ). Detections of IL-2 and IL-4 were performed using murine IL-2 and IL-4 ELISA kits purchased from Endogen Inc. (MA, U.S.A.) respectively. Assay of IFN-γ was performed using a mouse IFN-γ ELISA kit supplied by Genzyme Corporation (MA, U.S.A.). Test culture supernatants were assayed at 1 in 5 dilution according to the manufacturers' instructions. The results obtained are set forth in Table 7.

Example 25

This Example describes the general procedure used for the production of murine D15 -specific monoclonal antibodies.

BALB/c mice were immunized intraperitoneally with 20 to 50 μg of the N-terminal rD15 fragment (Example 11) emulsified in Freund's complete adjuvant. Two weeks later, the mice were given another injection of the same amount of immunogen in incomplete Freund's adjuvant (IFA). Three days before the fusion, the mice were boosted again with the same amount of immunogen in IFA. Hybridomas were produced by fusion of splenic lymphocytes from immunized mice with non-secreting Sp2/0 myeloma cells as previously described by Hamel et al. (1987). D15 -specific hybridomas were cloned by sequential limiting dilutions and screened for anti-D15 monoclonal antibody production. Eight D15 -specific hybridoma cell lines were identified, expanded and frozen in liquid nitrogen. One of the hybridoma cell lines, 6C8-F6-C6, has been partially characterized. The monoclonal antibody (MAb 6CS-F6-C6) reacts with peptide D15-P8. This MAb 6C8-F6-C6 was used to prepare the D15 -specific MAb affinity column and purify native D15 from *H. influenzae* cell paste (Example 13).

TABLE 1

PROTECTIVE EFFECT OF
PASSIVELY TAANSFERRED ANTI-N-TERMINAL RD15
FRAGMENT ANTIBODIES IN
THE INFANT RAT MODEL OF BACTEREMIA[1]

| | cfu/0.1 mL blood | | |
|---|---|---|---|
| Rabbit antisera | Pre-immune | Post-immunization | p value |
| Rb#434 | 510 (%)[2] | 6 (1/6) | <0.001 |
| Rb#435 | 910 (4/4) | 6 (1/4) | <0.001 |

[1]Five-day old infant rata were passively immunized with 0.15 mL of rabbit anti-N-terminal rD15 fragment s.c. One day later, the infant rats were challenged with 200 cfu of *H. influenzae* type b strain MinnA (0.1 mL, IP). The blood samples were taken from each rat 24 hours after the challenge and analysed for bacteria counts.
[2]The parentheses indicate the number of rats found to be bacteremic out of the total number of rats challenged.

TABLE 2

SEQUENCE OF OVERLAPPING SYNTHETIC PEPTIDES ENCOMPASSING THE ENTIRE D15 ANTIGEN SEQUENCE

| PEPTIDES | RESIDUES | SEQUENCES | SEQ ID NO: |
|---|---|---|---|
| D15-P1 | 20—49 | APFVAKDIRVDGVQGDLEQQIRASLPVRAG | 14 |
| D15-P2 | 45—74 | PVRAGQRVTDNDVAMIVRSLFVSGRFDDVK | 15 |
| D15-P3 | 68—99 | GRFDDVKAHQEGDVLVVSVVAKSIISDVKIKG | 16 |
| D15-P4 | 93—122 | SDVKIKGNSVIPTEALKQNLDANGFKVGDV | 17 |
| D15-P5 | 114—143 | ANGFKVGDVLIREKLNEFAKSVKEHYASVG | 18 |
| D15-P6 | 135—164 | VKEHYASVGRYNATVEPIVNTLPNNRAEIL | 19 |
| D15-P7 | 157—187 | PNNRAEILIQINEDDKAKLASLTFKGNESVS | 20 |
| D15-P8 | 180—209 | FKGNESVSSSTLQEQMELQPDSWWKKLWGNK | 21 |
| D15-P9 | 199—228 | PDSWWKLWGNKFEGAQFEKDLQSIRDYYLN | 22 |
| D15-P10 | 219—249 | LQSIRDYYLNNGYAKAQITKTDVQLNDEKTK | 23 |
| D15-P11 | 241—270 | VQLNDEKTKVNVTIDVNEGLQYDLRSARII | 24 |
| D15-P12 | 262—291 | YDLRSARIIGNLGGMSAELEPLLSALHLND | 25 |
| D15-P13 | 282—312 | PLLSALHLNDTFRRSDIADVENAIKAKLGER | 26 |
| D15-P14 | 304—333 | AIKAKLGERGYGSATVNSVPDFDDANKTLA | 27 |
| D15-P15 | 325—354 | FDDANKTLAITLVVDAGRRLTVRQLRFEGN | 28 |
| D15-P16 | 346—375 | VRQLRFEGNTVSADSTLRQEMRQQEGTWYN | 29 |
| D15-P17 | 367—396 | RQQEGTWYNSQLVELGKIRLDRTGFFETVE | 30 |
| D15-P18 | 390—416 | GFFETVENRIDPINGSNDEVDVVYKVK | 31 |
| D15-P19 | 410—435 | DVVYKVKERNTGSINFGIGYGTESGI | 32 |

TABLE 2-continued

SEQUENCE OF OVERLAPPING SYNTHETIC PEPTIDES ENCOMPASSING THE ENTIRE D15 ANTIGEN SEQUENCE

| PEPTIDES | RESIDUES | SEQUENCES | SEQ ID NO: |
|---|---|---|---|
| D15-P20 | 430–455 | GTESGISYQASVKQDNFLGTGAAVSI | 33 |
| D15-P21 | 450–477 | GAAVSIAGTKNDYGTSVNLGYTEPYFTK | 34 |
| D15-P22 | 471–497 | TEPYFTKDGVSLGGNVFFENYDNSKSD | 35 |
| D15-P23 | 491–516 | YDNSKSDTSSNYKRTTYGSNVTLGFP | 36 |
| D15-P24 | 511–538 | VTLGFPVNENNSYYVGLGHTYNKISNF | 37 |
| D15-P25 | 532–559 | YNKISNFALEYNRNLYIQSMKFKGNGIK | 38 |
| D15-P26 | 554–582 | KGNGIKTNDFDFSFGWNYNSLNRGYFPTK | 39 |
| D15-P27 | 577–602 | GYFPTKGVKASLGGRVTIPGSDNKYYK | 40 |
| D15-P28 | 596–625 | SDNKYYKLSADVQGFYPLDRDHLWVVSAK | 41 |
| D15-P29 | 619–646 | LWVVSAKASAGYANGFGNKRLPFYQTYT | 42 |
| D15-P30 | 641–666 | FYQTYTAGGIGSLRGFAYGSIGPNAI | 43 |
| D15-P31 | 662–688 | GPNAIYAEYGNGSGTGTFKKISSDVIG | 44 |
| D15-P32 | 681–709 | KISSDVIGGNAIATASAELIVPTPFVSDK | 45 |
| D15-P33 | 705–731 | FVSDKSQNTVRTSLFVDAASVWNTKWK | 46 |
| D15-P34 | 725–750 | VWNTKWKSDKNGLESDVLKRLPDYGK | 47 |
| D15-P35 | 745–771 | LPDYGKSSRIRASTGVGFQWQSPIGPL | 48 |
| D15-P36 | 769–798 | GPLVFSYAKPIKKYENDDVEQFQFSIGGSF | 49 |

TABLE 3

REACTIVITY OF RABBIT AND GUINEA PIG ANTI-N-TERMINAL rD15 FRAGMENT ANTISERA WITH D15 SYNTHETIC PEPTIDES

| | Reactive Titers | | | | |
|---|---|---|---|---|---|
| | Rabbit antisera | | Guinea pig antisera | | |
| Peptides | 3434 | 435 | 858 | 859 | 860 |
| D15-P1 | 400 | 1,600 | 6,400 | 6,400 | 6,400 |
| D15-P2 | 1,600 | <100 | 100 | 100 | <100 |
| D15-P3 | 400 | <100 | 100 | <100 | <100 |
| D15-P4 | 25,600 | 6,400 | <100 | <100 | <100 |
| D15-P5 | 6,400 | 400 | 1,600 | 25,600 | 400 |
| D15-P6 | 1,600 | 6,400 | 400 | 6,400 | 6,400 |
| D15-P7 | 6,400 | 6,400 | 25,600 | 409,600 | 409,600 |
| D15-P8 | 6,400 | 6,400 | 25,600 | 409,600 | 409,600 |
| D15-P9 | <100 | <100 | 400 | 1,600 | 1,600 |
| D15-P10 | <100 | <100 | 400 | 6,400 | <100 |

TABLE 4

INHIBITION OF ANTI-N-TERMINAL rD15 FRAGMENT ANTIBODY-INDUCED PROTECTION BY D15 PEPTIDES IN THE INFANT RAT MODEL OF BACTEREMIA

| Group # | Antibody | cfu/10 μL blood | cfu in each group/cfu in group #4 (control) (%) |
|---|---|---|---|
| 1 | Anti-D15 Ab + PBS | 60 ± 120 (3/7) | 3 |
| 2 | Anti-D15 Ab + peptides | 300 ± 240 (6/7) | 13 |
| 3 | Anti-D15 Ab + rD15 | 1,520 ± 1,280 (7/7) | 64 |
| 4 | PBS + peptides | 2,360 ± 1,200 (6/7) | 100 |

One half mL of rabbit anti-N-terminal rD15 fragment antiserum (Anti-rD15 fragment Ab) was mixed with either nine D15 peptides (100 μg of peptides D15-P2 to D15-P10, see TABLE 2) or with 600 μg of N-terminal rD15 fragment at room temperature for 1 hr. Antiserum and peptides mixed with PBS were used as controls. Seven-day old infant rats were injected s.c. with 0.2 mL of the various preparations. After 24 h, the infant rats were challenged I.P. with 200 cfu of H. influenzae type b strain MinnA. The blood samples were taken at 24 h after the challenge. The numbers in parentheses indicate the number of animals that were bacteremic out of the total number of animals challenged. The level of bacteremia is expressed as the mean of values obtained from seven infant rats tested individually ± one standard deviation (SD).

TABLE 5

INHIBITION OF THE IMMUNOPROTECTION ABILITY OF THE RABBIT ANTI-N-TERMINAL rD15 FRAGMENT ANTISERUM ABSORBED WITH D15 PEPTIDES (D15-P4 TO D15-P8) IN THE INFANT RAT MODEL OF BACTEREMIA

| Group # | Antibody | cfu/10 μL blood | cfu in each group/cfu in group #3 (%) |
|---|---|---|---|
| 1 | rD15 Ab + PBS | 220 ± 360 (3/6) | 8 |
| 2 | rD15 Ab + peptides | 2,960 ± 560 (6/6) | 106 |
| 3 | PBS + peptides | 2,800 ± 360 (6/6) | 100 |

TABLE 5-continued

INHIBITION OF THE IMMUNOPROTECTION ABILITY OF THE RABBIT ANTI-N-TERMINAL rD15 FRAGMENT ANTISERUM ABSORBED WITH D15 PEPTIDES (D15-P4 TO D15-P8) IN THE INFANT RAT MODEL OF BACTEREMIA

| Group # | Antibody | cfu/10 μL blood | cfu in each group/cfu in group #3 (%) |
|---|---|---|---|

One half mL of rabbit anti-rD15 fragment antiserum (rD15 Ab) was mixed with five D15 peptides (peptides P4 to P8, 250 μg of each peptide) at room temperature for 1 hr. Antiserum and peptides diluted in PBS were used as controls. Seven-day old infant rats were injected s.c. with 0.2 mL of the indicated material. After 24 h, the infant rats were challenged I.P. with 200 cfu of *H. influenzae* type b strain MinnA. The blood samples were collected 24 h after challenge. The numbers in parentheses indicate the number of animals that were bacteremia out of the total number of animals challenged. The level of bacteremia is expressed as the mean of values obtained from six infant rats tested individually ± one SD.

TABLE 6

REACTIVITY OF RABBIT, GUINEA PIG AND MOUSE ANTI-rD15 ANTISERA WITH D15 PEPTIDES

| | Reactive Titer[1] | | |
|---|---|---|---|
| Peptide | Rabbit[2] | Guinea Pig[3] | Mouse[4] |
| D15-P1 | − | − | + |
| D15-P2 | − | +++ | + |
| D15-P3 | − | − | + |
| D15-P4 | + | + | + |
| D15-P5 | − | − | + |
| D15-P6 | − | + | + |
| D15-P7 | − | − | + |
| D15-P8 | − | ++++ | ++++ |
| D15-P9 | − | − | + |
| D15-P10 | − | − | +++ |
| D15-P11 | − | − | +++ |
| D15-P12 | − | − | + |
| D15-P13 | − | − | + |
| D15-P14 | +++ | + | + |
| D15-P15 | − | − | + |
| D15-P16 | − | − | + |
| D15-P17 | − | − | + |
| D15-P18 | − | − | + |
| D15-P19 | − | − | + |
| D15-P20 | − | − | + |
| D15-P21 | − | − | + |
| D15-P22 | − | − | + |
| D15-P23 | − | − | + |
| D15-P24 | − | − | + |
| D15-P25 | − | − | + |
| D15-P26 | − | − | +++ |
| D15-P27 | − | + | + |
| D15-P28 | − | − | + |
| D15-P29 | − | − | + |
| D15-P30 | − | − | + |
| D15-P31 | − | − | + |
| D15-P32 | − | − | + |
| D15-P33 | − | − | + |
| D15-P34 | − | − | + |
| D15-P35 | − | − | + |
| D15-P36 | ++++ | − | + |

[1]The reactive titer is based on peptide-specific ELISAs. +, ++, +++, and ++++ represent reactive titers of animal antisera tested at 1/300, 1/1000, 1/2000 and 1/5000 dilutions, respectively; − means nonreactive.
[2]Titer represents the average value of two rabbit antisera rasied against rD15.
[3]Titer represents the average value of two guinea pig antisera raised against rD15.
[4]Titer represents the average value of five mouse antisera raised against r15.

TABLE 7

T-CELL STIMULATORY ACTIVITY OF D15 PEPTIDES

| | CYTOKINE RELEASE (pg/mL)[2] | | |
|---|---|---|---|
| Peptide | IL-2[2] | γ-IFN[3] | IL-4[4] |
| D15-P1 | — | — | — |
| D15-P2 | 122 | — | — |
| D15-P3 | 25 | — | — |
| D15-P4 | — | — | — |
| D15-P5 | *742* | *38,000* | *13* |
| D15-P6 | — | — | — |
| D15-P7 | — | — | — |
| D15-P8 | — | — | — |
| D15-P9 | — | — | — |
| D15-P10 | 108 | 1,900 | — |
| D15-P11 | — | — | — |
| D15-P12 | 1,052 | 6,100 | — |
| D15-P13 | *105* | *6,200* | *56* |
| D15-P14 | — | — | — |
| D15-P15 | — | — | — |
| D15-P16 | 48 | — | — |
| D15-P17 | — | — | — |
| D15-P18 | 32 | 4,800 | — |
| D15-P19 | 882 | 24,500 | — |
| D15-P20 | — | — | — |
| D15-P21 | — | — | — |
| D15-P22 | — | — | — |
| D15-P23 | 78 | — | — |
| D15-P24 | 103 | — | — |
| D15-P25 | — | — | — |
| D15-P26 | 572 | 6,700 | — |
| D15-P27 | *274* | *7,505* | *68* |
| D15-P28 | 142 | 742 | — |
| D15-P29 | — | — | — |
| D15-P30 | — | — | — |
| D15-P31 | — | — | — |
| D15-P32 | — | — | — |
| D15-P33 | — | — | — |
| D15-P34 | 82 | 603 | — |
| D15-P35 | 107 | 751 | — |
| D15-P36 | — | — | — |

[1]Results are expressed as mean values of triplicate cultures. All standard deviations were less that 15%. Immunodominant Th1-cell epitopes are highlighted with bold and Th0-cell epitopes are in italics.

TABLE 8

RABBIT AND GUINEA PIG ANTIBODY RESPONSES TO D15 PEPTIDES

| | Peptide-Specific ELISAs Reactive Titer[1] | |
|---|---|---|
| Immunogen | Rabbit[2] | Guinea Pig[3] |
| D15-P1 | 102,400 | 819,200 |
| D15-P2 | 204,800 | 1,637,400 |
| D15-P3 | 51,200 | 1,637,400 |
| D15-P4 | 204,800 | 819,200 |
| D15-P5 | 51,200 | 1,637,400 |
| D15-P6 | 51,200 | 403,600 |
| D15-P7 | 204,800 | 819,200 |
| D15-P8 | 51,200 | 409,600 |
| D15-P9 | 102,400 | 409,600 |
| D15-P10 | 102,400 | 819,200 |
| D15-P11 | 51,200 | 819,200 |
| D15-P12 | 102,400 | 204,800 |
| D15-P13 | NT[4] | 204,800 |
| D15-P14 | NT | 409,600 |
| D15-P15 | NT | 204,800 |
| D15-P16 | NT | 819,200 |
| D15-P17 | NT | 204,800 |
| D15-P18 | NT | 312,500 |
| D15-P19 | NT | 312.500 |
| D15-P20 | NT | 62,500 |

TABLE 8-continued

RABBIT AND GUINEA PIG ANTIBODY RESPONSES TO D15 PEPTIDES

| | Peptide-Specific ELISAs Reactive Titer[1] | |
|---|---|---|
| Immunogen | Rabbit[2] | Guinea Pig[3] |
| D15-P21 | NT | 62,500 |
| D15-P22 | NT | 12,500 |
| D15-P23 | NT | 1,562,500 |
| D15-P24 | NT | 312,500 |
| D15-P25 | NT | 62,500 |
| D15-P26 | NT | 500 |
| D15-P27 | NT | 1,500 |
| D15-P28 | NT | 1,250 |
| D15-P29 | NT | <500 |
| D15-P30 | NT | <500 |
| D15-P31 | NT | <500 |
| D15-P32 | NT | 12,500 |
| D15-P33 | NT | 12,500 |
| D15-P34 | NT | 62,500 |
| D15-P35 | NT | 1,250 |
| D15-P36 | NT | 12,500 |

[1]The reactive titer is based on peptide-specific ELISAs. A titer below 500 indicates that the peptide is not immunogenic.
[2]Titers represent the average value of obtained for two rabbit antisera raised against the D15 peptide.
[3]Titers represent the average value obtained for two guinea pig antisera raised against the D15 peptide.
[4]NT: not tested.

TABLE 9

RABBIT IgG ANTIBODY RESPONSE TO D15-PRP CONJUGATE

| | Reactive Titer Against[2] | | | |
|---|---|---|---|---|
| | PRP | | rD15 | |
| Rabit[1] # | 2 doses | 3 doses | 2 doses | 3 doses |
| 489-1 | 1,600 | 3,200 | 1,600 | 6,400 |
| 490-1 | 1,600 | 1,600 | 6,400 | 25,600 |

[1]Rabbits were immunized intramuscularly with rD15-PRP conjugates (5 to 50 μg PRP equivalent) mixed with 3 mg ALPO$_4$ per mL, followed by two booster doses (half amount of the same immunogen) at 2 week intervals.
[2]Reactive titres is based on PRP specific and D-15 specific ELISAs.

SUMMARY OF THE DISCLOSURE

In summary of this disclosure, the present invention provides purified and isolated nucleic acid molecules containing genes encoding the D15 outer membrane protein, the sequences of these genes and the derived amino acid sequences thereof. The invention also provides peptides corresponding to portions of the D35 outer membrane protein. In addition, the invention provides antibodies raised against D15 outer membrane protein, fragments and peptides. The genes, DNA sequences, antibodies and peptides are useful for diagnosis, immunization and the generation of diagnostic and immunological reagents. Vaccines based on expressed recombinant D35, portions thereof or peptides derived from the provided sequences can be prepared for prevention of *H. influenza* disease. Modification are possible within the scope of the invention.

REFERENCES

O'Hagan (1992).
Ulman et al., 1993.
Berns C. A. and Thomas C. A. (1965) J. Mol. Biol. 11:476–490.
Thomas W. R. and Rossi A. A. (1986) Infect. Immun. 52:812–817.
Thomas W. R. et al. (1990) Infect. and Immun. 58:1909–1913.
Carlone G. M. et al. (1986) J. Clin. Microbiol. 24:330–331.
Smith, D. B. and Johnson K. S. (1988) Gene 67:31–40.
Harkness, R. et al. (1992) J. Bacteriol. 174:2425–2430.
Hamel et al. (1987) J. Med. Microbiol. 23:163–170.
Mills et al. (1993) Infect. Immun. 61:399–410.
Trinchieri, (1993) Immunol. Today 14:335–338.
Hope, T. P. (1986) J. Immunol. Methods 88:1–18.
Zangwill et al., 1993. MMWR 42:1–15.
Loeb et al. 1987. Infect. Immun. 55:2612–2618.
Panezutti, 1993. Infect. Immun. 61: 1867–1872.

What we claim is:

1. A purified and isolated nucleic acid molecule consisting of a DNA sequence selected from the group consisting of:
   (a) a DNA sequence consisting of SEQ ID NOS: 1, 3, 5, 7 or 9, and
   (b) a DNA sequence encoding an amino acid sequence consisting of SEQ ID NOS: 2,4, 6, 8 or 10.

2. A purified and isolated nucleic acid molecule consisting of a DNA sequence encoding a functional D15 outer membrane protein of a strain of *Haemophilus influenzae* of molecular weight as determined by SDS-PAGE of about 80 kDa and including the consensus sequence having SEQ ID NO: 55.

3. A recombinant plasmid for transformation of a host, comprising a plasmid vector into which has been inserted a nucleic acid molecule as claimed in claim 1.

4. A recombinant plasmid for transformation of a host, comprising a plasmid vector into which has been inserted a nucleic acid molecule as claimed in claim 2.

5. A recombinant vector for transformation of a host, comprising expression means operatively coupled to a nucleic acid molecule as claimed in claim 1 for expression of a gene product consisting of a D15 outer membrane protein of *Haemophilus influenzae* having a molecular weight as determined by SDS-PAGE of about 80 kDa or a polypeptide fragment thereof.

6. A recombinant vector for transformation of a host, comprising expression means operationaly coupled to a nucleic acid molecule as claimed in claim 2 for expression of a gene product which consists of a D15 outer membrane protein of *Haemophilus influenzae* of molecular weight as determined by SDS-PAGE of about 80 kDa.

7. The recombinant vector of claim 5 or 6, wherein the nucleic acid molecule further comprises a nucleic acid sequence encoding a leader sequence for export of said gene product from said host.

8. A method of producing a D15 outer membrane protein of a strain of *Haemophilus influenzae* having a molecular weight as determined by SDS-PAGE of about 80 kDa, which comprises:

assembling a recombinant vector as claimed in claim 5, transforming a host cell with said recombinant vector, growing the host cell to express the D15 outer membrane protein, and isolating and purifying the expressed D15 outer membrane protein.

9. A method of producing a D15 outer membrane protein of a strain of *Haemophilus influenzae* having a molecular weight as determined by SDS-PAGE of about 80 kDa, which comprises:

assembling a recombinant vector as claimed in claim 6, transforming a host cell with said recombinant vector, growing the host cell to express the D15 outer membrane protein, and isolating and purifying the expressed D15 outer membrane protein.

10. A recombinant nucleic acid fragment encoding an immunogenic peptide of a purified and isolated D15 outer membrane protein having a molecular weight as determined by SDS-PAGE of about 80 kDa, wherein said immunogenic peptide is selected from the group consisting of SEQ ID NOS. 14–38, 40, 41 and 45–49.

* * * * *

SEQUENCE LISTING (1) GENERAL INFORMATION:

(iii) NUMBER OF SEQUENCES: 55

(2) INFORMATION FOR SEQ ID NO: 1:

(i) SEQUENCE CHARACTERISTICS:
      (A) LENGTH: 2949 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS (B) LOCATION: 75..2465

(xi) SEQUENCE DESCRIPTION: SEQ ID NO: 1:

| | | | | | | | | | | | | | | |
|---|---|---|---|---|---|---|---|---|---|---|---|---|---|---|
| GATTACGCCA | AGCTTAACGG | TGTTTGCATT | ATTTAATGAT | TTTTTACGTC | TATAATTTAT | 60 |

```
ATAGGATACA ATCG ATG AAA AAA CTT CTA ATC GCA AGT TTA TTA TTC GGT         110
                Met Lys Lys Leu Leu Ile Ala Ser Leu Leu Phe Gly
                 1               5                          10

ACG ACA ACG ACT GTG TTT GCC GCA CCT TTT GTG GCA AAA GAT ATT CGT         158
Thr Thr Thr Thr Val Phe Ala Ala Pro Phe Val Ala Lys Asp Ile Arg
         15                  20                  25

GTG GAT GGT GTT CAA GGT GAC TTA GAA CAA CAA ATC CGA GCA AGT TTA         206
Val Asp Gly Val Gln Gly Asp Leu Glu Gln Gln Ile Arg Ala Ser Leu
 30                  35                  40

CCT GTT CGT GCC GGT CAG CGT GTG ACT GAC AAT GAT GTG GCT AAT ATT         254
Pro Val Arg Ala Gly Gln Arg Val Thr Asp Asn Asp Val Ala Asn Ile
 45                  50                  55                  60

GTC CGC TCT TTA TTC GTA AGT GGT CGA TTC GAT GAT GTG AAA GCG CAT         302
Val Arg Ser Leu Phe Val Ser Gly Arg Phe Asp Asp Val Lys Ala His
                 65                  70                  75

CAA GAA GGC GAT GTG CTT GTT GTT AGC GTT GTG GCT AAA TCG ATC ATT         350
Gln Glu Gly Asp Val Leu Val Val Ser Val Val Ala Lys Ser Ile Ile
             80                  85                  90

TCA GAT GTT AAA ATC AAA GGT AAC TCT GTT ATT CCC ACT GAA GCA CTT         398
Ser Asp Val Lys Ile Lys Gly Asn Ser Val Ile Pro Thr Glu Ala Leu
         95                 100                 105

AAA CAA AAC TTA GAT GCT AAC GGG TTT AAA GTT GGC GAT GTT TTA ATT         446
Lys Gln Asn Leu Asp Ala Asn Gly Phe Lys Val Gly Asp Val Leu Ile
110                 115                 120

CGA GAA AAA TTA AAT GAA TTT GCC AAA AGT GTA AAA GAG CAC TAT GCA         494
Arg Glu Lys Leu Asn Glu Phe Ala Lys Ser Val Lys Glu His Tyr Ala
125                 130                 135                 140

AGT GTA GGT CGC TAT AAC GCA ACA GTT GAA CCT ATT GTC AAT ACG CTA         542
Ser Val Gly Arg Tyr Asn Ala Thr Val Glu Pro Ile Val Asn Thr Leu
                145                 150                 155

CCA AAT AAT CGC GCT GAA ATT TTA ATT CAA ATC AAT GAA GAT GAT AAA         590
Pro Asn Asn Arg Ala Glu Ile Leu Ile Gln Ile Asn Glu Asp Asp Lys
            160                 165                 170

GCA AAA TTG GCA TCA TTA ACT TTC AAG GGG AAC GAA TCT GTT AGT AGC         638
Ala Lys Leu Ala Ser Leu Thr Phe Lys Gly Asn Glu Ser Val Ser Ser
        175                 180                 185

AGT ACA TTA CAA GAA CAA ATG GAA TTA CAA CCT GAT TCT TGG TGG AAA         686
Ser Thr Leu Gln Glu Gln Met Glu Leu Gln Pro Asp Ser Trp Trp Lys
    190                 195                 200

TTA TGG GGA AAT AAA TTT GAA GGT GCG CAA TTC GAG AAA GAT TTG CAG         734
Leu Trp Gly Asn Lys Phe Glu Gly Ala Gln Phe Glu Lys Asp Leu Gln
205                 210                 215                 220

TCA ATT CGT GAT TAT TAT TTA AAT AAT GGC TAT GCC AAA GCA CAA ATT         782
Ser Ile Arg Asp Tyr Tyr Leu Asn Asn Gly Tyr Ala Lys Ala Gln Ile
                225                 230                 235

ACT AAA ACG GAT GTT CAG CTA AAT GAT GAA AAA ACA AAA GTT AAT GTA         830
Thr Lys Thr Asp Val Gln Leu Asn Asp Glu Lys Thr Lys Val Asn Val
            240                 245                 250

ACC ATT GAT GTA AAT GAA GGT TTA CAG TAT GAC CTT CGT AGT GCA CGC         878
Thr Ile Asp Val Asn Glu Gly Leu Gln Tyr Asp Leu Arg Ser Ala Arg
        255                 260                 265

ATT ATA GGT AAT CTG GGA GGT ATG TCT GCC GAG CTT GAA CCT TTA CTT         926
Ile Ile Gly Asn Leu Gly Gly Met Ser Ala Glu Leu Glu Pro Leu Leu
    270                 275                 280

TCA GCA TTA CAT TTA AAT GAT ACT TTC CGC CGT AGT GAT ATT GCA GAT         974
```

```
Ser Ala Leu His Leu Asn Asp Thr Phe Arg Arg Ser Asp Ile Ala Asp
285                 290                 295                 300

GTA GAA AAT GCA ATT AAA GCA AAA CTT GGA GAA CGC GGT TAC GGT AGC    1022
Val Glu Asn Ala Ile Lys Ala Lys Leu Gly Glu Arg Gly Tyr Gly Ser
                    305                 310                 315

GCA ACG GTA AAT TCA GTA CCT GAT TTT GAT GAT GCA AAT AAA ACA TTA    1070
Ala Thr Val Asn Ser Val Pro Asp Phe Asp Asp Ala Asn Lys Thr Leu
                320                 325                 330

GCG ATA ACC CTT GTT GTT GAT GCT GGA CGA CGT TTA ACT GTT CGC CAA    1118
Ala Ile Thr Leu Val Val Asp Ala Gly Arg Arg Leu Thr Val Arg Gln
            335                 340                 345

CTT CGC TTT GAA GGA AAT ACC GTT TCT GCT GAT AGC ACT TTA CGT CAG    1166
Leu Arg Phe Glu Gly Asn Thr Val Ser Ala Asp Ser Thr Leu Arg Gln
        350                 355                 360

GAA ATG CGC CAA CAA GAA GGA ACT TGG TAT AAT TCA CAA TTA GTT GAG    1214
Glu Met Arg Gln Gln Glu Gly Thr Trp Tyr Asn Ser Gln Leu Val Glu
365                 370                 375                 380

TTA GGA AAA ATT CGC TTA GAT CGT ACA GGT TTC TTC GAA ACA GTC GAA    1262
Leu Gly Lys Ile Arg Leu Asp Arg Thr Gly Phe Phe Glu Thr Val Glu
                    385                 390                 395

AAC CGA ATT GAT CCT ATC AAT GGT AGT AAT GAT GAA GTG GAT GTC GTA    1310
Asn Arg Ile Asp Pro Ile Asn Gly Ser Asn Asp Glu Val Asp Val Val
                400                 405                 410

TAT AAA GTC AAA GAA CGT AAC ACG GGT AGT ATC AAC TTT GGT ATT GGT    1358
Tyr Lys Val Lys Glu Arg Asn Thr Gly Ser Ile Asn Phe Gly Ile Gly
            415                 420                 425

TAC GGT ACA GAG AGT GGT ATT AGT TAT CAA GCA AGT GTT AAA CAA GAT    1406
Tyr Gly Thr Glu Ser Gly Ile Ser Tyr Gln Ala Ser Val Lys Gln Asp
        430                 435                 440

AAT TTC TTG GGA ACA GGG GCG GCA GTA AGT ATA GCT GGT ACG AAA AAT    1454
Asn Phe Leu Gly Thr Gly Ala Ala Val Ser Ile Ala Gly Thr Lys Asn
445                 450                 455                 460

GAT TAT GGT ACG AGT GTC AAT TTG GGT TAT ACC GAG CCC TAT TTT ACT    1502
Asp Tyr Gly Thr Ser Val Asn Leu Gly Tyr Thr Glu Pro Tyr Phe Thr
                    465                 470                 475

AAA GAT GGT GTA AGT CTT GGT GGA AAT GTT TTC TTT GAA AAC TAC GAT    1550
Lys Asp Gly Val Ser Leu Gly Gly Asn Val Phe Phe Glu Asn Tyr Asp
                480                 485                 490

AAC TCT AAA AGT GAT ACA TCC TCT AAC TAT AAG CGT ACG ACT TAC GGA    1598
Asn Ser Lys Ser Asp Thr Ser Ser Asn Tyr Lys Arg Thr Thr Tyr Gly
            495                 500                 505

AGT AAT GTT ACT TTA GGT TTC CCT GTA AAT GAA AAT AAC TCC TAT TAT    1646
Ser Asn Val Thr Leu Gly Phe Pro Val Asn Glu Asn Asn Ser Tyr Tyr
        510                 515                 520

GTA GGA TTA GGT CAT ACC TAT AAT AAA ATT AGT AAC TTT GCT CTA GAA    1694
Val Gly Leu Gly His Thr Tyr Asn Lys Ile Ser Asn Phe Ala Leu Glu
525                 530                 535                 540

TAT AAC CGT AAT TTA TAT ATT CAA TCA ATG AAA TTT AAA GGT AAT GGC    1742
Tyr Asn Arg Asn Leu Tyr Ile Gln Ser Met Lys Phe Lys Gly Asn Gly
                    545                 550                 555

ATT AAA ACA AAT GAC TTT GAT TTT TCT TTT GGT TGG AAC TAT AAC AGC    1790
Ile Lys Thr Asn Asp Phe Asp Phe Ser Phe Gly Trp Asn Tyr Asn Ser
                560                 565                 570

CTT AAT AGA GGC TAT TTC CCA ACT AAA GGG GTT AAA GCA AGT CTT GGT    1838
Leu Asn Arg Gly Tyr Phe Pro Thr Lys Gly Val Lys Ala Ser Leu Gly
            575                 580                 585

GGA CGA GTT ACT ATT CCA GGT TCT GAT AAC AAA TAC TAC AAA CTA AGT    1886
Gly Arg Val Thr Ile Pro Gly Ser Asp Asn Lys Tyr Tyr Lys Leu Ser
        590                 595                 600
```

```
GCA GAT GTA CAG GGT TTC TAC CCA TTA GAC AGA GAT CAC CTC TGG GTT      1934
Ala Asp Val Gln Gly Phe Tyr Pro Leu Asp Arg Asp His Leu Trp Val
605                 610                 615                 620

GTA TCT GCA AAA GCA TCT GCA GGA TAT GCA AAT GGT TTT GGA AAC AAG      1982
Val Ser Ala Lys Ala Ser Ala Gly Tyr Ala Asn Gly Phe Gly Asn Lys
                625                 630                 635

CGT TTA CCG TTC TAT CAA ACT TAT ACA GCG GGT GGC ATC GGT TCA TTA      2030
Arg Leu Pro Phe Tyr Gln Thr Tyr Thr Ala Gly Gly Ile Gly Ser Leu
            640                 645                 650

CGT GGT TTT GCT TAT GGT AGT ATT GGA CCT AAC GCA ATT TAT GCC GAA      2078
Arg Gly Phe Ala Tyr Gly Ser Ile Gly Pro Asn Ala Ile Tyr Ala Glu
        655                 660                 665

TAT GGT AAT GGT AGT GGT ACT GGT ACT TTT AAG AAG ATA AGT TCT GAT      2126
Tyr Gly Asn Gly Ser Gly Thr Gly Thr Phe Lys Lys Ile Ser Ser Asp
    670                 675                 680

GTG ATT GGT GGT AAT GCA ATC GCT ACA GCT AGC GCA GAG TTA ATT GTG      2174
Val Ile Gly Gly Asn Ala Ile Ala Thr Ala Ser Ala Glu Leu Ile Val
685                 690                 695                 700

CCA ACT CCA TTT GTG AGC GAT AAG AGC CAA AAT ACG GTC CGA ACC TCC      2222
Pro Thr Pro Phe Val Ser Asp Lys Ser Gln Asn Thr Val Arg Thr Ser
                705                 710                 715

TTA TTT GTT GAT GCG GCA AGT GTT TGG AAT ACT AAA TGG AAA TCA GAT      2270
Leu Phe Val Asp Ala Ala Ser Val Trp Asn Thr Lys Trp Lys Ser Asp
            720                 725                 730

AAA AAT GGA TTA GAG AGC GAT GTA TTA AAA AGA TTG CCT GAT TAT GGC      2318
Lys Asn Gly Leu Glu Ser Asp Val Leu Lys Arg Leu Pro Asp Tyr Gly
        735                 740                 745

AAA TCA AGC CGT ATT CGC GCC TCT ACA GGT GTC GGA TTC CAA TGG CAA      2366
Lys Ser Ser Arg Ile Arg Ala Ser Thr Gly Val Gly Phe Gln Trp Gln
    750                 755                 760

TCT CCT ATT GGG CCA TTG GTA TTC TCT TAT GCC AAA CCA ATT AAA AAA      2414
Ser Pro Ile Gly Pro Leu Val Phe Ser Tyr Ala Lys Pro Ile Lys Lys
765                 770                 775                 780

TAT GAA AAT GAT GAT GTC GAA CAG TTC CAA TTT AGT ATT GGA GGT TCT      2462
Tyr Glu Asn Asp Asp Val Glu Gln Phe Gln Phe Ser Ile Gly Gly Ser
                785                 790                 795

TTC TAATAAATTG AACTTTTTTC TTCATCAGAA CTCAAAAACA ACGTTCTCTG           2515
Phe

CCTAATTTAA TTGGGCAGAG AAAATATTAA ACCCATCATT TAATTAAGGA TATTTATCAA    2575

ATGAAAAACA TCGCAAAAGT AACCGCACTT GCTTTAGGTA TTGCACTTGC TTCAGGCTAT    2635

GCTTCCGCTG AAGAAAAAAT TGCTTTCATT AATGCAGGTA TATTTTTCAA CATCACCCAG    2695

ATCGCCAAGC GGTAGCAGAT AAACTTGATG CTGAATTTAA ACCTGTAGCT GAGAAATTAG    2755

CAGCAAGCAA AAAAGAAGTT GATGATAAAA TTGCTGCTGC TCGTAAAAAA GTAGAAGCAA    2815

AAGTTGCGGC TTTAGAAAAA GATGCACCTC GCTTACGTCA AGCTGATATT CAAAAACGCC    2875

AACAGGAGAT TAATAAATTA GGTGCGGCTG AAGATGCTGA ATTACAAAAA TTAATGCAAG    2935

AACAAGATAA AAAA                                                     2949

(2) INFORMATION FOR SEQ ID NO: 2:

(i) SEQUENCE CHARACTERISTICS:
            (A) LENGTH: 797 amino acids
            (B) TYPE: amino acid
            (D) TOPOLOGY: linear (ii) MOLECULE TYPE: protein (xi) SEQUENCE DESCRIPTION: SEQ ID NO: 2:
```

-continued

```
Met Lys Lys Leu Leu Ile Ala Ser Leu Leu Phe Gly Thr Thr Thr Thr
 1               5                   10                  15

Val Phe Ala Ala Pro Phe Val Ala Lys Asp Ile Arg Val Asp Gly Val
            20                  25                  30

Gln Gly Asp Leu Glu Gln Gln Ile Arg Ala Ser Leu Pro Val Arg Ala
        35                  40                  45

Gly Gln Arg Val Thr Asp Asn Asp Val Ala Asn Ile Val Arg Ser Leu
    50                  55                  60

Phe Val Ser Gly Arg Phe Asp Asp Val Lys Ala His Gln Glu Gly Asp
65                  70                  75                  80

Val Leu Val Val Ser Val Ala Lys Ser Ile Ile Ser Asp Val Lys
                85                  90                  95

Ile Lys Gly Asn Ser Val Ile Pro Thr Glu Ala Leu Lys Gln Asn Leu
                100                 105                 110

Asp Ala Asn Gly Phe Lys Val Gly Asp Val Leu Ile Arg Glu Lys Leu
            115                 120                 125

Asn Glu Phe Ala Lys Ser Val Lys Glu His Tyr Ala Ser Val Gly Arg
    130                 135                 140

Tyr Asn Ala Thr Val Glu Pro Ile Val Asn Thr Leu Pro Asn Asn Arg
145                 150                 155                 160

Ala Glu Ile Leu Ile Gln Ile Asn Glu Asp Asp Lys Ala Lys Leu Ala
                165                 170                 175

Ser Leu Thr Phe Lys Gly Asn Glu Ser Val Ser Ser Thr Leu Gln
            180                 185                 190

Glu Gln Met Glu Leu Gln Pro Asp Ser Trp Trp Lys Leu Trp Gly Asn
    195                 200                 205

Lys Phe Glu Gly Ala Gln Phe Glu Lys Asp Leu Gln Ser Ile Arg Asp
210                 215                 220

Tyr Tyr Leu Asn Asn Gly Tyr Ala Lys Ala Gln Ile Thr Lys Thr Asp
225                 230                 235                 240

Val Gln Leu Asn Asp Glu Lys Thr Lys Val Asn Val Thr Ile Asp Val
            245                 250                 255

Asn Glu Gly Leu Gln Tyr Asp Leu Arg Ser Ala Arg Ile Ile Gly Asn
                260                 265                 270

Leu Gly Gly Met Ser Ala Glu Leu Glu Pro Leu Leu Ser Ala Leu His
            275                 280                 285

Leu Asn Asp Thr Phe Arg Arg Ser Asp Ile Ala Asp Val Glu Asn Ala
    290                 295                 300

Ile Lys Ala Lys Leu Gly Glu Arg Gly Tyr Gly Ser Ala Thr Val Asn
305                 310                 315                 320

Ser Val Pro Asp Phe Asp Ala Asn Lys Thr Leu Ala Ile Thr Leu
            325                 330                 335

Val Val Asp Ala Gly Arg Arg Leu Thr Val Arg Gln Leu Arg Phe Glu
            340                 345                 350

Gly Asn Thr Val Ser Ala Asp Ser Thr Leu Arg Gln Glu Met Arg Gln
        355                 360                 365

Gln Glu Gly Thr Trp Tyr Asn Ser Gln Leu Val Glu Leu Gly Lys Ile
    370                 375                 380

Arg Leu Asp Arg Thr Gly Phe Phe Glu Thr Val Glu Asn Arg Ile Asp
385                 390                 395                 400

Pro Ile Asn Gly Ser Asn Asp Glu Val Asp Val Tyr Lys Val Lys
            405                 410                 415

Glu Arg Asn Thr Gly Ser Ile Asn Phe Gly Ile Gly Tyr Gly Thr Glu
```

```
              420                 425                 430
Ser Gly Ile Ser Tyr Gln Ala Ser Val Lys Gln Asp Asn Phe Leu Gly
            435                 440                 445

Thr Gly Ala Ala Val Ser Ile Ala Gly Thr Lys Asn Asp Tyr Gly Thr
450                 455                 460

Ser Val Asn Leu Gly Tyr Thr Glu Pro Tyr Phe Thr Lys Asp Gly Val
465                 470                 475                 480

Ser Leu Gly Gly Asn Val Phe Phe Glu Asn Tyr Asp Asn Ser Lys Ser
                485                 490                 495

Asp Thr Ser Ser Asn Tyr Lys Arg Thr Thr Tyr Gly Ser Asn Val Thr
                500                 505                 510

Leu Gly Phe Pro Val Asn Glu Asn Asn Ser Tyr Val Gly Leu Gly
            515                 520                 525

His Thr Tyr Asn Lys Ile Ser Asn Phe Ala Leu Glu Tyr Asn Arg Asn
            530                 535                 540

Leu Tyr Ile Gln Ser Met Lys Phe Lys Gly Asn Gly Ile Lys Thr Asn
545                 550                 555                 560

Asp Phe Asp Phe Ser Phe Gly Trp Asn Tyr Asn Ser Leu Asn Arg Gly
                565                 570                 575

Tyr Phe Pro Thr Lys Gly Val Lys Ala Ser Leu Gly Gly Arg Val Thr
            580                 585                 590

Ile Pro Gly Ser Asp Asn Lys Tyr Tyr Lys Leu Ser Ala Asp Val Gln
            595                 600                 605

Gly Phe Tyr Pro Leu Asp Arg Asp His Leu Trp Val Val Ser Ala Lys
            610                 615                 620

Ala Ser Ala Gly Tyr Ala Asn Gly Phe Gly Asn Lys Arg Leu Pro Phe
625                 630                 635                 640

Tyr Gln Thr Tyr Thr Ala Gly Gly Ile Gly Ser Leu Arg Gly Phe Ala
                645                 650                 655

Tyr Gly Ser Ile Gly Pro Asn Ala Ile Tyr Ala Glu Tyr Gly Asn Gly
                660                 665                 670

Ser Gly Thr Gly Thr Phe Lys Lys Ile Ser Ser Asp Val Ile Gly Gly
            675                 680                 685

Asn Ala Ile Ala Thr Ala Ser Ala Glu Leu Ile Val Pro Thr Pro Phe
690                 695                 700

Val Ser Asp Lys Ser Gln Asn Thr Val Arg Thr Ser Leu Phe Val Asp
705                 710                 715                 720

Ala Ala Ser Val Trp Asn Thr Lys Trp Lys Ser Asp Lys Asn Gly Leu
                725                 730                 735

Glu Ser Asp Val Leu Lys Arg Leu Pro Asp Tyr Gly Lys Ser Ser Arg
            740                 745                 750

Ile Arg Ala Ser Thr Gly Val Gly Phe Gln Trp Gln Ser Pro Ile Gly
            755                 760                 765

Pro Leu Val Phe Ser Tyr Ala Lys Pro Ile Lys Lys Tyr Glu Asn Asp
            770                 775                 780

Asp Val Glu Gln Phe Gln Phe Ser Ile Gly Gly Ser Phe
785                 790                 795

(2) INFORMATION FOR SEQ ID NO: 3:

(i) SEQUENCE CHARACTERISTICS:
        (A) LENGTH: 2984 base pairs
        (B) TYPE: nucleic acid
        (C) STRANDEDNESS: single
        (D) TOPOLOGY: linear
```

-continued (ii) MOLECULE TYPE: DNA (genomic)

(ix) FEATURE:
    (A) NAME/KEY: CDS
    (B) LOCATION: 374..2764

(xi) SEQUENCE DESCRIPTION: SEQ ID NO: 3:

```
ACAGGACAGC TTTCCCTTTT AACCTTGAAA ATATTAGGGA AATTACTTCC TGGCGATTTG      60

TCATTAAATA ATTTAAGTGG GCCAATTTCT ATTGCAAAAG GTGCTGGCCC ATCAGCAAAT     120

ATTGGATTGG TGTATTTTTT AAGTTTTATG GCACTGATTA GTGTAAATTT AGGGATTATG     180

AATTTATTTC CATTACCAGT ATTAGATGGC GGTCATTTAG TTTTTTTAAC AATGGAAGCT     240

GTTAAAGGAA AACCTGTTTC TGAGCGGGTG CAAAGCATCT GTTATCGAAT TGGCGCAGCA     300

CTGTTATTAA GCTTAACGGT GTTTGCATTA TTTAATGATT TTTTACGTCT ATAATTTATA     360

TAGGATACAA TCG ATG AAA AAA CTT CTA ATC GCA AGT TTA TTA TTC GGT        409
             Met Lys Lys Leu Leu Ile Ala Ser Leu Leu Phe Gly
               1               5                  10

ACG ACA ACG ACT GTG TTT GCC GCA CCT TTT GTG GCA AAA GAT ATT CGT        457
Thr Thr Thr Thr Val Phe Ala Ala Pro Phe Val Ala Lys Asp Ile Arg
         15                  20                  25

GTG GAT GGT GTT CAA GGT GAC TTA GAA CAA CAA ATC CGA GCA AGT TTA        505
Val Asp Gly Val Gln Gly Asp Leu Glu Gln Gln Ile Arg Ala Ser Leu
 30                  35                  40

CCT GTT CGT GCC GGT CAG CGT GTG ACT GAC AAT GAT GTG GCT AAT ATT        553
Pro Val Arg Ala Gly Gln Arg Val Thr Asp Asn Asp Val Ala Asn Ile
 45                  50                  55                  60

GTC CGC TCT TTA TTC GTA AGT GGT CGA TTC GAT GAT GTG AAA GCG CAT        601
Val Arg Ser Leu Phe Val Ser Gly Arg Phe Asp Asp Val Lys Ala His
                 65                  70                  75

CAA GAA GGC GAT GTG CTT GTT GTT AGC GTT GTG GCT AAA TCG ATC ATT        649
Gln Glu Gly Asp Val Leu Val Val Ser Val Val Ala Lys Ser Ile Ile
             80                  85                  90

TCA GAT GTT AAA ATC AAA GGT AAC TCT GTT ATT CCC ACT GAA GCA CTT        697
Ser Asp Val Lys Ile Lys Gly Asn Ser Val Ile Pro Thr Glu Ala Leu
         95                 100                 105

AAA CAA AAC TTA GAT GCT AAC GGG TTT AAA GTT GGC GAT GTT TTA ATT        745
Lys Gln Asn Leu Asp Ala Asn Gly Phe Lys Val Gly Asp Val Leu Ile
110                 115                 120

CGA GAA AAA TTA AAT GAA TTT GCC AAA AGT GTA AAA GAG CAC TAT GCA        793
Arg Glu Lys Leu Asn Glu Phe Ala Lys Ser Val Lys Glu His Tyr Ala
125                 130                 135                 140

AGT GTA GGT CGC TAT AAC GCA ACA GTT GAA CCT ATT GTC AAT ACG CTA        841
Ser Val Gly Arg Tyr Asn Ala Thr Val Glu Pro Ile Val Asn Thr Leu
                145                 150                 155

CCA AAT AAT CGC GCT GAA ATT TTA ATT CAA ATC AAT GAA GAT GAT AAA        889
Pro Asn Asn Arg Ala Glu Ile Leu Ile Gln Ile Asn Glu Asp Asp Lys
            160                 165                 170

GCA AAA TTG GCA TCA TTA ACT TTC AAG GGG AAC GAA TCT GTT AGT AGC        937
Ala Lys Leu Ala Ser Leu Thr Phe Lys Gly Asn Glu Ser Val Ser Ser
        175                 180                 185

AGT ACA TTA CAA GAA CAA ATG GAA TTA CAA CCT GAT TCT TGG TGG AAA        985
Ser Thr Leu Gln Glu Gln Met Glu Leu Gln Pro Asp Ser Trp Trp Lys
190                 195                 200

TTA TGG GGA AAT AAA TTT GAA GGT GCG CAA TTC GAG AAA GAT TTG CAG       1033
Leu Trp Gly Asn Lys Phe Glu Gly Ala Gln Phe Glu Lys Asp Leu Gln
205                 210                 215                 220

TCA ATT CGT GAT TAT TAT TTA AAT AAT GGC TAT GCC AAA GCA CAA ATT       1081
Ser Ile Arg Asp Tyr Tyr Leu Asn Asn Gly Tyr Ala Lys Ala Gln Ile
```

-continued

```
                    225                 230                 235
ACT AAA ACG GAT GTT CAG CTA AAT GAT GAA AAA ACA AAA GTT AAT GTA        1129
Thr Lys Thr Asp Val Gln Leu Asn Asp Glu Lys Thr Lys Val Asn Val
            240                 245                 250

ACC ATT GAT GTA AAT GAA GGT TTA CAG TAT GAC CTT CGT AGT GCA CGC        1177
Thr Ile Asp Val Asn Glu Gly Leu Gln Tyr Asp Leu Arg Ser Ala Arg
            255                 260                 265

ATT ATA GGT AAT CTG GGA GGT ATG TCT GCC GAG CTT GAA CCT TTA CTT        1225
Ile Ile Gly Asn Leu Gly Gly Met Ser Ala Glu Leu Glu Pro Leu Leu
            270                 275                 280

TCA GCA TTA CAT TTA AAT GAT ACT TTC CGC CGT AGT GAT ATT GCA GAT        1273
Ser Ala Leu His Leu Asn Asp Thr Phe Arg Arg Ser Asp Ile Ala Asp
285                 290                 295                 300

GTA GAA AAT GCA ATT AAA GCA AAA CTT GGA GAA CGC GGT TAC GGT AGC        1321
Val Glu Asn Ala Ile Lys Ala Lys Leu Gly Glu Arg Gly Tyr Gly Ser
                305                 310                 315

GCA ACG GTA AAT TCA GTA CCT GAT TTT GAT GAT GCA AAT AAA ACA TTA        1369
Ala Thr Val Asn Ser Val Pro Asp Phe Asp Asp Ala Asn Lys Thr Leu
                320                 325                 330

GCG ATA ACC CTT GTT GTT GAT GCT GGA CGA CGT TTA ACT GTT CGC CAA        1417
Ala Ile Thr Leu Val Val Asp Ala Gly Arg Arg Leu Thr Val Arg Gln
            335                 340                 345

CTT CGC TTT GAA GGA AAT ACC GTT TCT GCT GAT AGC ACT TTA CGT CAG        1465
Leu Arg Phe Glu Gly Asn Thr Val Ser Ala Asp Ser Thr Leu Arg Gln
            350                 355                 360

GAA ATG CGC CAA CAA GAA GGA ACT TGG TAT AAT TCA CAA TTA GTT GAG        1513
Glu Met Arg Gln Gln Glu Gly Thr Trp Tyr Asn Ser Gln Leu Val Glu
365                 370                 375                 380

TTA GGA AAA ATT CGC TTA GAT CGT ACA GGT TTC TTC GAA ACA GTC GAA        1561
Leu Gly Lys Ile Arg Leu Asp Arg Thr Gly Phe Phe Glu Thr Val Glu
                385                 390                 395

AAC CGA ATT GAT CCT ATC AAT GGT AGT AAT GAT GAA GTG GAT GTC GTA        1609
Asn Arg Ile Asp Pro Ile Asn Gly Ser Asn Asp Glu Val Asp Val Val
                400                 405                 410

TAT AAA GTC AAA GAA CGT AAC ACG GGT AGT ATC AAC TTT GGT ATT GGT        1657
Tyr Lys Val Lys Glu Arg Asn Thr Gly Ser Ile Asn Phe Gly Ile Gly
            415                 420                 425

TAC GGT ACA GAG AGT GGT ATT AGT TAT CAA GCA AGT GTT AAA CAA GAT        1705
Tyr Gly Thr Glu Ser Gly Ile Ser Tyr Gln Ala Ser Val Lys Gln Asp
            430                 435                 440

AAT TTC TTG GGA ACA GGG GCG GCA GTA AGT ATA GCT GGT ACG AAA AAT        1753
Asn Phe Leu Gly Thr Gly Ala Ala Val Ser Ile Ala Gly Thr Lys Asn
445                 450                 455                 460

GAT TAT GGT ACG AGT GTC AAT TTG GGT TAT ACC GAG CCC TAT TTT ACT        1801
Asp Tyr Gly Thr Ser Val Asn Leu Gly Tyr Thr Glu Pro Tyr Phe Thr
                465                 470                 475

AAA GAT GGT GTA AGT CTT GGT GGA AAT GTT TTC TTT GAA AAC TAC GAT        1849
Lys Asp Gly Val Ser Leu Gly Gly Asn Val Phe Phe Glu Asn Tyr Asp
                480                 485                 490

AAC TCT AAA AGT GAT ACA TCC TCT AAC TAT AAG CGT ACG ACT TAC GGA        1897
Asn Ser Lys Ser Asp Thr Ser Ser Asn Tyr Lys Arg Thr Thr Tyr Gly
            495                 500                 505

AGT AAT GTT ACT TTA GGT TTC CCT GTA AAT GAA AAT AAC TCC TAT TAT        1945
Ser Asn Val Thr Leu Gly Phe Pro Val Asn Glu Asn Asn Ser Tyr Tyr
            510                 515                 520

GTA GGA TTA GGT CAT ACC TAT AAT AAA ATT AGT AAC TTT GCT CTA GAA        1993
Val Gly Leu Gly His Thr Tyr Asn Lys Ile Ser Asn Phe Ala Leu Glu
525                 530                 535                 540

TAT AAC CGT AAT TTA TAT ATT CAA TCA ATG AAA TTT AAA GGT AAT GGC        2041
```

```
Tyr Asn Arg Asn Leu Tyr Ile Gln Ser Met Lys Phe Lys Gly Asn Gly
            545                 550                 555

ATT AAA ACA AAT GAC TTT GAT TTT TCT TTT GGT TGG AAC TAT AAC AGC    2089
Ile Lys Thr Asn Asp Phe Asp Phe Ser Phe Gly Trp Asn Tyr Asn Ser
            560                 565                 570

CTT AAT AGA GGC TAT TTC CCA ACT AAA GGG GTT AAA GCA AGT CTT GGT    2137
Leu Asn Arg Gly Tyr Phe Pro Thr Lys Gly Val Lys Ala Ser Leu Gly
            575                 580                 585

GGA CGA GTT ACT ATT CCA GGT TCT GAT AAC AAA TAC TAC AAA CTA AGT    2185
Gly Arg Val Thr Ile Pro Gly Ser Asp Asn Lys Tyr Tyr Lys Leu Ser
            590                 595                 600

GCA GAT GTA CAG GGT TTC TAC CCA TTA GAC AGA GAT CAC CTC TGG GTT    2233
Ala Asp Val Gln Gly Phe Tyr Pro Leu Asp Arg Asp His Leu Trp Val
605                 610                 615                 620

GTA TCT GCA AAA GCA TCT GCA GGA TAT GCA AAT GGT TTT GGA AAC AAG    2281
Val Ser Ala Lys Ala Ser Ala Gly Tyr Ala Asn Gly Phe Gly Asn Lys
            625                 630                 635

CGT TTA CCG TTC TAT CAA ACT TAT ACA GCG GGT GGC ATC GGT TCA TTA    2329
Arg Leu Pro Phe Tyr Gln Thr Tyr Thr Ala Gly Gly Ile Gly Ser Leu
            640                 645                 650

CGT GGT TTT GCT TAT GGT AGT ATT GGA CCT AAC GCA ATT TAT GCC GAA    2377
Arg Gly Phe Ala Tyr Gly Ser Ile Gly Pro Asn Ala Ile Tyr Ala Glu
            655                 660                 665

TAT GGT AAT GGT AGT GGT ACT GGT ACT TTT AAG AAG ATA AGT TCT GAT    2425
Tyr Gly Asn Gly Ser Gly Thr Gly Thr Phe Lys Lys Ile Ser Ser Asp
            670                 675                 680

GTG ATT GGT GGT AAT GCA ATC GCT ACA GCT AGC GCA GAG TTA ATT GTG    2473
Val Ile Gly Gly Asn Ala Ile Ala Thr Ala Ser Ala Glu Leu Ile Val
685                 690                 695                 700

CCA ACT CCA TTT GTG AGC GAT AAG AGC CAA AAT ACG GTC CGA ACC TCC    2521
Pro Thr Pro Phe Val Ser Asp Lys Ser Gln Asn Thr Val Arg Thr Ser
            705                 710                 715

TTA TTT GTT GAT GCG GCA AGT GTT TGG AAT ACT AAA TGG AAA TCA GAT    2569
Leu Phe Val Asp Ala Ala Ser Val Trp Asn Thr Lys Trp Lys Ser Asp
            720                 725                 730

AAA AAT GGA TTA GAG AGC GAT GTA TTA AAA AGA TTG CCT GAT TAT GGC    2617
Lys Asn Gly Leu Glu Ser Asp Val Leu Lys Arg Leu Pro Asp Tyr Gly
            735                 740                 745

AAA TCA AGC CGT ATT CGC GCC TCT ACA GGT GTC GGA TTC CAA TGG CAA    2665
Lys Ser Ser Arg Ile Arg Ala Ser Thr Gly Val Gly Phe Gln Trp Gln
            750                 755                 760

TCT CCT ATT GGG CCA TTG GTA TTC TCT TAT GCC AAA CCA ATT AAA AAA    2713
Ser Pro Ile Gly Pro Leu Val Phe Ser Tyr Ala Lys Pro Ile Lys Lys
765                 770                 775                 780

TAT GAA AAT GAT GAT GTC GAA CAG TTC CAA TTT AGT ATT GGA GGT TCT    2761
Tyr Glu Asn Asp Asp Val Glu Gln Phe Gln Phe Ser Ile Gly Gly Ser
            785                 790                 795

TTC TAATAAATTG AACTTTTTTC TTCATCAGAA CTCAAAAACA ACGTTCTCTG         2814
Phe

CCTAATTTAA TTGGGCAGAG AAAATATTAA ACCCATCATT TAATTAAGGA TATTTATCAA  2874

ATGAAAAACA TCGCAAAAGT AACCGCACTT GCTTTAGGTA TTGCACTTGC TTCAGGCTAT  2934

GCTTCCGCTG AAGAAAAAAT TGCTTTCATT AATGCACTTA TATTTTTCAA            2984

(2) INFORMATION FOR SEQ ID NO: 4:

(i) SEQUENCE CHARACTERISTICS:
        (A) LENGTH: 797 amino acids
        (B) TYPE: amino acid
        (D) TOPOLOGY: linear
```

(ii) MOLECULE TYPE: protein (xi) SEQUENCE DESCRIPTION: SEQ ID NO: 4:

| Met | Lys | Lys | Leu | Leu | Ile | Ala | Ser | Leu | Leu | Phe | Gly | Thr | Thr | Thr | Thr |
|---|---|---|---|---|---|---|---|---|---|---|---|---|---|---|---|
| 1 | | | | 5 | | | | | 10 | | | | | 15 | |

| Val | Phe | Ala | Ala | Pro | Phe | Val | Ala | Lys | Asp | Ile | Arg | Val | Asp | Gly | Val |
| | | | 20 | | | | | 25 | | | | | 30 | | |

| Gln | Gly | Asp | Leu | Glu | Gln | Gln | Ile | Arg | Ala | Ser | Leu | Pro | Val | Arg | Ala |
| | | 35 | | | | | 40 | | | | | 45 | | | |

| Gly | Gln | Arg | Val | Thr | Asp | Asn | Asp | Val | Ala | Asn | Ile | Val | Arg | Ser | Leu |
| | 50 | | | | | 55 | | | | | 60 | | | | |

| Phe | Val | Ser | Gly | Arg | Phe | Asp | Asp | Val | Lys | Ala | His | Gln | Glu | Gly | Asp |
| 65 | | | | 70 | | | | | 75 | | | | | 80 | |

| Val | Leu | Val | Val | Ser | Val | Val | Ala | Lys | Ser | Ile | Ile | Ser | Asp | Val | Lys |
| | | | | 85 | | | | | 90 | | | | | 95 | |

| Ile | Lys | Gly | Asn | Ser | Val | Ile | Pro | Thr | Glu | Ala | Leu | Lys | Gln | Asn | Leu |
| | | | | 100 | | | | | 105 | | | | | 110 | |

| Asp | Ala | Asn | Gly | Phe | Lys | Val | Gly | Asp | Val | Leu | Ile | Arg | Glu | Lys | Leu |
| | | | 115 | | | | | 120 | | | | | 125 | | |

| Asn | Glu | Phe | Ala | Lys | Ser | Val | Lys | Glu | His | Tyr | Ala | Ser | Val | Gly | Arg |
| | 130 | | | | | 135 | | | | | 140 | | | | |

| Tyr | Asn | Ala | Thr | Val | Glu | Pro | Ile | Val | Asn | Thr | Leu | Pro | Asn | Asn | Arg |
| 145 | | | | | 150 | | | | | 155 | | | | | 160 |

| Ala | Glu | Ile | Leu | Ile | Gln | Ile | Asn | Glu | Asp | Asp | Lys | Ala | Lys | Leu | Ala |
| | | | | 165 | | | | | 170 | | | | | 175 | |

| Ser | Leu | Thr | Phe | Lys | Gly | Asn | Glu | Ser | Val | Ser | Ser | Ser | Thr | Leu | Gln |
| | | | | 180 | | | | | 185 | | | | | 190 | |

| Glu | Gln | Met | Glu | Leu | Gln | Pro | Asp | Ser | Trp | Trp | Lys | Leu | Trp | Gly | Asn |
| | | | 195 | | | | | 200 | | | | | 205 | | |

| Lys | Phe | Glu | Gly | Ala | Gln | Phe | Glu | Lys | Asp | Leu | Gln | Ser | Ile | Arg | Asp |
| | 210 | | | | | 215 | | | | | 220 | | | | |

| Tyr | Tyr | Leu | Asn | Asn | Gly | Tyr | Ala | Lys | Ala | Gln | Ile | Thr | Lys | Thr | Asp |
| 225 | | | | | 230 | | | | | 235 | | | | | 240 |

| Val | Gln | Leu | Asn | Asp | Glu | Lys | Thr | Lys | Val | Asn | Val | Thr | Ile | Asp | Val |
| | | | | 245 | | | | | 250 | | | | | 255 | |

| Asn | Glu | Gly | Leu | Gln | Tyr | Asp | Leu | Arg | Ser | Ala | Arg | Ile | Ile | Gly | Asn |
| | | | | 260 | | | | | 265 | | | | | 270 | |

| Leu | Gly | Gly | Met | Ser | Ala | Glu | Leu | Glu | Pro | Leu | Leu | Ser | Ala | Leu | His |
| | | | 275 | | | | | 280 | | | | | 285 | | |

| Leu | Asn | Asp | Thr | Phe | Arg | Arg | Ser | Asp | Ile | Ala | Asp | Val | Glu | Asn | Ala |
| | 290 | | | | | 295 | | | | | 300 | | | | |

| Ile | Lys | Ala | Lys | Leu | Gly | Glu | Arg | Gly | Tyr | Gly | Ser | Ala | Thr | Val | Asn |
| 305 | | | | | 310 | | | | | 315 | | | | | 320 |

| Ser | Val | Pro | Asp | Phe | Asp | Asp | Ala | Asn | Lys | Thr | Leu | Ala | Ile | Thr | Leu |
| | | | | 325 | | | | | 330 | | | | | 335 | |

| Val | Val | Asp | Ala | Gly | Arg | Arg | Leu | Thr | Val | Arg | Gln | Leu | Arg | Phe | Glu |
| | | | 340 | | | | | 345 | | | | | 350 | | |

| Gly | Asn | Thr | Val | Ser | Ala | Asp | Ser | Thr | Leu | Arg | Gln | Glu | Met | Arg | Gln |
| | 355 | | | | | 360 | | | | | 365 | | | | |

| Gln | Glu | Gly | Thr | Trp | Tyr | Asn | Ser | Gln | Leu | Val | Glu | Leu | Gly | Lys | Ile |
| | 370 | | | | | 375 | | | | | 380 | | | | |

| Arg | Leu | Asp | Arg | Thr | Gly | Phe | Phe | Glu | Thr | Val | Glu | Asn | Arg | Ile | Asp |
| 385 | | | | | 390 | | | | | 395 | | | | | 400 |

```
Pro Ile Asn Gly Ser Asn Asp Glu Val Asp Val Val Tyr Lys Val Lys
            405                 410                 415
Glu Arg Asn Thr Gly Ser Ile Asn Phe Gly Ile Gly Tyr Gly Thr Glu
            420                 425                 430
Ser Gly Ile Ser Tyr Gln Ala Ser Val Lys Gln Asp Asn Phe Leu Gly
            435                 440                 445
Thr Gly Ala Ala Val Ser Ile Ala Gly Thr Lys Asn Asp Tyr Gly Thr
            450                 455                 460
Ser Val Asn Leu Gly Tyr Thr Glu Pro Tyr Phe Thr Lys Asp Gly Val
465                 470                 475                 480
Ser Leu Gly Gly Asn Val Phe Phe Glu Asn Tyr Asp Asn Ser Lys Ser
            485                 490                 495
Asp Thr Ser Ser Asn Tyr Lys Arg Thr Thr Tyr Gly Ser Asn Val Thr
            500                 505                 510
Leu Gly Phe Pro Val Asn Glu Asn Ser Tyr Tyr Val Gly Leu Gly
            515                 520                 525
His Thr Tyr Asn Lys Ile Ser Asn Phe Ala Leu Glu Tyr Asn Arg Asn
            530                 535                 540
Leu Tyr Ile Gln Ser Met Lys Phe Lys Gly Asn Gly Ile Lys Thr Asn
545                 550                 555                 560
Asp Phe Asp Phe Ser Phe Gly Trp Asn Tyr Asn Ser Leu Asn Arg Gly
            565                 570                 575
Tyr Phe Pro Thr Lys Gly Val Lys Ala Ser Leu Gly Gly Arg Val Thr
            580                 585                 590
Ile Pro Gly Ser Asp Asn Lys Tyr Tyr Lys Leu Ser Ala Asp Val Gln
            595                 600                 605
Gly Phe Tyr Pro Leu Asp Arg Asp His Leu Trp Val Val Ser Ala Lys
            610                 615                 620
Ala Ser Ala Gly Tyr Ala Asn Gly Phe Gly Asn Lys Arg Leu Pro Phe
625                 630                 635                 640
Tyr Gln Thr Tyr Thr Ala Gly Gly Ile Gly Ser Leu Arg Gly Phe Ala
            645                 650                 655
Tyr Gly Ser Ile Gly Pro Asn Ala Ile Tyr Ala Glu Tyr Gly Asn Gly
            660                 665                 670
Ser Gly Thr Gly Thr Phe Lys Lys Ile Ser Ser Asp Val Ile Gly Gly
            675                 680                 685
Asn Ala Ile Ala Thr Ala Ser Ala Glu Leu Ile Val Pro Thr Pro Phe
            690                 695                 700
Val Ser Asp Lys Ser Gln Asn Thr Val Arg Thr Ser Leu Phe Val Asp
705                 710                 715                 720
Ala Ala Ser Val Trp Asn Thr Lys Trp Lys Ser Asp Lys Asn Gly Leu
            725                 730                 735
Glu Ser Asp Val Leu Lys Arg Leu Pro Asp Tyr Gly Lys Ser Ser Arg
            740                 745                 750
Ile Arg Ala Ser Thr Gly Val Gly Phe Gln Trp Gln Ser Pro Ile Gly
            755                 760                 765
Pro Leu Val Phe Ser Tyr Ala Lys Pro Ile Lys Lys Tyr Glu Asn Asp
            770                 775                 780
Asp Val Glu Gln Phe Gln Phe Ser Ile Gly Gly Ser Phe
785                 790                 795

(2) INFORMATION FOR SEQ ID NO: 5:
```

(i) SEQUENCE CHARACTERISTICS:
    (A) LENGTH: 2950 base pairs
    (B) TYPE: nucleic acid
    (C) STRANDEDNESS: single
    (D) TOPOLOGY: linear (ii) MOLECULE TYPE: DNA (genomic)

(ix) FEATURE:
    (A) NAME/KEY: CDS
    (B) LOCATION: 334..2724

(xi) SEQUENCE DESCRIPTION: SEQ ID NO: 5:

```
AATCACTTAC TGGCGATTTG TCATTAAATA ATTTAAGTGG GCCAATTTCT ATTGCAAAAG      60

GTGCTGGCAC ATCAGCAAAT ATTGGATTGG TGTATTTTTT AAGTTTTATG GCACTGATTA     120

GTGTAAATTT AGGGATTATG AATTTATTTC CATTACCAGT ATTAGATGGC GGTCATTTAG     180

TTTTTTTAAC AATGGAAGCT GTTAAAGGAA AACCTGTTTC TGAGCGGGTG CAAAGCATCT     240

GTTATCGAAT TGGCGCAGCA CTGTTATTAA GCTTAACGGT GTTTGCATTA TTTAATGATT     300

TTTTACGTCT ATAATTTATA TAGGATACAA TCG ATG AAA AAA CTT CTA ATC GCA      354
                                    Met Lys Lys Leu Leu Ile Ala
                                      1               5

AGT TTA TTA TTC GGT ACG ACA ACG ACT GTG TTT GCC GCA CCT TTT GTG       402
Ser Leu Leu Phe Gly Thr Thr Thr Thr Val Phe Ala Ala Pro Phe Val
         10                  15                  20

GCA AAA GAT ATT CGT GTG GAT GGT GTT CAA GGT GAC TTA GAA CAA CAA       450
Ala Lys Asp Ile Arg Val Asp Gly Val Gln Gly Asp Leu Glu Gln Gln
 25                  30                  35

ATC CGA GCA AGT TTA CCT GTT CGT GCC GGT CAG CGT GTG ACT GAC AAT       498
Ile Arg Ala Ser Leu Pro Val Arg Ala Gly Gln Arg Val Thr Asp Asn
 40                  45                  50                  55

GAT GTG GCT AAT ATT GTC CGC TCT TTA TTC GTA AGT GGT CGA TTC GAT       546
Asp Val Ala Asn Ile Val Arg Ser Leu Phe Val Ser Gly Arg Phe Asp
                 60                  65                  70

GAT GTG AAA GCG CAT CAA GAA GGC GAT GTG CTT GTT GTT AGC GTT GTG       594
Asp Val Lys Ala His Gln Glu Gly Asp Val Leu Val Val Ser Val Val
             75                  80                  85

GCT AAA TCG ATC ATT TCA GAT GTT AAA ATC AAA GGT AAC TCT GTT ATT       642
Ala Lys Ser Ile Ile Ser Asp Val Lys Ile Lys Gly Asn Ser Val Ile
         90                  95                 100

CCC ACT GAA GCA CTT AAA CAA AAC TTA GAT GCT AAC GGG TTT AAA GTT       690
Pro Thr Glu Ala Leu Lys Gln Asn Leu Asp Ala Asn Gly Phe Lys Val
    105                 110                 115

GGC GAT GTT TTA ATT CGA GAA AAA TTA AAT GAA TTT GCC AAA AGT GTA       738
Gly Asp Val Leu Ile Arg Glu Lys Leu Asn Glu Phe Ala Lys Ser Val
120                 125                 130                 135

AAA GAG CAC TAT GCA AGT GTA GGT CGC TAT AAC GCA ACA GTT GAA CCT       786
Lys Glu His Tyr Ala Ser Val Gly Arg Tyr Asn Ala Thr Val Glu Pro
                140                 145                 150

ATT GTC AAT ACG CTA CCA AAT AAT CGC GCT GAA ATT TTA ATT CAA ATC       834
Ile Val Asn Thr Leu Pro Asn Asn Arg Ala Glu Ile Leu Ile Gln Ile
            155                 160                 165

AAT GAA GAT GAT AAA GCA AAA TTG GCA TCA TTA ACT TTC AAG GGG AAC       882
Asn Glu Asp Asp Lys Ala Lys Leu Ala Ser Leu Thr Phe Lys Gly Asn
        170                 175                 180

GAA TCT GTT AGT AGC AGT ACA TTA CAA GAA CAA ATG GAA TTA CAA CCT       930
Glu Ser Val Ser Ser Ser Thr Leu Gln Glu Gln Met Glu Leu Gln Pro
185                 190                 195

GAT TCT TGG TGG AAA TTA TGG GGA AAT AAA TTT GAA GGT GCG CAA TTC       978
Asp Ser Trp Trp Lys Leu Trp Gly Asn Lys Phe Glu Gly Ala Gln Phe
200                 205                 210                 215
```

```
GAG AAA GAT TTG CAG TCA ATT CGT GAT TAT TAT TTA AAT AAT GGC TAT     1026
Glu Lys Asp Leu Gln Ser Ile Arg Asp Tyr Tyr Leu Asn Asn Gly Tyr
                220                 225                 230

GCC AAA GCA CAA ATT ACT AAA ACG GAT GTT CAG CTA AAT GAT GAA AAA     1074
Ala Lys Ala Gln Ile Thr Lys Thr Asp Val Gln Leu Asn Asp Glu Lys
                235                 240                 245

ACA AAA GTT AAT GTA ACC ATT GAT GTA AAT GAA GGT TTA CAG TAT GAC     1122
Thr Lys Val Asn Val Thr Ile Asp Val Asn Glu Gly Leu Gln Tyr Asp
                250                 255                 260

CTT CGT AGT GCA CGC ATT ATA GGT AAT CTG GGA GGT ATG TCT GCC GAG     1170
Leu Arg Ser Ala Arg Ile Ile Gly Asn Leu Gly Gly Met Ser Ala Glu
        265                 270                 275

CTT GAA CCT TTA CTT TCA GCA TTA CAT TTA AAT GAT ACT TTC CGC CGT     1218
Leu Glu Pro Leu Leu Ser Ala Leu His Leu Asn Asp Thr Phe Arg Arg
280                 285                 290                 295

AGT GAT ATT GCA GAT GTA GAA AAT GCA ATT AAA GCA AAA CTT GGA GAA     1266
Ser Asp Ile Ala Asp Val Glu Asn Ala Ile Lys Ala Lys Leu Gly Glu
                300                 305                 310

CGC GGT TAC GGT AGC GCA ACG GTA AAT TCA GTA CCT GAT TTT GAT GAT     1314
Arg Gly Tyr Gly Ser Ala Thr Val Asn Ser Val Pro Asp Phe Asp Asp
                315                 320                 325

GCA AAT AAA ACA TTA GCG ATA ACC CTT GTT GTT GAT GCT GGA CGA CGT     1362
Ala Asn Lys Thr Leu Ala Ile Thr Leu Val Val Asp Ala Gly Arg Arg
            330                 335                 340

TTA ACT GTT CGC CAA CTT CGC TTT GAA GGA AAT ACC GTT TCT GCT GAT     1410
Leu Thr Val Arg Gln Leu Arg Phe Glu Gly Asn Thr Val Ser Ala Asp
        345                 350                 355

AGC ACT TTA CGT CAG GAA ATG CGC CAA CAA GAA GGA ACT TGG TAT AAT     1458
Ser Thr Leu Arg Gln Glu Met Arg Gln Gln Glu Gly Thr Trp Tyr Asn
360                 365                 370                 375

TCA CAA TTA GTT GAG TTA GGA AAA ATT CGC TTA GAT CGT ACA GGT TTC     1506
Ser Gln Leu Val Glu Leu Gly Lys Ile Arg Leu Asp Arg Thr Gly Phe
                380                 385                 390

TTC GAA ACA GTC GAA AAC CGA ATT GAT CCT ATC AAT GGT AGT AAT GAT     1554
Phe Glu Thr Val Glu Asn Arg Ile Asp Pro Ile Asn Gly Ser Asn Asp
                395                 400                 405

GAA GTG GAT GTC GTA TAT AAA GTC AAA GAA CGT AAC ACG GGT AGT ATC     1602
Glu Val Asp Val Val Tyr Lys Val Lys Glu Arg Asn Thr Gly Ser Ile
            410                 415                 420

AAC TTT GGT ATT GGT TAC GGT ACA GAG AGT GGT ATT AGT TAT CAA GCA     1650
Asn Phe Gly Ile Gly Tyr Gly Thr Glu Ser Gly Ile Ser Tyr Gln Ala
        425                 430                 435

AGT GTT AAA CAA GAT AAT TTC TTG GGA ACA GGG GCG GCA GTA AGT ATA     1698
Ser Val Lys Gln Asp Asn Phe Leu Gly Thr Gly Ala Ala Val Ser Ile
440                 445                 450                 455

GCT GGT ACG AAA AAT GAT TAT GGT ACG AGT GTC AAT TTG GGT TAT ACC     1746
Ala Gly Thr Lys Asn Asp Tyr Gly Thr Ser Val Asn Leu Gly Tyr Thr
                460                 465                 470

GAG CCC TAT TTT ACT AAA GAT GGT GTA AGT CTT GGT GGA AAT GTT TTC     1794
Glu Pro Tyr Phe Thr Lys Asp Gly Val Ser Leu Gly Gly Asn Val Phe
            475                 480                 485

TTT GAA AAC TAC GAT AAC TCT AAA AGT GAT ACA TCC TCT AAC TAT AAG     1842
Phe Glu Asn Tyr Asp Asn Ser Lys Ser Asp Thr Ser Ser Asn Tyr Lys
        490                 495                 500

CGT ACG ACT TAC GGA AGT AAT GTT ACT TTA GGT TTC CCT GTA AAT GAA     1890
Arg Thr Thr Tyr Gly Ser Asn Val Thr Leu Gly Phe Pro Val Asn Glu
505                 510                 515

AAT AAC TCC TAT TAT GTA GGA TTA GGT CAT ACC TAT AAT AAA ATT AGT     1938
Asn Asn Ser Tyr Tyr Val Gly Leu Gly His Thr Tyr Asn Lys Ile Ser
```

```
          520              525              530              535
AAC TTT GCT CTA GAA TAT AAC CGT AAT TTA TAT ATT CAA TCA ATG AAA        1986
Asn Phe Ala Leu Glu Tyr Asn Arg Asn Leu Tyr Ile Gln Ser Met Lys
                540              545              550

TTT AAA GGT AAT GGC ATT AAA ACA AAT GAC TTT GAT TTT TCT TTT GGT        2034
Phe Lys Gly Asn Gly Ile Lys Thr Asn Asp Phe Asp Phe Ser Phe Gly
                555              560              565

TGG AAC TAT AAC AGC CTT AAT AGA GGC TAT TTC CCA ACT AAA GGG GTT        2082
Trp Asn Tyr Asn Ser Leu Asn Arg Gly Tyr Phe Pro Thr Lys Gly Val
                570              575              580

AAA GCA AGT CTT GGT GGA CGA GTT ACT ATT CCA GGT TCT GAT AAC AAA        2130
Lys Ala Ser Leu Gly Gly Arg Val Thr Ile Pro Gly Ser Asp Asn Lys
                585              590              595

TAC TAC AAA CTA AGT GCA GAT GTA CAG GGT TTC TAC CCA TTA GAC AGA        2178
Tyr Tyr Lys Leu Ser Ala Asp Val Gln Gly Phe Tyr Pro Leu Asp Arg
600              605              610              615

GAT CAC CTC TGG GTT GTA TCT GCA AAA GCA TCT GCA GGA TAT GCA AAT        2226
Asp His Leu Trp Val Val Ser Ala Lys Ala Ser Ala Gly Tyr Ala Asn
                620              625              630

GGT TTT GGA AAC AAG CGT TTA CCG TTC TAT CAA ACT TAT ACA GCG GGT        2274
Gly Phe Gly Asn Lys Arg Leu Pro Phe Tyr Gln Thr Tyr Thr Ala Gly
                635              640              645

GGC ATC GGT TCA TTA CGT GGT TTT GCT TAT GGT AGT ATT GGA CCT AAC        2322
Gly Ile Gly Ser Leu Arg Gly Phe Ala Tyr Gly Ser Ile Gly Pro Asn
                650              655              660

GCA ATT TAT GCC GAA TAT GGT AAT GGT AGT GGT ACT GGT ACT TTT AAG        2370
Ala Ile Tyr Ala Glu Tyr Gly Asn Gly Ser Gly Thr Gly Thr Phe Lys
                665              670              675

AAG ATA AGT TCT GAT GTG ATT GGT GGT AAT GCA ATC GCT ACA GCT AGC        2418
Lys Ile Ser Ser Asp Val Ile Gly Gly Asn Ala Ile Ala Thr Ala Ser
680              685              690              695

GCA GAG TTA ATT GTG CCA ACT CCA TTT GTG AGC GAT AAG AGC CAA AAT        2466
Ala Glu Leu Ile Val Pro Thr Pro Phe Val Ser Asp Lys Ser Gln Asn
                700              705              710

ACG GTC CGA ACC TCC TTA TTT GTT GAT GCG GCA AGT GTT TGG AAT ACT        2514
Thr Val Arg Thr Ser Leu Phe Val Asp Ala Ala Ser Val Trp Asn Thr
                715              720              725

AAA TGG AAA TCA GAT AAA AAT GGA TTA GAG AGC GAT GTA TTA AAA AGA        2562
Lys Trp Lys Ser Asp Lys Asn Gly Leu Glu Ser Asp Val Leu Lys Arg
                730              735              740

TTG CCT GAT TAT GGC AAA TCA AGC CGT ATT CGC GCC TCT ACA GGT GTC        2610
Leu Pro Asp Tyr Gly Lys Ser Ser Arg Ile Arg Ala Ser Thr Gly Val
                745              750              755

GGA TTC CAA TGG CAA TCT CCT ATT GGG CCA TTG GTA TTC TCT TAT GCC        2658
Gly Phe Gln Trp Gln Ser Pro Ile Gly Pro Leu Val Phe Ser Tyr Ala
760              765              770              775

AAA CCA ATT AAA AAA TAT GAA AAT GAT GAT GTC GAA CAG TTC CAA TTT        2706
Lys Pro Ile Lys Lys Tyr Glu Asn Asp Asp Val Glu Gln Phe Gln Phe
                780              785              790

AGT ATT GGA GGT TCT TTC TAATAAATTG AACTTTTTTC TTCATCAGAA               2754
Ser Ile Gly Gly Ser Phe
                795

CTCAAAAACA ACGTTCTCTG CCTAATTTAA TTGGGCAGAG AAAATATTAA ACCCATCATT     2814

TAATTAAGGA TATTTATCAA ATGAAAAACA TCGCAAAAGT AACCGCACTT GCTTTAGGTA     2874

TTGCACTTGC TTCAGGCTAT GCTTCCGCTG AAGAAAAAAT TGCTTTCATT AATGCGGGTT     2934

ATATTTCAAG GCAAGG                                                     2950
```

-continued (2) INFORMATION FOR SEQ ID NO: 6:

(i) SEQUENCE CHARACTERISTICS:
        (A) LENGTH: 797 amino acids
        (B) TYPE: amino acid
        (D) TOPOLOGY: linear (ii) MOLECULE TYPE: protein (xi) SEQUENCE DESCRIPTION: SEQ ID NO: 6:

```
Met Lys Lys Leu Leu Ile Ala Ser Leu Leu Phe Gly Thr Thr Thr Thr
 1               5                  10                  15

Val Phe Ala Ala Pro Phe Val Ala Lys Asp Ile Arg Val Asp Gly Val
                20                  25                  30

Gln Gly Asp Leu Glu Gln Gln Ile Arg Ala Ser Leu Pro Val Arg Ala
            35                  40                  45

Gly Gln Arg Val Thr Asp Asn Asp Val Ala Asn Ile Val Arg Ser Leu
        50                  55                  60

Phe Val Ser Gly Arg Phe Asp Asp Val Lys Ala His Gln Glu Gly Asp
65                  70                  75                  80

Val Leu Val Val Ser Val Ala Lys Ser Ile Ile Ser Asp Val Lys
                85                  90                  95

Ile Lys Gly Asn Ser Val Ile Pro Thr Glu Ala Leu Lys Gln Asn Leu
                100                 105                 110

Asp Ala Asn Gly Phe Lys Val Gly Asp Val Leu Ile Arg Glu Lys Leu
            115                 120                 125

Asn Glu Phe Ala Lys Ser Val Lys Glu His Tyr Ala Ser Val Gly Arg
        130                 135                 140

Tyr Asn Ala Thr Val Glu Pro Ile Val Asn Thr Leu Pro Asn Asn Arg
145                 150                 155                 160

Ala Glu Ile Leu Ile Gln Ile Asn Glu Asp Asp Lys Ala Lys Leu Ala
                165                 170                 175

Ser Leu Thr Phe Lys Gly Asn Glu Ser Val Ser Ser Thr Leu Gln
            180                 185                 190

Glu Gln Met Glu Leu Gln Pro Asp Ser Trp Trp Lys Leu Trp Gly Asn
        195                 200                 205

Lys Phe Glu Gly Ala Gln Phe Glu Lys Asp Leu Gln Ser Ile Arg Asp
210                 215                 220

Tyr Tyr Leu Asn Asn Gly Tyr Ala Lys Ala Gln Ile Thr Lys Thr Asp
225                 230                 235                 240

Val Gln Leu Asn Asp Glu Lys Thr Lys Val Asn Val Thr Ile Asp Val
                245                 250                 255

Asn Glu Gly Leu Gln Tyr Asp Leu Arg Ser Ala Arg Ile Ile Gly Asn
            260                 265                 270

Leu Gly Gly Met Ser Ala Glu Leu Glu Pro Leu Leu Ser Ala Leu His
        275                 280                 285

Leu Asn Asp Thr Phe Arg Arg Ser Asp Ile Ala Asp Val Glu Asn Ala
290                 295                 300

Ile Lys Ala Lys Leu Gly Glu Arg Gly Tyr Gly Ser Ala Thr Val Asn
305                 310                 315                 320

Ser Val Pro Asp Phe Asp Ala Asn Lys Thr Leu Ala Ile Thr Leu
                325                 330                 335

Val Val Asp Ala Gly Arg Arg Leu Thr Val Arg Gln Leu Arg Phe Glu
            340                 345                 350

Gly Asn Thr Val Ser Ala Asp Ser Thr Leu Arg Gln Glu Met Arg Gln
        355                 360                 365
```

-continued

```
Gln Glu Gly Thr Trp Tyr Asn Ser Gln Leu Val Glu Leu Gly Lys Ile
    370                 375                 380

Arg Leu Asp Arg Thr Gly Phe Phe Glu Thr Val Glu Asn Arg Ile Asp
385                 390                 395                 400

Pro Ile Asn Gly Ser Asn Asp Glu Val Asp Val Val Tyr Lys Val Lys
                405                 410                 415

Glu Arg Asn Thr Gly Ser Ile Asn Phe Gly Ile Gly Tyr Gly Thr Glu
                420                 425                 430

Ser Gly Ile Ser Tyr Gln Ala Ser Val Lys Gln Asp Asn Phe Leu Gly
                435                 440                 445

Thr Gly Ala Ala Val Ser Ile Ala Gly Thr Lys Asn Asp Tyr Gly Thr
    450                 455                 460

Ser Val Asn Leu Gly Tyr Thr Glu Pro Tyr Phe Thr Lys Asp Gly Val
465                 470                 475                 480

Ser Leu Gly Gly Asn Val Phe Phe Glu Asn Tyr Asp Asn Ser Lys Ser
                485                 490                 495

Asp Thr Ser Ser Asn Tyr Lys Arg Thr Thr Tyr Gly Ser Asn Val Thr
                500                 505                 510

Leu Gly Phe Pro Val Asn Glu Asn Asn Ser Tyr Tyr Val Gly Leu Gly
                515                 520                 525

His Thr Tyr Asn Lys Ile Ser Asn Phe Ala Leu Glu Tyr Asn Arg Asn
    530                 535                 540

Leu Tyr Ile Gln Ser Met Lys Phe Lys Gly Asn Gly Ile Lys Thr Asn
545                 550                 555                 560

Asp Phe Asp Phe Ser Phe Gly Trp Asn Tyr Asn Ser Leu Asn Arg Gly
                565                 570                 575

Tyr Phe Pro Thr Lys Gly Val Lys Ala Ser Leu Gly Gly Arg Val Thr
                580                 585                 590

Ile Pro Gly Ser Asp Asn Lys Tyr Tyr Lys Leu Ser Ala Asp Val Gln
                595                 600                 605

Gly Phe Tyr Pro Leu Asp Arg Asp His Leu Trp Val Val Ser Ala Lys
    610                 615                 620

Ala Ser Ala Gly Tyr Ala Asn Gly Phe Gly Asn Lys Arg Leu Pro Phe
625                 630                 635                 640

Tyr Gln Thr Tyr Thr Ala Gly Gly Ile Gly Ser Leu Arg Gly Phe Ala
                645                 650                 655

Tyr Gly Ser Ile Gly Pro Asn Ala Ile Tyr Ala Glu Tyr Gly Asn Gly
                660                 665                 670

Ser Gly Thr Gly Thr Phe Lys Lys Ile Ser Ser Asp Val Ile Gly Gly
                675                 680                 685

Asn Ala Ile Ala Thr Ala Ser Ala Glu Leu Ile Val Pro Thr Pro Phe
    690                 695                 700

Val Ser Asp Lys Ser Gln Asn Thr Val Arg Thr Ser Leu Phe Val Asp
705                 710                 715                 720

Ala Ala Ser Val Trp Asn Thr Trp Lys Ser Asp Lys Asn Gly Leu
                725                 730                 735

Glu Ser Asp Val Leu Lys Arg Leu Pro Asp Tyr Gly Lys Ser Ser Arg
                740                 745                 750

Ile Arg Ala Ser Thr Gly Val Gly Phe Gln Trp Gln Ser Pro Ile Gly
    755                 760                 765

Pro Leu Val Phe Ser Tyr Ala Lys Pro Ile Lys Lys Tyr Glu Asn Asp
770                 775                 780
```

Asp Val Glu Gln Phe Gln Phe Ser Ile Gly Gly Ser Phe
785                 790                 795

(2) INFORMATION FOR SEQ ID NO: 7:

(i) SEQUENCE CHARACTERISTICS:
        (A) LENGTH: 2974 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 386..2761

(xi) SEQUENCE DESCRIPTION: SEQ ID NO: 7:

```
GGCATTGAAA AAACAGGACA GCTTTCCCTT TTAACCTTGA AAATATTAGG GAAATTACTT      60

ACTGGCGATT TGTCATTAAA TAATTTAAGT GGGCCAATTT CTATTGCAAA AGGTGCTGGC     120

GCATCAGCAA ATATTGGATT GGTGTATTTT TTAAGTTTTA TGGCATTGAT TAGTGTAAAT     180

TTAGGGATTA TGAATTTATT TCCATTACCA GTATTAGATG GCGGTCATTT AGTTTTTTTA     240

ACAATGGAAG CTGTTAAAGG AAAACCTGTT TCTGAGCGGG TGCAAAGCAT CTGTTATCGA     300

ATTGGCGCAG CACTGTTATT AAGCTTAACG GTGTTTGCAT TATTTAATGA TTTTTTACGT     360

CTATAATTTA TATAGGATAC AATCG ATG AAA AAA CTT CTA ATC GCA AGT TTA      412
                          Met Lys Lys Leu Leu Ile Ala Ser Leu
                           1                 5
```

```
TTA TTC GGT ACG ACA ACG ACT GTG TTT GCC GCA CCT TTT GTG GCA AAA      460
Leu Phe Gly Thr Thr Thr Thr Val Phe Ala Ala Pro Phe Val Ala Lys
 10                  15                  20                  25

GAT ATT CGT GTG GAT GGT GTT CAA GGT GAC TTA GAA CAA CAA ATC CGA      508
Asp Ile Arg Val Asp Gly Val Gln Gly Asp Leu Glu Gln Gln Ile Arg
             30                  35                  40

GCA AGT TTA CCT GTT CGT GCC GGT CAG CGT GTG ACT GAC AAT GAT GTG      556
Ala Ser Leu Pro Val Arg Ala Gly Gln Arg Val Thr Asp Asn Asp Val
         45                  50                  55

GCT AAT ATT GTC CGC TCT TTA TTC GTA AGT GGT CGA TTC GAT GAT GTG      604
Ala Asn Ile Val Arg Ser Leu Phe Val Ser Gly Arg Phe Asp Asp Val
     60                  65                  70

AAA GCG CAT CAA GAA GGC GAT GTG CTT GTT GTT AGC GTT GTG GCT AAA      652
Lys Ala His Gln Glu Gly Asp Val Leu Val Val Ser Val Val Ala Lys
 75                  80                  85

TCG ATC ATT TCA GAT GTT AAA ATC AAA GGT AAC TCT ATT ATT CCA CCT      700
Ser Ile Ile Ser Asp Val Lys Ile Lys Gly Asn Ser Ile Ile Pro Pro
 90                  95                 100                 105

GAA GCA CTA AAA CAA AAC TTA GAT GCT AAC GGG TTT AAA GTT GGC GAT      748
Glu Ala Leu Lys Gln Asn Leu Asp Ala Asn Gly Phe Lys Val Gly Asp
             110                 115                 120

ATT TTA ATT CGA GAA AAA TTA AAT GAA TTT GCC CAA AGT GTA AAA GAG      796
Ile Leu Ile Arg Glu Lys Leu Asn Glu Phe Ala Gln Ser Val Lys Glu
         125                 130                 135

CAC TAT GCA AGT GTA GGT CGC TAT AAC GCA ACC GTT GAA CCT ATT GTC      844
His Tyr Ala Ser Val Gly Arg Tyr Asn Ala Thr Val Glu Pro Ile Val
     140                 145                 150

AAT ACG CTA CCA AAT AAT CGC GCT GAA ATT TTA ATT CAA ATC AAT GAA      892
Asn Thr Leu Pro Asn Asn Arg Ala Glu Ile Leu Ile Gln Ile Asn Glu
 155                 160                 165

GAT GAT AAA GCC AAA TTG GCA TCA TTA ACT TTC AAG GGG AAC GAA TCT      940
Asp Asp Lys Ala Lys Leu Ala Ser Leu Thr Phe Lys Gly Asn Glu Ser
170                  175                 180                 185
```

```
GTT AGT AGC AGT ACA TTA CAA GAA CAA ATG GAA TTA CAA CCT GAT TCT      988
Val Ser Ser Ser Thr Leu Gln Glu Gln Met Glu Leu Gln Pro Asp Ser
            190                 195                 200

TGG TGG AAA TTA TGG GGA AAT AAA TTT GAA GGT GCG CAA TTC GAG AAA     1036
Trp Trp Lys Leu Trp Gly Asn Lys Phe Glu Gly Ala Gln Phe Glu Lys
            205                 210                 215

GAT TTG CAG GCA ATT CGT GAT TAT TAT TTA AAT AAT GGC TAT GCC AAA     1084
Asp Leu Gln Ala Ile Arg Asp Tyr Tyr Leu Asn Asn Gly Tyr Ala Lys
            220                 225                 230

GCA CAA ATC ACT AAA GCG GAT GTT CAG CTA AAT GAT GAA AAA ACA AAA     1132
Ala Gln Ile Thr Lys Ala Asp Val Gln Leu Asn Asp Glu Lys Thr Lys
            235                 240                 245

GTT AAT GTA ACC ATT GAT GTA AAT GAA GGT TTA CAG TAT GAC CTT CGT     1180
Val Asn Val Thr Ile Asp Val Asn Glu Gly Leu Gln Tyr Asp Leu Arg
250                 255                 260                 265

AGT GCA CGC ATT ATA GGT AAT CTG GGA GGT ATG TCT GCC GAG CTT GAA     1228
Ser Ala Arg Ile Ile Gly Asn Leu Gly Gly Met Ser Ala Glu Leu Glu
            270                 275                 280

CCT TTA CTT TCA GCA TTA CAT TTA AAT GAT ACT TTC CGC CGT AGT GAT     1276
Pro Leu Leu Ser Ala Leu His Leu Asn Asp Thr Phe Arg Arg Ser Asp
            285                 290                 295

ATT GCA GAT GTA GAA AAT GCA ATT AAA GCA AAA CTT GGG GAA CGA GGT     1324
Ile Ala Asp Val Glu Asn Ala Ile Lys Ala Lys Leu Gly Glu Arg Gly
            300                 305                 310

TAC GGT AAC ACA ACA GTA AAT TCT GTA CCT GAT TTT GAC GAT GCA AAT     1372
Tyr Gly Asn Thr Thr Val Asn Ser Val Pro Asp Phe Asp Asp Ala Asn
315                 320                 325

AAA ACA TTA GCG ATA ACC TTT GTT GTT GAT GCT GGA CGA CGT TTA ACT     1420
Lys Thr Leu Ala Ile Thr Phe Val Val Asp Ala Gly Arg Arg Leu Thr
330                 335                 340                 345

GTT CAC CAA CTT CGC TTT GAA GGA AAT ACC GTT TCT GCT GAT AGT ACT     1468
Val His Gln Leu Arg Phe Glu Gly Asn Thr Val Ser Ala Asp Ser Thr
            350                 355                 360

TTA CGT CAG GAA ATG CGC CAA CAA GAA GGA ACT TGG TAT AAT TCA CAA     1516
Leu Arg Gln Glu Met Arg Gln Gln Glu Gly Thr Trp Tyr Asn Ser Gln
            365                 370                 375

TTA GTT GAG TTA GGA AAA ATT CGC TTA GAT CGT ACA GGT TTC TTC GAA     1564
Leu Val Glu Leu Gly Lys Ile Arg Leu Asp Arg Thr Gly Phe Phe Glu
            380                 385                 390

ACA GTT GAA AAC CGA ATT GAT CCT ATC AAT GGT AGC AAT GAT GAA GTG     1612
Thr Val Glu Asn Arg Ile Asp Pro Ile Asn Gly Ser Asn Asp Glu Val
            395                 400                 405

GAT GTC GTA TAT AAA GTC AAA GAA CGT AAC ACG GGT AGT ATC AAC TTT     1660
Asp Val Val Tyr Lys Val Lys Glu Arg Asn Thr Gly Ser Ile Asn Phe
410                 415                 420                 425

GGT ATT GGT TAC GGT ACA GAG AGT GGT ATT AGT TAT CAA GCA AGT GTC     1708
Gly Ile Gly Tyr Gly Thr Glu Ser Gly Ile Ser Tyr Gln Ala Ser Val
            430                 435                 440

AAA CAA GAT AAT TTC TTG GGA ACA GGG GCG GCA GTA AGT ATA GCT GGT     1756
Lys Gln Asp Asn Phe Leu Gly Thr Gly Ala Ala Val Ser Ile Ala Gly
            445                 450                 455

ACG AAA AAT GAT TAT GGT ACG AGT GTC AAT TTG GGT TAT ACC GAG CCC     1804
Thr Lys Asn Asp Tyr Gly Thr Ser Val Asn Leu Gly Tyr Thr Glu Pro
            460                 465                 470

TAT TTT ACT AAA GAT GGT GTA AGT CTT GGT GGA AAT GTT TTC TTT GAA     1852
Tyr Phe Thr Lys Asp Gly Val Ser Leu Gly Gly Asn Val Phe Phe Glu
            475                 480                 485

AAC TAC GAT AAC TCT AAA AGT GAT ACA TCC TCT AAC TAT AAG CGT ACG     1900
Asn Tyr Asp Asn Ser Lys Ser Asp Thr Ser Ser Asn Tyr Lys Arg Thr
```

```
                490                    495                    500                    505
ACT TAT GGA AGT AAT GTT ACT TTA GGT TTC CCT GTA AAT GAA AAT AAC                        1948
Thr Tyr Gly Ser Asn Val Thr Leu Gly Phe Pro Val Asn Glu Asn Asn
                510                    515                    520

TCC TAT TAT GTA GGA TTA GGC CAT ACC TAT AAT AAA ATT AGT AAC TTT                        1996
Ser Tyr Tyr Val Gly Leu Gly His Thr Tyr Asn Lys Ile Ser Asn Phe
                525                    530                    535

GCT CTA GAA TAT AAC CGT AAT TTA TAT ATT CAA TCA ATG AAA TTT AAA                        2044
Ala Leu Glu Tyr Asn Arg Asn Leu Tyr Ile Gln Ser Met Lys Phe Lys
                540                    545                    550

GGT AAT GGC ATT AAA ACA AAT GAC TTT GAT TTT TCT TTT GGT TGG AAC                        2092
Gly Asn Gly Ile Lys Thr Asn Asp Phe Asp Phe Ser Phe Gly Trp Asn
    555                    560                    565

TAT AAC AGC CTT AAT AGA GGC TAT TTC CCA ACT AAA GGG GTT AAA GCA                        2140
Tyr Asn Ser Leu Asn Arg Gly Tyr Phe Pro Thr Lys Gly Val Lys Ala
570                    575                    580                    585

AGT CTT GGT GGA CGA GTT ACA ATT CCA GGT TCT GAT AAC AAA TAC TAC                        2188
Ser Leu Gly Gly Arg Val Thr Ile Pro Gly Ser Asp Asn Lys Tyr Tyr
                590                    595                    600

AAA CTA AGT GCA GAT GTA CAG GGT TTC TAC CCA TTA GAC AGA GAT CAC                        2236
Lys Leu Ser Ala Asp Val Gln Gly Phe Tyr Pro Leu Asp Arg Asp His
                605                    610                    615

CTC TGG GTT GTA TCT GCA AAA GCA TCT GCA GGA TAT GCA AAT GGT TTT                        2284
Leu Trp Val Val Ser Ala Lys Ala Ser Ala Gly Tyr Ala Asn Gly Phe
                620                    625                    630

GGA AAC AAG CGT TTA CCG TTC TAT CAA ACT TAT ACA GCG GGT GGC ATT                        2332
Gly Asn Lys Arg Leu Pro Phe Tyr Gln Thr Tyr Thr Ala Gly Gly Ile
    635                    640                    645

GGT TCA TTA CGC GGT TTT GCT TAT GGT AGC ATT GGG CCT AAC GCA ATT                        2380
Gly Ser Leu Arg Gly Phe Ala Tyr Gly Ser Ile Gly Pro Asn Ala Ile
650                    655                    660                    665

TAT CAA GGT CAA AAT AAT AAA TTT AAT AAG ATA AGT TCT GAT GTG ATT                        2428
Tyr Gln Gly Gln Asn Asn Lys Phe Asn Lys Ile Ser Ser Asp Val Ile
                670                    675                    680

GGT GGT AAT GCA ATC GCT ACA GCT AGC GCA GAG TTA ATT GTG CCA ACT                        2476
Gly Gly Asn Ala Ile Ala Thr Ala Ser Ala Glu Leu Ile Val Pro Thr
                685                    690                    695

CCA TTT GTG AGT GAT AAG AGT CAA AAT ACA GTC CGA ACC TCC CTA TTT                        2524
Pro Phe Val Ser Asp Lys Ser Gln Asn Thr Val Arg Thr Ser Leu Phe
                700                    705                    710

GTT GAT GCG GCA AGT GTT TGG AAT ACT AAA TGG AAA TCA GAT AAA AAT                        2572
Val Asp Ala Ala Ser Val Trp Asn Thr Lys Trp Lys Ser Asp Lys Asn
    715                    720                    725

GGA TTA GAG AGC AAT GTC TTG AAA GAC TTA CCC GAT TAT GGC AAA TCA                        2620
Gly Leu Glu Ser Asn Val Leu Lys Asp Leu Pro Asp Tyr Gly Lys Ser
730                    735                    740                    745

AGC CGT ACT CGC GCC TCT ACA GGT GTC GGA TTC CAA TGG CAA TCT CCT                        2668
Ser Arg Thr Arg Ala Ser Thr Gly Val Gly Phe Gln Trp Gln Ser Pro
                750                    755                    760

AGT GGA CCA GTG GTA TTT TCT TAT GCT AAA CCA ATT AAA AAA TAT GAA                        2716
Ser Gly Pro Val Val Phe Ser Tyr Ala Lys Pro Ile Lys Lys Tyr Glu
                765                    770                    775

AAT GAT GAT GTC GAA CAG TTC CAA TTT AGT ATT GGG GGT TCT TTC                            2761
Asn Asp Asp Val Glu Gln Phe Gln Phe Ser Ile Gly Gly Ser Phe
                780                    785                    790

TAATAAATTG AACTTTTTTC GTCATCAGAA CTCAAAAACA ACGTTCTCTG CCTAATTTAA                      2821

TTGGGCAGAG AAAATATTAA AACCATCATT TAATTAAGGA TATTTATCAA ATGAAAAACA                      2881

TCGCCAAAGT AACCGCACTT GCTTTAGGTA TTGCACTTGC TTCAGGCTAT GCTGCAGCTG                      2941
```

AAGAAAAAAT TGCTTTTATT AATGCAGGTT ATA 2974

(2) INFORMATION FOR SEQ ID NO: 8:

(i) SEQUENCE CHARACTERISTICS:
        (A) LENGTH: 792 amino acids
        (B) TYPE: amino acid
        (D) TOPOLOGY: linear (ii) MOLECULE TYPE: protein (xi) SEQUENCE DESCRIPTION: SEQ ID NO: 8:

```
Met Lys Lys Leu Leu Ile Ala Ser Leu Leu Phe Gly Thr Thr Thr Thr
 1               5                  10                  15

Val Phe Ala Ala Pro Phe Val Ala Lys Asp Ile Arg Val Asp Gly Val
                20                  25                  30

Gln Gly Asp Leu Glu Gln Gln Ile Arg Ala Ser Leu Pro Val Arg Ala
            35                  40                  45

Gly Gln Arg Val Thr Asp Asn Asp Val Ala Asn Ile Val Arg Ser Leu
        50                  55                  60

Phe Val Ser Gly Arg Phe Asp Asp Val Lys Ala His Gln Glu Gly Asp
 65                 70                  75                  80

Val Leu Val Val Ser Val Ala Lys Ser Ile Ser Asp Val Lys
                85                  90                  95

Ile Lys Gly Asn Ser Ile Ile Pro Pro Glu Ala Leu Lys Gln Asn Leu
            100                 105                 110

Asp Ala Asn Gly Phe Lys Val Gly Asp Ile Leu Ile Arg Glu Lys Leu
        115                 120                 125

Asn Glu Phe Ala Gln Ser Val Lys Glu His Tyr Ala Ser Val Gly Arg
130                 135                 140

Tyr Asn Ala Thr Val Glu Pro Ile Val Asn Thr Leu Pro Asn Asn Arg
145                 150                 155                 160

Ala Glu Ile Leu Ile Gln Ile Asn Glu Asp Asp Lys Ala Lys Leu Ala
                165                 170                 175

Ser Leu Thr Phe Lys Gly Asn Glu Ser Val Ser Ser Ser Thr Leu Gln
            180                 185                 190

Glu Gln Met Glu Leu Gln Pro Asp Ser Trp Trp Lys Leu Trp Gly Asn
        195                 200                 205

Lys Phe Glu Gly Ala Gln Phe Glu Lys Asp Leu Gln Ala Ile Arg Asp
210                 215                 220

Tyr Tyr Leu Asn Asn Gly Tyr Ala Lys Ala Gln Ile Thr Lys Ala Asp
225                 230                 235                 240

Val Gln Leu Asn Asp Glu Lys Thr Lys Val Asn Val Thr Ile Asp Val
                245                 250                 255

Asn Glu Gly Leu Gln Tyr Asp Leu Arg Ser Ala Arg Ile Ile Gly Asn
            260                 265                 270

Leu Gly Gly Met Ser Ala Glu Leu Glu Pro Leu Leu Ser Ala Leu His
        275                 280                 285

Leu Asn Asp Thr Phe Arg Arg Ser Asp Ile Ala Asp Val Glu Asn Ala
290                 295                 300

Ile Lys Ala Lys Leu Gly Glu Arg Gly Tyr Gly Asn Thr Thr Val Asn
305                 310                 315                 320

Ser Val Pro Asp Phe Asp Asp Ala Asn Lys Thr Leu Ala Ile Thr Phe
                325                 330                 335

Val Val Asp Ala Gly Arg Arg Leu Thr Val His Gln Leu Arg Phe Glu
```

-continued

```
                340                 345                 350
Gly Asn Thr Val Ser Ala Asp Ser Thr Leu Arg Gln Glu Met Arg Gln
            355                 360                 365

Gln Glu Gly Thr Trp Tyr Asn Ser Gln Leu Val Glu Leu Gly Lys Ile
370                 375                 380

Arg Leu Asp Arg Thr Gly Phe Phe Glu Thr Val Glu Asn Arg Ile Asp
385                 390                 395                 400

Pro Ile Asn Gly Ser Asn Asp Glu Val Asp Val Tyr Lys Val Lys
                405                 410                 415

Glu Arg Asn Thr Gly Ser Ile Asn Phe Gly Ile Gly Tyr Gly Thr Glu
            420                 425                 430

Ser Gly Ile Ser Tyr Gln Ala Ser Val Lys Gln Asp Asn Phe Leu Gly
            435                 440                 445

Thr Gly Ala Ala Val Ser Ile Ala Gly Thr Lys Asn Asp Tyr Gly Thr
450                 455                 460

Ser Val Asn Leu Gly Tyr Thr Glu Pro Tyr Phe Thr Lys Asp Gly Val
465                 470                 475                 480

Ser Leu Gly Gly Asn Val Phe Phe Glu Asn Tyr Asp Asn Ser Lys Ser
                485                 490                 495

Asp Thr Ser Ser Asn Tyr Lys Arg Thr Thr Tyr Gly Ser Asn Val Thr
            500                 505                 510

Leu Gly Phe Pro Val Asn Glu Asn Asn Ser Tyr Tyr Val Gly Leu Gly
            515                 520                 525

His Thr Tyr Asn Lys Ile Ser Asn Phe Ala Leu Glu Tyr Asn Arg Asn
            530                 535                 540

Leu Tyr Ile Gln Ser Met Lys Phe Lys Gly Asn Gly Ile Lys Thr Asn
545                 550                 555                 560

Asp Phe Asp Phe Ser Phe Gly Trp Asn Tyr Asn Ser Leu Asn Arg Gly
                565                 570                 575

Tyr Phe Pro Thr Lys Gly Val Lys Ala Ser Leu Gly Gly Arg Val Thr
            580                 585                 590

Ile Pro Gly Ser Asp Asn Lys Tyr Tyr Lys Leu Ser Ala Asp Val Gln
            595                 600                 605

Gly Phe Tyr Pro Leu Asp Arg Asp His Leu Trp Val Val Ser Ala Lys
            610                 615                 620

Ala Ser Ala Gly Tyr Ala Asn Gly Phe Gly Asn Lys Arg Leu Pro Phe
625                 630                 635                 640

Tyr Gln Thr Tyr Thr Ala Gly Gly Ile Gly Ser Leu Arg Gly Phe Ala
                645                 650                 655

Tyr Gly Ser Ile Gly Pro Asn Ala Ile Tyr Gln Gly Gln Asn Asn Lys
            660                 665                 670

Phe Asn Lys Ile Ser Ser Asp Val Ile Gly Gly Asn Ala Ile Ala Thr
            675                 680                 685

Ala Ser Ala Glu Leu Ile Val Pro Thr Pro Phe Val Ser Asp Lys Ser
690                 695                 700

Gln Asn Thr Val Arg Thr Ser Leu Phe Val Asp Ala Ala Ser Val Trp
705                 710                 715                 720

Asn Thr Lys Trp Lys Ser Asp Lys Asn Gly Leu Glu Ser Asn Val Leu
                725                 730                 735

Lys Asp Leu Pro Asp Tyr Gly Lys Ser Ser Arg Thr Arg Ala Ser Thr
            740                 745                 750

Gly Val Gly Phe Gln Trp Gln Ser Pro Ser Gly Pro Val Val Phe Ser
            755                 760                 765
```

(2) INFORMATION FOR SEQ ID NO: 9:

(i) SEQUENCE CHARACTERISTICS:
        (A) LENGTH: 2989 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 390..2768

(xi) SEQUENCE DESCRIPTION: SEQ ID NO: 9:

```
Tyr Ala Lys Pro Ile Lys Lys Tyr Glu Asn Asp Val Glu Gln Phe
    770                 775                 780

Gln Phe Ser Ile Gly Gly Ser Phe
785                 790

AAAAGGCATT GAAAAAACAG GACAACTTTC CCTTTTAAACC TTGAAAATAT TAGGGAAATT      60

ACTTACTGGC GATTTGTCAT TAAATAATTT AAGTGGGCCA ATTTCTATTG CAAAAGGTGC     120

TGGTGCATCA GCAAATATTG GATTGGTGTA TTTTTTAAGT TTTATGGCAT TGATTAGTGT     180

AAATTTAGGG ATTATGAATT TATTTCCATT ACCAGTATTA GATGGCGGTC ATTTAGTTTT     240

TTTAACAATG GAAGCTGTTA AAGGAAAACC TGTTTCTGAG CGGGTGCAAA GCATCTGTTA     300

TCGAATTGGC GCAGCACTGT TATTAAGCTT AACGGTGTTT GCATTATTTA ATGATTTTTT     360

ACGTCTATAA TTTATATAGG ATACAATCG ATG AAA AAA CTT CTA ATC GCA AGT      413
                                 Met Lys Lys Leu Leu Ile Ala Ser
                                   1               5

TTA TTA TTC GGT GCG ACA ACG ACT GTG TTT GCC GCA CCT TTT GTG CCA      461
Leu Leu Phe Gly Ala Thr Thr Thr Val Phe Ala Ala Pro Phe Val Pro
    10              15                  20

AAA GAT ATT CGT GTG GAT GGT GTT CAA GGT GAC TTA GAA CAA CAA ATC      509
Lys Asp Ile Arg Val Asp Gly Val Gln Gly Asp Leu Glu Gln Gln Ile
 25              30                  35                  40

CGA GCA AGT TTA CCT GTT CGT GCT GGT CAG CGT GTG ACT GAC AAT GAT      557
Arg Ala Ser Leu Pro Val Arg Ala Gly Gln Arg Val Thr Asp Asn Asp
                45                  50                  55

GTG GCT AAT ATT GTC CGC TCT TTA TTC GTA AGT GGT CGA TTC GAT GAT      605
Val Ala Asn Ile Val Arg Ser Leu Phe Val Ser Gly Arg Phe Asp Asp
                    60                  65                  70

GTG AAA GCG CAT CAA GAA GGC GAT GTG CTT GTT GTT AGC GTT GTG GCT      653
Val Lys Ala His Gln Glu Gly Asp Val Leu Val Val Ser Val Val Ala
     75                  80                  85

AAA TCG ATC ATT TCA GAT GTT AAA ATC AAA GGT AAC TCT GTT ATT CCC      701
Lys Ser Ile Ile Ser Asp Val Lys Ile Lys Gly Asn Ser Val Ile Pro
 90                  95                 100

ACT GAA GCA CTT AAA CAA AAC TTA GAT GCT AAC GGG TTT AAA GTT GGC      749
Thr Glu Ala Leu Lys Gln Asn Leu Asp Ala Asn Gly Phe Lys Val Gly
105                 110                 115                 120

GAT GTT TTA ATT CGA GAA AAA TTA AAT GAA TTT GCC AAA AGT GTA AAA      797
Asp Val Leu Ile Arg Glu Lys Leu Asn Glu Phe Ala Lys Ser Val Lys
                125                 130                 135

GAG CAC TAT GCA AGT GTA GGT CGC TAT AAC GCA ACC GTT GAA CCT ATT      845
Glu His Tyr Ala Ser Val Gly Arg Tyr Asn Ala Thr Val Glu Pro Ile
                140                 145                 150

GTC AAT ACG CTG CCA AAT AAT CGT GCT GAA ATT TTA ATT CAA ATC AAT      893
Val Asn Thr Leu Pro Asn Asn Arg Ala Glu Ile Leu Ile Gln Ile Asn
                    155                 160                 165
```

-continued

```
GAA GAT GAT AAA GCA AAA TTG GCA TCA TTA ACT TTC AAG GGG AAC GAA      941
Glu Asp Asp Lys Ala Lys Leu Ala Ser Leu Thr Phe Lys Gly Asn Glu
    170                 175                 180

TCT GTT AGT AGC AGT ACA TTA CAA GAA CAA ATG GAA TTA CAA CCT GAT      989
Ser Val Ser Ser Ser Thr Leu Gln Glu Gln Met Glu Leu Gln Pro Asp
185                 190                 195                 200

TCT TGG TGG AAA TTA TGG GGA AAT AAA TTT GAA GGT GCG CAA TTC GAG     1037
Ser Trp Trp Lys Leu Trp Gly Asn Lys Phe Glu Gly Ala Gln Phe Glu
                205                 210                 215

AAA GAT CTG CAG GCA ATT CGT GAT TAT TAT TTA AAT AAT GGC TAT GCC     1085
Lys Asp Leu Gln Ala Ile Arg Asp Tyr Tyr Leu Asn Asn Gly Tyr Ala
            220                 225                 230

AAA GCA CAA ATC ACT AAA ACG GAT GTT CAG CTA AAT GAT GAA AAA ACA     1133
Lys Ala Gln Ile Thr Lys Thr Asp Val Gln Leu Asn Asp Glu Lys Thr
        235                 240                 245

AAA GTT AAT GTA ACC ATT GAT GTA AAT GAA GGT TTA CAG TAT GAC CTT     1181
Lys Val Asn Val Thr Ile Asp Val Asn Glu Gly Leu Gln Tyr Asp Leu
250                 255                 260

CGT AGT GCA CGC ATT ATA GGT AAT CTG GGA GGT ATG TCT GCC GAG CTT     1229
Arg Ser Ala Arg Ile Ile Gly Asn Leu Gly Gly Met Ser Ala Glu Leu
265                 270                 275                 280

GAA CCT TTA CTT TCA GCA TTA CAT TTA AAT GAT ACT TTC CGC CGT AGT     1277
Glu Pro Leu Leu Ser Ala Leu His Leu Asn Asp Thr Phe Arg Arg Ser
                285                 290                 295

GAT ATT GCA GAT GTA GAA AAT GCA ATT AAA GCA AAA CTT GGG GAA CGA     1325
Asp Ile Ala Asp Val Glu Asn Ala Ile Lys Ala Lys Leu Gly Glu Arg
            300                 305                 310

GGT TAC GGT AAC ACA ACA GTA AAT TCT GTA CCT GAT TTT GAC GAT GCA     1373
Gly Tyr Gly Asn Thr Thr Val Asn Ser Val Pro Asp Phe Asp Asp Ala
        315                 320                 325

AAT AAA ACA TTA GCG ATA ACC TTT GTT GTT GAT GCT GGA CGA CGT TTA     1421
Asn Lys Thr Leu Ala Ile Thr Phe Val Val Asp Ala Gly Arg Arg Leu
330                 335                 340

ACT GTT CGC CAA CTT CGC TTT GAA GGA AAT ACC GTT TCT GCT GAT AGT     1469
Thr Val Arg Gln Leu Arg Phe Glu Gly Asn Thr Val Ser Ala Asp Ser
345                 350                 355                 360

ACT TTA CGT CAG GAA ATG CGA CAA CAA GAA GGA ACT TGG TAT AAT TCA     1517
Thr Leu Arg Gln Glu Met Arg Gln Gln Glu Gly Thr Trp Tyr Asn Ser
                365                 370                 375

CAA TTA GTT GAG TTA GGA AAA ATT CGC TTA GAT CGT ACA GGT TTC TTC     1565
Gln Leu Val Glu Leu Gly Lys Ile Arg Leu Asp Arg Thr Gly Phe Phe
            380                 385                 390

GAA ACA GTT GAA AAC CGA ATT GAT CCT ATC AAT GGT AGC AAT GAT GAA     1613
Glu Thr Val Glu Asn Arg Ile Asp Pro Ile Asn Gly Ser Asn Asp Glu
        395                 400                 405

GTG GAT GTC GTA TAT AAA GTC AAA GAA CGT AAC ACG GGT AGT ATC AAC     1661
Val Asp Val Val Tyr Lys Val Lys Glu Arg Asn Thr Gly Ser Ile Asn
410                 415                 420

TTT GGT ATT GGT TAC GGT ACA GAG AGT GGT ATC AGT TAT CAA ACA AGT     1709
Phe Gly Ile Gly Tyr Gly Thr Glu Ser Gly Ile Ser Tyr Gln Thr Ser
425                 430                 435                 440

ATT AAA CAA GAT AAT TTC TTG GGA ACA GGG GCG GCA GTA AGT ATA GCT     1757
Ile Lys Gln Asp Asn Phe Leu Gly Thr Gly Ala Ala Val Ser Ile Ala
                445                 450                 455

GGT ACG AAA AAT GAT TAT GGT ACG AGT GTC AAT TTG GGT TAT ACC GAA     1805
Gly Thr Lys Asn Asp Tyr Gly Thr Ser Val Asn Leu Gly Tyr Thr Glu
            460                 465                 470

CCC TAT TTT ACT AAA GAT GGT GTA AGT CTT GGT GGA AAT ATT TTC TTT     1853
Pro Tyr Phe Thr Lys Asp Gly Val Ser Leu Gly Gly Asn Ile Phe Phe
```

```
                    475                    480                    485
GAA AAC TAC GAT AAC TCT AAA AGT GAT ACA TCC TCT AAC TAT AAG CGT              1901
Glu Asn Tyr Asp Asn Ser Lys Ser Asp Thr Ser Ser Asn Tyr Lys Arg
    490                 495                 500

ACG ACT TAT GGA AGT AAT GTT ACT TTA GGT TTC CCT GTA AAT GAA AAT              1949
Thr Thr Tyr Gly Ser Asn Val Thr Leu Gly Phe Pro Val Asn Glu Asn
505                 510                 515                 520

AAC TCC TAT TAT GTA GGA TTA GGC CAT ACC TAT AAT AAA ATT AGT AAC              1997
Asn Ser Tyr Tyr Val Gly Leu Gly His Thr Tyr Asn Lys Ile Ser Asn
                525                 530                 535

TTT GCT CTA GAA TAT AAC CGT AAT TTA TAT ATT CAA TCA ATG AAA TTT              2045
Phe Ala Leu Glu Tyr Asn Arg Asn Leu Tyr Ile Gln Ser Met Lys Phe
            540                 545                 550

AAA GGT AAT GGC ATT AAA ACA AAT GAC TTT GAT TTT TCT TTT GGT TGG              2093
Lys Gly Asn Gly Ile Lys Thr Asn Asp Phe Asp Phe Ser Phe Gly Trp
        555                 560                 565

AAC TAT AAC AGC CTT AAT AGA GGC TAT TTC CCA ACT AAA GGG GTT AAA              2141
Asn Tyr Asn Ser Leu Asn Arg Gly Tyr Phe Pro Thr Lys Gly Val Lys
    570                 575                 580

GCA AGT CTT GGT GGA CGA GTT ACT ATT CCA GGT TCT GAT AAC AAA TAC              2189
Ala Ser Leu Gly Gly Arg Val Thr Ile Pro Gly Ser Asp Asn Lys Tyr
585                 590                 595                 600

TAC AAA CTA AGT GCA GAT GTA CAG GGT TTC TAC CCA TTA GAC AGA GAT              2237
Tyr Lys Leu Ser Ala Asp Val Gln Gly Phe Tyr Pro Leu Asp Arg Asp
                605                 610                 615

CAC CGC TGG GTT GTA TCT GCA AAA GCA TCT GCA GGA TAT GCA AAT GGT              2285
His Arg Trp Val Val Ser Ala Lys Ala Ser Ala Gly Tyr Ala Asn Gly
            620                 625                 630

TTT GGA AAC AAG CGT TTA CCG TTC TAT CAA ACT TAT ACA GCG GGT GGC              2333
Phe Gly Asn Lys Arg Leu Pro Phe Tyr Gln Thr Tyr Thr Ala Gly Gly
        635                 640                 645

ATT GGT TCA TTA CGC GGT TTT GCT TAT GGT AGT ATT GGG CCT AAT GCA              2381
Ile Gly Ser Leu Arg Gly Phe Ala Tyr Gly Ser Ile Gly Pro Asn Ala
    650                 655                 660

ATT TAT GCC GAA CAT GGT AAT GGT ACT TTT AAT AAG ATA AGT TCT GAT              2429
Ile Tyr Ala Glu His Gly Asn Gly Thr Phe Asn Lys Ile Ser Ser Asp
665                 670                 675                 680

GTG ATT GGT GGT AAT GCA ATC ACA ACT GCG AGT GCA GAA CTT ATT GTA              2477
Val Ile Gly Gly Asn Ala Ile Thr Thr Ala Ser Ala Glu Leu Ile Val
                685                 690                 695

CCA ACT CCA TTT GTG AGT GAT AAA AGC CAA AAT ACA GTC CGA ACC TCC              2525
Pro Thr Pro Phe Val Ser Asp Lys Ser Gln Asn Thr Val Arg Thr Ser
            700                 705                 710

CTA TTT GTT GAT GCG GCA AGT GTT TGG AAT ACT AAA TGG AAA TCA GAT              2573
Leu Phe Val Asp Ala Ala Ser Val Trp Asn Thr Lys Trp Lys Ser Asp
        715                 720                 725

AAA AAT GGA TTA GAG AGC AAG GTC TTG AAA GAC TTA CCT GAT TAT GGC              2621
Lys Asn Gly Leu Glu Ser Lys Val Leu Lys Asp Leu Pro Asp Tyr Gly
    730                 735                 740

AAA TCA AGC CGT ATT CGC GCC TCT ACA GGT GTC GGA TTC CAA TGG CAA              2669
Lys Ser Ser Arg Ile Arg Ala Ser Thr Gly Val Gly Phe Gln Trp Gln
745                 750                 755                 760

TCT CCT ATT GGA CCA TTG GTA TTT TCT TAT GCT AAA CCA ATT AAA AAA              2717
Ser Pro Ile Gly Pro Leu Val Phe Ser Tyr Ala Lys Pro Ile Lys Lys
                765                 770                 775

TAT GAA AAT GAT GAT GTC GAA CAG TTC CAA TTT AGT ATT GGG GGC TCT              2765
Tyr Glu Asn Asp Asp Val Glu Gln Phe Gln Phe Ser Ile Gly Gly Ser
            780                 785                 790

TTC TAATAAATTG AACTTTTTTC GTCATCAGAA CTCAAAAACG ACGTTCTCTG                   2818
```

Phe

CCTAATTGAA TTGGGCAGAG AAAATATTAA ACCCATCATT TAATTAAGGA TATTTATCAA   2878

ATGAAAAACA TCGCAAAAGT AACCGCACTT GCTTTAGGTT TTGCACTTGC TTCAGGCTAT   2938

GCTTCCGCTG AAGAAAAAAT TGCTTTCATT AATGCAGGTT ATATTTTTCA A           2989

(2) INFORMATION FOR SEQ ID NO: 10:

(i) SEQUENCE CHARACTERISTICS:
        (A) LENGTH: 793 amino acids
        (B) TYPE: amino acid
        (D) TOPOLOGY: linear (ii) MOLECULE TYPE: protein (xi) SEQUENCE DESCRIPTION: SEQ ID NO: 10:

```
Met Lys Lys Leu Leu Ile Ala Ser Leu Leu Phe Gly Ala Thr Thr Thr
 1               5                  10                  15

Val Phe Ala Ala Pro Phe Val Pro Lys Asp Ile Arg Val Asp Gly Val
                20                  25                  30

Gln Gly Asp Leu Glu Gln Gln Ile Arg Ala Ser Leu Pro Val Arg Ala
            35                  40                  45

Gly Gln Arg Val Thr Asp Asn Asp Val Ala Asn Ile Val Arg Ser Leu
        50                  55                  60

Phe Val Ser Gly Arg Phe Asp Asp Val Lys Ala His Gln Glu Gly Asp
65                  70                  75                  80

Val Leu Val Val Ser Val Ala Lys Ser Ile Ile Ser Asp Val Lys
                85                  90                  95

Ile Lys Gly Asn Ser Val Ile Pro Thr Glu Ala Leu Lys Gln Asn Leu
                100                 105                 110

Asp Ala Asn Gly Phe Lys Val Gly Asp Val Leu Ile Arg Glu Lys Leu
            115                 120                 125

Asn Glu Phe Ala Lys Ser Val Lys Glu His Tyr Ala Ser Val Gly Arg
        130                 135                 140

Tyr Asn Ala Thr Val Glu Pro Ile Val Asn Thr Leu Pro Asn Asn Arg
145                 150                 155                 160

Ala Glu Ile Leu Ile Gln Ile Asn Glu Asp Asp Lys Ala Lys Leu Ala
                165                 170                 175

Ser Leu Thr Phe Lys Gly Asn Glu Ser Val Ser Ser Thr Leu Gln
            180                 185                 190

Glu Gln Met Glu Leu Gln Pro Asp Ser Trp Trp Lys Leu Trp Gly Asn
        195                 200                 205

Lys Phe Glu Gly Ala Gln Phe Glu Lys Asp Leu Gln Ala Ile Arg Asp
    210                 215                 220

Tyr Tyr Leu Asn Asn Gly Tyr Ala Lys Ala Gln Ile Thr Lys Thr Asp
225                 230                 235                 240

Val Gln Leu Asn Asp Glu Lys Thr Lys Val Asn Val Thr Ile Asp Val
                245                 250                 255

Asn Glu Gly Leu Gln Tyr Asp Leu Arg Ser Ala Arg Ile Ile Gly Asn
            260                 265                 270

Leu Gly Gly Met Ser Ala Glu Leu Glu Pro Leu Leu Ser Ala Leu His
        275                 280                 285

Leu Asn Asp Thr Phe Arg Arg Ser Asp Ile Ala Asp Val Glu Asn Ala
    290                 295                 300

Ile Lys Ala Lys Leu Gly Glu Arg Gly Tyr Gly Asn Thr Thr Val Asn
305                 310                 315                 320
```

```
Ser Val Pro Asp Phe Asp Asp Ala Asn Lys Thr Leu Ala Ile Thr Phe
            325                 330                 335

Val Val Asp Ala Gly Arg Arg Leu Thr Val Arg Gln Leu Arg Phe Glu
            340                 345                 350

Gly Asn Thr Val Ser Ala Asp Ser Thr Leu Arg Gln Glu Met Arg Gln
            355                 360                 365

Gln Glu Gly Thr Trp Tyr Asn Ser Gln Leu Val Glu Leu Gly Lys Ile
            370                 375                 380

Arg Leu Asp Arg Thr Gly Phe Phe Glu Thr Val Glu Asn Arg Ile Asp
385                 390                 395                 400

Pro Ile Asn Gly Ser Asn Asp Glu Val Asp Val Val Tyr Lys Val Lys
            405                 410                 415

Glu Arg Asn Thr Gly Ser Ile Asn Phe Gly Ile Gly Tyr Gly Thr Glu
            420                 425                 430

Ser Gly Ile Ser Tyr Gln Thr Ser Ile Lys Gln Asp Asn Phe Leu Gly
            435                 440                 445

Thr Gly Ala Ala Val Ser Ile Ala Gly Thr Lys Asn Asp Tyr Gly Thr
            450                 455                 460

Ser Val Asn Leu Gly Tyr Thr Glu Pro Tyr Phe Thr Lys Asp Gly Val
465                 470                 475                 480

Ser Leu Gly Gly Asn Ile Phe Phe Glu Asn Tyr Asp Asn Ser Lys Ser
            485                 490                 495

Asp Thr Ser Ser Asn Tyr Lys Arg Thr Thr Tyr Gly Ser Asn Val Thr
            500                 505                 510

Leu Gly Phe Pro Val Asn Glu Asn Asn Ser Tyr Tyr Val Gly Leu Gly
            515                 520                 525

His Thr Tyr Asn Lys Ile Ser Asn Phe Ala Leu Glu Tyr Asn Arg Asn
            530                 535                 540

Leu Tyr Ile Gln Ser Met Lys Phe Lys Gly Asn Gly Ile Lys Thr Asn
545                 550                 555                 560

Asp Phe Asp Phe Ser Phe Gly Trp Asn Tyr Asn Ser Leu Asn Arg Gly
            565                 570                 575

Tyr Phe Pro Thr Lys Gly Val Lys Ala Ser Leu Gly Gly Arg Val Thr
            580                 585                 590

Ile Pro Gly Ser Asp Asn Lys Tyr Tyr Lys Leu Ser Ala Asp Val Gln
            595                 600                 605

Gly Phe Tyr Pro Leu Asp Arg Asp His Arg Trp Val Val Ser Ala Lys
            610                 615                 620

Ala Ser Ala Gly Tyr Ala Asn Gly Phe Gly Asn Lys Arg Leu Pro Phe
625                 630                 635                 640

Tyr Gln Thr Tyr Thr Ala Gly Gly Ile Gly Ser Leu Arg Gly Phe Ala
            645                 650                 655

Tyr Gly Ser Ile Gly Pro Asn Ala Ile Tyr Ala Glu His Gly Asn Gly
            660                 665                 670

Thr Phe Asn Lys Ile Ser Ser Asp Val Ile Gly Gly Asn Ala Ile Thr
            675                 680                 685

Thr Ala Ser Ala Glu Leu Ile Val Pro Thr Pro Phe Val Ser Asp Lys
            690                 695                 700

Ser Gln Asn Thr Val Arg Thr Ser Leu Phe Val Asp Ala Ala Ser Val
705                 710                 715                 720

Trp Asn Thr Lys Trp Lys Ser Asp Lys Asn Gly Leu Glu Ser Lys Val
            725                 730                 735
```

-continued

```
Leu Lys Asp Leu Pro Asp Tyr Gly Lys Ser Ser Arg Ile Arg Ala Ser
            740                 745                 750

Thr Gly Val Gly Phe Gln Trp Gln Ser Pro Ile Gly Pro Leu Val Phe
        755                 760                 765

Ser Tyr Ala Lys Pro Ile Lys Lys Tyr Glu Asn Asp Val Glu Gln
770                 775                 780

Phe Gln Phe Ser Ile Gly Gly Ser Phe
785                 790
```

(2) INFORMATION FOR SEQ ID NO: 11:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 11:

```
Ala Pro Phe Val Ala Lys
1               5
```

(2) INFORMATION FOR SEQ ID NO: 12:

(i) SEQUENCE CHARACTERISTICS:
        (A) LENGTH: 23 amino acids
        (B) TYPE: amino acid
        (C) STRANDEDNESS: single
        (D) TOPOLOGY: linear (xi) SEQUENCE DESCRIPTION: SEQ ID NO: 12:

```
Ser Leu Phe Val Ser Gly Arg Phe Asp Asp Val Lys Ala His Gln Glu
1               5                   10                  15

Gly Asp Val Leu Val Val Ser
            20
```

(2) INFORMATION FOR SEQ ID NO: 13:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 13:

```
Met Ser Pro Ile Leu Gly Tyr Trp Lys
1               5
```

(2) INFORMATION FOR SEQ ID NO: 14:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 14:

```
Ala Pro Phe Val Ala Lys Asp Ile Arg Val Asp Gly Val Gln Gly Asp
1               5                   10                  15

Leu Glu Gln Gln Ile Arg Ala Ser Leu Pro Val Arg Ala Gly
            20                  25                  30
```

(2) INFORMATION FOR SEQ ID NO: 15:

(i) SEQUENCE CHARACTERISTICS:
        (A) LENGTH: 30 amino acids

```
    (B) TYPE: amino acid
    (C) STRANDEDNESS: single
    (D) TOPOLOGY: linear (xi) SEQUENCE DESCRIPTION: SEQ ID NO: 15:

Pro Val Arg Ala Gly Gln Arg Val Thr Asp Asn Asp Val Ala Met Ile
1               5                   10                  15

Val Arg Ser Leu Phe Val Ser Gly Arg Phe Asp Asp Val Lys
            20                  25                  30

(2) INFORMATION FOR SEQ ID NO: 16:

(i) SEQUENCE CHARACTERISTICS:
        (A) LENGTH: 32 amino acids
        (B) TYPE: amino acid
        (C) STRANDEDNESS: single
        (D) TOPOLOGY: linear (xi) SEQUENCE DESCRIPTION: SEQ ID NO: 16:

Gly Arg Phe Asp Asp Val Lys Ala His Gln Glu Gly Asp Val Leu Val
1               5                   10                  15

Val Ser Val Ala Lys Ser Ile Ile Ser Asp Val Lys Ile Lys Gly
            20                  25                  30

(2) INFORMATION FOR SEQ ID NO: 17:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 17:

Ser Asp Val Lys Ile Lys Gly Asn Ser Val Ile Pro Thr Glu Ala Leu
1               5                   10                  15

Lys Gln Asn Leu Asp Ala Asn Gly Phe Lys Val Gly Asp Val
            20                  25                  30

(2) INFORMATION FOR SEQ ID NO: 18:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 18:

Ala Asn Gly Phe Lys Val Gly Asp Val Leu Ile Arg Glu Lys Leu Asn
1               5                   10                  15

Glu Phe Ala Lys Ser Val Lys Glu His Tyr Ala Ser Val Gly
            20                  25                  30

(2) INFORMATION FOR SEQ ID NO: 19:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 19:

Val Lys Glu His Tyr Ala Ser Val Gly Arg Tyr Asn Ala Thr Val Glu
1               5                   10                  15

Pro Ile Val Asn Thr Leu Pro Asn Asn Arg Ala Glu Ile Leu
            20                  25                  30
```

(2) INFORMATION FOR SEQ ID NO: 20:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 20:

Pro Asn Asn Arg Ala Glu Ile Leu Ile Gln Ile Asn Glu Asp Asp Lys
    1               5                   10                  15

Ala Lys Leu Ala Ser Leu Thr Phe Lys Gly Asn Glu Ser Val Ser
                20                  25                  30

(2) INFORMATION FOR SEQ ID NO: 21:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 21:

Phe Lys Gly Asn Glu Ser Val Ser Ser Thr Leu Gln Glu Gln Met
    1               5                   10                  15

Glu Leu Gln Pro Asp Ser Trp Trp Lys Lys Leu Trp Gly Asn Lys
                20                  25                  30

(2) INFORMATION FOR SEQ ID NO: 22:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 22:

Pro Asp Ser Trp Trp Lys Leu Trp Gly Asn Lys Phe Glu Gly Ala Gln
    1               5                   10                  15

Phe Glu Lys Asp Leu Gln Ser Ile Arg Asp Tyr Tyr Leu Asn
                20                  25                  30

(2) INFORMATION FOR SEQ ID NO: 23:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 23:

Leu Gln Ser Ile Arg Asp Tyr Tyr Leu Asn Asn Gly Tyr Ala Lys Ala
    1               5                   10                  15

Gln Ile Thr Lys Thr Asp Val Gln Leu Asn Asp Glu Lys Thr Lys
                20                  25                  30

(2) INFORMATION FOR SEQ ID NO: 24:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 24:

```
    Val Gln Leu Asn Asp Glu Lys Thr Lys Val Asn Val Thr Ile Asp Val
    1               5                   10                  15

Asn Glu Gly Leu Gln Tyr Asp Leu Arg Ser Ala Arg Ile Ile
                20                  25                  30

(2) INFORMATION FOR SEQ ID NO: 25:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 25:

Tyr Asp Leu Arg Ser Ala Arg Ile Ile Gly Asn Leu Gly Gly Met Ser
    1               5                   10                  15

Ala Glu Leu Glu Pro Leu Leu Ser Ala Leu His Leu Asn Asp
                20                  25                  30

(2) INFORMATION FOR SEQ ID NO: 26:

(i) SEQUENCE CHARACTERISTICS:
        (A) LENGTH: 31 amino acids
        (B) TYPE: amino acid
        (C) STRANDEDNESS: single
        (D) TOPOLOGY: linear (xi) SEQUENCE DESCRIPTION: SEQ ID NO: 26:

Pro Leu Leu Ser Ala Leu His Leu Asn Asp Thr Phe Arg Arg Ser Asp
    1               5                   10                  15

Ile Ala Asp Val Glu Asn Ala Ile Lys Ala Lys Leu Gly Glu Arg
                20                  25                  30

(2) INFORMATION FOR SEQ ID NO: 27:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 27:

Ala Ile Lys Ala Lys Leu Gly Glu Arg Gly Tyr Gly Ser Ala Thr Val
    1               5                   10                  15

Asn Ser Val Pro Asp Phe Asp Asp Ala Asn Lys Thr Leu Ala
                20                  25                  30

(2) INFORMATION FOR SEQ ID NO: 28:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 28:

Phe Asp Asp Ala Asn Lys Thr Leu Ala Ile Thr Leu Val Val Asp Ala
    1               5                   10                  15

Gly Arg Arg Leu Thr Val Arg Gln Leu Arg Phe Glu Gly Asn
                20                  25                  30

(2) INFORMATION FOR SEQ ID NO: 29:

(i) SEQUENCE CHARACTERISTICS:
```

(A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 29:

Val Arg Gln Leu Arg Phe Glu Gly Asn Thr Val Ser Ala Asp Ser Thr
    1               5                   10                  15

Leu Arg Gln Glu Met Arg Gln Gln Glu Gly Thr Trp Tyr Asn
                20                  25                  30

(2) INFORMATION FOR SEQ ID NO: 30:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 30:

Arg Gln Gln Glu Gly Thr Trp Tyr Asn Ser Gln Leu Val Glu Leu Gly
    1               5                   10                  15

Lys Ile Arg Leu Asp Arg Thr Gly Phe Phe Glu Thr Val Glu
                20                  25                  30

(2) INFORMATION FOR SEQ ID NO: 31:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 31:

Gly Phe Phe Glu Thr Val Glu Asn Arg Ile Asp Pro Ile Asn Gly Ser
    1               5                   10                  15

Asn Asp Glu Val Asp Val Val Tyr Lys Val Lys
                20                  25

(2) INFORMATION FOR SEQ ID NO: 32:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 32:

Asp Val Val Tyr Lys Val Lys Glu Arg Asn Thr Gly Ser Ile Asn Phe
    1               5                   10                  15

Gly Ile Gly Tyr Gly Thr Glu Ser Gly Ile
                20                  25

(2) INFORMATION FOR SEQ ID NO: 33:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 33:

Gly Thr Glu Ser Gly Ile Ser Tyr Gln Ala Ser Val Lys Gln Asp Asn
    1               5                   10                  15

Phe Leu Gly Thr Gly Ala Ala Val Ser Ile

```
                20              25

(2) INFORMATION FOR SEQ ID NO: 34:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 34:

Gly Ala Ala Val Ser Ile Ala Gly Thr Lys Asn Asp Tyr Gly Thr Ser
    1               5                   10                  15

Val Asn Leu Gly Tyr Thr Glu Pro Tyr Phe Thr Lys
                20                  25

(2) INFORMATION FOR SEQ ID NO: 35:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 35:

Thr Glu Pro Tyr Phe Thr Lys Asp Gly Val Ser Leu Gly Gly Asn Val
    1               5                   10                  15

Phe Phe Glu Asn Tyr Asp Asn Ser Lys Ser Asp
                20                  25

(2) INFORMATION FOR SEQ ID NO: 36:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 36:

Tyr Asp Asn Ser Lys Ser Asp Thr Ser Ser Asn Tyr Lys Arg Thr Thr
    1               5                   10                  15

Tyr Gly Ser Asn Val Thr Leu Gly Phe Pro
                20                  25

(2) INFORMATION FOR SEQ ID NO: 37:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 37:

Val Thr Leu Gly Phe Pro Val Asn Glu Asn Asn Ser Tyr Tyr Val Gly
    1               5                   10                  15

Leu Gly His Thr Tyr Asn Lys Ile Ser Asn Phe
                20                  25

(2) INFORMATION FOR SEQ ID NO: 38:

(i) SEQUENCE CHARACTERISTICS:
        (A) LENGTH: 28 amino acids
        (B) TYPE: amino acid
        (C) STRANDEDNESS: single
        (D) TOPOLOGY: linear
```

(xi) SEQUENCE DESCRIPTION: SEQ ID NO: 38:

Tyr Asn Lys Ile Ser Asn Phe Ala Leu Glu Tyr Asn Arg Asn Leu Tyr
1               5                   10                  15

Ile Gln Ser Met Lys Phe Lys Gly Asn Gly Ile Lys
            20                  25

(2) INFORMATION FOR SEQ ID NO: 39:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO: 39:

Lys Gly Asn Gly Ile Lys Thr Asn Asp Phe Asp Phe Ser Phe Gly Trp
1               5                   10                  15

Asn Tyr Asn Ser Leu Asn Arg Gly Tyr Phe Pro Thr Lys
            20                  25

(2) INFORMATION FOR SEQ ID NO: 40:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 40:

Gly Tyr Phe Pro Thr Lys Gly Val Lys Ala Ser Leu Gly Gly Arg Val
1               5                   10                  15

Thr Ile Pro Gly Ser Asp Asn Lys Tyr Tyr Lys
            20                  25

(2) INFORMATION FOR SEQ ID NO: 41:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO: 41:

Ser Asp Asn Lys Tyr Tyr Lys Leu Ser Ala Asp Val Gln Gly Phe Tyr
1               5                   10                  15

Pro Leu Asp Arg Asp His Leu Trp Val Val Ser Ala Lys
            20                  25

(2) INFORMATION FOR SEQ ID NO: 42:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO: 42:

Leu Trp Val Val Ser Ala Lys Ala Ser Ala Gly Tyr Ala Asn Gly Phe
1               5                   10                  15

Gly Asn Lys Arg Leu Pro Phe Tyr Gln Thr Tyr Thr
            20                  25

(2) INFORMATION FOR SEQ ID NO: 43:

(i) SEQUENCE CHARACTERISTICS:
    (A) LENGTH: 26 amino acids
    (B) TYPE: amino acid
    (C) STRANDEDNESS: single
    (D) TOPOLOGY: linear (xi) SEQUENCE DESCRIPTION: SEQ ID NO: 43:

```
Phe Tyr Gln Thr Tyr Thr Ala Gly Gly Ile Gly Ser Leu Arg Gly Phe
1               5                   10                  15

Ala Tyr Gly Ser Ile Gly Pro Asn Ala Ile
            20                  25
```

(2) INFORMATION FOR SEQ ID NO: 44:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 44:

```
Gly Pro Asn Ala Ile Tyr Ala Glu Tyr Gly Asn Gly Ser Gly Thr Gly
1               5                   10                  15

Thr Phe Lys Lys Ile Ser Ser Asp Val Ile Gly
            20                  25
```

(2) INFORMATION FOR SEQ ID NO: 45:

(i) SEQUENCE CHARACTERISTICS:
        (A) LENGTH: 29 amino acids
        (B) TYPE: amino acid
        (C) STRANDEDNESS: single
        (D) TOPOLOGY: linear (xi) SEQUENCE DESCRIPTION: SEQ ID NO: 45:

```
Lys Ile Ser Ser Asp Val Ile Gly Gly Asn Ala Ile Ala Thr Ala Ser
1               5                   10                  15

Ala Glu Leu Ile Val Pro Thr Pro Phe Val Ser Asp Lys
            20                  25
```

(2) INFORMATION FOR SEQ ID NO: 46:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 46:

```
Phe Val Ser Asp Lys Ser Gln Asn Thr Val Arg Thr Ser Leu Phe Val
1               5                   10                  15

Asp Ala Ala Ser Val Trp Asn Thr Lys Trp Lys
            20                  25
```

(2) INFORMATION FOR SEQ ID NO: 47:

(i) SEQUENCE CHARACTERISTICS:
        (A) LENGTH: 26 amino acids
        (B) TYPE: amino acid
        (C) STRANDEDNESS: single
        (D) TOPOLOGY: linear (xi) SEQUENCE DESCRIPTION: SEQ ID NO: 47:

```
Val Trp Asn Thr Lys Trp Lys Ser Asp Lys Asn Gly Leu Glu Ser Asp
1               5                   10                  15
```

```
      Val Leu Lys Arg Leu Pro Asp Tyr Gly Lys
                  20                  25
```

(2) INFORMATION FOR SEQ ID NO: 48:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO: 48:

```
    Leu Pro Asp Tyr Gly Lys Ser Ser Arg Ile Arg Ala Ser Thr Gly Val
    1               5                   10                  15

Gly Phe Gln Trp Gln Ser Pro Ile Gly Pro Leu
                20                  25
```

(2) INFORMATION FOR SEQ ID NO: 49:

(i) SEQUENCE CHARACTERISTICS:
        (A) LENGTH: 30 amino acids
        (B) TYPE: amino acid
        (C) STRANDEDNESS: single
        (D) TOPOLOGY: linear (xi) SEQUENCE DESCRIPTION: SEQ ID NO: 49:

```
    Gly Pro Leu Val Phe Ser Tyr Ala Lys Pro Ile Lys Lys Tyr Glu Asn
    1               5                   10                  15

Asp Asp Val Glu Gln Phe Gln Phe Ser Ile Gly Gly Ser Phe
                20                  25                  30
```

(2) INFORMATION FOR SEQ ID NO: 50:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (xi) SEQUENCE DESCRIPTION: SEQ ID NO: 50:

```
TATGGCACCT TTTGTGGCAA AAGATATTCG TGTGGATGGT GTTCAAGGTG ACTTAGAATC        60

AACAAACCGA GCAAGTTTAC CTGTTCGTG                                         89
```

(2) INFORMATION FOR SEQ ID NO: 51:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (xi) SEQUENCE DESCRIPTION: SEQ ID NO: 51:

```
ACCGTGGAAA ACACCGTTTT CTATAAGCAC ACCTACCACA AGTTCCACTG AATCTTGGTT        60

GTTTAGGCTC GTTCAAATGG ACAAGCACGG CC                                     92
```

(2) INFORMATION FOR SEQ ID NO: 52:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 52:

```
GGGGAATTCC AAAAGATGTT CGT                                                23
```

(2) INFORMATION FOR SEQ ID NO: 53:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 53:

```
CACGAATTCC CTGCAAATC                                                     19
```

(2) INFORMATION FOR SEQ ID NO: 54:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 54:

```
Met Ala Pro Phe Val Lys Asp
 1               5
```

(2) INFORMATION FOR SEQ ID NO: 55:

(i) SEQUENCE CHARACTERISTICS:
        (A) LENGTH: 2987 base pairs
        (B) TYPE: nucleic acid
        (C) STRANDEDNESS: single
        (D) TOPOLOGY: linear (xi) SEQUENCE DESCRIPTION: SEQ ID NO: 55:

```
AAAAGGCATT GAAAAAACAG GACAGCTTTC CCTTTTAACC TTGAAAATAT TAGGGAAATT       60
ACTTACTGGC GATTTGTCAT TAAATAATTT AAGTGGGCCA ATTTCTATTG CAAAAGGTGC      120
TGGCGCATCA GCAAATATTG GATTGGTGTA TTTTTTAAGT TTTATGGCAT GATTAGTGTA      180
AATTTAGGGA TTATGAATTT ATTTCCATTA CCAGTATTAG ATGGCGGTCA TTTAGTTTTT      240
TTAACAATGG AAGCTGTTAA AGGAAAACCT GTTTCTGAGC GGGTGCAAAG CATCTGTTAT      300
CGAATTGGCG CAGCACTGTT ATTAAGCTTA ACGGTGTTTG CATTATTTAA TGATTTTTTA      360
CGTCTATAAT TTATATAGGA TACAATCGAT GAAAAAACTT CTAATCGCAA GTTTATTATT      420
CGGTACGACA ACGACTGTGT TGCCGCACCC TTTTGTGGCA AAAGATATTC GTGTGGATGG      480
TGTTCAAGGT GACTTAGAAC AACAAATCCG AGCAAGTTTA CCTGTTCGTG CCGGTCAGCG      540
TGTGACTGAC AATGATGTGG CTAATATTGT CCGCTCTTTA TTCGTAAGTG GTCGATTCGA      600
TGATGTGAAA GCGCATCAAG AAGGCGATGT GCTTGTTGTT AGCGTTGTGG CTAAATCGAT      660
CATTTCAGAT GTTAAAATCA AAGGTAACTC TGTTATTCCC ACTGAAGCAC TTAAACAAAA      720
CTTAGATGCT AACGGGTTTA AAGTTGGCGA TGTTTTAATT CGAGAAAAAT TAAATGAATT      780
TGCCAAAAGT GTAAAAGAGC ACTATGCAAG TGTAGGTCGC TATAACGCAA CAGTTGAACC      840
TATTGTCAAT ACGCTACCAA ATAATCGCGC TGAAATTTTA ATTCAAATCA ATGAAGATGA      900
TAAAGCAAAA TTGGCATCAT TAACTTTCAA GGGGAACGAA TCTGTTAGTA GCAGTACATT      960
ACAAGAACAA ATGGAATTAC AACCTGATTC TTGGTGGAAA TTATGGGGAA ATAAATTTGA     1020
AGGTGCGCAA TTCGAGAAAG ATTTGCAGTC AATTCGTGAT TATTATTTAA ATAATGGCTA     1080
TGCCAAAGCA CAAATTACTA AAACGGATGT TCAGCTAAAT GATGAAAAAA CAAAAGTTAA     1140
```

-continued

```
TGTAACCATT GATGTAAATG AAGGTTTACA GTATGACCTT CGTAGTGCAC GCATTATAGG    1200

TAATCTGGGA GGTATGTCTG CCGAGCTTGA ACCTTTACTT TCAGCATTAC ATTTAAATGA    1260

TACTTTCCGC CGTAGTGATA TTGCAGATGT AGAAAATGCA ATTAAAGCAA AACTTGGAGA    1320

ACGCGGTTAC GGTAGCGCAA CGGTAAATTC AGTACCTGAT TTTGATGATG CAAATAAAAC    1380

ATTAGCGATA ACCCTTGTTG TTGATGCTGG ACGACGTTTA ACTGTTCGCC AACTTCGCTT    1440

TGAAGGAAAT ACCGTTTCTG CTGATAGCAC TTTACGTCAG GAAATGCGCC AACAAGAAGG    1500

AACTTGGTAT AATTCACAAT TAGTTGAGTT AGGAAAAATT CGCTTAGATC GTACAGGTTT    1560

CTTCGAAACA GTCGAAAACC GAATTGATCC TATCAATGGT AGTAATGATG AAGTGGATGT    1620

CGTATATAAA GTCAAAGAAC GTAACACGGG TAGTATCAAC TTTGGTATTG GTTACGGTAC    1680

AGAGAGTGGT ATTAGTTATC AAGCAAGTGT TAAACAAGAT AATTTCTTGG GAACAGGGGC    1740

GGCAGTAAGT ATAGCTGGTA CGAAAAATGA TTATGGTACG AGTGTCAATT TGGGTTATAC    1800

CGAGCCCTAT TTTACTAAAG ATGGTGTAAG TCTTGGTGGA AATGTTTTCT TTGAAAACTA    1860

CGATAACTCT AAAAGTGATA CATCCTCTAA CTATAAGCGT ACGACTTACG GAAGTAATGT    1920

TACTTTAGGT TTCCCTGTAA ATGAAAATAA CTCCTATTAT GTAGGATTAG GTCATACCTA    1980

TAATAAAATT AGTAACTTTG CTCTAGAATA TAACCGTAAT TTATATATTC AATCAATGAA    2040

ATTTAAAGGT AATGGCATTA AAACAAATGA CTTTGATTTT TCTTTTGGTT GGAACTATAA    2100

CAGCCTTAAT AGAGGCTATT TCCCAACTAA AGGGGTTAAA GCAAGTCTTG GTGGACGAGT    2160

TACTATTCCA GGTTCTGATA ACAAATACTA CAAACTAAGT GCAGATGTAC AGGGTTTCTA    2220

CCCATTAGAC AGAGATCACC TCTGGGTTGT ATCTGCAAAA GCATCTGCAG GATATGCAAA    2280

TGGTTTTGGA AACAAGCGTT TACCGTTCTA TCAAACTTAT ACAGCGGGTG GCATCGGTTC    2340

ATTACGTGGT TTTGCTTATG GTAGTATTGG ACCTAACGCA ATTTATGCCG AATATGGTAA    2400

TGGTAGTGGT ACTGGTACTT TTAAGAAGAT AAGTTCTGAT GTGATTGGTG GTAATGCAAT    2460

CGCTACAGCT AGCGCAGAGT TAATTGTGCC AACTCCATTT GTGAGCGATA AGAGCCAAAA    2520

TACGGTCCGA ACCTCCTTAT TTGTTGATGC GGCAAGTGTT TGGAATACTA AATGGAAATC    2580

AGATAAAAAT GGATTAGAGA GCGATGTATT AAAAAGATTG CCTGATTATG GCAAATCAAG    2640

CCGTATTCGC GCCTCTACAG GTGTCGGATT CCAATGGCAA TCTCCTATTG GGCCATTGGT    2700

ATTCTCTTAT GCCAAACCAA TTAAAAAATA TGAAAATGAT GATGTCGAAC AGTTCCAATT    2760

TAGTATTGGA GGTTCTTTCT AATAAATTGA ACTTTTTTCT TCATCAGAAC TCAAAAACAA    2820

CGTTCTCTGC CTAATTTAAT TGGGCAGAGA AAATATTAAA CCCATCATTT AATTAAGGAT    2880

ATTTATCAAA TGAAAAACAT CGCAAAAGTA ACCGCACTTG CTTTAGGTAT TGCACTTGCT    2940

TCAGGCTATG CTTCCGCTGA AGAAAAAATT GCTTTCATTA ATGCAGT                 2987
```